(12) United States Patent
Wright et al.

(10) Patent No.: US 10,174,337 B2
(45) Date of Patent: *Jan. 8, 2019

(54) HERBICIDE RESISTANCE GENES

(71) Applicant: Dow AgroSciences LLC, Indianapolis, IN (US)

(72) Inventors: Terry Wright, Westfield, IN (US); Justin Lira, Fishers, IN (US); Donald Merlo, Carmel, IN (US); Nicole Arnold, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 554 days.

This patent is subject to a terminal disclaimer.

(21) Appl. No.: 14/820,893

(22) Filed: Aug. 7, 2015

(65) Prior Publication Data

US 2015/0344903 A1 Dec. 3, 2015

Related U.S. Application Data

(63) Continuation of application No. 12/951,813, filed on Nov. 22, 2010, now Pat. No. 9,127,289, which is a continuation of application No. 11/587,893, filed as application No. PCT/US2005/014737 on May 2, 2005, now Pat. No. 7,838,733.

(60) Provisional application No. 60/567,052, filed on Apr. 30, 2004.

(51) Int. Cl.
*C12N 15/82* (2006.01)
*C12N 9/02* (2006.01)

(52) U.S. Cl.
CPC ....... *C12N 15/8274* (2013.01); *C12N 9/0069* (2013.01); *C12N 15/8209* (2013.01)

(58) Field of Classification Search
None
See application file for complete search history.

(56) References Cited

U.S. PATENT DOCUMENTS

| 7,838,733 B2 * | 11/2010 | Wright | C12N 9/0069 800/300 |
| 9,127,289 B2 * | 9/2015 | Wright | C12N 9/0069 800/300 |
| 2003/0041357 A1 * | 2/2003 | Jepson | C07K 14/415 800/300 |

OTHER PUBLICATIONS

Spencer et al 1992, Plant Molecular Biology 18: 201-210.*
Kohler Oct. 1, 2002, Genbank Accession No. Q8KSC8.*

* cited by examiner

*Primary Examiner* — David H Kruse
(74) *Attorney, Agent, or Firm* — Barnes & Thornburg LLP

(57) ABSTRACT

The subject invention provides novel plants that are not only resistant to 2,4-D and other phenoxy auxin herbicides, but also to aryloxyphenoxypropionate herbicides. Heretofore, there was no expectation or suggestion that a plant with both of these advantageous properties could be produced by the introduction of a single gene. The subject invention also includes plants that produce one or more enzymes of the subject invention alone or "stacked" together with another herbicide resistance gene, preferably a glyphosate resistance gene, so as to provide broader and more robust weed control, increased treatment flexibility, and improved herbicide resistance management options. More specifically, preferred enzymes and genes for use according to the subject invention are referred to herein as AAD (aryloxyalkanoate dioxygenase) genes and proteins. No α-ketoglutarate-dependent dioxygenase enzyme has previously been reported to have the ability to degrade herbicides of different chemical classes and modes of action. This highly novel discovery is the basis of significant herbicide tolerant crop trait opportunities as well as development of selectable marker technology. The subject invention also includes related methods of controlling weeds. The subject invention enables novel combinations of herbicides to be used in new ways. Furthermore, the subject invention provides novel methods of preventing the formation of, and controlling, weeds that are resistant (or naturally more tolerant) to one or more herbicides such as glyphosate.

13 Claims, 24 Drawing Sheets

Specification includes a Sequence Listing.

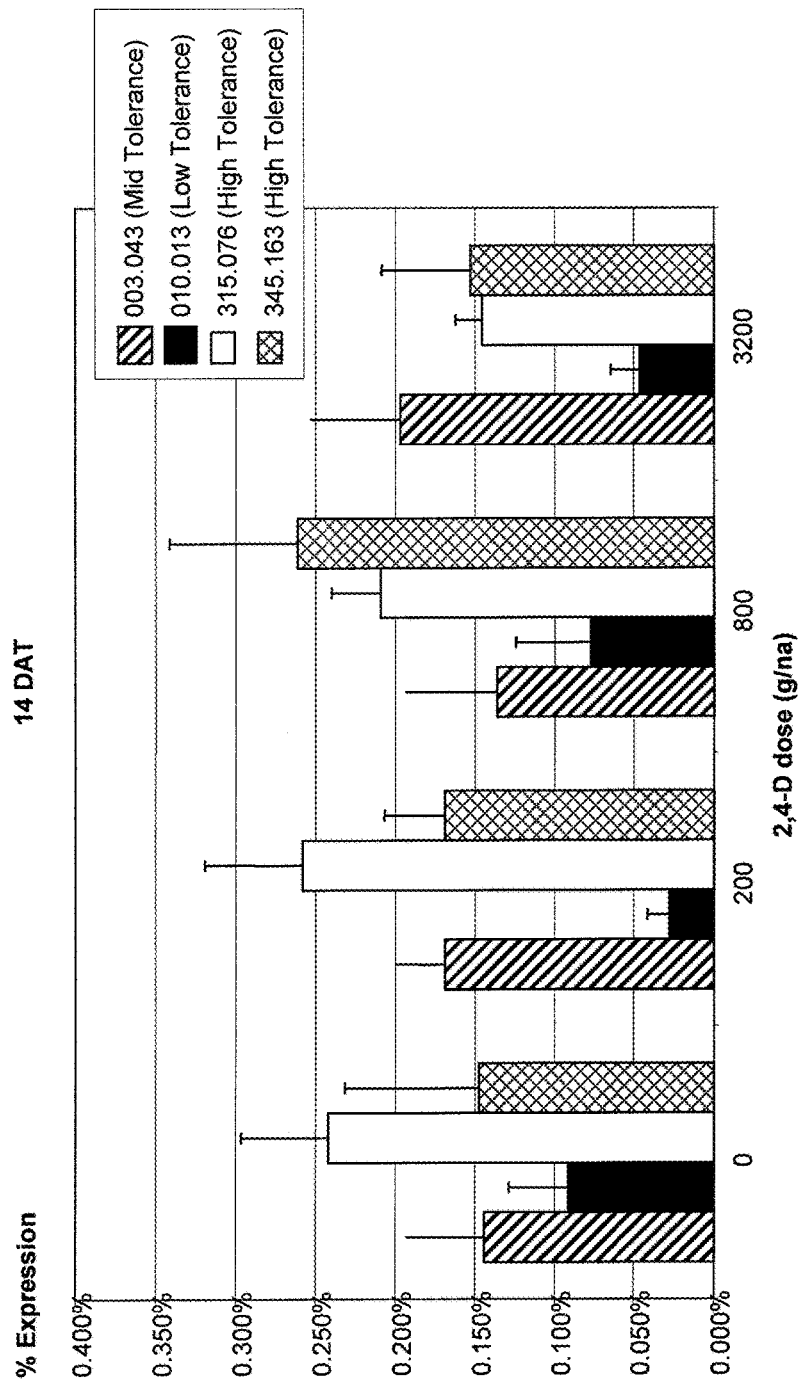

SEQUENCE LISTING

```
<160> NUMBER OF SEQ ID NOS: 32

<210> SEQ ID NO 1
<211> LENGTH: 50
<212> TYPE: DNA
<213> ORGANISM: Artificial Sequence
<220> FEATURE:
<223> OTHER INFORMATION: Forward primer used to amplify the rdpA/AAD-1
      (v1) gene

<400> SEQUENCE: 1
tctagaagga gatataccat gcatgctgca ctgtccccc tctcccagcg              50

<210> SEQ ID NO 2
<211> LENGTH: 38
<212> TYPE: DNA
<213> ORGANISM: Artificial Sequence
<220> FEATURE:
<223> OTHER INFORMATION: Reverse primer used to amplify the rdpA/AAD-1
```

(v1) gene

<400> SEQUENCE: 2
ctcgagttac tagcgcgccg ggcgcacgcc accgaccg                              38

<210> SEQ ID NO 3
<211> LENGTH: 915
<212> TYPE: DNA
<213> ORGANISM: Sphingobium herbicidovorans
<220> FEATURE:
<221> NAME/KEY: misc_feature
<222> LOCATION: (1)..(18)
<223> OTHER INFORMATION: Primer linker
<220> FEATURE:
<221> NAME/KEY: misc_feature
<222> LOCATION: (907)..(915)
<223> OTHER INFORMATION: Primer linker

<400> SEQUENCE: 3
tctagaagga gatataccat gcatgctgca ctgtccccc tctcccagcg ctttgagcgc      60
atcgcggtcc agccgctgac cggcgtcctg ggcgccgaga tcaccggcgt cgacctgcgc     120
gagccgctcg acgacagcac ctggaacgaa atcctcgacg cgttccacac ttaccaggtc     180
atctattttc ccggccaggc gatcaccaac gaacagcaca tcgccttcag ccggcgcttc     240
ggccccgtcg atcccgtgcc cctgctcaag agcatcgaag ggtatccaga ggtgcagatg     300
atccgccgcg aagccaacga aagcgggcgt gtgatcggtg aygactggca caccgacagc     360
accttcctgg acgcaccgcc ggccgccgtg gtgatgcgcg cgatcgacgt gcccgagcat     420
ggcggcgaca ccggttttct gagcatgtac accgcgtggg agacgctgtc gcccaccatg     480
caggccacca tcgaagggtt gaacgtagtg cacagcgcca cgcgtgtgtt cggctcgctc     540
taccaggccc agaaccggcg cttcagcaac accagcgtca aggtgatgga cgtcgacgcg     600
ggcgaccgtg aaaccgtgca ccccctggtg gtgacccatc cgggcagcgg ccgcaagggc     660
ctgtacgtga accaggtcta ttgccagcgc atcgagggca tgaccgatgc cgaaagcaaa     720
ccgctgctgc agttcctgta cgagcatgcg acacggttcg atttcacctg ccgcgtgcgc     780
tggaagaagg accaggtcct ggtctgggac aacctgtgca cgatgcaccg ggccgtaccc     840
gactacgcgg gcaagttccg ctacctgacg cgcaccacgg tcggtggcgt gcgcccggcg     900
cgctagtaac tcgag                                                     915

<210> SEQ ID NO 4
<211> LENGTH: 897
<212> TYPE: DNA
<213> ORGANISM: Artificial Sequence
<220> FEATURE:
<223> OTHER INFORMATION: AAD-1 (v2) primary sequence
<220> FEATURE:
<221> NAME/KEY: misc_feature
<222> LOCATION: (1)..(2)
<223> OTHER INFORMATION: primer linker
<220> FEATURE:
<221> NAME/KEY: misc_feature
<222> LOCATION: (891)..(897)
<223> OTHER INFORMATION: primer linker

<400> SEQUENCE: 4
ccatggctgc tgcactgtcc ccctctccc agcgctttga gcgcatcgcg gtccagccgc      60
tgaccggcgt cctgggcgcc gagatcaccg gcgtcgacct gcgcgagccg ctcgacgaca    120
gcacctggaa cgaaatcctc gacgcgttcc acacttacca ggtcatctat tttcccggcc    180
aggcgatcac caacgaacag cacatcgcct tcagccggcg cttcggcccc gtcgatcccg    240

```
tgcccctgct caagagcatc gaagggtatc cagaggtgca gatgatccgc cgcgaagcca    300
acgaaagcgg gcgtgtgatc ggtgatgact ggcacaccga cagcaccttc ctggacgcac    360
cgccggccgc cgtggtgatg cgcgcgatcg acgtgcccga gcatggcggc gacaccggtt    420
ttctgagcat gtacaccgcg tgggagacgc tgtcgcccac catgcaggcc accatcgaag    480
ggttgaacgt agtgcacagc gccacgcgtg tgttcggctc gctctaccag gcccagaacc    540
ggcgcttcag caacaccagc gtcaaggtga tggacgtcga cgcgggcgac cgtgaaaccg    600 tgcacccct ggtggtgacc catccgggca gcggctgcaa gggcctgtac gtgaaccagg    660
tctattgcca gcgcatcgag ggcatgaccg atgccgaaag caaaccgctg ctgcagttcc    720
tgtacgagca tgcgacacgg ttcgatttca cctgccgcgt gcgctggaag aaggaccagg    780
tcctggtctg ggacaacctg tgcacgatgc accgggccgt acccgactac gcgggcaagt    840
tccgctacct gacgcgcacc acggtcggtg gcgtgcgccc ggcgcgctag tgagctc       897

<210> SEQ ID NO 5
<211> LENGTH: 919
<212> TYPE: DNA
<213> ORGANISM: Artificial Sequence
<220> FEATURE:
<223> OTHER INFORMATION: AAD-1 (v3) primary sequence
<220> FEATURE:
<221> NAME/KEY: misc_feature
<222> LOCATION: (1)..(2)
<223> OTHER INFORMATION: primer linker
<220> FEATURE:
<221> NAME/KEY: misc_feature
<222> LOCATION: (6)..(8)
<223> OTHER INFORMATION: additional alanine codon (GCT)
<220> FEATURE:
<221> NAME/KEY: misc_feature
<222> LOCATION: (894)..(919)
<223> OTHER INFORMATION: primer linker

<400> SEQUENCE: 5
ccatggctca tgctgccctc agccctctct cccaacgctt tgagagaata gctgtccagc     60
cactcactgg tgtccttggt gctgagatca ctggagtgga cttgagggaa ccacttgatg    120
acagcacctg gaatgagata ttggatgcct ccacactta ccaagtcatc tactttcctg     180
gccaagcaat caccaatgag cagcacattg cattctcaag aaggtttgga ccagttgatc    240
cagtgcctct tctcaagagc attgaaggct atccagaggt tcagatgatc cgcagagaag    300
ccaatgagtc tggaagggtg attggtgatg actggcacac agactccact ttccttgatg    360
cacctccagc tgctgttgtg atgagggcca tagatgttcc tgagcatggc ggagacactg    420
ggttcctttc aatgtacaca gcttgggaga ccttgtctcc aaccatgcaa gccaccatcg    480
aagggctcaa cgttgtgcac tctgccacac gtgtgttcgg ttccctctac aagcacaga     540 accgtcgctt cagcaacacc tcagtcaagg tgatggatgt tgatgctggt gacagagaga    600
cagtccatcc cttggttgtg actcatcctg gctctggaag gaaaggcctt tatgtgaatc    660
aagtctactg tcagagaatt gagggcatga cagatgcaga atcaaagcca ttgcttcagt    720
tcctctatga gcatgccacc agatttgact tcacttgccg tgtgaggtgg aagaaagacc    780
aagtccttgt ctgggacaac ttgtgcacca tgcaccgtgc tgttcctgac tatgctggca    840
agttcagata cttgactcgc accacagttg gtggagttag gcctgccgc tgagtagtta    900 gcttaatcac ctagagctc                                                919

<210> SEQ ID NO 6
```

```
<211> LENGTH: 30
<212> TYPE: DNA
<213> ORGANISM: Artificial Sequence
<220> FEATURE:
<223> OTHER INFORMATION: rdpA(ncoI) 5' primer

<400> SEQUENCE: 6
cccatggctg ctgcactgtc cccctctcc                                        30

<210> SEQ ID NO 7
<211> LENGTH: 33
<212> TYPE: DNA
<213> ORGANISM: Artificial Sequence
<220> FEATURE:
<223> OTHER INFORMATION: 3'saci primer

<400> SEQUENCE: 7
gagctcacta gcgcgccggg cgcacgccac cga                                   33

<210> SEQ ID NO 8
<211> LENGTH: 36
<212> TYPE: DNA
<213> ORGANISM: Artificial Sequence
<220> FEATURE:
<223> OTHER INFORMATION: BstEII/ Del NotI 5' primer

<400> SEQUENCE: 8
tggtggtgac ccatccgggc agcggctgca agggcc                                36

<210> SEQ ID NO 9
<211> LENGTH: 295
<212> TYPE: PRT
<213> ORGANISM: Sphingobium herbicidovorans

<400> SEQUENCE: 9
```

Met His Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
            20                  25                  30

Leu Arg Glu Pro Leu Asp Asp Ser Thr Trp Asn Glu Ile Leu Asp Ala
        35                  40                  45

Phe His Thr Tyr Gln Val Ile Tyr Phe Pro Gly Gln Ala Ile Thr Asn
    50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Ala Ala Val Val Met Arg Ala
        115                 120                 125

Ile Asp Val Pro Glu His Gly Gly Asp Thr Gly Phe Leu Ser Met Tyr
    130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro

```
                195                 200                 205
Gly Ser Gly Arg Lys Gly Leu Tyr Val Asn Gln Val Tyr Cys Gln Arg
    210                 215                 220

Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
                260                 265                 270

Val Pro Asp Tyr Ala Gly Lys Phe Arg Tyr Leu Thr Arg Thr Thr Val
                275                 280                 285

Gly Gly Val Arg Pro Ala Arg
                290                 295

<210> SEQ ID NO 10
<211> LENGTH: 295
<212> TYPE: PRT
<213> ORGANISM: Artificial Sequence
<220> FEATURE:
<223> OTHER INFORMATION: AAD-1 v2 Translation
<220> FEATURE:
<221> NAME/KEY: MISC_FEATURE
<222> LOCATION: (2)..(2)
<223> OTHER INFORMATION: Different from v1
<220> FEATURE:
<221> NAME/KEY: MISC_FEATURE
<222> LOCATION: (212)..(212)
<223> OTHER INFORMATION: Different from v1

<400> SEQUENCE: 10

Met Ala Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
                20                  25                  30

Leu Arg Glu Pro Leu Asp Asp Ser Thr Trp Asn Glu Ile Leu Asp Ala
            35                  40                  45

Phe His Thr Tyr Gln Val Ile Tyr Phe Pro Gly Gln Ala Ile Thr Asn
    50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Pro Ala Ala Val Val Met Arg Ala
        115                 120                 125

Ile Asp Val Pro Glu His Gly Gly Asp Thr Gly Phe Leu Ser Met Tyr
    130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro
        195                 200                 205

Gly Ser Gly Cys Lys Gly Leu Tyr Val Asn Gln Val Tyr Cys Gln Arg
    210                 215                 220
```

```
Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
            260                 265                 270

Val Pro Asp Tyr Ala Gly Lys Phe Arg Tyr Leu Thr Arg Thr Thr Val
        275                 280                 285

Gly Gly Val Arg Pro Ala Arg
    290                 295
```

<210> SEQ ID NO 11
<211> LENGTH: 296
<212> TYPE: PRT
<213> ORGANISM: Artificial Sequence
<220> FEATURE:
<223> OTHER INFORMATION: AAD-1 v3 Translation
<220> FEATURE:
<221> NAME/KEY: MISC_FEATURE
<222> LOCATION: (2)..(3)
<223> OTHER INFORMATION: Different from V1

<400> SEQUENCE: 11

```
Met Ala His Ala Ala Leu Ser Pro Leu Ser Gln Arg Phe Glu Arg Ile
1               5                   10                  15

Ala Val Gln Pro Leu Thr Gly Val Leu Gly Ala Glu Ile Thr Gly Val
                20                  25                  30

Asp Leu Arg Glu Pro Leu Asp Asp Ser Thr Trp Asn Glu Ile Leu Asp
            35                  40                  45

Ala Phe His Thr Tyr Gln Val Ile Tyr Phe Pro Gly Gln Ala Ile Thr
        50                  55                  60

Asn Glu Gln His Ile Ala Phe Ser Arg Arg Phe Gly Pro Val Asp Pro
65                  70                  75                  80

Val Pro Leu Leu Lys Ser Ile Glu Gly Tyr Pro Glu Val Gln Met Ile
                85                  90                  95

Arg Arg Glu Ala Asn Glu Ser Gly Arg Val Ile Gly Asp Asp Trp His
            100                 105                 110

Thr Asp Ser Thr Phe Leu Asp Ala Pro Pro Ala Ala Val Val Met Arg
        115                 120                 125

Ala Ile Asp Val Pro Glu His Gly Gly Asp Thr Gly Phe Leu Ser Met
    130                 135                 140

Tyr Thr Ala Trp Glu Thr Leu Ser Pro Thr Met Gln Ala Thr Ile Glu
145                 150                 155                 160

Gly Leu Asn Val Val His Ser Ala Thr Arg Val Phe Gly Ser Leu Tyr
                165                 170                 175

Gln Ala Gln Asn Arg Arg Phe Ser Asn Thr Ser Val Lys Val Met Asp
            180                 185                 190

Val Asp Ala Gly Asp Arg Glu Thr Val His Pro Leu Val Val Thr His
        195                 200                 205

Pro Gly Ser Gly Arg Lys Gly Leu Tyr Val Asn Gln Val Tyr Cys Gln
    210                 215                 220

Arg Ile Glu Gly Met Thr Asp Ala Glu Ser Lys Pro Leu Leu Gln Phe
225                 230                 235                 240

Leu Tyr Glu His Ala Thr Arg Phe Asp Phe Thr Cys Arg Val Arg Trp
                245                 250                 255

Lys Lys Asp Gln Val Leu Val Trp Asp Asn Leu Cys Thr Met His Arg
```

```
                 260                 265                 270
Ala Val Pro Asp Tyr Ala Gly Lys Phe Arg Tyr Leu Thr Arg Thr Thr
            275                 280                 285

Val Gly Gly Val Arg Pro Ala Arg
        290                 295

<210> SEQ ID NO 12
<211> LENGTH: 888
<212> TYPE: DNA
<213> ORGANISM: Bradyrhizobium japonicum USDA 110

<400> SEQUENCE: 12
atgacgatcg ccatccggca gcttcagacg cattttgtcg gccaggtttc cggcctcgat      60
ttgcgaaagc cgctcacgcc gggcgaggcc cgcgaggtcg agtccgccat ggacaaatac     120
gcggtgctcg ttttccacga ccaggacatc accgacgagc agcagatggc tttcgcgctg     180
aacttcggcc agcgcgagga cgcgcgcggc ggcacggtca ccaaggagaa ggactaccgg     240
ctgcaatccg gcctgaacga cgtctccaat ctcggcaagg acggcaagcc gctggccaag     300
gacagccgca cgcacctgtt caatctcggc aactgcctct ggcactccga cagctcgttc     360
cgtcccattc ccgcaaaatt ctcgctgctg tcggcgcgcg tggtgaaccc gacggggggc     420
aacaccgaat cgcggacat gcgcgccgcc tatgacgcgc tcgacgacga gccaaggcc     480 gaaatcgagg acctcgtctg cgagcactcg ctgatgtatt cgcgcggctc gctcggcttc     540
accgagtaca ccgacgaaga gaagcagatg ttcaagccgg tcctgcaacg cctcgtgcgc     600
acccatccgg tccaccgccg caagtcgctg tatctctcgt cgcatgccgg caagatcgcc     660
agcatgagcg tgccggaggg gcggctgctg ttgcgcgatc tcaacgagca cgcgacgcag     720
ccggaattcg tctacgtcca caatggaag ctgcatgacc tcgtgatgtg ggacaaccgc     780
cagaccatgc accgcgtccg ccgctacgac cagtcccagc cccgcgacat gccgcgcg     840 acggtggcgg ggacggagcc gacggtgcag cagcaggcgg cggagtag              888

<210> SEQ ID NO 13
<211> LENGTH: 289
<212> TYPE: PRT
<213> ORGANISM: Bradyrhizobium japonicum USDA 110

<400> SEQUENCE: 13

Met Thr Ile Ala Ile Arg Gln Leu Gln Thr His Phe Val Gly Gln Val
1               5                  10                  15

Ser Gly Leu Asp Leu Arg Lys Pro Leu Thr Pro Gly Glu Ala Arg Glu
            20                  25                  30

Val Glu Ser Ala Met Asp Lys Tyr Ala Val Leu Val Phe His Asp Gln
        35                  40                  45

Asp Ile Thr Asp Glu Gln Gln Met Ala Phe Ala Leu Asn Phe Gly Gln
    50                  55                  60

Arg Glu Asp Ala Arg Gly Gly Thr Val Thr Lys Glu Lys Asp Tyr Arg
65                  70                  75                  80

Leu Gln Ser Gly Leu Asn Asp Val Ser Asn Leu Gly Lys Asp Gly Lys
                85                  90                  95

Pro Leu Ala Lys Asp Ser Arg Thr His Leu Phe Asn Leu Gly Asn Cys
            100                 105                 110

Leu Trp His Ser Asp Ser Ser Phe Arg Pro Ile Pro Ala Lys Phe Ser
        115                 120                 125

Leu Leu Ser Ala Arg Val Val Asn Pro Thr Gly Gly Asn Thr Glu Phe
```

```
            130                 135                 140
Ala Asp Met Arg Ala Ala Tyr Asp Ala Leu Asp Asp Glu Thr Lys Ala
145                 150                 155                 160

Glu Ile Glu Asp Leu Val Cys Glu His Ser Leu Met Tyr Ser Arg Gly
                165                 170                 175

Ser Leu Gly Phe Thr Glu Tyr Thr Asp Glu Glu Lys Gln Met Phe Lys
            180                 185                 190

Pro Val Leu Gln Arg Leu Val Arg Thr His Pro Val His Arg Arg Lys
        195                 200                 205

Ser Leu Tyr Leu Ser Ser His Ala Gly Lys Ile Ala Ser Met Ser Val
    210                 215                 220

Pro Glu Gly Arg Leu Leu Leu Arg Asp Leu Asn Glu His Ala Thr Gln
225                 230                 235                 240

Pro Glu Phe Val Tyr Val His Lys Trp Lys Leu His Asp Leu Val Met
                245                 250                 255

Trp Asp Asn Arg Gln Thr Met His Arg Val Arg Arg Tyr Asp Gln Ser
            260                 265                 270

Gln Pro Arg Asp Met Arg Arg Ala Thr Val Ala Gly Thr Glu Pro Thr
        275                 280                 285

Val
```

<210> SEQ ID NO 14
<211> LENGTH: 34
<212> TYPE: DNA
<213> ORGANISM: Artificial Sequence
<220> FEATURE:
<223> OTHER INFORMATION: brjap 5'(speI)

<400> SEQUENCE: 14
actagtaaca aagaaggaga tataccatga cgat        34

<210> SEQ ID NO 15
<211> LENGTH: 33
<212> TYPE: DNA
<213> ORGANISM: Artificial Sequence
<220> FEATURE:
<223> OTHER INFORMATION: br jap 3' (xhoI)

<400> SEQUENCE: 15
ttctcgagct atcactccgc cgcctgctgc tgc         33

<210> SEQ ID NO 16
<211> LENGTH: 17
<212> TYPE: DNA
<213> ORGANISM: Artificial Sequence
<220> FEATURE:
<223> OTHER INFORMATION: M13 forward primer

<400> SEQUENCE: 16
gtaaaacgac ggccagt                           17

<210> SEQ ID NO 17
<211> LENGTH: 17
<212> TYPE: DNA
<213> ORGANISM: Artificial Sequence
<220> FEATURE:
<223> OTHER INFORMATION: M13 reverse primer

<400> SEQUENCE: 17
caggaaacag ctatgac                           17

<210> SEQ ID NO 18
<211> LENGTH: 32
<212> TYPE: DNA
<213> ORGANISM: Artificial Sequence
<220> FEATURE:
<223> OTHER INFORMATION: NcoI of Brady

<400> SEQUENCE: 18
tataccacat gtcgatcgcc atccggcagc tt                          32

<210> SEQ ID NO 19
<211> LENGTH: 33
<212> TYPE: DNA
<213> ORGANISM: Artificial Sequence
<220> FEATURE:
<223> OTHER INFORMATION: SacI of Brady

<400> SEQUENCE: 19
gagctcctat cactccgccg cctgctgctg cac                         33

<210> SEQ ID NO 20
<211> LENGTH: 525
<212> TYPE: PRT
<213> ORGANISM: Glycine max

<400> SEQUENCE: 20

Met Ala Gln Val Ser Arg Val His Asn Leu Ala Gln Ser Thr Gln Ile
1               5                   10                  15

Phe Gly His Ser Ser Asn Ser Asn Lys Leu Lys Ser Val Asn Ser Val
            20                  25                  30

Ser Leu Arg Pro Arg Leu Trp Gly Ala Ser Lys Ser Arg Ile Pro Met
        35                  40                  45

His Lys Asn Gly Ser Phe Met Gly Asn Phe Asn Val Gly Lys Gly Asn
    50                  55                  60

Ser Gly Val Phe Lys Val Ser Ala Ser Val Ala Ala Glu Lys Pro
65                  70                  75                  80

Ser Thr Ser Pro Glu Ile Val Leu Glu Pro Ile Lys Asp Phe Ser Gly
                85                  90                  95

Thr Ile Thr Leu Pro Gly Ser Lys Ser Leu Ser Asn Arg Ile Leu Leu
            100                 105                 110

Leu Ala Ala Leu Ser Glu Gly Thr Thr Val Val Asp Asn Leu Leu Tyr
        115                 120                 125

Ser Glu Asp Ile His Tyr Met Leu Gly Ala Leu Arg Thr Leu Gly Leu
    130                 135                 140

Arg Val Glu Asp Asp Lys Thr Thr Lys Gln Ala Ile Val Glu Gly Cys
145                 150                 155                 160

Gly Gly Leu Phe Pro Thr Ser Lys Glu Ser Lys Asp Glu Ile Asn Leu
                165                 170                 175

Phe Leu Gly Asn Ala Gly Thr Ala Met Arg Pro Leu Thr Ala Ala Val
            180                 185                 190

Val Ala Ala Gly Gly Asn Ala Ser Tyr Val Leu Asp Gly Val Pro Arg
        195                 200                 205

Met Arg Glu Arg Pro Ile Gly Asp Leu Val Ala Gly Leu Lys Gln Leu
    210                 215                 220

Gly Ala Asp Val Asp Cys Phe Leu Gly Thr Asn Cys Pro Pro Val Arg
225                 230                 235                 240

Val Asn Gly Lys Gly Gly Leu Pro Gly Gly Lys Val Lys Leu Ser Gly
                245                 250                 255

```
Ser Val Ser Ser Gln Tyr Leu Thr Ala Leu Met Ala Ala Pro Leu
            260                 265                 270

Ala Leu Gly Asp Val Glu Ile Glu Ile Val Asp Lys Leu Ile Ser Val
        275                 280                 285

Pro Tyr Val Glu Met Thr Leu Lys Leu Met Glu Arg Phe Gly Val Ser
    290                 295                 300

Val Glu His Ser Gly Asn Trp Asp Arg Phe Leu Val His Gly Gly Gln
305                 310                 315                 320

Lys Tyr Lys Ser Pro Gly Asn Ala Phe Val Glu Gly Asp Ala Ser Ser
                325                 330                 335

Ala Ser Tyr Leu Leu Ala Gly Ala Ala Ile Thr Gly Gly Thr Ile Thr
            340                 345                 350

Val Asn Gly Cys Gly Thr Ser Ser Leu Gln Gly Asp Val Lys Phe Ala
            355                 360                 365

Glu Val Leu Glu Lys Met Gly Ala Lys Val Thr Trp Ser Glu Asn Ser
370                 375                 380

Val Thr Val Ser Gly Pro Pro Arg Asp Phe Ser Gly Arg Lys Val Leu
385                 390                 395                 400

Arg Gly Ile Asp Val Asn Met Asn Lys Met Pro Asp Val Ala Met Thr
                405                 410                 415

Leu Ala Val Val Ala Leu Phe Ala Asn Gly Pro Thr Ala Ile Arg Asp
                420                 425                 430

Val Ala Ser Trp Arg Val Lys Glu Thr Glu Arg Met Ile Ala Ile Cys
            435                 440                 445

Thr Glu Leu Arg Lys Leu Gly Ala Thr Val Glu Glu Gly Pro Asp Tyr
    450                 455                 460

Cys Val Ile Thr Pro Pro Glu Lys Leu Asn Val Thr Ala Ile Asp Thr
465                 470                 475                 480

Tyr Asp Asp His Arg Met Ala Met Ala Phe Ser Leu Ala Ala Cys Gly
                485                 490                 495

Asp Val Pro Val Thr Ile Lys Asp Pro Gly Cys Thr Arg Lys Thr Phe
            500                 505                 510

Pro Asp Tyr Phe Glu Val Leu Glu Arg Leu Thr Lys His
            515                 520                 525

<210> SEQ ID NO 21
<211> LENGTH: 525
<212> TYPE: PRT
<213> ORGANISM: Artificial sequence
<220> FEATURE:
<223> OTHER INFORMATION: Doubly mutated Soybean EPSPS protein: threonine
      183 converted to isoleucine; proline 187 converted to serine

<400> SEQUENCE: 21

Met Ala Gln Val Ser Arg Val His Asn Leu Ala Gln Ser Thr Gln Ile
1               5                   10                  15

Phe Gly His Ser Ser Asn Ser Asn Lys Leu Lys Ser Val Asn Ser Val
                20                  25                  30

Ser Leu Arg Pro Arg Leu Trp Gly Ala Ser Lys Ser Arg Ile Pro Met
            35                  40                  45

His Lys Asn Gly Ser Phe Met Gly Asn Phe Asn Val Gly Lys Gly Asn
        50                  55                  60

Ser Gly Val Phe Lys Val Ser Ala Ser Val Ala Ala Ala Glu Lys Pro
65                  70                  75                  80

Ser Thr Ser Pro Glu Ile Val Leu Glu Pro Ile Lys Asp Phe Ser Gly
```

```
            85                  90                  95
Thr Ile Thr Leu Pro Gly Ser Lys Ser Leu Ser Asn Arg Ile Leu Leu
            100                 105                 110

Leu Ala Ala Leu Ser Glu Gly Thr Thr Val Val Asp Asn Leu Leu Tyr
            115                 120                 125

Ser Glu Asp Ile His Tyr Met Leu Gly Ala Leu Arg Thr Leu Gly Leu
            130                 135                 140

Arg Val Glu Asp Lys Thr Thr Lys Gln Ala Ile Val Glu Gly Cys
145                 150                 155                 160

Gly Gly Leu Phe Pro Thr Ser Lys Glu Ser Lys Asp Glu Ile Asn Leu
            165                 170                 175

Phe Leu Gly Asn Ala Gly Ile Ala Met Arg Ser Leu Thr Ala Ala Val
            180                 185                 190

Val Ala Ala Gly Gly Asn Ala Ser Tyr Val Leu Asp Gly Val Pro Arg
            195                 200                 205

Met Arg Glu Arg Pro Ile Gly Asp Leu Val Ala Gly Leu Lys Gln Leu
            210                 215                 220

Gly Ala Asp Val Asp Cys Phe Leu Gly Thr Asn Cys Pro Pro Val Arg
225                 230                 235                 240

Val Asn Gly Lys Gly Gly Leu Pro Gly Gly Lys Val Lys Leu Ser Gly
            245                 250                 255

Ser Val Ser Ser Gln Tyr Leu Thr Ala Leu Leu Met Ala Ala Pro Leu
            260                 265                 270

Ala Leu Gly Asp Val Glu Ile Glu Ile Val Asp Lys Leu Ile Ser Val
            275                 280                 285

Pro Tyr Val Glu Met Thr Leu Lys Leu Met Glu Arg Phe Gly Val Ser
            290                 295                 300

Val Glu His Ser Gly Asn Trp Asp Arg Phe Leu Val His Gly Gly Gln
305                 310                 315                 320

Lys Tyr Lys Ser Pro Gly Asn Ala Phe Val Glu Gly Asp Ala Ser Ser
            325                 330                 335

Ala Ser Tyr Leu Leu Ala Gly Ala Ala Ile Thr Gly Gly Thr Ile Thr
            340                 345                 350

Val Asn Gly Cys Gly Thr Ser Ser Leu Gln Gly Asp Val Lys Phe Ala
            355                 360                 365

Glu Val Leu Glu Lys Met Gly Ala Lys Val Thr Trp Ser Glu Asn Ser
            370                 375                 380

Val Thr Val Ser Gly Pro Pro Arg Asp Phe Ser Gly Arg Lys Val Leu
385                 390                 395                 400

Arg Gly Ile Asp Val Asn Met Asn Lys Met Pro Asp Val Ala Met Thr
            405                 410                 415

Leu Ala Val Val Ala Leu Phe Ala Asn Gly Pro Thr Ala Ile Arg Asp
            420                 425                 430

Val Ala Ser Trp Arg Val Lys Glu Thr Glu Arg Met Ile Ala Ile Cys
            435                 440                 445

Thr Glu Leu Arg Lys Leu Gly Ala Thr Val Glu Glu Gly Pro Asp Tyr
            450                 455                 460

Cys Val Ile Thr Pro Pro Glu Lys Leu Asn Val Thr Ala Ile Asp Thr
465                 470                 475                 480

Tyr Asp Asp His Arg Met Ala Met Ala Phe Ser Leu Ala Ala Cys Gly
            485                 490                 495

Asp Val Pro Val Thr Ile Lys Asp Pro Gly Cys Thr Arg Lys Thr Phe
            500                 505                 510
```

Pro Asp Tyr Phe Glu Val Leu Glu Arg Leu Thr Lys His
        515                 520                 525

<210> SEQ ID NO 22
<211> LENGTH: 1604
<212> TYPE: DNA
<213> ORGANISM: Artificial sequence
<220> FEATURE:
<223> OTHER INFORMATION: Soybean-biased DNA sequence encoding
      doubly-mutated EPSPS disclosed in SEQ ID NO:21, with added
      sequence
<220> FEATURE:
<221> NAME/KEY: misc_feature
<222> LOCATION: (1)..(1575)
<223> OTHER INFORMATION: Coding sequence of soybean-biased DNA sequence
      encoding the EPSPSprotien of SEQ ID NO:21
<220> FEATURE:
<221> NAME/KEY: misc_feature
<222> LOCATION: (1576)..(1578)
<223> OTHER INFORMATION: Translation terminator tga
<220> FEATURE:
<221> NAME/KEY: misc_feature
<222> LOCATION: (1579)..(1604)
<223> OTHER INFORMATION: Sequence included to introduce translation stop
      codons in all six open reading frames, and to introduce a SacI
      restriction enzyme recognition site for cloning purposes

<400> SEQUENCE: 22

```
atggctcaag tctcccgtgt tcacaatctt gctcagtcaa cccaaatctt tggacattca       60
agcaactcaa acaaactgaa gtctgtgaat tctgtctcac ttcgcccacg cctttgggga      120
gcatccaaga gtcgcatacc aatgcacaag aatgggagtt tcatgggcaa cttcaatgtt      180
gggaaaggca attctggtgt cttcaaagtt tcagcttctg ttgcagccgc agagaaaccc      240
agcacttccc ctgagattgt tcttgaaccc attaaggact tcagtggaac aatcactctg      300
cctggatcaa agagtctttc aaacagaata cttctcttgg cagctctgag tgaaggaacc      360
actgtagttg acaaccttt gtactctgaa gatattcatt acatgttggg tgctctcaga      420
actcttgggt tgagagttga agatgacaag accacaaaac aagccatagt tgaaggatgt      480
ggtgggttgt ttccaacaag caaagaatcc aaagatgaga tcaacttgtt tcttggcaat      540
gctggaattg caatgagaag cctcactgct gcagtagttg cagctggtgg aatgcaagt       600 tatgtccttg atggtgtccc cagaatgagg gaaaggccca tcggtgacct tgtggctggc      660
ctgaaacagc ttggagcaga tgttgattgc ttcttgggca caaactgccc tccagtgaga      720
gtgaatggga agggaggttt gcctggtgga aaggtcaaac tgagtggatc agtctcttcc      780
cagtatctga ctgccttgct catggctgcc cctctggctt gggtgatgt ggagattgaa       840 atagtggaca gttgatttc tgttccatat gtggaaatga ccctcaaact catggagagg      900
tttggagttt ctgttgaaca ttctggcaac tgggatcgtt tccttgtaca tggaggtcag      960
aagtacaaaa gccctggcaa tgcctttgtt gaagggatg caagctctgc ttcctatctc      1020
ttggctgggg ctgccatcac tggtgggacc atcactgtga atggctgtgg cacctcatcc      1080
cttcaaggtg atgtaaagtt tgcagaggtc ttggagaaaa tgggtgccaa ggtcacctgg      1140
tctgagaaca gtgtaactgt gtctggacct cccagagact tcagtggcag aaaggttctc      1200
cgtggaattg atgtgaacat gaacaagatg ccagatgtgg ccatgaccct cgctgttgta      1260
gccctgtttg caaatggacc aactgcaatc cgtgatgttg cttcatggag ggtgaaggag      1320
acagagagga tgattgccat tgcacagaa ctccgcaaac ttggtgcaac agttgaagag      1380
ggaccagatt actgtgtgat aacccacct gagaagctca atgtgacagc cattgacacc      1440
```

-continued

```
tatgatgacc acagaatggc aatggctttc tcccttgctg cctgtggtga tgtgcctgtg    1500
actatcaaag accctgggtg cacaaggaag acatttccag actactttga agttttggag    1560
aggttgacaa agcactgagt agttagctta atcacctaga gctc                      1604
```

```
<210> SEQ ID NO 23
<211> LENGTH: 20
<212> TYPE: DNA
<213> ORGANISM: Artificial sequence
<220> FEATURE:
<223> OTHER INFORMATION: Primer Pat 5-3

<400> SEQUENCE: 23 agatacccctt ggttggttgc                                                  20
```

```
<210> SEQ ID NO 24
<211> LENGTH: 20
<212> TYPE: DNA
<213> ORGANISM: Artificial sequence
<220> FEATURE:
<223> OTHER INFORMATION: Primer Pat 3-3

<400> SEQUENCE: 24
cagatggatc gtttggaagg                                                  20
```

```
<210> SEQ ID NO 25
<211> LENGTH: 23
<212> TYPE: DNA
<213> ORGANISM: Artificial sequence
<220> FEATURE:
<223> OTHER INFORMATION: AAD-1 PTU forward primer

<400> SEQUENCE: 25
ataatgccag cctgttaaac gcc                                              23
```

```
<210> SEQ ID NO 26
<211> LENGTH: 23
<212> TYPE: DNA
<213> ORGANISM: Artificial sequence
<220> FEATURE:
<223> OTHER INFORMATION: AAD-1 PTU reverse primer

<400> SEQUENCE: 26
ctcaagcata tgaatgacct cga                                              23
```

```
<210> SEQ ID NO 27
<211> LENGTH: 22
<212> TYPE: DNA
<213> ORGANISM: Artificial sequence
<220> FEATURE:
<223> OTHER INFORMATION: Forward primer for Coding Region PCR AAD-1
      (RdpAcodF)

<400> SEQUENCE: 27
atggctcatg ctgccctcag cc                                               22
```

```
<210> SEQ ID NO 28
<211> LENGTH: 22
<212> TYPE: DNA
<213> ORGANISM: Artificial sequence
<220> FEATURE:
<223> OTHER INFORMATION: Reverse primer for Coding Region PCR AAD-1
      (RdpAcodR)

<400> SEQUENCE: 28
cgggcaggcc taactccacc aa                                               22
```

<210> SEQ ID NO 29
<211> LENGTH: 932
<212> TYPE: DNA
<213> ORGANISM: Artificial sequence
<220> FEATURE:
<223> OTHER INFORMATION: AAD-2 v2 plant-optimized nucleotide

<400> SEQUENCE: 29

```
ccatggctac catagcaatc agacagctcc agacccactt tgtgggtcaa gtttctggat      60
tggacctcag aaagccactc actcctggag aagccagaga agttgaatca gctatggaca     120
agtacgcagt tcttgtcttc catgaccaag acatcacaga tgagcaacag atggcctttg     180
ccctcaactt tggtcagagg gaggatgcac gtggtggcac tgtcaccaaa gagaaggatt     240
accgtcttca gtctggcctc aatgatgttt ccaacttggg caagatgga aagccacttg      300
ccaaggacag ccgcacccat tgttcaacc ttggaaactg cttgtggcat tctgactcca      360
gcttcagacc aatcccagcc aagttcagcc tcctttctgc tcgtgttgtg aacccaactg     420
gtgggaacac tgagtttgct gacatgagag ctgcctatga tgctcttgac gatgaaacca     480
aagctgagat tgaggacctt gtgtgtgagc actctctcat gtactcaagg ggctcacttg     540
gcttcactga gtacacagat gaagagaagc aaatgttcaa gcccgtcttg cagcgcttgg     600
tccgcacaca ccctgtgcac cgtcgcaaat cactctacct ctccagccat gccgaaaga     660
ttgccagcat gtccgtccct gaagggaggc tccttttgag ggatttgaat gaacatgcta     720
ctcagcctga gttcgtctat gttcacaaat ggaagttgca tgatcttgtg atgtgggaca     780
ataggcaaac catgcacaga gtgaggagat atgaccagtc ccaacccaga gacatgcgcc     840
gtgcaacagt tgctgggacc gagcccacag tgcaacagca agcagcagag tgagtagtta     900
gcttaatcac ctagagctcg gtcaccagat ct                                    932
```

<210> SEQ ID NO 30
<211> LENGTH: 296
<212> TYPE: PRT
<213> ORGANISM: Artificial sequence
<220> FEATURE:
<223> OTHER INFORMATION: Translated AAD-2 v2 protein

<400> SEQUENCE: 30

Met Ala Thr Ile Ala Ile Arg Gln Leu Gln Thr His Phe Val Gly Gln
1               5                   10                  15

Val Ser Gly Leu Asp Leu Arg Lys Pro Leu Thr Pro Gly Glu Ala Arg
            20                  25                  30

Glu Val Glu Ser Ala Met Asp Lys Tyr Ala Val Leu Val Phe His Asp
        35                  40                  45

Gln Asp Ile Thr Asp Glu Gln Gln Met Ala Phe Ala Leu Asn Phe Gly
    50                  55                  60

Gln Arg Glu Asp Ala Arg Gly Gly Thr Val Thr Lys Glu Lys Asp Tyr
65                  70                  75                  80

Arg Leu Gln Ser Gly Leu Asn Asp Val Ser Asn Leu Gly Lys Asp Gly
                85                  90                  95

Lys Pro Leu Ala Lys Asp Ser Arg Thr His Leu Phe Asn Leu Gly Asn
            100                 105                 110

Cys Leu Trp His Ser Asp Ser Ser Phe Arg Pro Ile Pro Ala Lys Phe
        115                 120                 125

Ser Leu Leu Ser Ala Arg Val Val Asn Pro Thr Gly Gly Asn Thr Glu
    130                 135                 140

```
Phe Ala Asp Met Arg Ala Ala Tyr Asp Ala Leu Asp Asp Glu Thr Lys
145                 150                 155                 160

Ala Glu Ile Glu Asp Leu Val Cys Glu His Ser Leu Met Tyr Ser Arg
                165                 170                 175

Gly Ser Leu Gly Phe Thr Glu Tyr Thr Asp Glu Glu Lys Gln Met Phe
            180                 185                 190

Lys Pro Val Leu Gln Arg Leu Val Arg Thr His Pro Val His Arg Arg
            195                 200                 205

Lys Ser Leu Tyr Leu Ser Ser His Ala Gly Lys Ile Ala Ser Met Ser
        210                 215                 220

Val Pro Glu Gly Arg Leu Leu Leu Arg Asp Leu Asn Glu His Ala Thr
225                 230                 235                 240

Gln Pro Glu Phe Val Tyr Val His Lys Trp Lys Leu His Asp Leu Val
                245                 250                 255

Met Trp Asp Asn Arg Gln Thr Met His Arg Val Arg Arg Tyr Asp Gln
                260                 265                 270

Ser Gln Pro Arg Asp Met Arg Arg Ala Thr Val Ala Gly Thr Glu Pro
            275                 280                 285

Thr Val Gln Gln Gln Ala Ala Glu
    290                 295

<210> SEQ ID NO 31
<211> LENGTH: 22
<212> TYPE: DNA
<213> ORGANISM: Artificial sequence
<220> FEATURE:
<223> OTHER INFORMATION: Southern fragment PCR AAD-1 forward primer

<400> SEQUENCE: 31
atggctcatg ctgccctcag cc                                        22

<210> SEQ ID NO 32
<211> LENGTH: 21
<212> TYPE: DNA
<213> ORGANISM: Artificial sequence
<220> FEATURE:
<223> OTHER INFORMATION: Southern fragment PCR AAD-1 reverse primer

<400> SEQUENCE: 32
gggcaggcct aactccacca a                                         21
```

HERBICIDE RESISTANCE GENES

CROSS-REFERENCE TO RELATED APPLICATION

This application is a continuation application of U.S. Ser. No. 12/951,813, filed Nov. 22, 2010, which is a divisional of U.S. Ser. No. 11/587,893, filed May 22, 2008, now patented as U.S. Pat. No. 7,838,733, which is a national stage entry of PCT/US2005/014737, filed May 2, 2005, which claims the benefit of U.S. Provisional Application Ser. No. 60/567,052, filed Apr. 30, 2004, which are hereby incorporated by reference in their entirety, including any figures, tables, nucleic acid sequences, amino acid sequences, or drawings.

BACKGROUND OF THE INVENTION

Weeds can quickly deplete soil of valuable nutrients needed by crops and other desirable plants. There are many different types of herbicides presently used for the control of weeds. One extremely popular herbicide is glyphosate.

Crops, such as corn, soybeans, canola, cotton, sugar beets, wheat, turf, and rice, have been developed that are resistant to glyphosate. Thus, fields with actively growing glyphosate resistant corn, for example, can be sprayed to control weeds without significantly damaging the corn plants.

With the introduction of genetically engineered, glyphosate tolerant crops (GTCs) in the mid-1990's, growers were enabled with a simple, convenient, flexible, and inexpensive tool for controlling a wide spectrum of broadleaf and grass weeds unparalleled in agriculture. Consequently, producers were quick to adopt GTCs and in many instances abandon many of the accepted best agronomic practices such as crop rotation, herbicide mode of action rotation, tank mixing, incorporation of mechanical with chemical and cultural weed control. Currently glyphosate tolerant soybean, cotton, corn, and canola are commercially available in the United States and elsewhere in the Western Hemisphere. More GTCs (e.g., wheat, rice, sugar beets, turf, etc.) are poised for introduction pending global market acceptance. Many other glyphosate resistant species are in experimental to development stages (e.g., alfalfa, sugar cane, sunflower, beets, peas, carrot, cucumber, lettuce, onion, strawberry, tomato, and tobacco; forestry species like poplar and sweetgum; and horticultural species like marigold, petunia, and begonias; see "isb.vt.edu/cfdocs/fieldtests1.cfm, 2005" website). Additionally, the cost of glyphosate has dropped dramatically in recent years to the point that few conventional weed control programs can effectively compete on price and performance with glyphosate GTC systems.

Glyphosate has been used successfully in burndown and other non-crop areas for total vegetation control for more than 15 years. In many instances, as with GTCs, glyphosate has been used 1-3 times per year for 3, 5, 10, up to 15 years in a row. These circumstances have led to an over-reliance on glyphosate and GTC technology and have placed a heavy selection pressure on native weed species for plants that are naturally more tolerant to glyphosate or which have developed a mechanism to resist glyphosate's herbicidal activity.

Extensive use of glyphosate-only weed control programs is resulting in the selection of glyphosate-resistant weeds, and is selecting for the propagation of weed species that are inherently more tolerant to glyphosate than most target species (i.e., weed shifts). (Ng et al., 2003; Simarmata et al., 2003; Lorraine-Colwill et al., 2003; Sfiligoj, 2004; Miller et al., 2003; Heap, 2005; Murphy et al., 2002; Martin et al., 2002.) Although glyphosate has been widely used globally for more than 15 years, only a handful of weeds have been reported to have developed resistance to glyphosate (Heap, 2005); however, most of these have been identified in the past 3-5 years. Resistant weeds include both grass and broadleaf species—*Lolium rigidum*, *Lolium multiflorum*, *Eleusine indica*, *Ambrosia artemisiifolia*, *Conyza canadensis*, *Conyza bonariensis*, and *Plantago lanceolata*. Additionally, weeds that had previously not been an agronomic problem prior to the wide use of GTCs are now becoming more prevalent and difficult to control in the context of GTCs, which comprise >80% of U.S. cotton and soybean acres and >20% of U.S. corn acres (Gianessi, 2005). These weed shifts are occurring predominantly with (but not exclusively) difficult-to-control broadleaf weeds. Some examples include *Ipomoea*, *Amaranthus*, *Chenopodium*, *Taraxacum*, and *Commelina* species.

In areas where growers are faced with glyphosate resistant weeds or a shift to more difficult-to-control weed species, growers can compensate for glyphosate's weaknesses by tank mixing or alternating with other herbicides that will control the missed weeds. One popular and efficacious tankmix partner for controlling broadleaf escapes in many instances has been 2,4-diclorophenoxyacetic acid (2,4-D). 2,4-D has been used agronomically and in non-crop situations for broad spectrum, broadleaf weed control for more than 60 years. Individual cases of more tolerant species have been reported, but 2,4-D remains one of the most widely used herbicides globally. A limitation to further use of 2,4-D is that its selectivity in dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting (Agriliance, 2003).

2,4-D is in the phenoxy acid class of herbicides, as are MCPA, mecoprop, and dichlorprop. 2,4-D has been used in many monocot crops (such as corn, wheat, and rice) for the selective control of broadleaf weeds without severely damaging the desired crop plants. 2,4-D is a synthetic auxin derivative that acts to deregulate normal cell-hormone homeostasis and impede balanced, controlled growth; however, the exact mode of action is still not known.

2,4-D has different levels of selectivity on certain plants (e.g., dicots are more sensitive than grasses). Differential metabolism of 2,4-D by different plants is one explanation for varying levels of selectivity. In general, plants metabolize 2,4-D slowly, so varying plant response to 2,4-D may be more likely explained by different activity at the target site(s) (WSSA, 2002). Plant metabolism of 2,4-D typically occurs via a two-phase mechanism, typically hydroxylation followed by conjugation with amino acids or glucose (WSSA, 2002).

Over time, microbial populations have developed an alternative and efficient pathway for degradation of this particular xenobiotic, which results in the complete mineralization of 2,4-D. Successive applications of the herbicide select for microbes that can utilize the herbicide as a carbon source for growth, giving them a competitive advantage in the soil. For this reason, 2,4-D is currently formulated to have a relatively short soil half-life, and no significant carryover effects to subsequent crops are encountered. This adds to the herbicidal utility of 2,4-D.

One organism that has been extensively researched for its ability to degrade 2,4-D is *Ralstonia eutropha* (Streber et al., 1987). The gene that codes for the first enzymatic step in the mineralization pathway is tfdA. See U.S. Pat. No. 6,153,401 and GENBANK Acc. No. M16730. TfdA catalyzes the conversion of 2,4-D acid to dichlorophenol (DCP) via an α-ketoglutarate-dependent dioxygenase reaction (Smejkal et al., 2001). DCP has little herbicidal activity compared to 2,4-D. TfdA has been used in transgenic plants to impart 2,4-D resistance in dicot plants (e.g., cotton and tobacco) normally sensitive to 2,4-D (Streber et al. (1989), Lyon et al. (1989), Lyon (1993), and U.S. Pat. No. 5,608,147).

A large number of tfdA-type genes that encode proteins capable of degrading 2,4-D have been identified from the environment and deposited into the Genbank database. Many homologues are similar to tfdA (>85% amino acid identity) and have similar enzymatic properties to tfdA. However, there are a number of homologues that have a significantly lower identity to tfdA (25-50%), yet have the characteristic residues associated with α-ketoglutarate dioxygenase $Fe^{+2}$ dioxygenases. It is therefore not obvious what the substrate specificities of these divergent dioxygenases are.

One unique example with low homology to tfdA (28% amino acid identity) is rdpA from *Sphingobium herbicidovorans* (Kohler et al., 1999, Westendorf et al., 2002). This enzyme has been shown to catalyze the first step in (R)-dichlorprop (and other (R)-phenoxypropionic acids) as well as 2,4-D (a phenoxyacetic acid) mineralization (Westendorf et al., 2003). Although the organisms that degrade phenoxypropionic acid were described some time ago, little progress had been made in characterizing this pathway until recently (Horvath et al., 1990). An additional complication to dichlorprop degradation is the stereospecificity (R vs. S) involved in both the uptake (Kohler, 1999) and initial oxidation of dichlorprop (Westendorf et al., 2003). Heterologous expression of rdpA in other microbes, or transformation of this gene into plants, has not heretofore been reported. Literature has focused primarily around close homologues of tfdA that primarily degrade achiral phenoxyacetic acids (e.g., 2,4-D).

Development of new herbicide-tolerant crop (HTC) technologies has been limited in success due largely to the efficacy, low cost, and convenience of GTCs. Consequently, a very high rate of adoption for GTCs has occurred among producers. This created little incentive for developing new HTC technologies.

Aryloxyalkanoate chemical substructures are a common entity of many commercialized herbicides including the phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). However, these classes of herbicides are all quite distinct, and no evidence exists in the current literature for common degradation pathways among these chemical classes. Discovery of a multifunctional enzyme for the degradation of herbicides covering multiple modes would be both unique and valuable as an HTC trait.

BRIEF SUMMARY OF THE INVENTION

The subject invention provides novel plants that are not only resistant to 2,4-D, but also to AOPP herbicides. Heretofore, there was no expectation or suggestion that a plant with both of these advantageous properties could be produced by the introduction of a single gene. The subject invention also includes plants that produce one or more enzymes of the subject invention "stacked" together with one or more other herbicide resistance genes, including, but not limited to, glyphosate-, imidazolinone-, and glufosinate-resistance genes, so as to provide herbicide-tolerant plants compatible with broader and more robust weed control and herbicide resistance management options. The present invention further includes methods and compositions utilizing homologues of the genes and proteins exemplified herein.

In some embodiments, the invention provides monocot and dicot plants tolerant to 2,4-D, AOPP, and one or more commercially available herbicides (e.g., glyphosate, imidazolinones, glufosinate, sulfonylureas, dicamba, bromoxynil, and others). Vectors comprising nucleic acid sequences responsible for such herbicide tolerance are also disclosed, as are methods of using such tolerant plants and combinations of herbicides for weed control and prevention of weed population shifts. The subject invention enables novel combinations of herbicides to be used in new ways. Furthermore, the subject invention provides novel methods of preventing the development of, and controlling, strains of weeds that are resistant to one or more herbicides such as glyphosate. The subject invention enables novel uses of novel combinations of herbicides and crops, including preplant application to an area to be planted immediately prior to planting with seed for plants that would otherwise be sensitive to that herbicide (such as 2,4-D).

The subject invention relates in part to the identification of an enzyme that is not only able to degrade 2,4-D, but also surprisingly possesses novel properties, which distinguish the enzyme of the subject invention from previously known tfdA proteins, for example. More specifically, the subject invention relates to the use of an enzyme that is capable of degrading both 2,4-D and AOPP herbicides, in an enantiospecific manner. No α-ketoglutarate-dependent dioxygenase enzyme has previously been reported to have the ability to degrade herbicides of different chemical classes and modes of action. The preferred enzyme and gene for use according to the subject invention are referred to herein as AAD-1 (AryloxyAlkanoate Dioxygenase). This highly novel discovery is the basis of significant HTC trait and selectable marker opportunities.

There was no prior motivation to produce plants comprising an AAD-1 gene (preferably an AAD-1 polynucleotide that has a sequence optimized for expression in one or more types of plants, as exemplified herein), and there was no expectation that such plants could effectively produce an AAD-1 enzyme to render the plants resistant to not only phenoxy acid herbicides (such as 2,4-D) but also AOPP herbicides (such as quizalofop, haloxyfop, et al.). Thus, the subject invention provides many advantages that were not heretofore thought to be possible in the art.

This invention also relates in part to the identification and use of genes encoding aryloxyalkanoate dioxygenase enzymes that are capable of degrading phenoxy auxin and aryloxyphenoxypropionate herbicides. Methods of screening proteins for these activities are within the scope of the subject invention. Thus, the subject invention includes degradation of 2,4-dichlorophenoxyacetic acid, other phenoxyalkanoate auxin herbicides, and aryloxyphenoxypropionate herbicides by a recombinantly expressed AAD-1 enzyme. The subject invention also includes methods of controlling weeds wherein said methods comprise applying one or more AOPP, phenoxy auxin, or other aryloxyalkanoate herbicides to plants comprising an AAD-1 gene. The subject invention also provides methods of using an AAD-1 gene as a selectable marker for identifying plant cells and whole plants transformed with AAD-1, optionally including one, two, or more exogenous genes simultaneously inserted into target plant cells. Methods of the subject invention include selecting transformed cells that are resistant to appropriate levels of an herbicide. The subject invention further includes methods of preparing a polypeptide, having the biological activity of aryloxyalkanoate dioxygenase, by culturing plants and/or cells of the subject invention.

BRIEF DESCRIPTION OF THE FIGURES

FIGS. 9A, 9B, and 9C show injury of Arabidopsis plants after 2,4-D treatment. Four different lines were each treated with four different doses of 2,4-D and their injury was graded 4 (panel A) and 14 (panel B) days after treatment. Their expression of AAD-1 (v3) in leaves was also determined using ELISA (panel C). The results were mean±SEM of five leaves from five different plants received the same treatment.

BRIEF DESCRIPTION OF THE SEQUENCES

Figure 1:
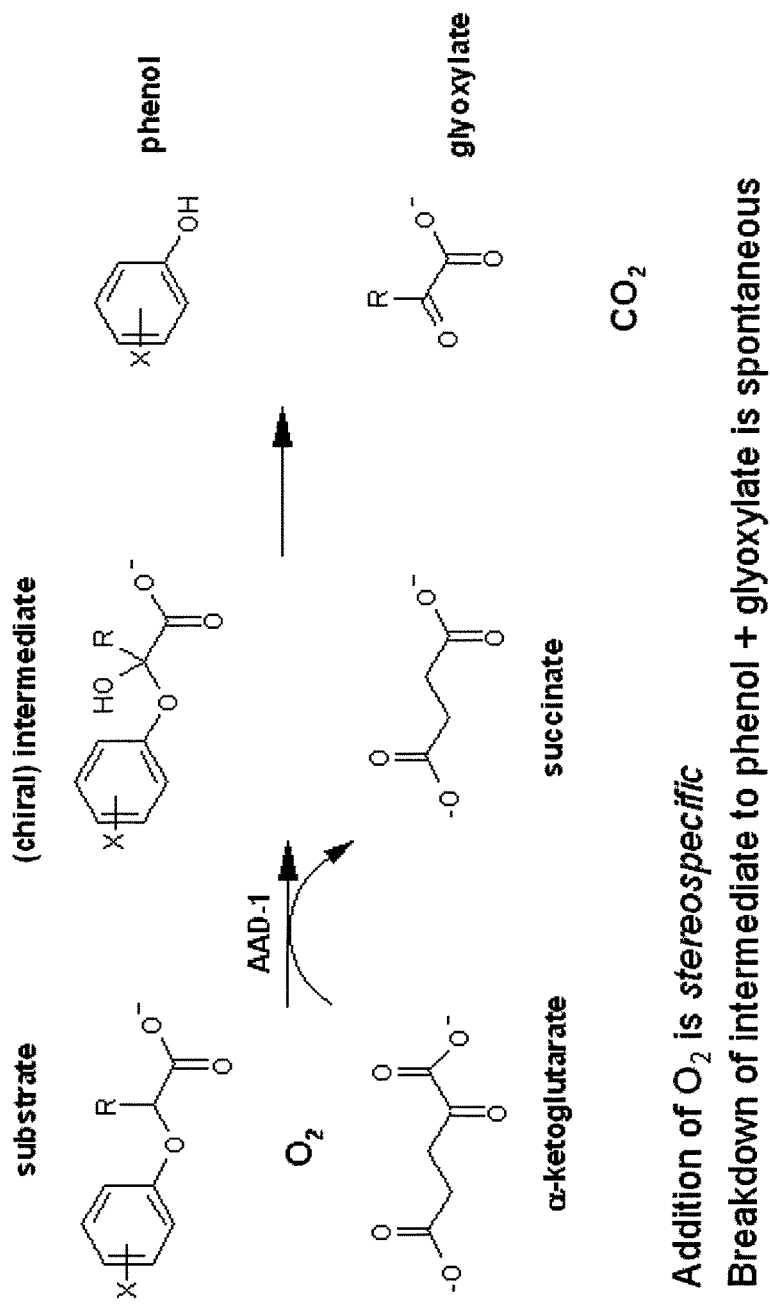
FIG. 1 shows a general scheme for dioxygenase cleavage of phenoxy auxin or AOPP herbicides.

SEQ ID NO:1 is the sequence of a forward primer used to amplify the rdpA/AAD-1 (v1) gene.

SEQ ID NO:2 is the sequence of a reverse primer used to amplify the rdpA/AAD-1 (v1) gene.

SEQ ID NO:3 is the nucleotide sequence of AAD-1 (v1) from Sphingobium herbicidovorans.

SEQ ID NO:4 is the nucleic acid sequence of the native AAD-1 gene with internal NotI restriction site removed. This gene is designated AAD-1 (v2). DNA sequencing confirmed that the correct PCR product was generated, but an inadvertent change was made at amino acid #212 from arginine to cysteine.

SEQ ID NO:5 is a "plant-optimized" DNA sequence AAD-1 (v3). This "gene" encodes SEQ ID NO:11, which is the same as SEQ ID NO:9 except for the addition of an alanine residue at the second position. The additional alanine codon (GCT) was included to encode an Nco I site (CCATGG) spanning the ATG start codon, to enable subsequent cloning operations.

SEQ ID NO:6 ("rdpA(ncoI)") and SEQ ID NO:7 ("3'saci") were used to amplify a DNA fragment using the Fail Safe PCR System (Epicenter).

SEQ ID NO:8 is another PCR primer ("BstEII/Del NotI") that was used with the "3' SacI" primer.

SEQ ID NO:9 is the native amino acid sequence encoded by the AAD-1 (v1) gene from Sphingobium herbicidovorans.

SEQ ID NO:10 is the amino acid sequence encoded by the AAD-1 (v2) DNA sequence of SEQ ID NO:4.

SEQ ID NO:11 is the amino acid sequence encoded by the AAD-1 (v3) plant-optimized DNA sequence of SEQ ID NO:5.

SEQ ID NO:12 is the DNA sequence of the native AAD-2 (v1) gene.

SEQ ID NO:13 is the amino acid sequence of the AAD-2 (v1) protein.

SEQ ID NO:14 is a forward primer used to amplify AAD-2 (v1) DNA for cloning.

SEQ ID NO:15 is a reverse primer used to amplify AAD-2 (v1) DNA for cloning.

SEQ ID NO:16 is the M13 forward primer.

SEQ ID NO:17 is the M13 reverse primer.

SEQ ID NO:18 is a forward primer used to amplify AAD-2 (v1) DNA for cloning.

SEQ ID NO:19 is a reverse primer used to amplify AAD-2 (v1) DNA for cloning.

SEQ ID NO:20 is the native soybean EPSPS protein.

SEQ ID NO:21 is a doubly mutated soybean EPSPS protein sequence, containing a mutation at residue 183 (threonine of native protein replaced with isoleucine), and at residue 187 (proline in native protein replaced with serine).

SEQ ID NO:22 is the soybean-biased DNA sequence that encodes the EPSPS protein of SEQ ID NO:21.

SEQ ID NO:23 is primer Pat 5-3.

SEQ ID NO:24 is primer Pat 3-3.

SEQ ID NO:25 is forward primer AAD-1 PTU.

SEQ ID NO:26 is reverse primer AAD-1 PTU.

SEQ ID NO:27 is the forward primer for the Coding Region PCR AAD-1.

SEQ ID NO:28 is the reverse primer for the Coding Region PCR AAD-1.

SEQ ID NO:29 is the AAD-2 (v2) nucleotide (plant optimized).

SEQ ID NO:30 is the translated AAD-2 (v2) protein sequence.

SEQ ID NO:31 is the Southern fragment PCR AAD-1 forward primer.

SEQ ID NO:32 is the Southern fragment PCR AAD-1 reverse primer.

DETAILED DESCRIPTION OF THE INVENTION

The subject development of a 2,4-D resistance gene and subsequent resistant crops provides excellent options for controlling broadleaf, glyphosate-resistant (or highly tolerant and shifted) weed species for in-crop applications. 2,4-D is a broad-spectrum, relatively inexpensive, and robust broadleaf herbicide that would provide excellent utility for growers if greater crop tolerance could be provided in dicot and monocot crops alike. 2,4-D-tolerant transgenic dicot crops would also have greater flexibility in the timing and rate of application. An additional utility of an herbicide tolerance trait for 2,4-D would be its utility to prevent damage to normally sensitive crops from 2,4-D drift, volatilization, inversion (or other off-site movement phenomenon), misapplication, vandalism and the like. An additional benefit of the AAD-1 gene is that unlike all tfdA homologues characterized to date, AAD-1 is able to degrade the R-enantiomers (herbicidally active isomers) of the chiral phenoxy auxins (e.g., dichlorprop and mecoprop) in addition to achiral phenoxy auxins (e.g., 2,4-D, MCPA, 4-chlorophenoxyacetic acid). See Table 1. Multiple mixes of different phenoxy auxin combinations have been used globally to address specific weed spectra and environmental conditions in various regions. Use of the AAD-1 gene in plants would afford protection to a much wider spectrum of phenoxy auxin herbicides, thereby increasing the flexibility and spectra of weeds that can be controlled, protecting from drift or other off-site phenoxy herbicide injury for the full breadth of commercially available phenoxy auxins.

Table 1.

Commercially available phenoxy auxins. Reference to phenoxy auxin herbicides is generally made to the active acid but some are commercially formulated as any of a variety of corresponding ester formulations and these are likewise considered as substrates for AAD-1 enzyme in planta as general plant esterases convert these esters to the active acids in planta. Likewise reference can also be for the corresponding organic or inorganic salt of the corresponding acid. When chiral propionic acid, salt, or ester herbicides are indicated, racemic (R,S) or optically purified (R or S) enantiomers are considered the same herbicides for the purpose of naming these herbicides, even though different CAS numbers may correspond to optically pure compounds. Possible use rate ranges can be as stand-alone treatments or in combination with other herbicides in both crop and non-crop uses.

TABLE 1

Commercially available phenoxy auxins.

| Chemical name | CAS no | Possible use rate ranges (g ae/ha) | Preferred use rate ranges (g ae/ha) | Structure |
|---|---|---|---|---|
| 2,4-D | 94-75-7 | 25-4000 | 280-1120 | 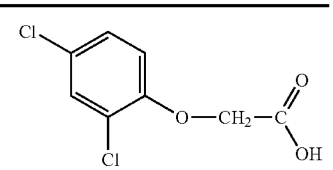 |
| 2,4,5-T | 93-76-5 | 25-4000 | 25-4000 | 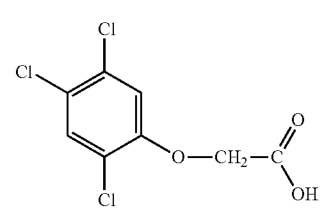 [SMILES: O=C(O)COc1cc(Cl)c(Cl)cc1Cl] |

TABLE 1-continued

Commercially available phenoxy auxins.

| Chemical name | CAS no | Possible use rate ranges (g ae/ha) | Preferred use rate ranges (g ae/ha) | Structure |
|---|---|---|---|---|
| 4-CPA | 122-88-3 | 25-4000 | 25-4000 | 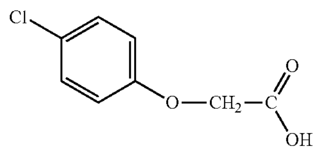 [SMILES: O=C(O)COc1ccc(Cl)cc1] |
| 3,4-DA | 588-22-7 | 25-4000 | 25-4000 | 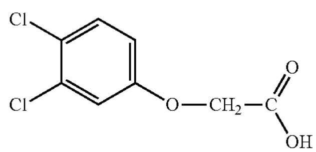 [SMILES: O=C(O)COc1ccc(Cl)c(Cl)c1] |
| MCPA | 94-74-6 | 25-4000 | 125-1550 | 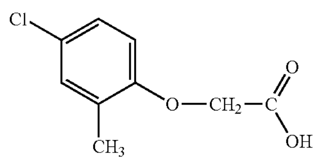 |
| Dichlorprop | 120-36-5 | 25-12000 | 100-2240 | 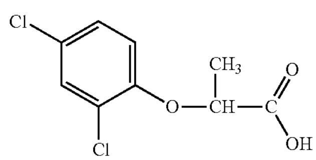 |
| Mecoprop | 7085-19-0 | 25-4000 | 250-3360 | 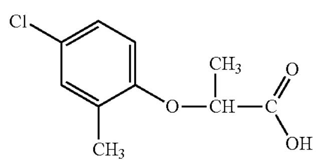 |
| Cloprop | 101-10-0 | 25-4000 | 25-4000 | 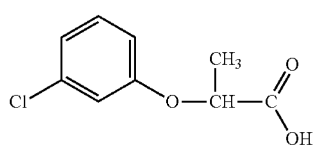 |
| 4-CPP | 3307-39-9 | 25-4000 | 25-4000 | 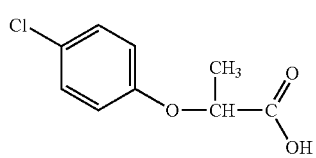 |
| Fenoprop | 93-72-1 | 25-4000 | 25-4000 | 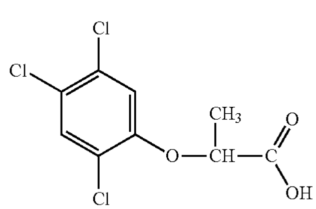 |
| 3,4-DP | 3307-41-3 | 25-4000 | 25-4000 | 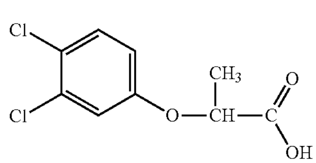 |

An additional benefit of the AAD-1 gene is its unprecedented ability to concomitantly degrade a host of commercial and non-commercial graminicidal compounds of the general class aryloxyphenoxypropionates (AOPPs). See Table 2. This attribute may allow the use of any of a number of AOPP compounds in transgenic crops containing AAD-1, where tolerance in those crops had not previously warranted use in those crops. These will most commonly include grass crops such as corn, rice, wheat, barley, rye, oats, *sorghum*, warm and cool-season turf species, grass pasture species, and many others, but could also include dicot crops where AOPP tolerance (naturally present in most dicots) is not at commercially acceptable levels to allow AOPP use in said dicot crop.

Table 2.

AOPP graminicidal compounds listed by accepted common names. Reference to AOPP herbicides is generally made to the active acid but most are commercially formulated as any of a variety of corresponding ester formulations and these are likewise considered as substrates for AAD-1 enzyme in planta as general plant esterases convert these esters to the active acids in planta. Likewise reference can also be for the corresponding organic or inorganic salt of the corresponding acid. When chiral propionic acid, salt, or ester herbicides are indicated, racemic (R,S) or optically purified (R or S) enantiomers are considered the same herbicides for the purpose of naming these herbicides, even though different CAS numbers may correspond to optically pure compounds. Possible use rate ranges can be as stand-alone treatments or in combination with other herbicides in both crop and non-crop uses.

TABLE 2

AOPP graminicidal compounds listed by accepted common names.

| Chemical name | CAS no | Possible use rate ranges (g ae/ha) | Preferred use rate ranges (g ae/ha) | Structure |
| --- | --- | --- | --- | --- |
| Chlorazifop | 72492-94-7 | 10-2000 | 10-2000 | 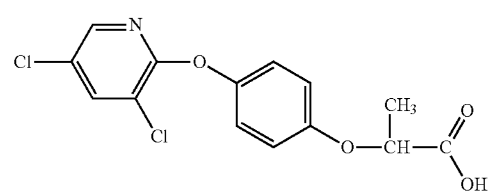 [SMILES: CC(Oc1ccc(Oc2ncc(Cl)cc2Cl)cc1)C(=O)O] |
| Clodinafop | 105512-06-9 | 10-2000 | 20-200 | 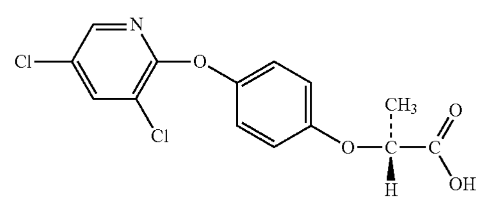 |
| Clofop | 59621-49-7 | 10-2000 | 10-2000 | 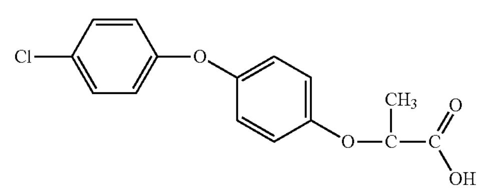 [SMILES: CC(Oc1ccc(Oc2ccc(Cl)cc2)cc1)C(=O)O] |
| Cyhalofop | 122008-85-9 | 10-2000 | 105-560 | 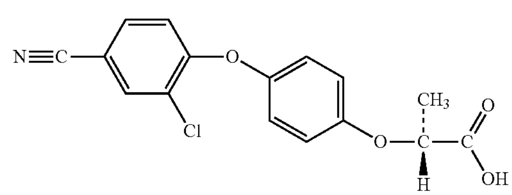 |
| Diclofop | 71283-65-3 | 10-2000 | 280-2000 | 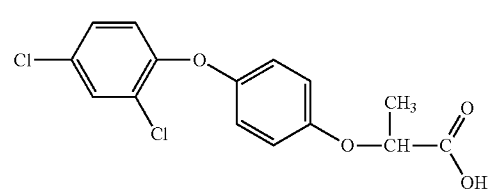 [SMILES: CC(Oc1ccc(Oc2ccc(Cl)cc2Cl)cc1)C(=O)O] |

TABLE 2-continued

AOPP graminicidal compounds listed by accepted common names.

| Chemical name | CAS no | Possible use rate ranges (g ae/ha) | Preferred use rate ranges (g ae/ha) | Structure |
|---|---|---|---|---|
| Fenoxaprop | 66441-23-4 | 10-2000 | 20-200 | 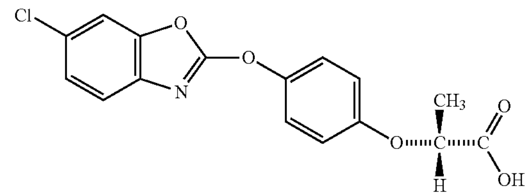 |
| Fenthiaprop | 95721-12-3 | 10-2000 | 10-2000 | 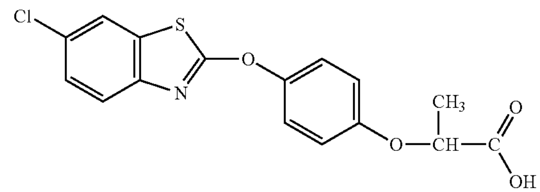 [SMILES: CC(Oc1ccc(Oc2nc3ccc(Cl)cc3s2)cc1)C(=O)O] |
| Fluazifop | 69335-91-7 | 10-2000 | 25-420 | 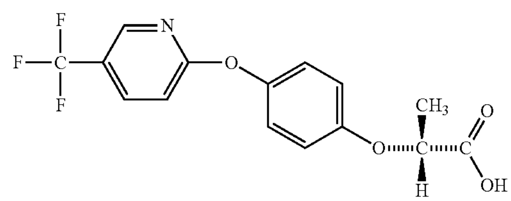 |
| Haloxyfop | 69806-40-2 | 10-2000 | 20-600 | 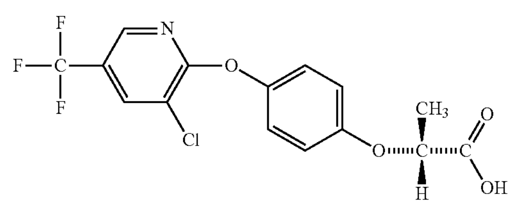 |
| Isoxapyrifop | 87757-18-4 | 10-2000 | 30-240 | 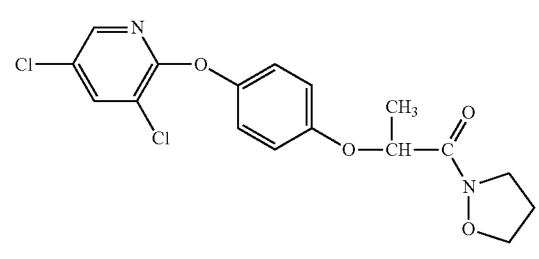 [SMILES: CC(Oc1ccc(Oc2ncc(Cl)cc2Cl)cc1)C(=O)N1CCCO1] |
| Metamifop | 256412-89-2 | 10-2000 | 35-280 | 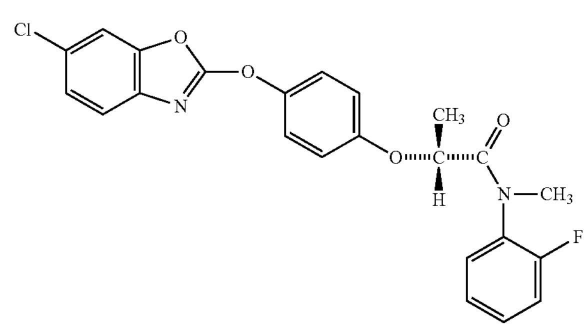 |

TABLE 2-continued

AOPP graminicidal compounds listed by accepted common names.

| Chemical name | CAS no | Possible use rate ranges (g ae/ha) | Preferred use rate ranges (g ae/ha) | Structure |
|---|---|---|---|---|
| Propaquizafop | 111479-05-1 | 10-2000 | 30-240 | 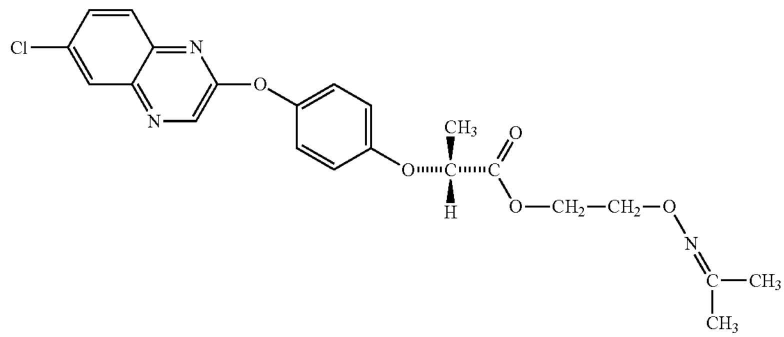 |
| Quizalofop | 76578-14-8 | 10-2000 | 20-240 | 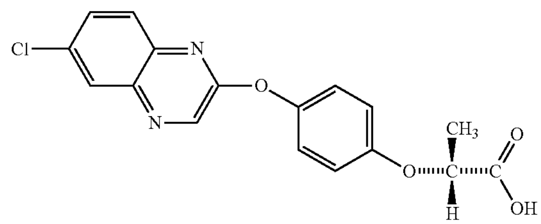 |
| Trifop | 58597-74-4 | 10-2000 | 10-2000 | 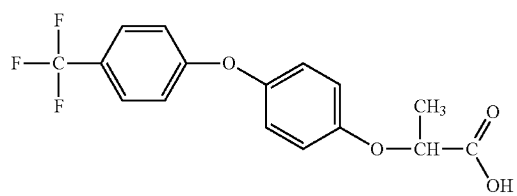 [SMILES: CC(Oc1ccc(Oc2ccc(C(F)(F)F)cc2)cc1)C(=O)O] |

A single gene (AAD-1) has now been identified which, when genetically engineered for expression in plants, has the properties to allow the use of phenoxy auxin herbicides in plants where inherent tolerance never existed or was not sufficiently high to allow use of these herbicides. Additionally, AAD-1 can provide protection in planta to AOPP herbicides where natural tolerance also was not sufficient to allow selectivity. Plants containing AAD-1 alone now may be treated sequentially or tank mixed with one, two, or a combination of several phenoxy auxin herbicides. The rate for each phenoxy auxin herbicide may range from 25 to 4000 g ae/ha, and more typically from 100 to 2000 g ae/ha for the control of a broad spectrum of dicot weeds. Likewise, one, two, or a mixture of several AOPP graminicidal compounds may be applied to plants expressing AAD-1 with reduced risk of injury from said herbicides. The rate for each AOPP may range from 10 to 2000 g ae/ha, and more typically from 20-500 g ae/ha for the control of a broad spectrum of monocot weeds. Combinations of these different chemistry classes and herbicides with different modes of action and spectra in the same field (either sequentially or in tank mix combination) shall provide control of most potential weeds for which herbicidal control is desired.

Glyphosate is used extensively because it controls a very wide spectrum of broadleaf and grass weed species. However, repeated use of glyphosate in GTCs and in non-crop applications has, and will continue to, select for weed shifts to naturally more tolerant species or glyphosate-resistant biotypes. Tankmix herbicide partners used at efficacious rates that offer control of the same species but having different modes of action is prescribed by most herbicide resistance management strategies as a method to delay the appearance of resistant weeds. Stacking AAD-1 with a glyphosate tolerance trait (and/or with other herbicide-tolerance traits) could provide a mechanism to allow for the control of glyphosate resistant weed species (either grass weed species with one or more AOPP herbicides, or broadleaf weed species with one or more phenoxy auxins) in GTCs by enabling the use of glyphosate, phenoxy auxin(s) (e.g., 2,4-D) and AOPP herbicide(s) (e.g., quizalofop) selectively in the same crop. Applications of these herbicides could be simultaneously in a tank mixture comprising two or more herbicides of different modes of action; individual applications of single herbicide composition in sequential applications as pre-plant, preemergence, or postemergence and split timing of applications ranging from 2 hours to 3 months; or, alternatively, any combination of any number of herbicides representing each chemical class can be applied at any timing within 7 months of planting the crop up to harvest of the crop (or the preharvest interval for the individual herbicide, whichever is shortest).

It is important to have flexibility in controlling a broad spectrum of grass and broadleaf weeds in terms of timing of application, rate of individual herbicides, and the ability to control difficult or resistant weeds. Glyphosate applications in a crop with a glyphosate resistance gene/AAD-1 stack could range from 250-2500 g ae/ha; phenoxy auxin herbicide(s) (one or more) could be applied from 25-4000 g ae/ha; and AOPP herbicide(s) (one or more) could be applied from 10-2000 g ae/ha. The optimal combination(s) and timing of these application(s) will depend on the particular situation, species, and environment, and will be best determined by a person skilled in the art of weed control and having the benefit of the subject disclosure.

Herbicide formulations (e.g., ester, acid, or salt formulation; or soluble concentrate, emulsifiable concentrate, or soluble liquid) and tankmix additives (e.g., adjuvants or compatibility agents) can significantly affect weed control from a given herbicide or combination of one or more herbicides. Any combination of these with any of the aforementioned herbicide chemistries is within the scope of this invention.

One skilled in the art would also see the benefit of combining two or more modes of action for increasing the spectrum of weeds controlled and/or for the control of naturally more tolerant species or resistant weed species could also extend to chemistries for which herbicide tolerance was enabled in crops through human involvement (either transgenically or non-transgenically) beyond GTCs. Indeed, traits encoding glyphosate resistance (e.g., resistant plant or bacterial EPSPS, GOX, GA7), glufosinate resistance (e.g., Pat, bar), acetolactate synthase (ALS)-inhibiting herbicide resistance (e.g., imidazolinone, sulfonylurea, triazolopyrimidine sulfonanilide, pyrmidinylthiobenzoates, and other chemistries=AHAS, Csr1, SurA, et al.), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Regarding additional herbicides, some additional preferred ALS inhibitors include the triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include mesotrione, isoxaflutole, and sulcotrione. Some preferred PPO inhibitors include flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-1 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

The subject invention relates in part to the identification of an enzyme that is not only able to degrade 2,4-D, but also surprisingly possesses novel properties, which distinguish the enzyme of the subject invention from previously known tfdA proteins, for example. Even though this enzyme has very low homology to tfdA, the genes of the subject invention can still be generally classified in the same overall family of α-ketoglutarate-dependent dioxygenases. This family of proteins is characterized by three conserved histidine residues in a "$HX(D/E)X_{23-26}(T/S)X_{114-183}HX_{10-13}R$" motif which comprises the active site. The histidines coordinate $Fe^{+2}$ ion in the active site that is essential for catalytic activity (Hogan et al., 2000). The preliminary in vitro expression experiments discussed herein were tailored to help select for novel attributes.

More specifically, the subject invention relates in part to the use of an enzyme that is not only capable of degrading 2,4-D, but also AOPP herbicides. No α-ketoglutarate-dependent dioxygenase enzyme has previously been reported to have the ability to degrade herbicides of different chemical classes and modes of action. Preferred enzymes and genes for use according to the subject invention are referred to herein as AAD-1 (AryloxyAlkanoate Dioxygenase) genes and proteins.

This invention also relates in part to the identification and use of genes encoding aryloxyalkanoate dioxygenase enzymes that are capable of degrading phenoxy auxin and aryloxyphenoxypropionate herbicides. Thus, the subject invention relates in part to the degradation of 2,4-dichlorophenoxyacetic acid, other phenoxyalkanoic auxin herbicides, and aryloxyphenoxyalkanoate herbicides by a recombinantly expressed AAD-1 enzyme.

The subject proteins tested positive for 2,4-D conversion to 2,4-dichlorophenol ("DCP"; herbicidally inactive) in analytical and biological assays. Partially purified proteins of the subject invention can rapidly convert 2,4-D to DCP (ranging from 50-100% conversion) in vitro. An additional advantage that AAD-1-transformed plants provide is that parent herbicide(s) are metabolized to inactive forms, thereby reducing the potential for harvesting herbicidal residues in grain or stover.

The subject invention also includes methods of controlling weeds wherein said methods comprise applying an AOPP herbicide and/or a phenoxy auxin herbicide to plants comprising an AAD-1 gene.

In light of these discoveries, novel plants that comprise a polynucleotide encoding this type of enzyme are now provided. Heretofore, there was no motivation to produce such plants, and there was no expectation that such plants could effectively produce this enzyme to render the plants resistant to not only phenoxy acid herbicides (such as 2,4-D) but also AOPP herbicides. Thus, the subject invention provides many advantages that were not heretofore thought to be possible in the art.

Publicly available strains (deposited in culture collections like ATCC or DSMZ) can be acquired and screened, using techniques disclosed herein, for novel genes. Sequences disclosed herein can be used to amplify and clone the homologous genes into a recombinant expression system for further screening and testing according to the subject invention.

As discussed above in the Background section, one organism that has been extensively researched for its ability to degrade 2,4-D is Ralstonia eutropha (Streber et al., 1987). The gene that codes for the first enzyme in the degradation pathway is tfdA. See U.S. Pat. No. 6,153,401 and GENBANK Acc. No. M16730. TfdA catalyzes the conversion of 2,4-D acid to herbicidally inactive DCP via an α-ketoglutarate-dependent dioxygenase reaction (Smejkal et al., 2001). TfdA has been used in transgenic plants to impart 2,4-D resistance in dicot plants (e.g., cotton and tobacco) normally sensitive to 2,4-D (Streber et al., 1989; Lyon et al., 1989; Lyon et al., 1993). A large number of tfdA-type genes that encode proteins capable of degrading 2,4-D have been identified from the environment and deposited into the Genbank database. Many homologues are quite similar to tfdA (>85% amino acid identity) and have similar enzymatic properties to tfdA. However, a small collection of α-ketoglutarate-dependent dioxygenase homologues are presently identified that have a low level of homology to tfdA.

RdpA, from *Sphingobium herbicidovorans* (Westendorf et al., 2002), is one unique example with low homology (28% amino acid identity). This enzyme has been shown to catalyze the first step in (R)-dichlorprop (and other (R)-phenoxypropionic acids) as well as 2,4-D (a phenoxyacetic acid) mineralization (Westendorf et al., 2003). Although the organism responsible for phenoxypropionic acid degradation has been known for some time, little progress has been made in characterizing this pathway until recently (Horvath et al., 1990). An additional complication to dichlorprop degradation is the stereospecificity (R vs. S) involved in both the uptake (Kohler, 1999) and initial oxidation of dichlorprop (Westendorf et al., 2003). Heterologous expression of rdpA in other microbes or transformation of this gene into plants, heretofore, was not reported. Literature has focused primarily around close homologues of tfdA that primarily degrade achiral phenoxyacetic acids. There was no prior expectation that rdpA or AAD-1 genes could be successfully expressed in plants to render the plants resistant to 2,4-D (not to mention the completely surprising AOPP resistance).

As described in more detail in the Examples below, rdpA was cloned from *Sphingobium herbicidovorans* and tested for substrate promiscuity among various herbicide chemical classes. This α-ketoglutarate-dependent dioxygenase enzyme purified in its native form had previously been shown to degrade 2,4-D and dichlorprop (Westendorf et al., 2002 and 2003). However, no α-ketoglutarate-dependent dioxygenase enzyme has previously been reported to have the ability to degrade herbicides of different chemical classes and modes of action. RdpA has never been expressed in plants, nor was there any motivation to do so because development of new HTC technologies has been limited due largely to the efficacy, low cost, and convenience of GTCs (Devine, 2005).

In light of the novel activity, proteins and genes of the subject invention are referred to herein as AAD-1 proteins and genes. AAD-1 was presently confirmed to degrade a variety of phenoxyacetic and phenoxypropionic auxin herbicides in vitro. However, this enzyme, as reported for the first time herein, was surprisingly found to also be capable of degrading additional substrates of the class of aryloxyalkanoate molecules. Substrates of significant agronomic importance are the aryloxyphenoxypropionate (AOPP) grass herbicides. This highly novel discovery is the basis of significant Herbicide Tolerant Crop (HTC) and selectable marker trait opportunities.

The broad spectrum grass AOPP herbicides are reported herein to be excellent substrates for AAD-1 as well as 2,4-D, dichlorprop, and other phenoxy auxins. This enzyme is unique in its ability to deliver herbicide degradative activity to a range of broad spectrum broadleaf herbicides (phenoxy auxins) and a range of broad spectrum, highly active grass herbicides (AOPPs).

Thus, the subject invention relates in part to the degradation of 2,4-dichlorophenoxyacetic acid, other phenoxyalkanoic auxin herbicides, and aryloxyphenoxy-alkanoate herbicides by a recombinantly expressed aryloxyalkanoate dioxygenase enzyme (AAD-1). This invention also relates in part to identification and uses of genes encoding an aryloxyalkanoate dioxygenase degrading enzyme (AAD-1) capable of degrading phenoxy auxin and aryloxyphenoxypropionate herbicides.

The subject enzyme enables transgenic expression resulting in tolerance to combinations of herbicides that would control nearly all broadleaf and grass weeds. AAD-1 can serve as an excellent herbicide tolerant crop (HTC) trait to stack with other HTC traits (e.g., glyphosate resistance, glufosinate resistance, imidazolinone resistance, bromoxynil resistance, et al.), and insect resistance traits (Cry1F, Cry1Ab, Cry 34/45, et al.) for example. Additionally, AAD-1 can serve as a selectable marker to aid in selection of primary transformants of plants genetically engineered with a second gene or group of genes.

In addition, the subject microbial gene has been redesigned such that the protein is encoded by codons having a bias toward both monocot and dicot plant usage (hemicot). *Arabidopsis*, corn, tobacco, cotton, soybean, canola, and rice have been transformed with AAD-1-containing constructs and have demonstrated high levels of resistance to both the phenoxy auxin and AOPP herbicides. Thus, the subject invention also relates to "plant optimized" genes that encode proteins of the subject invention. As shown below in Example 6, the exemplified rebuilt gene was more efficacious in conveying herbicide resistance to the plant, as compared to the bacterial gene.

Oxyalkanoate groups are useful for introducing a stable acid functionality into herbicides. The acidic group can impart phloem mobility by "acid trapping," a desirable attribute for herbicide action and therefore could be incorporated into new herbicides for mobility purposes. Aspects of the subject invention also provide a mechanism of creating HTCs. There exist many potential commercial and experimental herbicides that can serve as substrates for AAD-1. Thus, the use of the subject genes can also result in herbicide tolerance to those other herbicides as well.

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

Additionally, glyphosate tolerant crops grown worldwide are prevalent. Many times in rotation with other glyphosate tolerant crops, control of glyphosate-resistant volunteers may be difficult in rotational crops. Thus, the use of the subject transgenic traits, stacked or transformed individually into crops, provides a tool for controlling other HTC volunteer crops.

This invention can be applied in the context of commercializing a 2,4-D resistance trait stacked with current glyphosate resistance traits in soybeans, for example. Thus, this invention provides a tool to combat broadleaf weed species shifts and/or selection of herbicide resistant broadleaf weeds, which culminates from extremely high reliance by growers on glyphosate for weed control with various crops.

The transgenic expression of the subject AAD-1 genes is exemplified in, for example, *Arabidopsis*, corn (maize), tobacco, cotton, rice, soybean, and canola. However, the subject invention can be applied to any other desired types of plants. Soybeans are a preferred crop for transformation according to the subject invention. However, this invention can be applied to multiple other grass and other broadleaf crops. Likewise, 2,4-D can be more positively utilized in grass crops where tolerance to 2,4-D is moderate, and increased tolerance via this trait would provide growers the opportunity to use 2,4-D at more efficacious rates and over a wider application timing without the risk of crop injury.

Still further, the subject invention provides a single gene that can provide resistance to herbicides that control broadleaf weed (auxins) and grass weeds (AOPPs). This gene may be utilized in multiple crops to enable the use of a broad spectrum herbicide combination. The subject invention can also control weeds resistant to current chemicals, and aids in the control of shifting weed spectra resulting from current agronomic practices. The subject AAD-1 can also be used in efforts to effectively detoxify additional herbicide substrates to non-herbicidal forms. Thus, the subject invention provides for the development of additional HTC traits and/or selectable marker technology.

Separate from, or in addition to, using the subject genes to produce HTCs, the subject genes can also be used as selectable markers for successfully selecting transformants in cell cultures, greenhouses, and in the field. There is high inherent value for the subject genes simply as a selectable marker for biotechnology projects. The promiscuity of AAD-1 for other phenoxyalkanoic auxinic herbicides provides many opportunities to utilize this gene for HTC and/or selectable marker purposes.

One gene of the subject invention, referred to herein as AAD-1 (aryloxyalkanoate dioxygenase), was cloned from *Sphingobium herbicidovorans* (ATCC 700291) by PCR into pET 280-S/S (designated pDAB 3203) and expressed in BL-21 Star *E. coli*. When this gene is overexpressed (by induction of 1 mM IPTG and culture lysate combined with the following reaction mix: 112.5 µg/ml 2,4-D, 1 mM Ascorbic acid, 1 mM α-ketoglutarate, 50 µM $Fe(NH_4)_2(SO_4)_2$, the recombinantly produced enzyme degrades 2,4-D into herbicidally inactive DCP (as determined by HPLC, mass spectrometry, colorimetric assay, and *Arabidopsis* plate assay). Additionally, AAD-1 has been demonstrated to convert the following herbicides into their corresponding inactive phenol: dichlorprop, mecoprop, haloxyfop, dichlofop, and others (See Tables 3 and 4).

Table 3: Effect of purified AAD-1 (v1) on various herbicidal auxins and auxin analogs. Substrates were assayed at 1 mM in 25 mM MOPS pH 6.8, 200 µM $Fe^{2+}$, 200 µM Na ascorbate, 1 mM α-ketoglutarate using either 1 µg or 10 µg (10×) purified AAD-1 (v1) per 0.16 ml assay.

TABLE 3

Effect of purified AAD-1 (v1) on various herbicidal auxins and auxin analogs

| STRUCTURE | Registry ID | Compound | AAD1 | AAD1 (10X) |
|---|---|---|---|---|
| 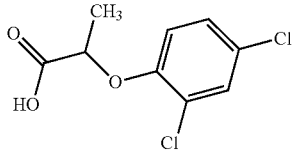 | 117613 | (R,S)-dichlorprop | 0.566 | 2.594 |
| 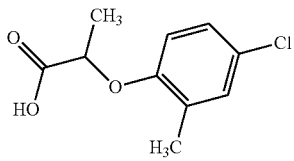 | 188874 | (R,S)-mecoprop | 0.341 | 2.085 |
| 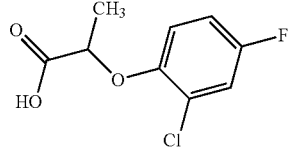 | 83293 | (R,S)-2-chloro, 4-fluorophenoxy-proprionate | 0.304 | 2.358 |
| 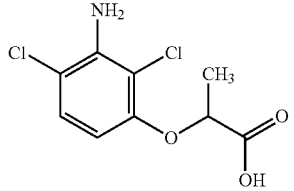 | 11113675 | (R,S)-3-aminodichlorpop | 0.228 | 2.676 |
| 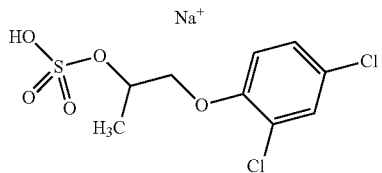 [SMILES: [Na+] ; CC(COc1ccc(Cl)cc1Cl)OS(=O)(=O)O] | 188476 | | 0.077 | 0.687 |

TABLE 3-continued
Effect of purified AAD-1 (v1) on various herbicidal auxins and auxin analogs
| STRUCTURE | Registry ID | Compound | AAD1 | AAD1 (10X) |
|---|---|---|---|---|
| 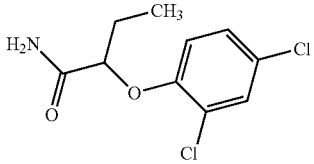 | 192132 | | 0.064 | 0.204 |
| 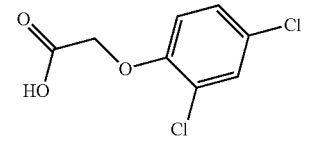 [SMILES: O=C(O)COc1ccc(Cl)cc1Cl] | 195517 | 2,4-D | 0.034 | 0.383 |
| 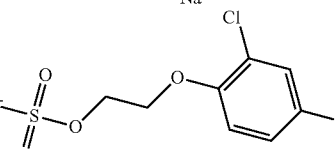 | 398166 | sesone | 0.02 | 0.177 |
| 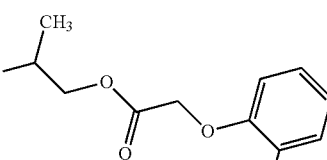 | 190252 | | 0.008 | 0.211 |
| 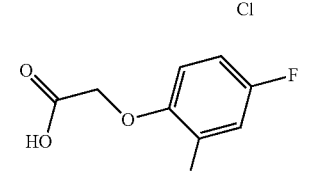 | 124988 | | 0.007 | 0.058 |
| 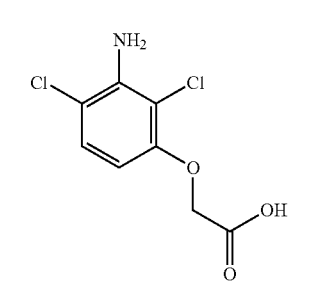 [SMILES: Nc1c(Cl)ccc(OCC(=O)O)c1Cl] | 11263526 | | 0.004 | 0.069 |
| 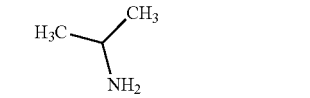 | 178577 | | 0.003 | 0.021 |
| 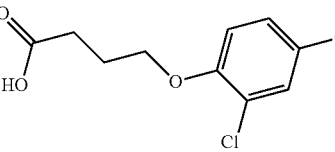 | | | | |

TABLE 3-continued

Effect of purified AAD-1 (v1) on various herbicidal auxins and auxin analogs

| STRUCTURE | Registry ID | Compound | AAD1 | AAD1 (10X) |
|---|---|---|---|---|
| 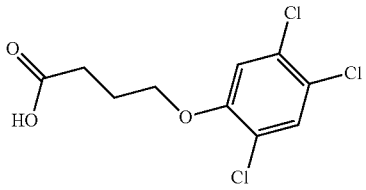 Na+ | 178587 | | 0.003 | 0.02 |
| 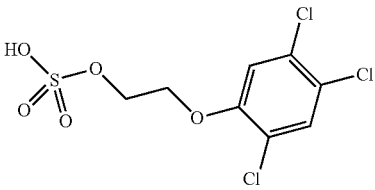 Na+ | 188527 | | 0.003 | 0.036 |

Table 4: Effect of purified AAD-1 (v1) on various AOPP graminicides and analogs, and on cloquintocet. Substrates were assayed at 1 mM in 25 mM MOPS pH 6.8, 200 μM $Fe^{2+}$, 200 μM Na ascorbate, 1 mM α-ketoglutarate using either 1 μg or 10 μg (10×) purified AAD-1 (v1) per 0.16 ml assay.

TABLE 4

Effect of purified AAD-1 (v1) on various AOPP graminicides and analogs, and on cloquintocet.

| STRUCTURE | Registry ID | Compound | AAD1 | AAD1 (10X) |
|---|---|---|---|---|
| 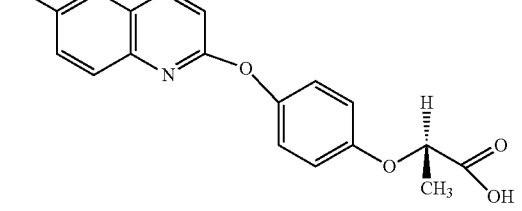 | 18706 | (R)-quizalofop | 0.43 | 2.1 |
| 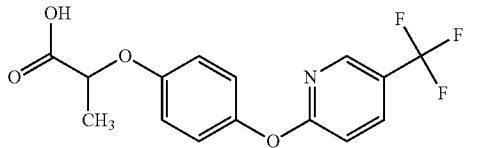 [SMILES: CC(Oc1ccc(Oc2ccc(C(F)(F)F)cn2)cc1)C(=O)O] | 67131 | (R,S)-fluazifop | 0.427 | 2.17 |
| 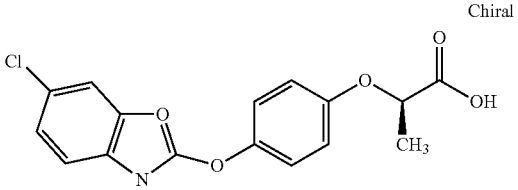 Chiral | 11044492 | (R)-fenoxaprop | 0.408 | 0.597 |
| 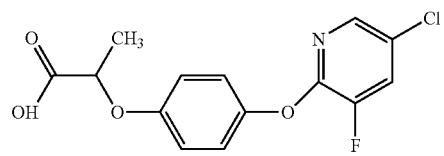 [SMILES: CC(Oc1ccc(Oc2ncc(Cl)cc2F)cc1)C(=O)O] | 34697 | (R,S)-clodinofop | 0.295 | 1.98 |

TABLE 4-continued

Effect of purified AAD-1 (v1) on various AOPP graminicides and analogs, and on cloquintocet.

| STRUCTURE | Registry ID | Compound | AAD1 | AAD1 (10X) |
|---|---|---|---|---|
| 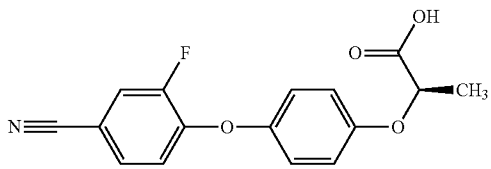 [SMILES: C[C@@H](Oc1ccc(Oc2ccc(C#N)cc2F)cc1)C(=O)O] | 14603 | (R)-cyhalofop | 0.222 | 1.989 |
| 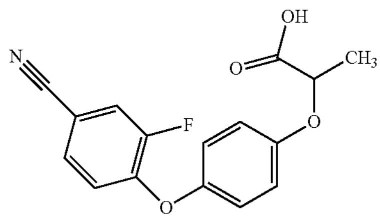 [SMILES: CC(Oc1ccc(Oc2ccc(C#N)cc2F)cc1)C(=O)O] | 14623 | (R,S)-cyhalofop | 0.215 | 1.815 |
| 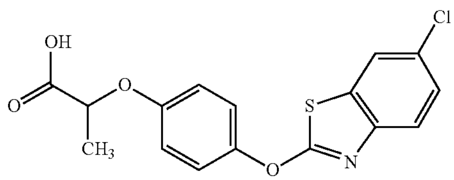 [SMILES: CC(Oc1ccc(Oc2nc3ccc(Cl)cc3s2)cc1)C(=O)O] | 62942 | (R,S)-fenthiaprop | 0.199 | 1.055 |
| 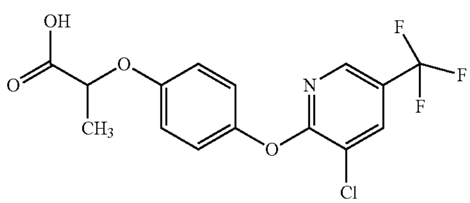 [SMILES: CC(Oc1ccc(Oc2ncc(C(F)(F)F)cc2Cl)cc1)C(=O)O] | 66905 | haloxyfop | 0.172 | 1.63 |
| 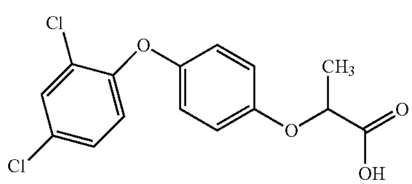 [SMILES: CC(Oc1ccc(Oc2ccc(Cl)cc2Cl)cc1)C(=O)O] | 460511 | (R,S)-diclofop | 0.155 | 1.663 |
| 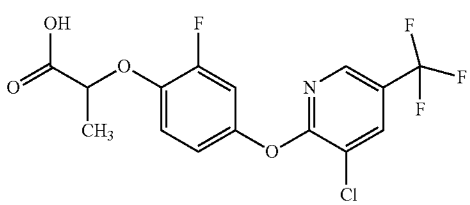 [SMILES: CC(Oc1ccc(Oc2ncc(C(F)(F)F)cc2Cl)cc1F)C(=O)O] | 25646 | | 0.144 | 1.69 |
| 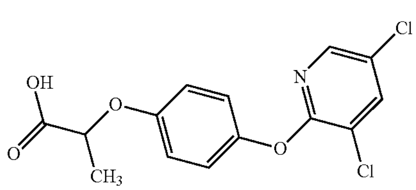 [SMILES: CC(Oc1ccc(Oc2ncc(Cl)cc2Cl)cc1)C(=O)O] | 70222 | (R,S)-chlorazifop | 0.128 | 1.584 |
| 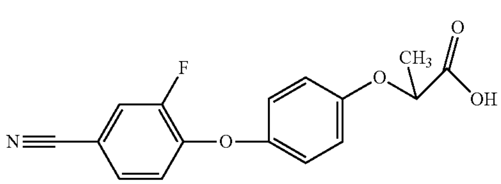 [SMILES: CC(Oc1ccc(Oc2ccc(C#N)cc2F)cc1)C(=O)O] | 199608 | cyhalofop | 0.114 | 1.26 |

TABLE 4-continued

Effect of purified AAD-1 (v1) on various AOPP graminicides and analogs, and on cloquintocet.

| STRUCTURE | Registry ID | Compound | AAD1 | AAD1 (10X) |
|---|---|---|---|---|
| [structure] | 43865 | haloxyfop-oxyacetate | 0.004 | 0.053 |
| [structure] | 7466 | (S)-cyhalofop | 0.003 | 0.017 |
| [structure] | 204558 | Cloquintocet | 0 | 0.001 |

Proteins (and Source Isolates) of the Subject Invention.

The present invention provides functional proteins. By "functional activity" (or "active") it is meant herein that the proteins/enzymes for use according to the subject invention have the ability to degrade or diminish the activity of a herbicide (alone or in combination with other proteins). Plants producing proteins of the subject invention will preferably produce "an effective amount" of the protein so that when the plant is treated with a herbicide, the level of protein expression is sufficient to render the plant completely or partially resistant or tolerant to the herbicide (at a typical rate, unless otherwise specified; typical application rates can be found in the well-known *Herbicide Handbook* (Weed Science Society of America, Eighth Edition, 2002), for example). The herbicide can be applied at rates that would normally kill the target plant, at normal field use rates and concentrations. (Because of the subject invention, the level and/or concentration can optionally be higher than those that were previously used.) Preferably, plant cells and plants of the subject invention are protected against growth inhibition or injury caused by herbicide treatment. Transformed plants and plant cells of the subject invention are preferably rendered resistant or tolerant to an herbicide, as discussed herein, meaning that the transformed plant and plant cells can grow in the presence of effective amounts of one or more herbicides as discussed herein. Preferred proteins of the subject invention have catalytic activity to metabolize one or more aryloxyalkanoate compounds.

Transfer of the functional activity to plant or bacterial systems can involve a nucleic acid sequence, encoding the amino acid sequence for a protein of the subject invention, integrated into a protein expression vector appropriate to the host in which the vector will reside. One way to obtain a nucleic acid sequence encoding a protein with functional activity is to isolate the native genetic material from the bacterial species which produce the protein of interest, using information deduced from the protein's amino acid sequence, as disclosed herein. The native sequences can be optimized for expression in plants, for example, as discussed in more detail below. Optimized polynucleotide can also be designed based on the protein sequence.

The subject invention provides classes of proteins having novel activities as identified herein. One way to characterize these classes of proteins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining proteins for use according to the subject invention. For example, antibodies to the proteins disclosed herein can be used to identify and isolate other proteins from a mixture of proteins. Specifically, antibodies may be raised to the portions of the proteins that are most conserved or most distinct, as compared to other related proteins. These antibodies can then be used to specifically identify equivalent proteins with the characteristic activity by immunoprecipitation, enzyme linked immunosorbent assay (ELISA), or immuno-blotting. Antibodies to the proteins disclosed herein, or to equivalent proteins, or to fragments of these proteins, can be readily prepared using standard procedures. Such antibodies are an aspect of the subject invention. Antibodies of the subject invention include monoclonal and polyclonal antibodies, preferably produced in response to an exemplified or suggested protein.

One skilled in the art would readily recognize that proteins (and genes) of the subject invention can be obtained from a variety of sources. Since entire herbicide degradation operons are known to be encoded on transposable elements such as plasmids, as well as genomically integrated, proteins of the subject invention can be obtained from a wide variety of microorganisms, for example, including recombinant and/or wild-type bacteria. Other members of the orders Firmicutes and Proteobacteria, and specific genera with known rdpA's, such as *Sphingobium, Delftia, Rodoferax*, and *Comamonas* for example, can be used as source isolates.

Mutants of bacterial isolates can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

A protein "from" or "obtainable from" any of the subject isolates referred to or suggested herein means that the protein (or a similar protein) can be obtained from the isolate or some other source, such as another bacterial strain or a plant. "Derived from" also has this connotation, and includes proteins obtainable from a given type of bacterium that are modified for expression in a plant, for example. One skilled in the art will readily recognize that, given the disclosure of a bacterial gene and protein, a plant can be engineered to produce the protein. Antibody preparations, nucleic acid probes (DNA, RNA, or PNA, for example), and the like can be prepared using the polynucleotide and/or amino acid sequences disclosed herein and used to screen and recover other related genes from other (natural) sources.

Standard molecular biology techniques may be used to clone and sequence the proteins and genes described herein. Additional information may be found in Sambrook et al., 1989, which is incorporated herein by reference.

Polynucleotides and Probes.

The subject invention further provides nucleotide sequences that encode proteins for use according to the subject invention. The subject invention further provides methods of identifying and characterizing genes that encode proteins having the desired herbicidal activity. In one embodiment, the subject invention provides unique nucleotide sequences that are useful as hybridization probes and/or primers for PCR techniques. The primers produce characteristic gene fragments that can be used in the identification, characterization, and/or isolation of specific genes of interest. The nucleotide sequences of the subject invention encode proteins that are distinct from previously described proteins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art. The level of gene expression and temporal/tissue specific expression can greatly impact the utility of the invention. Generally, greater levels of protein expression of a degradative gene will result in faster and more complete degradation of a substrate (in this case a target herbicide). Promoters will be desired to express the target gene at high levels unless the high expression has a consequential negative impact on the health of the plant. Typically, one would wish to have the AAD-1 gene constitutively expressed in all tissues for complete protection of the plant at all growth stages. However, one could alternatively use a vegetatively expressed resistance gene; this would allow use of the target herbicide in-crop for weed control and would subsequently control sexual reproduction of the target crop by application during the flowering stage.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA molecules are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of genes of interest will be amplified by the procedure, thus identifying the presence of the gene(s) of interest.

Further aspects of the subject invention include genes and isolates identified using the methods and nucleotide sequences disclosed herein. The genes thus identified can encode herbicidal resistance proteins of the subject invention.

Proteins and genes for use according to the subject invention can be identified and obtained by using oligonucleotide probes, for example. These probes are detectable nucleotide sequences that can be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes) and/or other synthetic (non-natural) bases. Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter. 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying genes of the subject invention. The nucleotide segments used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a gene (and the protein it encodes), for example, is by its ability to hybridize (under any of the conditions specifically disclosed herein) with a known or specifically exemplified gene.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes can be performed by standard methods (see, e.g., Maniatis et al. 1982). In general, hybridization and subsequent washes can be carried out under conditions that allow for detection of target sequences. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. 1983):

$$Tm=81.5° C.+16.6 \text{ Log } [Na+]+0.41(\% \text{ } G+C)-0.61(\% \text{ formamide})-600/\text{length of duplex in base pairs.}$$

Washes can typically be carried out as follows:
(1) Twice at room temperature for 15 minutes in 1×SSPE, 0.1% SDS (low stringency wash).
(2) Once at Tm-20° C. for 15 minutes in 0.2×SSPE, 0.1% SDS (moderate stringency wash).

For oligonucleotide probes, hybridization can be carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

$$Tm(° C.)=2(\text{number } T/A \text{ base pairs})+4(\text{number } G/C \text{ base pairs})$$

(Suggs et al., 1981).

Washes can typically be out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:
Low: 1 or 2×SSPE, room temperature
Low: 1 or 2×SSPE, 42° C.
Moderate: 0.2× or 1×SSPE, 65° C.
High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR Technology.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are preferably oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

Exemplified DNA sequences, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of Genes and Proteins.

The subject genes and proteins can be fused to other genes and proteins to produce chimeric or fusion proteins. The genes and proteins useful according to the subject invention include not only the specifically exemplified full-length sequences, but also portions, segments and/or fragments (including contiguous fragments and internal and/or terminal deletions compared to the full-length molecules) of these sequences, variants, mutants, chimerics, and fusions thereof. Proteins of the subject invention can have substituted amino acids so long as they retain desired functional activity. "Variant" genes have nucleotide sequences that encode the same proteins or equivalent proteins having activity equivalent or similar to an exemplified protein. The terms "variant proteins" and "equivalent proteins" refer to proteins having the same or essentially the same biological/functional activity against the target pests and equivalent sequences as the exemplified proteins. As used herein, reference to an "equivalent" sequence refers to sequences having amino acid substitutions, deletions, additions, or insertions that improve or do not adversely affect activity to a significant extent. Fragments retaining activity are also included in this definition. Fragments and other equivalents that retain the same or similar function or activity as a corresponding fragment of an exemplified protein are within the scope of the subject invention. Changes, such as amino acid substitutions or additions, can be made for a variety of purposes, such as increasing (or decreasing) protease stability of the protein (without materially/substantially decreasing the functional activity of the protein), removing or adding a restriction site, and the like. Variations of genes may be readily constructed using standard techniques for making point mutations, for example.

In addition, U.S. Pat. No. 5,605,793, for example, describes methods for generating additional molecular diversity by using DNA reassembly after random or focused fragmentation. This can be referred to as gene "shuffling," which typically involves mixing fragments (of a desired size) of two or more different DNA molecules, followed by repeated rounds of renaturation. This can improve the activity of a protein encoded by a starting gene. The result is a chimeric protein having improved activity, altered substrate specificity, increased enzyme stability, altered stereospecificity, or other characteristics.

"Shuffling" can be designed and targeted after obtaining and examining the atomic 3D (three dimensional) coordinates and crystal structure of a protein of interest. Thus, "focused shuffling" can be directed to certain segments of a protein that are ideal for modification, such as surface-exposed segments, and preferably not internal segments that are involved with protein folding and essential 3D structural integrity.

Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques, for example, can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, or 297 contiguous residues (amino acid or nucleotide), corresponding to a segment (of the same size) in any of the exemplified or suggested sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes that encode active fragments may be obtained using a variety of restriction enzymes. Proteases may be used to directly obtain active fragments of these proteins.

It is within the scope of the invention as disclosed herein that proteins can be truncated and still retain functional activity. By "truncated protein" it is meant that a portion of a protein may be cleaved off while the remaining truncated protein retains and exhibits the desired activity after cleavage. Cleavage can be achieved by various proteases. Furthermore, effectively cleaved proteins can be produced using molecular biology techniques wherein the DNA bases encoding said protein are removed either through digestion with restriction endonucleases or other techniques available to the skilled artisan. After truncation, said proteins can be expressed in heterologous systems such as E. coli, baculoviruses, plant-based viral systems, yeast, and the like and then placed in insect assays as disclosed herein to determine activity. It is well-known in the art that truncated proteins can be successfully produced so that they retain functional activity while having less than the entire, full-length sequence. For example, B.t. proteins can be used in a truncated (core protein) form (see, e.g., Hofte et al. (1989), and Adang et al. (1985)). As used herein, the term "protein" can include functionally active truncations.

In some cases, especially for expression in plants, it can be advantageous to use truncated genes that express truncated proteins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein.

Certain proteins of the subject invention have been specifically exemplified herein. As these proteins are merely exemplary of the proteins of the subject invention, it should be readily apparent that the subject invention comprises variant or equivalent proteins (and nucleotide sequences coding for equivalents thereof) having the same or similar activity of the exemplified proteins. Equivalent proteins will have amino acid similarity (and/or homology) with an exemplified protein. The amino acid identity will typically be at least 60%, preferably at least 75%, more preferably at least 80%, even more preferably at least 90%, and can be at least 95%. Preferred proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits.

Unless otherwise specified, as used herein, percent sequence identity and/or similarity of two nucleic acids is determined using the algorithm of Karlin and Altschul, 1990, modified as in Karlin and Altschul 1993. Such an algorithm is incorporated into the NBLAST and XBLAST programs of Altschul et al., 1990. BLAST nucleotide searches are performed with the NBLAST program, score=100, wordlength=12. Gapped BLAST can be used as described in Altschul et al., 1997. When utilizing BLAST and Gapped BLAST programs, the default parameters of the respective programs (NBLAST and XBLAST) are used. See NCBI/NIH website. To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

Various properties and three-dimensional features of the protein can also be changed without adversely affecting the activity/functionality of the protein. Conservative amino acid substitutions can be tolerated/made to not adversely affect the activity and/or three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 5 provides a listing of examples of amino acids belonging to each class.

TABLE 5

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. However, preferred substitutions do not significantly detract from the functional/biological activity of the protein.

As used herein, reference to "isolated" polynucleotides and/or "purified" proteins refers to these molecules when they are not associated with the other molecules with which they would be found in nature. Thus, reference to "isolated" and/or "purified" signifies the involvement of the "hand of man" as described herein. For example, a bacterial "gene" of the subject invention put into a plant for expression is an "isolated polynucleotide." Likewise, a protein derived from a bacterial protein and produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, proteins. These variant DNA sequences are within the scope of the subject invention. This is also discussed in more detail below in the section entitled "Optimization of sequence for expression in plants."

Optimization of Sequence for Expression in Plants.

To obtain high expression of heterologous genes in plants it is generally preferred to reengineer the genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial protein is reengineering of a heterologous gene for optimal expression, using codon bias more closely aligned with the target plant sequence, whether a dicot or monocot species. Sequences can also be optimized for expression in any of the more particular types of plants discussed elsewhere herein.

Transgenic Hosts.

The protein-encoding genes of the subject invention can be introduced into a wide variety of microbial or plant hosts. The subject invention includes transgenic plant cells and transgenic plants. Preferred plants (and plant cells) are corn, *Arabidopsis*, tobacco, soybeans, cotton, canola, rice, wheat, turf and pasture grasses, and the like. Other types of transgenic plants can also be made according to the subject invention, such as fruits, vegetables, and trees. More generally, dicots and/or monocots can be used in various aspects of the subject invention.

In preferred embodiments, expression of the gene results, directly or indirectly, in the intracellular production (and maintenance) of the protein(s) of interest. Plants can be rendered herbicide-resistant in this manner. Such hosts can be referred to as transgenic, recombinant, transformed, and/or transfected hosts and/or cells. In some aspects of this invention (when cloning and preparing the gene of interest, for example), microbial (preferably bacterial) cells can be produced and used according to standard techniques, with the benefit of the subject disclosure.

Plant cells transfected with a polynucleotide of the subject invention can be regenerated into whole plants. The subject invention includes cell cultures including tissue cell cultures, liquid cultures, and plated cultures. Seeds produced by and/or used to generate plants of the subject invention are also included within the scope of the subject invention. Other plant tissues and parts are also included in the subject invention. The subject invention likewise includes methods of producing plants or cells comprising a polynucleotide of the subject invention. One preferred method of producing such plants is by planting a seed of the subject invention.

Insertion of Genes to Form Transgenic Hosts.

One aspect of the subject invention is the transformation/transfection of plants, plant cells, and other host cells with polynucleotides of the subject invention that express proteins of the subject invention. Plants transformed in this manner can be rendered resistant to a variety of herbicides with different modes of action.

A wide variety of methods are available for introducing a gene encoding a desired protein into the target host under conditions that allow for stable maintenance and expression of the gene. These methods are well known to those skilled in the art and are described, for example, in U.S. Pat. No. 5,135,867.

Vectors comprising an AAD-1 polynucleotide are included in the scope of the subject invention. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the protein can be inserted into the vector at a suitable restriction site. The resulting plasmid is used for transformation in *E. coli*. The *E. coli* cells are cultivated in a suitable nutrient medium, then harvested and lysed. The plasmid is recovered by purification away from genomic DNA. Sequence analysis, restriction analysis, electrophoresis, and other biochemical-molecular biological methods are generally carried out as methods of analysis. After each manipulation, the DNA sequence used can be restriction digested and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985); Fraley et al. (1986); and An et al. (1985).

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), silicon carbide whiskers, aerosol beaming, PEG, or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters, 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can be cultivated advantageously with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial protein are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. Plant selectable markers also typically can provide resistance to various herbicides such as glufosinate, (PA7), glyphosate (EPSPS), imazethyapyr (AHAS), and many others. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a protein expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to Dow-Elanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149, 645, 5,469,976, 5,464,763 and 4,940,838 and 4,693,976 to Schilperoot; European Patent Applications 116718, 290799, 320500, all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Syngenta; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca, now Syngenta. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plants can be transformed with a viral vector using the methods described in U.S. Pat. No. 5,569,597 to Mycogen Plant Science and Ciba-Geigy (now Syngenta), as well as U.S. Pat. Nos. 5,589,367 and 5,316,931, both to Biosource, now Large Scale Biology.

As mentioned previously, the manner in which the DNA construct is introduced into the plant host is not critical to this invention. Any method that provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al. (1980) and EPO 0 120 515. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial protein is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos or glufosinate); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in Weising et al., 1988. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, osmotin UTR sequences, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active (or inactive) during a certain stage of the plant's development as well as active in plant tissues and organs. Examples of such include but are not limited to pollen-specific, embryo-specific, corn-silk-specific, cotton-fiber-specific, root-specific, seed-endosperm-specific, or vegetative phase-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical (tetracycline responsive), and stress. Other desirable transcription and translation elements that function in plants may be used. Numerous plant-specific gene transfer vectors are known in the art.

Plant RNA viral based systems can also be used to express bacterial protein. In so doing, the gene encoding a protein can be inserted into the coat promoter region of a suitable plant virus which will infect the host plant of interest. The protein can then be expressed thus providing protection of the plant from herbicide damage. Plant RNA viral based systems are described in U.S. Pat. No. 5,500,360 to Mycogen Plant Sciences, Inc. and U.S. Pat. Nos. 5,316,931 and 5,589,367 to Biosource, now Large Scale Biology.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Method for Identifying Genes that Impart Resistance to 2,4-D in Planta As a way to identify genes which possess herbicide degrading activities in planta, it is possible to mine current public databases such as NCBI (National Center for Biotechnology Information). To begin the process, it is necessary to have a functional gene sequence already identified that encodes a protein with the desired characteristics (i.e., α-ketoglutarate dioxygenase activity). This protein sequence is then used as the input for the BLAST (Basic Local Alignment Search Tool) (Altschul et al., 1997) algorithm to compare against available NCBI protein sequences deposited. Using default settings, this search returns upwards of 100 homologous protein sequences at varying levels. These range from highly identical (85-98%) to very low identity (23-32%) at the amino acid level. Traditionally only sequences with high homology would be expected to retain similar properties to the input sequence. In this case we chose only those sequences with ≤50% homology. We go on to exemplify that cloning and recombinantly expressing homologues with as little as 27% amino acid conservation can be used to impart commercial levels of resistance not only to the intended herbicide, but also to substrates never previously tested with these enzymes.

PCR and Cloning of Gene into pET.

A single gene (rdpA) was identified from the NCBI database (see the ncbi.nlm.nih.gov website; accession #AF516752) as a homologue with only 28% amino acid identity to tfdA from Ralstonia eutropha. Percent identity was determined by first translating both the rdpA and tfdA DNA sequences deposited in the database to proteins, then using ClustalW in the VectorNTI software package to perform the multiple sequence alignment.

The strain of Sphingobium herbicidovorans containing the rdpA gene was obtained from ATCC (American Type Culture Collection strain #700291). The lyophilized strain was revived according to ATCC protocol and stored at −80° C. in 20% glycerol for internal use as Dow Bacterial strain DB 536. From this freezer stock, a plate of Tryptic Soy Agar was then struck out with a loopful of cells for isolation, and incubated at 28° C. for 3 days.

A single colony was used to inoculate 100 ml of Tryptic Soy Broth in a 500 ml tri-baffled flask, which was incubated overnight at 28° C. on a floor shaker at 150 rpm. From this, total DNA was isolated with the gram negative protocol of Qiagen's DNeasy kit (Qiagen cat. #69504). The following primers were designed to amplify the target gene from genomic DNA, Forward: 5' TCTAGAAGGAGATATACC ATG CAT GCT GCA CTG TCC CCC CTC TCC CAG CG 3' [(SEQ ID NO:1) (added Xba I restriction site and Ribosome Binding Site (RBS))] and Reverse: 5' CTCGAGTTA CTA GCG CGC CGG GCG CAC GCC ACC GAC CG 3' [(SEQ ID NO:2)(added extra stop codon and Xho I site)].

Twenty microliter reactions were set up as follows: MasterMix 8 µl, ea. primer 1 µl (50 pmoles/µl), gDNA 2.5 µl, H₂O 7.5 µl. PCR was then carried out under the following conditions: 94° C. 45 sec, 52° C. 1.5 minute, 72° C. 1.5 minute, for 30 cycles, followed by a final cycle of 72° C. 5 minute, using Eppendorf's Master Taq kit (Eppendorf cat. #0032 002.250). The resulting ~1 kb PCR product was cloned into pCR 2.1 (Invitrogen cat. #K4550-40) following the included protocol, with chemically competent TOP10F' E. coli as the host strain, for verification of nucleotide sequence.

Ten of the resulting white colonies were picked into 4 ml Luria Broth+50 µg/ml Kanamycin (LB K), and grown overnight at 37° C. with agitation. Plasmids were purified from each culture using Promega Wizard Plus SV kit (Promega cat. #A1460) and following the included protocol. Sequencing was carried out with Beckman CEQ Quick Start Kit (Beckman Coulter cat. #608120) using M13 Forward (5' GTA AAA CGA CGG CCA GT 3') (SEQ ID NO:16) and Reverse (5' CAG GAA ACA GCT ATG AC 3') (SEQ ID NO:17) primers, per manufacturers instructions. This gene sequence (SEQ ID NO:3), and its corresponding protein (SEQ ID NO:9) was given a new general designation for internal consistency AAD-1 (v1) (AryloxyAlkanoate Dioxygenase).

Using the restriction enzymes corresponding to the sites added with the primer linkers (Xba 1, Xho 1) AAD-1 (v1) was cut out of the pCR2.1 vector and ligated into a pET 280 streptomycin/spectinomycin resistant vector. Ligated products were then transformed into TOP10F' E. coli, and plated on to Luria Broth+50 µg/ml Streptomycin & Spectinomycin (LB S/S) agar plates. To differentiate between AAD-1 (v1): pET 280 and pCR2.1:pET 280 ligations, approximately 20 isolated colonies were picked into 6 ml of LB S/S, and grown at 37° C. for 4 hours with agitation.

Each culture was then spotted onto LB K plates, which were incubated at 37° C. overnight. Colonies that grew on the LB K were assumed to have the pCR2.1 vector ligated in, and were discarded. Plasmids were isolated from the remaining cultures as before. This expression construct was given the designation pDAB 3203.

Example 2—Expression and Testing 2.1—HPLC Analysis.

Plasmid pDAB 3203 was maintained frozen at −80° C. in TOP10F' cells (Invitrogen) as Dow Recombinant strain DR 1878. For expression, plasmid DNA purified from TOP10F' culture using Promega's Wizard kit (Fisher cat. #PR-A1460) was transformed into BL-21 Star (DE3) cells (Invitrogen cat. #C6010-03) following manufacturer's protocol. After transformation, 50 µl of the cells were plated onto LB S/S agar plates and incubated overnight at 37° C.

The next morning, all colonies from the entire plate were scraped into 100 mls LB in a 500 ml tri-baffled flask and incubated at 37° C./200 rpm for 1 hr. Gene expression was then induced with 1 mM IPTG, and incubated for 4 hrs at 30° C./200 rpm. All 100 ml of culture was centrifuged at 4000 rpm for 20 min. The supernatants were then discarded, and the pellets were resuspended in 10 ml of 50 mM MOPS. These were then subjected to three 45-sec rounds of sonication to lyse the cells. Following this, lysates were centrifuged at 15,000 rpm to remove cell debris. The supernatant was pipetted off and stored at 4° C. To check for recombinant expression, a 20 µl aliquot was run on a 4-20% Tris Glycine gel (Invitrogen cat. #EC60255).

After expression was confirmed, enzyme activity was tested as follows. First, an aliquot of the cell extract was desalted with a PD-10 cartridge (Amersham cat. #17-0435-01). This was then used for subsequent herbicide enzyme reactions.

For each reaction, the following were combined: 2,4-D (125 µg/ml), [Ascorbate (1 mM), Ferrous ion (50 µM), α-ketoglutarate (1 mM), in 100 mM MOPS], cell extract (100 µl). This reaction was then incubated at room temp for 30 min., after which the reaction was stopped with the addition of 0.1 N HCl until pH was between 2 and 3. Half of the reaction volume (~500 µl) was set aside for bioassay, the remaining volume was organically extracted using Solid Phase Extraction tubes (Fisher cat. #11-131-6), eluting with 400 µl of Acetonitrile+0.05% TFA.

The extracts were then tested on HPLC for loss of the 2,4-D peak or presence of any additional peaks resulting from the degradation or modification of 2,4-D. Conditions for the HPLC were: Luna 10µ C18(2) 250×4.6 mm (Phenomenex cat. #00G-4253-E0), run at 50% ACN+0.05% TFA: 50% $H_2O$+0.05% TFA to 100% ACN+0.05% TFA over 5 min.

2.2—Plate Test Bioassays for Herbicide Degradation.

Plant bioassays were used to determine if in vitro enzymatic herbicide transformation resulted in a concomitant loss in herbicidal activity. Because of the selective nature of the herbicides being tested (i.e., monocot plants controlled by AOPP herbicides and dicot plants controlled by auxinic herbicides), wildtype *Agrostis palustris* var. Pencross and *Arabidopsis thaliana* var. Columbia were used as monocot and dicot test species, respectively. Each species is amenable to germination and growth in small Petri dishes.

*Arabidopsis* seeds were surface sterilized for 10 min. in 50% commercial bleach/deionized water (v/v) with 1 µL of Tween-20 added as a wetting agent with vigorous agitation (shaker table @ 250 rpm). Bleach solution was decanted inside a sterile hood and rinsed three times with sterile water. Bentgrass seeds were surface sterilized for 20 minutes in a like manner.

Twenty to thirty sterilized seeds for each test species used were added onto a sterile, solidified agar Plate Test Medium (PTM) [2.5 mM $KNO_3$, 2.5 mM $KH_2PO_4$, 50 mM $FeSO_4$, 10 mM NaEDTA (pH 8.0), 2 mM $MgSO_4$, 2 mM $Ca(NO_3)_2$, 70 µM $H_3BO_3$, 14 µM $MnCl_2$, 0.5 µM $CuSO_4$, 1 µM $ZnSO_4$, 0.2 µM $NaMoO_4.2H_2O$, 10 µM NaCl, 10 nM $CoCl_2.H_2O$, 0.8% (w/v) sucrose, 0.4% agarose (w/v)] for bioassay in 60×15-mm Petri dishes (Falcon 1007). PTM was additionally modified by adding up to six rates of test herbicide standards or herbicide-enzyme test solution dilutions such that the four-fold concentration increments covered a rate range of three orders of magnitude with the $GR_{50}$ rate (50% growth reduction) approximately in the center of the range.

For herbicide-enzyme test solutions, the maximal concentration was determined based on the nominal concentration before any subsequent enzymatic degradation would occur. Seeds were evenly spread by adding 3 ml of melted PTM of the same composition, swirling, and allowing to solidify. Plates were sealed and maintained under sterile conditions in a low light growth chamber (24 h $day^{-1}$, 100 $\mu E/m^2$ $s^1$, 23° C.) for 7 days. Root length or root+shoot length were measured for five randomly chosen *Arabidopsis* and bentgrass plants, respectively, average mean length (percent of untreated control) vs. nominal herbicide concentration and $GR_{50}$ determined.

This bioassay was used to confirm the loss of herbicidal activity as a result of AAD-1 (v1) degradation of the oxyalkanoate side chain from various agronomically relevant herbicides. In several instances, the anticipated phenol product co-eluted with the parent acid on HPLC and the bioassay served as the primary screen for herbicide degradation. Tables 6 and 7 represent herbicidal substrates tested.

TABLE 6

*Arabidopsis* plate test bioassay for commercial phenoxy and pyridinyloxyalkanoate auxin substrates.

| | $GR_{50}$ (nM) | | | | |
|---|---|---|---|---|---|
| Chemical tested | Chemical alone | Chemical + Blank Vector * | Chemical + AAD-1 v1 | $GR_{50}$ ratio ** | Structure |
| 2,4-D | 22 | 17 | 267 | 16 | (structure: 2,4-dichlorophenoxyacetic acid) |
| DCP | >1000 | nd | nd | nd | (structure: 2,4-dichlorophenol) |

TABLE 6-continued

Arabidopsis plate test bioassay for commercial phenoxy and pyridinyloxyalkanoate auxin substrates.

| Chemical tested | GR$_{50}$ (nM) | | | GR$_{50}$ ratio ** | Structure |
|---|---|---|---|---|---|
| | Chemical alone | Chemical + Blank Vector * | Chemical + AAD-1 vl | | |
| Dichlorprop | nd | 30 | 1000 | 33 | 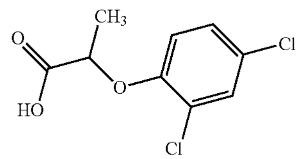 |
| Triclopyr | 255 | 1000 | 1000 | 1 | 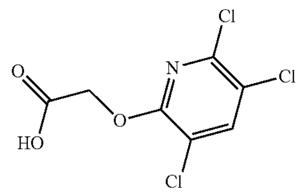 [SMILES: O=C(O)COc1nc(Cl)c(Cl)cc1Cl] |
| Fluroxypyr | 2200 | 2250 | 1825 | <1 | 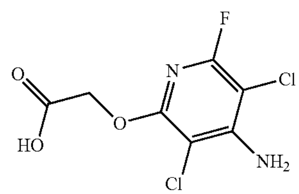 [SMILES: Nc1c(Cl)c(F)nc(OCC(=O)O)c1Cl] |

\* Blank vector represents of cell lysate treatment where *E. coli* pET vector had no gene insert.
\*\* GR50 ratio is a measure of the loss of herbicidal activity of enzyme-expressing lysate treatment vs blank vector treatments.
A number

TABLE 7

Bentgrass plate test bioassay for commercial aryloxyphenoxyalkanoate ACCase-inhibiting substrates.

| Chemical tested | GR$_{50}$ (nM) | | | GR$_{50}$ ratio ** | Structure |
|---|---|---|---|---|---|
| | Chemical alone | Chemical + Blank Vector * | Chemical + AAD-1 vl | | |
| Haloxyfop-RS | 28 | 21 | 520 | 25 | 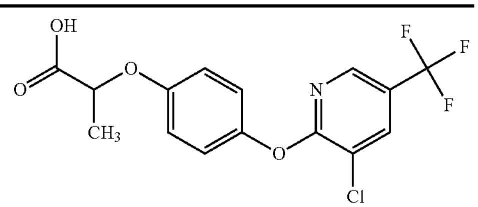 |
| Diclofop-RS | nd | 20 | 130 | 7 | 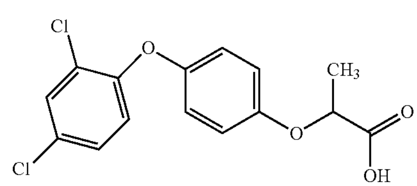 [SMILES: CC(Oc1ccc(Oc2ccc(Cl)cc2Cl)cc1)C(=O)O] |

\* Blank vector represents of cell lysate treatment where *E. coli* pET vector had no gene insert.
\*\* GR50 ratio is a measure of the loss of herbicidal activity of enzyme-expressing lysate treatment vs blank vector treatments. A number 2.3—HPLC Results.

From the literature, it was known that dioxygenase enzymes in this class require α-ketoglutarate as a co-substrate (for a general scheme, see FIG. 1) and ferrous ion to bind in the active site. Other experiments in the literature have shown that the addition of ascorbate increased the enzymatic activity by maintaining the iron in the reduced state, thus preventing the enzyme for being degraded. Based on this previous work, initial assays were set up under the assumption that the subject enzyme would work in the same way as other members of this general class of enzyme.

Figure 2:
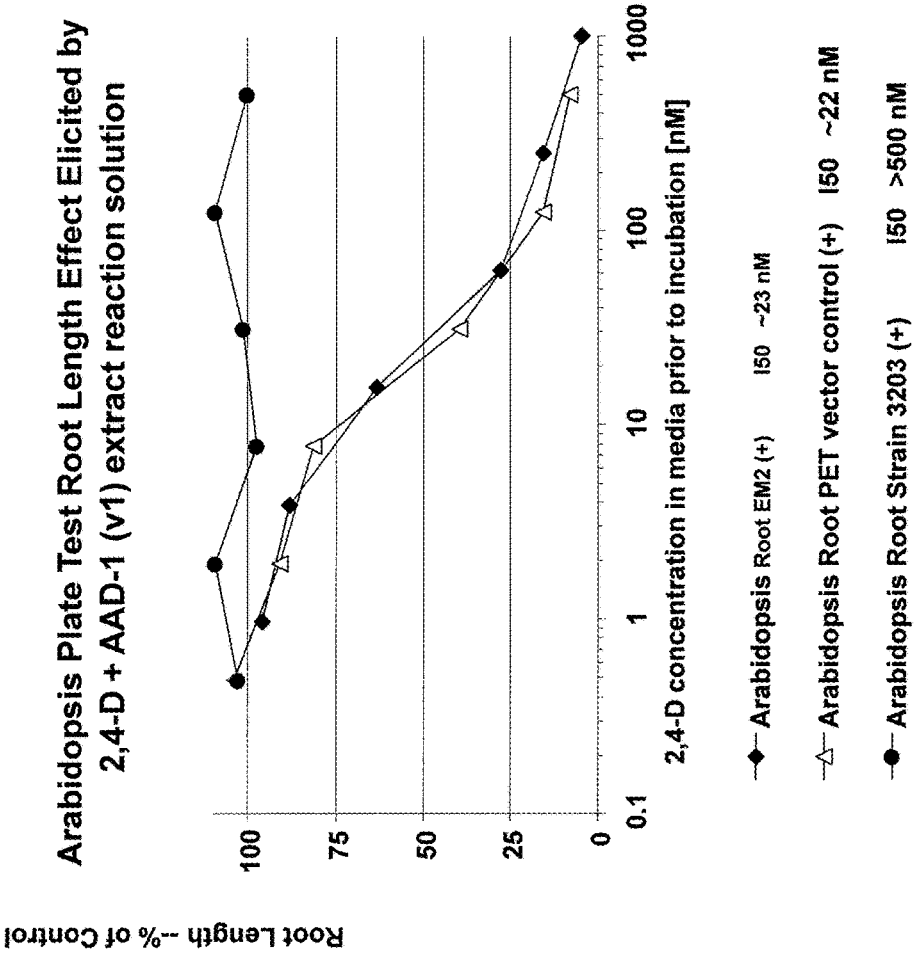
FIG. 2 shows loss of herbicidal activity from a 2,4-D solution treated with AAD-1.

Surprisingly, the initial HPLC results showed the presence of a new peak at 6.1 minute, in addition to a reduced 2,4-D peak at 5.5 min. This new peak was not present in the control assay. For an initial identification of the peak at 6.1 minutes, a DCP control was run under our assay conditions and predictably this also eluted at 6.1 minutes. The formation of this product was confirmed using a colorimetric assay to detect phenols (see example 3.1) as well as mass spectrometry. As expected, AAD-1 (v1) carries out a similar reaction as other members of this enzyme class. In the bioassay, these same samples were also shown to have an almost complete loss of 2,4-D herbicidal activity in the *Arabidopsis* plate assay (FIG. 2). Regardless of the specific conditions of the assay (i.e., longer incubations, more enzyme), only 50-75% of the 2,4-D could be degraded to DCP as measured by HPLC. In fact, longer induction of the BL-21 *E. coli* cells with IPTG only resulted in less active enzyme, even though more total recombinant protein was expressed.

After demonstrating degradation of 2,4-D, additional substrates were tested with similar ring substitutions (i.e., oxyacetates and oxypropionates). The first compounds tested were the pyridine analogs fluroxypyr and triclopyr, which are pyridinyloxyacetates. No enzyme activity was detected on either of these as substrates. Additional tests on various analogs of these two pyridinyloxyacetates with either the fluorine or the amino groups removed also were not degraded. Interestingly however, adding a fluorine to the 5 position of 2,4-D resulted in an almost total loss of enzyme degradation (see next section for additional results).

ACCase inhibitors, haloxyfop and diclofop, were then tested using the same conditions as with 2,4-D. (The corresponding phenol metabolites co-eluted with the parent compound under the HPLC conditions used.) The bioassay results from these samples showed loss of herbicidal activity against both haloxyfop (FIG. 3) and diclofop. These results were also confirmed by the colorimetric assay, which was also used to test a wider sampling of these compounds.

2.4—Plate Test Bioassays for Herbicide Degradation.

Bioassay tests results corroborated initial HPLC results that indicated loss of 2,4-D parent following incubation of 2,4-D solutions with unpurified recombinant AAD-1 (v1) extracts (FIG. 2). Additionally, the herbicidal activity of the phenoxypropionic acid, dichlorprop, was also effectively degraded. The ratio of the nominal $GR_{50}$ for herbicide+ enzyme solution versus the herbicide solution alone served as measure of loss of parent herbicide activity resulting from enzyme activity. A ratio of 2-3 typically correlated with 50-75% loss of parent herbicide activity (Table 6). Often a $GR_{50}$ could not be determined following enzyme treatment; de facto, no detectable herbicide activity remained.

Figure 3:
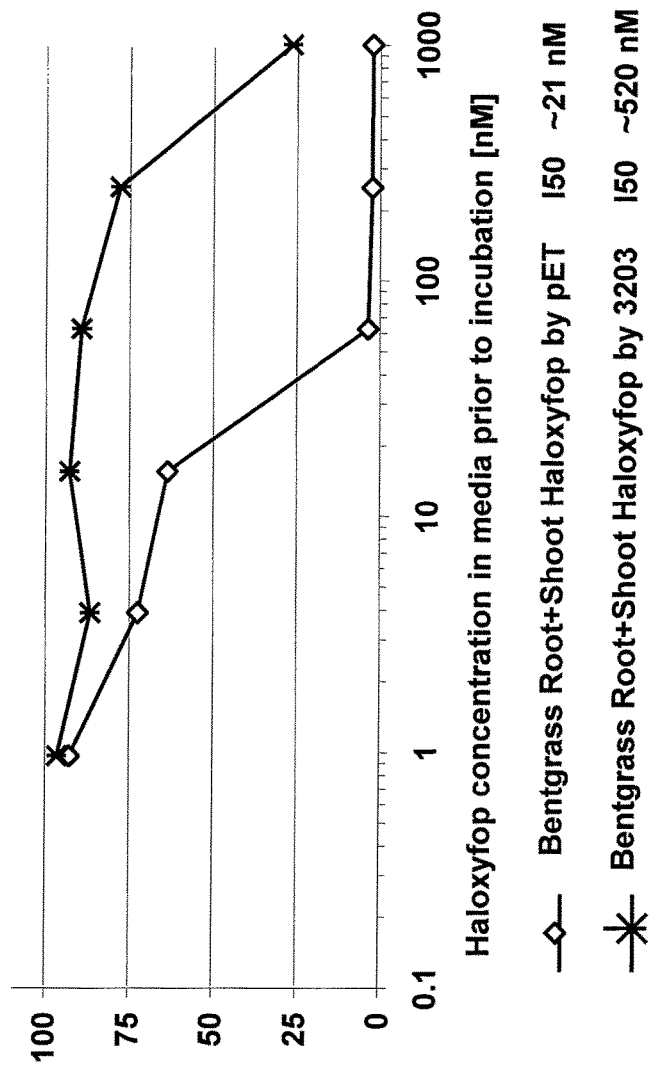
FIG. 3 shows loss of herbicidal activity from a haloxyfop solution treated with AAD-1.

The AOPP class of herbicides, too, served as excellent substrates for AAD-1 (v1) as shown by near complete degradation of graminicidal activity using the bentgrass plate bioassay (FIG. 3 and Table 7). These data are significant in that this is the first reported observation for any members of this class of enzyme to be active on herbicides outside the phenoxy auxins. The implications are that this enzyme is promiscuous enough to utilize chemicals with similar phenoxyalkanoate substructures even though they have completely different modes of action as herbicides.

Example 3—In Vitro Assay of AAD-1 (v1) Activity Via Colorimetric Phenol Detection 3.1—AAD-1 (v1) Assay.

Figure 4:
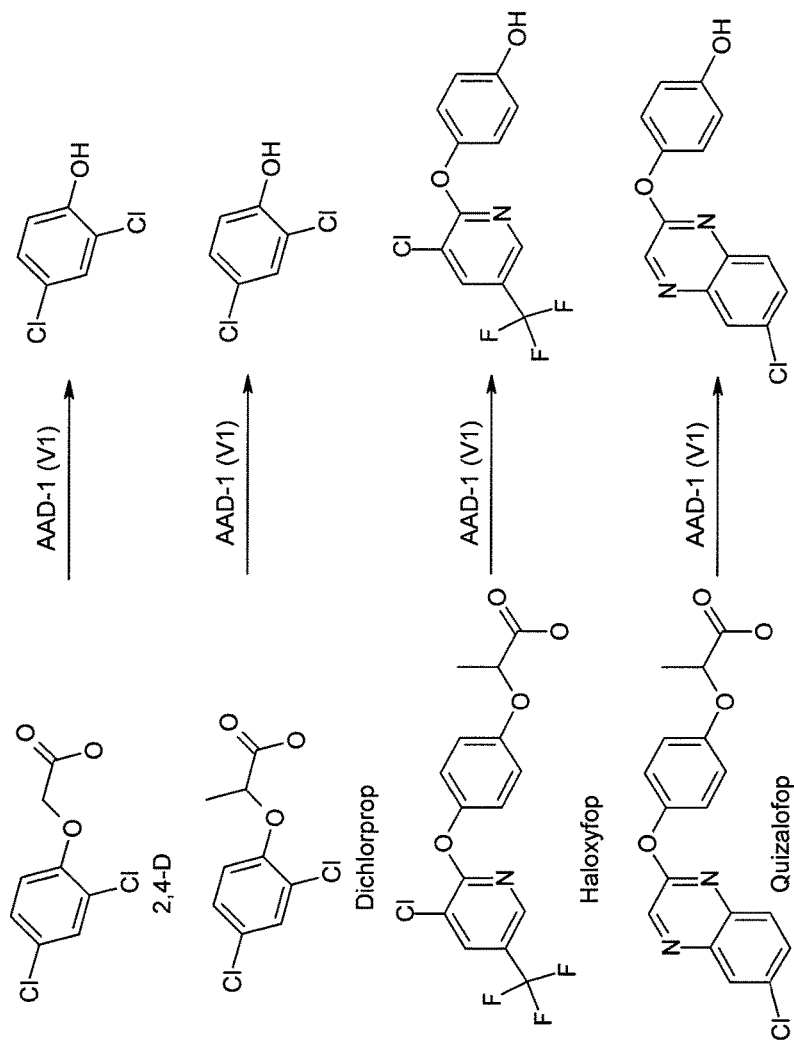
FIG. 4 shows anticipated phenols produced from representative herbicides catalyzed by AAD-1.

AAD-1 (v1) enzyme activity was measured by colorimetric detection of the product phenol using a protocol modified from that of Fukumori and Hausinger (1993) (*J. Biol. Chem.* 268: 24311-24317) to enable deployment in a 96-well microplate format. The colorimetric assay has been described for use in measuring the activity of dioxygenases cleaving 2,4-D and dichlorprop to release the product 2,4-dichlorophenol. However, other phenols could potentially be released from different aryloxyalkanoate herbicides such as haloxyfop and cyhalofop (see FIG. 4). The color yield from several phenols was compared to that of 2,4-dichlorophenol using the detection method previously described to ascertain which phenol products could be readily detected. Phenols and phenol analogs were tested at a final concentration of 100 μM in 0.15 ml 20 mM MOPS pH 6.75 containing 200 μM $NH_4(FeSO_4)_2$, 200 μM sodium ascorbate. The phenols derived from haloxyfop and cyhalofop had equivalent color yields to that of 2,4-dichlorophenol and so were readily detected. Pyridinols derived from fluroxypyr and triclopyr produced no significant color. The color yield of 2,4-dichlorophenol and the haloxyfop phenol was linear and proportional to the concentration of phenol in the assay up to ~500 μM. A calibration curve performed under standard assay conditions (160 μl final assay volume) indicated that an absorbance at 510 nm of 1.0 was obtained from 172 μM phenol.

Enzyme assays were performed in a total volume of 0.15 ml 20 mM MOPS pH 6.75 containing 200 μM $NH_4FeSO_4$, 200 μM sodium ascorbate, 1 mM α-ketoglutarate, the appropriate substrate (added from a 100 mM stock made up in DMSO), and enzyme. Assays were initiated by addition of the aryloxyalkanoate substrate, enzyme or α-ketoglutarate at time zero. After 15 minutes of incubation at 25° C., the reaction was terminated by addition of 10 μl 100 mM sodium EDTA. Color was developed by addition of 15 μl pH 10 buffer (3.09 g boric acid+3.73 g KCl+44 ml 1 N KOH), 1.5 μl 2% 4-aminoantipyrine and 1.5 μl 8% potassium ferricyanide. After 10 to 20 min, the absorbance at 510 nm was recorded in a spectrophotometric microplate reader. Blanks contained all reagents except for enzyme to account for the occasional slight contamination of some of the substrates by small amounts of phenols. Later assays were made more convenient by consolidating the additions as follows: the reaction was quenched by addition of 30 μl of a 1:1:1 mix of 50 mM Na EDTA; pH 10 buffer and 0.2% 4-aminoantipyrine, then adding 10 μl 0.8% potassium ferricyanide.

3.2—Extraction.

Activity of Recombinant AAD-1 (v1) Expressed in *Escherichia coli.*

*E. coli* cell pellets were resuspended in 0.1 M Tris, pH 7.4+1 mg/ml lysozyme (5 ml/cells from 250 ml culture; 20 ml/cells from 1 liter) at room temperature. After about 15 minutes with occasional shaking, the suspension was frozen in liquid nitrogen then thawed. DNase was added to 0.02 mg/ml final concentration and $MgCl_2$ to 1 mM. After the extract was no longer viscous, the extract was centrifuged for 15 min. The supernatant was passed over a BioRad 10DG column pre-equilibrated with 20 mM MOPS pH 6.75 and the eluant stored in aliquots at −70° C. Assays were either performed with these unpurified desalted extracts or with purified enzymes.

Figure 5:
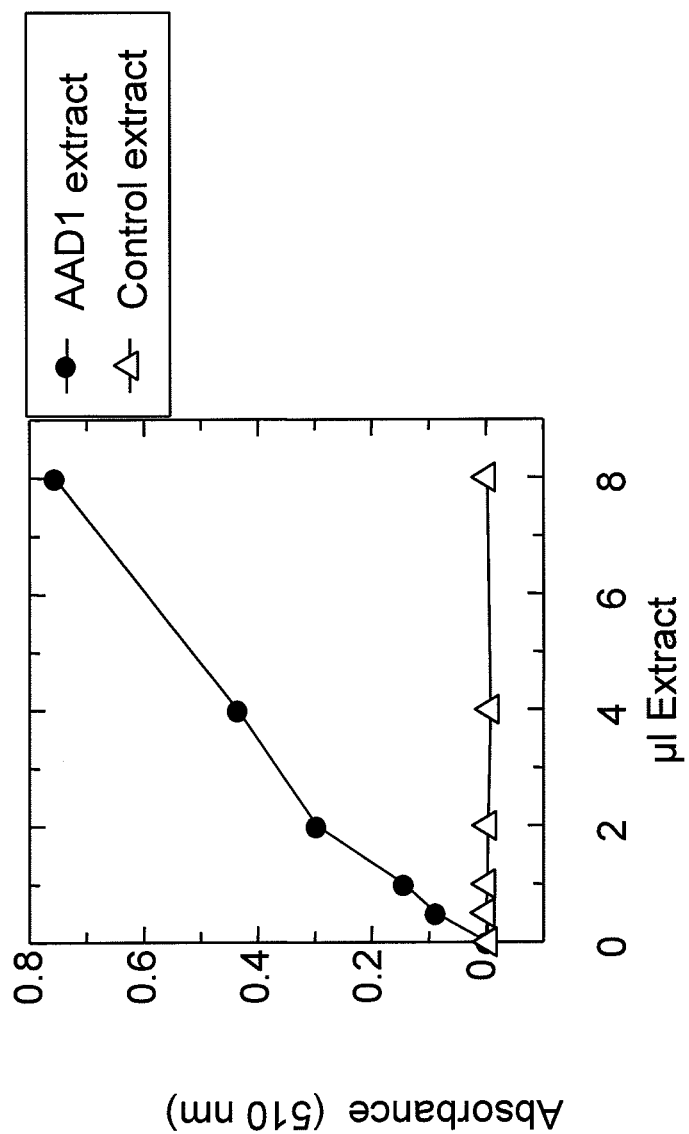
FIG. 5 shows 2,4-dichlorophenol production by recombinant AAD-1.

A cell pellet from a 250 ml culture of induced *E. coli* cells expressing pDAB3203 containing the gene encoding AAD-1 (v1) was extracted and assayed using the previously described protocols. The 2,4-D cleaving activity in the AAD-1 (v1) extract was compared to that from *E. coli* cells expressing a vector without AAD-1 (v1) using 1 mM 2,4-D and is shown in FIG. 5. The amount of 2,4-dichlorophenol formed is clearly proportional to the amount of extract added to the assay whereas the control extract contains no 2,4-D cleaving activity.

Figure 6B:
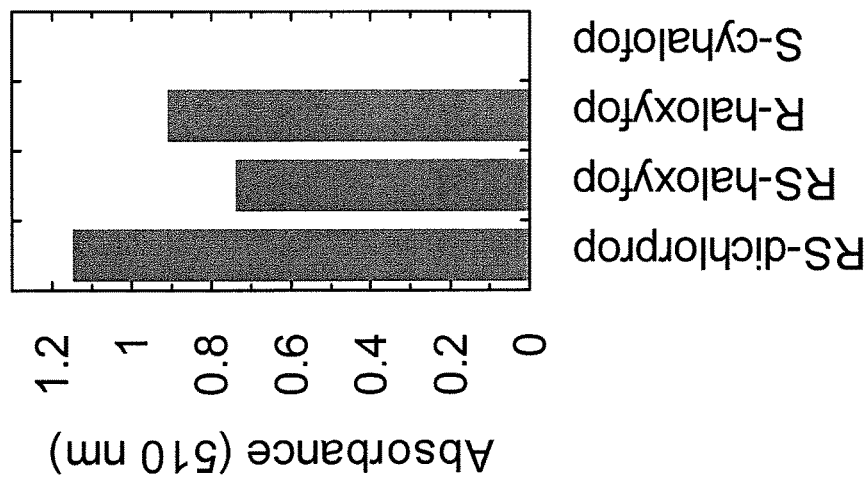
FIGS. 6A and 6B show phenol production by recombinant AAD-1 from various herbicide substrates.
Figure 6A:
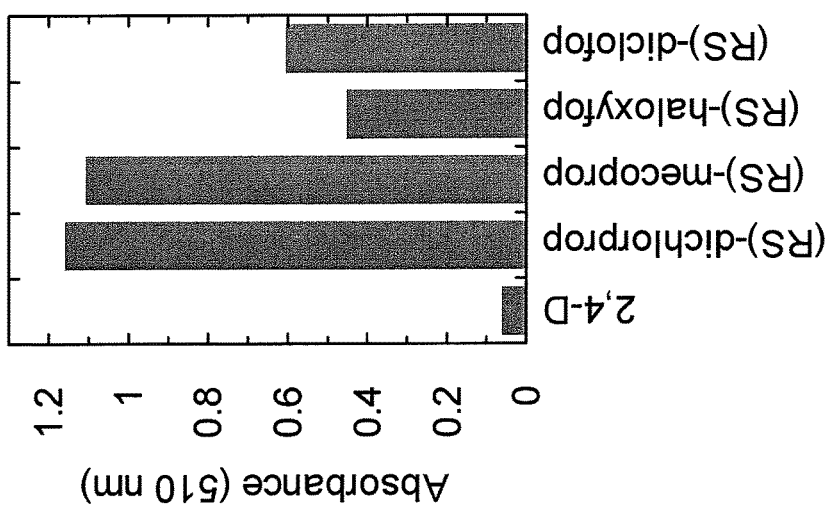

The activity of this extract was tested on four additional herbicides, (R,S)-dichlorprop, (R,S)-mecoprop, (R,S)-haloxyfop and (R,S)-diclofop in comparison to 2,4-D (all at a final concentration of 0.5 mM) using 4 µl of the *E. coli* extract per assay with a 15 min assay period. FIG. 6A shows that AAD-1 (v1) cleaved all five herbicides to yield a phenol with the relative activity on the substrates being dichlorprop=mecoprop>diclofop>haloxyfop>2,4-D. Thus AAD-1 (v1) has activity on graminicidal aryloxyphenoxypropionate herbicides as well as phenoxy auxins.

The AAD-1 (v1) extract was then tested using racemic (R,S)-haloxyfop, the R enantiomer of haloxyfop and the S-enantiomer of cyhalofop (all at 0.5 mM) as potential substrates to ascertain the likely enantiomeric specificity of AAD-1 (v1). The results are shown in FIG. 6B. The activity of the enzyme on (R)-haloxyfop was equivalent to that on (R,S)-haloxyfop whereas no activity could be seen on the S-enantiomer of cyhalofop indicating that AAD-1 (v1) has R specificity on AOPPs.

Example 4—Substrate Specificity of AAD-1 (v1)

4.1—Additional Substrates of AAD-1 (v1).

The substrate specificity of AAD-1 (v1) toward a variety of commercial and experimental herbicides was tested. Purified AAD-1 (v1) was used at either 1 or 10 µg per 160 µl assay and each substrate was tested at 1 mM with an assay time of 15 minutes. Table 3 shows the $A_{510}$ detected after the action of AAD-1 (v1) on a variety of aryloxyalkanoate auxinic herbicides and auxin analogs. The best substrate tested was dichlorprop, with mecoprop also being efficiently cleaved. Two other phenoxypropionates, the 4-fluoro and 3-amino analogs of dichlorprop, were also acted on effectively by AAD-1 (v1). AAD-1 (v1) produced small amounts of phenol from a variety of phenoxyacetates including 2,4-D. The relative rates on these substrates are better gauged from the assays using the higher amounts (10 µg) of AAD-1 (v1). From these data, 2,4-D is cleaved by AAD-1 (v1), as are two phenoxyalkylsulfonates, X188476 and X398166 (sesone).

Table 4 shows data for a variety of AOPP graminicide herbicides as AAD1 substrates, and also the safener cloquintocet. All the commercial AOPP herbicides tested were effectively cleaved by AAD-1 (v1). This is an unexpected discovery and greatly increases the potential utility of this enzyme for conferring resistance to a wide variety of graminicidal herbicides in transgenic uses, in addition to auxins. AAD-1 (v1) had the highest activity on quizalofop (76% of the dichlorprop rate) and lowest activity on cyhalofop (27% of the quizalofop rate, 21% of the dichlorprop rate). The aryloxyacetate analog of haloxyfop (X043865) was cleaved very slowly with only a small increase in $A_{510}$ using the higher (10 µg) amount of enzyme. This is consistent with higher activity of AAD-1 (v1) seen on phenoxypropionates relative to auxin phenoxyacetates. Minimal activity was detected on (S)-cyhalofop indicating that AAD-1 (v1) has a significant preference for the R enantiomers of aryloxypropionate substrates. Similarly, no activity was noted against the quinolinoxyacetate safener, cloquintocet, which is consistent with the observation that AAD-1 (v1) prefers aryloxypropionate substrates over phenoxy auxins.

Substrates X11115427, X124987 and MCPA were tested at 1 mM using 27 µg crude recombinant AAD-1 (v1) per assay. All three compounds were substrates for AAD-1 (v1) but with different relative effectiveness (Table 8). X11115427 was slightly better as a substrate than 2,4-D (125% of the 2,4-D rate) in contrast to the close analog 3-amino-dichlorprop, which is ~7-fold better than 2,4-D as a substrate (Table 3). The 5-F substitution appears to decrease the effectiveness of X11115427 as a substrate for AAD-1 (v1). The rates of product formation from 5-F-phenoxyacetate and MCPA were 32% and 55% that of 2,4-D respectively.

Table 8:

Effect of AAD-1 (v1) on three substrates relative to 2,4-D. Substrates were assayed as in Table 6 at 1 mM using a crude recombinant AAD-1 (v1) extract from *E. coli*.

TABLE 8

Effect of AAD-1 (v1) on three substrates relative to 2,4-D.

| Registry ID | MOLSTRUCTURE | Compound | A510 | % 2,4-D |
|---|---|---|---|---|
| 195517 | *(structure)* | 2,4-D | 0.177 | 100 |
| 11115427 | *(structure)* | (R,S)-3-amino, 5-F-dichlorprop | 0.221 | 125 |

TABLE 8-continued

Effect of AAD-1 (v1) on three substrates relative to 2,4-D.

| Registry ID | MOLSTRUCTURE | Compound | A510 | % 2,4-D |
|---|---|---|---|---|
| 124987 | (structure) | 5-F, 2,4-D | 0.056 | 32 |
| 192711 | (structure) | MCPA | 0.097 | 55 |

4.2—Kinetic Characterization.

Figure 7:
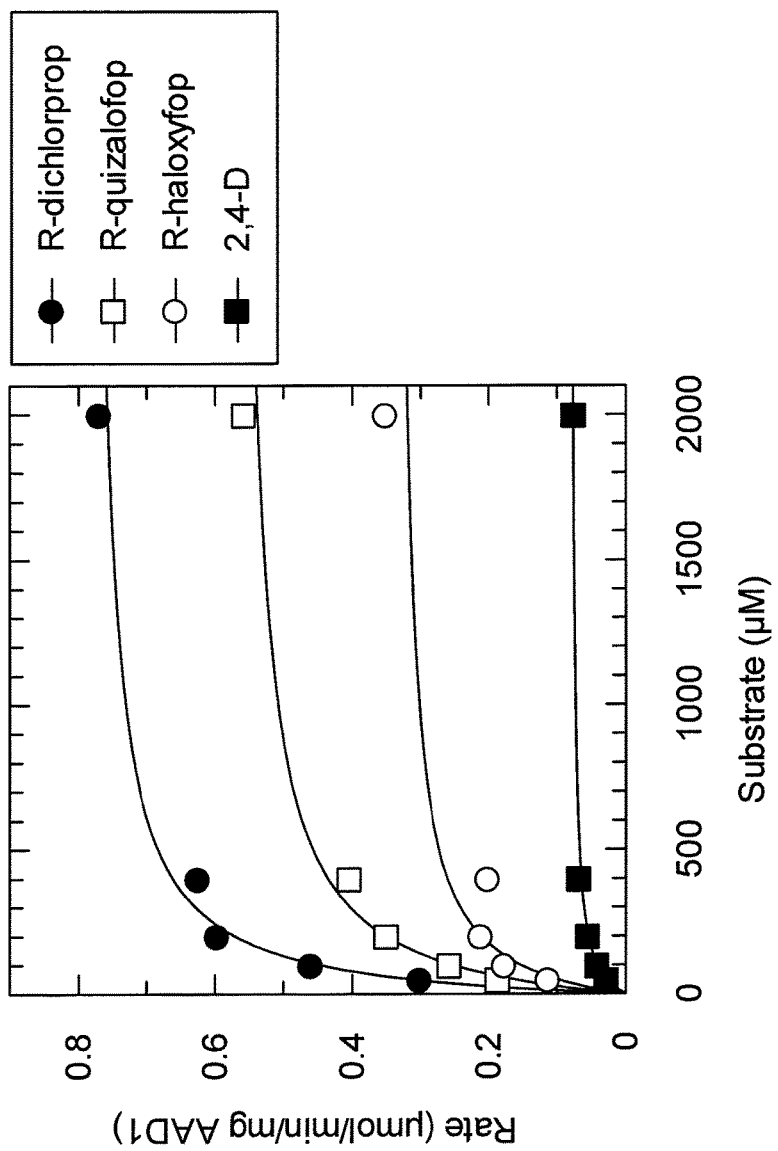
FIG. 7 shows AAD-1 reaction rate to substrate concentration for four herbicide substrates.

The $K_m$ and $k_{cat}$ values of purified AAD-1 (v1) (see Example 10) were determined for four herbicide substrates, (R)-dichlorprop, (R)-haloxyfop, (R)-quizalofop and 2,4-D under standard assay conditions (25 mM MOPS, pH 6.8; 200 µM Na ascorbate; 200 µM $Fe^{2+}$; 1 mM α-ketoglutarate; 25° C.). The dose response curves were fitted using Graft (Erithacus Software, UK), and the graphs and derived constants are shown in FIG. 7 and Table 9 respectively. The $K_m$ values for the four substrates were fairly similar (75-125 µM), but the $k_{cat}$ values varied significantly. (R)-dichlorprop had the highest $k_{cat}$ value and 2,4-D the lowest (10% that of (R)-dichlorprop). These $k_{cat}$ values were consistent with the range of values seen in the substrate specificity tests shown in Table 3 and Table 4 as these were performed at high (saturating) substrate concentrations (1 mM).

Table 9:

Kinetic Constants for AAD-1 (v1) Substrates. Kinetic constants were derived from the data in FIG. 7 using Grafit fitting to the Michaelis-Menten equation.

TABLE 9

Kinetic Constants for AAD-1 (v1) Substrates.

| Substrate | $K_m$ (µM) ± SE | $V_{max}$ (µmol $min^{-1}$ $mg^{-1}$ AAD1) ± SE | $k_{cat}$ ($min^{-1}$) | $k_{cat}/K_m$ ($min^{-1}$ $mN^{-1}$) |
|---|---|---|---|---|
| R-dichlorprop | 75 ± 10 | 0.79 ± 0.03 | 26.1 | 348 |
| R-quizalofop | 125 ± 20 | 0.57 ± 0.03 | 18.9 | 151 |
| R-haloxyfop | 120 ± 54 | 0.34 ± 0.04 | 11.2 | 94 |
| 2,4-D | 96 ± 8 | 0.57 ± 0.00 | 2.7 | 28 |

The relative $K_m$ and $k_{cat}$ values for dichlorprop and 2,4-D differ significantly from those published for the R-specific dioxygenase from *Delftia acidovorans* by Westendorf et al. (2003) (*Acta Biotechnol.* 23: 3-17). The published $k_{cat}/K_m$ value for 2,4-D is 0.6% that of dichlorprop, whereas in our studies, the $k_{cat}/K_m$ value for 2,4-D is 8% that of dichlorprop. Thus, in this study, AAD-1 (v1) is unexpectedly effective at catalyzing the cleavage of 2,4-D. This increases its potential utility for conferring diverse herbicide tolerance traits in transgenic applications.

4.3—Additional Substrates for AAD-1 (v1).

Three additional substrates were tested at 1 mM using 27 µg crude recombinant AAD-1 (v1) per assay; X11115427, X124987 and MCPA. The results are shown in Table 8. All three compounds were substrates for AAD-1 (v1) but with different relative effectiveness. X11115427 was only slightly better (125%) as a substrate than 2,4-D. This is in contrast to 3-aminodichlorprop which is >7 fold better than 2,4-D as a substrate (Table 3). Thus, the 5-F substitution has significantly decreased the effectiveness of X11115427 as a substrate for AAD-1 (v1). A similar pattern is seen with 5-F-2,4-D which is only 32% as effective as a substrate relative to 2,4-D. In this assay, MCPA was also less effective as a substrate of AAD-1 (v1) (55% relative to 2,4-D).

Example 5—Optimization of Sequence for Expression in Plants

5.1—Background.

To obtain high expression of heterologous genes in plants, it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial protein is reengineering of a heterologous gene for optimal expression.

One reason for the reengineering of a bacterial protein for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial protein for maize expression, more preferably referred to as plant optimized gene(s), is to generate a DNA sequence having a higher G+C content, and preferably one close to that of maize genes coding for metabolic enzymes. Another goal in the design of the plant optimized gene(s)

encoding a bacterial protein is to generate a DNA sequence in which the sequence modifications do not hinder translation.

Table 10 illustrates how high the G+C content is in maize. For the data in Table 10, coding regions of the genes were extracted from GenBank (Release 71) entries, and base compositions were calculated using the MacVector™ program (Accelerys, San Diego, Calif.). Intron sequences were ignored in the calculations.

TABLE 10

Compilation of G + C contents of protein coding regions of maize genes

| Protein Class.sup.a | Range % G + C | Mean % G + C.sup.b |
|---|---|---|
| Metabolic Enzymes (76) | 44.4-75.3 | 59.0 (.+−.8.0) |
| Structural Proteins (18) | 48.6-70.5 | 63.6 (.+−.6.7) |
| Regulatory Proteins (5) | 57.2-68.8 | 62.0 (.+−.4.9) |
| Uncharacterized Proteins (9) | 41.5-70.3 | 64.3 (.+−.7.2) |
| All Proteins (108) | 44.4-75.3 | 60.8 (.+−.5.2) |

.sup.a Number of genes in class given in parentheses.
.sup.b Standard deviations given in parentheses.
.sup.c Combined groups mean ignored in mean calculation Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within an mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial protein for maize (or other plant, such as cotton or soybean) expression, the codon bias of the plant has been determined. The codon bias for maize is the statistical codon distribution that the plant uses for coding its proteins and the preferred codon usage is shown in Table 11. After determining the bias, the percent frequency of the codons in the gene(s) of interest is determined. The primary codons preferred by the plant should be determined, as well as the second, third, and fourth choices of preferred codons when multiple choices exist. A new DNA sequence can then be designed which encodes the amino sequence of the bacterial protein, but the new DNA sequence differs from the native bacterial DNA sequence (encoding the protein) by the substitution of the plant (first preferred, second preferred, third preferred, or fourth preferred) codons to specify the amino acid at each position within the protein amino acid sequence. The new sequence is then analyzed for restriction enzyme sites that might have been created by the modification. The identified sites are further modified by replacing the codons with first, second, third, or fourth choice preferred codons. Other sites in the sequence which could affect transcription or translation of the gene of interest are the exon:intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 11

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

It is preferred that the plant optimized gene(s) encoding a bacterial protein contain about 63% of first choice codons, between about 22% to about 37% second choice codons, and between about 15% to about 0% third or fourth choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The method described above enables one skilled in the art to modify gene(s) that are foreign to a particular plant so that the genes are optimally expressed in plants. The method is further illustrated in PCT application WO 97/13402.

Thus, in order to design plant optimized genes encoding a bacterial protein, a DNA sequence is designed to encode the amino acid sequence of said protein utilizing a redundant genetic code established from a codon bias table compiled for the gene sequences for the particular plant. The resulting DNA sequence has a higher degree of codon diversity, a desirable base composition, can contain strategically placed restriction enzyme recognition sites, and lacks sequences that might interfere with transcription of the gene, or translation of the product mRNA. Thus, synthetic genes that are functionally equivalent to the proteins/genes of the subject invention can be used to transform hosts, including plants. Additional guidance regarding the production of synthetic genes can be found in, for example, U.S. Pat. No. 5,380,831.

5.2—Rebuild Analysis.

Extensive analysis of the 888 base pairs (bp) of the DNA sequence of the native AAD-1 (v1) coding region (SEQ ID NO:3) revealed the presence of several sequence motifs that are thought to be detrimental to optimal plant expression, as well as a non-optimal codon composition. To improve production of the recombinant protein in monocots as well as dicots, a "plant-optimized" DNA sequence (SEQ ID NO:5) was developed that encodes SEQ ID NO:11, which is the same as the native SEQ ID NO:9 except for the addition of an alanine residue at the second position. The additional alanine codon (GCT; underlined in SEQ ID NO:5) was included to encode an Nco I site (CCATGG) spanning the ATG start codon, to enable subsequent cloning operations. The proteins encoded by the native (v1) and plant-optimized (v3) coding regions are 99.3% identical, differing only at amino acid number 2. In contrast, the native (v1) and plant-optimized (v3) DNA sequences of the coding regions are only 77.7% identical. A sequence alignment was made of the native and plant-optimized DNAs, and Table 12 shows the differences in codon compositions of the native and plant-optimized sequences.

moter: Nt OSM 5'UTR: AAD-1 (v3): Nt OSM3'UTR: ORF1 polyA 3'UTR] (verified with Not I restriction digests). A Not I-Not I fragment containing the described cassette was then cloned into the Not I site of the binary vector pDAB3038. The resulting binary vector, pDAB721, containing the following cassette [AtUbi10 promoter: Nt OSM5'UTR: AAD-1 (v3): Nt OSM 3'UTR: ORF1 polyA 3'UTR: CsVMV promoter: PAT: ORF25/26 3'UTR] was restriction digested (with Bam HI, EcoR I, EcoR V, HinD III, Pac I, and Xmn I) for verification of the correct orientation. The verified completed construct (pDAB721) was used for transformation into *Agrobacterium* (see section 6.2).

TABLE 12

Codon composition comparison of native AAD-1 (v1) coding region and Plant-Optimized version.

| Amino Acid | Codon | Native Gene # | Native Gene % | Plant Opt Gene # | Plant Opt Gene % | Amino Acid | Codon | Native Gene # | Native Gene % | Plant Opt Gene # | Plant Opt Gene % |
|---|---|---|---|---|---|---|---|---|---|---|---|
| ALA (A) 22 | GCA | 2 | 9.1 | 5 | 22 | LEU (L) 22 | CTA | 0 | 0.0 | 0 | 0 |
|  | GCC | 10 | 45.5 | 8 | 35 |  | CTC | 5 | 22.7 | 7 | 32 |
|  | GCG | 9 | 40.9 | 0 | 0 |  | CTG | 16 | 72.7 | 0 | 0 |
|  | GCT | 1 | 4.5 | 10 | 43 |  | CTT | 0 | 0.0 | 8 | 36 |
| ARG (R) 23 | AGA | 0 | 0.0 | 7 | 30 |  | TTA | 0 | 0.0 | 0 | 0 |
|  | AGG | 0 | 0.0 | 7 | 30 |  | TTG | 1 | 4.5 | 7 | 32 |
|  | CGA | 0 | 0.0 | 0 | 0 | LYS (K) 7 | AAA | 1 | 14.3 | 2 | 29 |
|  | CGC | 16 | 69.6 | 5 | 22 |  | AAG | 6 | 85.7 | 5 | 71 |
|  | CGG | 4 | 17.4 | 0 | 0 | MET (M) | ATG | 8 | 100 | 8 | 100 |
|  | CGT | 3 | 13.0 | 4 | 17 | PHE (F) 13 | TTC | 10 | 76.9 | 9 | 69 |
| ASN (N) 8 | AAC | 8 | 100.0 | 4 | 50 |  | TTT | 3 | 23.1 | 4 | 31 |
|  | AAT | 0 | 0.0 | 4 | 50 | PRO (P) 17 | CCA | 1 | 5.9 | 8 | 47 |
| ASP (D) 19 | GAC | 15 | 78.9 | 10 | 53 |  | CCC | 9 | 52.9 | 1 | 6 |
|  | GAT | 4 | 21.1 | 9 | 47 |  | CCG | 7 | 41.2 | 0 | 0 |
| CYS (C) 3 | TGC | 3 | 100.0 | 2 | 67 |  | CCT | 0 | 0.0 | 8 | 47 |
|  | TGT | 0 | 0.0 | 1 | 33 | SER (S) 15 | AGC | 11 | 73.3 | 4 | 27 |
| END 1 | TAA | 0 | 0.0 | 0 | 0 |  | AGT | 0 | 0.0 | 0 | 0 |
|  | TAG | 1 | 100.0 | 0 | 0 |  | TCA | 0 | 0.0 | 4 | 27 |
|  | TGA | 0 | 0.0 | 1 | 100 |  | TCC | 2 | 13.3 | 3 | 20 |
| GLN (Q) 13 | CAA | 0 | 0.0 | 7 | 54 |  | TCG | 2 | 13.3 | 0 | 0 |
|  | CAG | 13 | 100.0 | 6 | 46 |  | TCT | 0 | 0.0 | 4 | 27 |
| GLU (E) 16 | GAA | 8 | 50.0 | 5 | 31 | THR (T) 23 | ACA | 1 | 4.3 | 6 | 26 |
|  | GAG | 8 | 50.0 | 11 | 69 |  | ACC | 16 | 69.6 | 9 | 39 |
| GLY (G) 21 | GGA | 0 | 0.0 | 6 | 29 |  | ACG | 5 | 21.7 | 0 | 0 |
|  | GGC | 15 | 71.4 | 7 | 33 |  | ACT | 1 | 4.3 | 8 | 35 |
|  | GGG | 3 | 14.3 | 2 | 10 | TRP (W) | TGG | 5 | 100 | 5 | 100 |
|  | GGT | 3 | 14.3 | 6 | 29 | TYR (Y) 10 | TAC | 7 | 70.0 | 6 | 60 |
| HIS (H) 10 | CAC | 6 | 60.0 | 5 | 50 |  | TAT | 3 | 30.0 | 4 | 40 |
|  | CAT | 4 | 40.0 | 5 | 50 | VAL (V) 28 | GTA | 2 | 7.1 | 0 | 0 |
| ILE (I) 12 | ATA | 0 | 0.0 | 3 | 25 |  | GTC | 11 | 39.3 | 8 | 29 |
|  | ATC | 12 | 100.0 | 5 | 42 |  | GTG | 15 | 53.6 | 10 | 36 |
|  | ATT | 0 | 0.0 | 4 | 33 |  | GTT | 0 | 0.0 | 10 | 36 |
|  | Totals | 148 |  | 149 |  |  | Totals | 148 |  | 148 |  |

5.3—Completion of Binary Vectors.

5.3.1—Rebuilt AAD-1 (v3).

The plant optimized gene AAD-1 (v3) was received from Picoscript (the gene rebuild design was completed (see above) and out-sourced to Picoscript for construction) and sequence verified (SEQ ID NO:5) internally, to confirm that no alterations of the expected sequence were present. The sequencing reactions were carried out with M13 Forward (SEQ ID NO:16) and M13 Reverse (SEQ ID NO:17) primers using the Beckman Coulter "Dye Terminator Cycle Sequencing with Quick Start Kit" reagents as before. Sequence data was analyzed and results indicated that no anomalies were present in the plant optimized AAD-1 (v3) DNA sequence. The AAD-1 (v3) gene was cloned into pDAB726 as an Nco I-Sac I fragment. The resulting construct was designated pDAB720, containing: [AtUbi10 pro- 5.3.2—Native AAD1 (v1) and Modified AAD-1 (v2).

The AAD-1 (v1) gene (SEQ ID NO:3) was PCR amplified from pDAB3203. During the PCR reaction, alterations were made within the primers to introduce the NcoI and SacI restriction sites in the 5' primer and 3' primer, respectively. The primers "rdpA(ncoI)" [CCC ATG GCT GCT GCA CTG TCC CCC CTC TCC] (SEQ ID NO:6) and "3'saci" [GAG CTC ACT AGC GCG CCG GGC GCA CGC CAC CGA] (SEQ ID NO:7) were used to amplify a DNA fragment using the Fail Safe PCR System (Epicenter).

The PCR amplicon was ligated into the pCR 2.1 TOPO TA cloning vector (Invitrogen) and sequence verified with M13 Forward (SEQ ID NO:16) and M13 Reverse (SEQ ID NO:17) primers using the Beckman Coulter "Dye Terminator Cycle Sequencing with Quick Start Kit" sequencing reagents.

Sequence data identified a clone with the correct sequence. During analysis a superfluous NotI restriction site was identified toward the 3' end of AAD-1 (v1). This site was removed to facilitate cloning into pDAB3038. To remove the additional site a PCR reaction was performed with an internal 5' primer. The NotI site was altered by incorporating a new codon for an amino acid to remove the spurious NotI site. This change would alter the arginine at position 212 to a cysteine. The PCR primers "BstEII/Del NotI" [TGG TGG TGA CCC ATC CGG GCA GCG GCT GCA AGG GCC] (SEQ ID NO:8) and "3' saci" (SEQ ID NO:7) were used.

A PCR reaction was completed using the Fail Safe PCR System (Epicenter) and the resulting fragment was cloned into the pCR 2.1 TOPO TA cloning kit (Invitrogen). Confirmation of the correct PCR product was completed by DNA sequencing, and the "fixed" gene was given the designation AAD-1 (v2) (SEQ ID NO:4).

A sequencing reaction using the M13 Reverse primer (SEQ ID NO:17) and the Beckman Coulter "Dye Terminator Cycle Sequencing with Quick Start Kit" sequencing reagents indicated that the correct PCR fragment had been isolated. This construct was digested with the BstEII and SacI enzymes. The resulting fragment was cloned into the pCR2.1 AAD-1 (v2) construct (pCR2.1 Delta NotI) and confirmed via restriction enzyme digestion.

The modified AAD-1 (v2) gene was then cloned into pDAB726 as a NcoI/SacI DNA fragment. The resulting construct (pDAB708) was verified with restriction digests. This construct was then cloned into the binary pDAB3038 as a NotI-NotI fragment. The final resulting construct was given the designation pDAB766, containing the [AtUbi10 promoter: Nt OSM5'UTR: AAD-1 (v2): Nt OSM 3'UTR: ORF1 polyA 3'UTR: CsVMV promoter: PAT: ORF25/26 3'UTR] and was restriction digested for verification of the correct orientation. The completed construct was then used for transformation into *Agrobacterium*.

5.3.3—Design of a Soybean-Codon-Biased DNA Sequence Encoding a Soybean EPSPS Having Mutations that Confer Glyphosate Tolerance.

This example teaches the design of a new DNA sequence that encodes a mutated soybean 5-enolpyruvoylshikimate 3-phosphate synthase (EPSPS), but is optimized for expression in soybean cells. The amino acid sequence of a triply-mutated soybean EPSPS is disclosed as SEQ ID NO:5 of WO 2004/009761. The mutated amino acids in the so-disclosed sequence are at residue 183 (threonine of native protein replaced with isoleucine), residue 186 (arginine in native protein replaced with lysine), and residue 187 (proline in native protein replaced with serine). Thus, one can deduce the amino acid sequence of the native soybean EPSPS protein by replacing the substituted amino acids of SEQ ID NO:5 of WO 2004/009761 with the native amino acids at the appropriate positions. Such native protein sequence is presented herein as SEQ ID NO:20. A doubly mutated soybean EPSPS protein sequence, containing a mutation at residue 183 (threonine of native protein replaced with isoleucine), and at residue 187 (proline in native protein replaced with serine) is presented herein as SEQ ID NO:21.

A codon usage table for soybean (*Glycine max*) protein coding sequences, calculated from 362,096 codons (approximately 870 coding sequences), was obtained from the "kazusa.or.jp/codon" World Wide Web site. Those data were reformatted as displayed in Table 13. Columns D and H of Table 13 present the distributions (in % of usage for all codons for that amino acid) of synonymous codons for each amino acid, as found in the protein coding regions of soybean gene. It is evident that some synonymous codons for some amino acids (an amino acid may be specified by 1, 2, 3, 4, or 6 codons) are present relatively rarely in soybean protein coding regions (for example, compare usage of GCG and GCT codons to specify alanine). A biased soybean codon usage table was calculated from the data in Table 13. Codons found in soybean genes less than about 10% of total occurrences for the particular amino acid were ignored. To balance the distribution of the remaining codon choices for an amino acid, a weighted average representation for each codon was calculated, using the formula:

Weighted % of $C1=1/(\% C1+\% C2+\% C3+\text{etc.})\times\%$ $C1\times100$ where C1 is the codon in question, C2, C3, etc. represent the remaining synonymous codons, and the % values for the relevant codons are taken from columns D and H of Table 13 (ignoring the rare codon values in bold font). The Weighted % value for each codon is given in Columns C and G of Table 13. TGA was arbitrarily chosen as the translation terminator. The biased codon usage frequencies were then entered into a specialized genetic code table for use by the OptGene™ gene design program (Ocimum Biosolutions LLC, Indianapolis, Ind.).

TABLE 13

Synonymous codon representation in soybean protein coding sequences, and calculation of a biased codon representation set for soybean-optimized synthetic gene design.

| A<br>Amino Acid | B<br>Codon | C<br>Weighted % | D<br>Soybean % | E<br>Amino Acid | F<br>Codon | G<br>Weighted % | H<br>Soybean % |
|---|---|---|---|---|---|---|---|
| ALA (A) | GCA | 33.1 | 30.3 | LEU (L) | CTA | DNU | 9.1 |
|  | GCC | 24.5 | 22.5 |  | CTC | 22.4 | 18.1 |
|  | GCG | DNU* | 8.5 |  | CTG | 16.3 | 13.2 |
|  | GCT | 42.3 | 38.7 |  | CTT | 31.5 | 25.5 |
| ARG (R) | AGA | 36.0 | 30.9 |  | TTA | DNU | 9.8 |
|  | AGG | 32.2 | 27.6 |  | TTG | 29.9 | 24.2 |
|  | CGA | DNU | 8.2 | LYS (K) | AAA | 42.5 | 42.5 |
|  | CGC | 14.8 | 12.7 |  | AAG | 57.5 | 57.5 |
|  | CGG | DNU | 6.0 | MET (M) | ATG | 100.0 | 100 |
|  | CGT | 16.9 | 14.5 | PHE (F) | TTC | 49.2 | 49.2 |
| ASN (N) | AAC | 50.0 | 50.0 |  | TTT | 50.8 | 50.8 |
|  | AAT | 50.0 | 50.0 | PRO (P) | CCA | 39.8 | 36.5 |
| ASP (D) | GAC | 38.1 | 38.1 |  | CCC | 20.9 | 19.2 |
|  | GAT | 61.9 | 61.9 |  | CCG | DNU | 8.3 |
| CYS (C) | TGC | 50.0 | 50.0 |  | CCT | 39.3 | 36.0 |
|  | TGT | 50.0 | 50.0 | SER (S) | AGC | 16.0 | 15.1 |

TABLE 13-continued

Synonymous codon representation in soybean protein coding sequences, and calculation of a biased codon representation set for soybean-optimized synthetic gene design.

| A Amino Acid | B Codon | C Weighted % | D Soybean % | E Amino Acid | F Codon | G Weighted % | H Soybean % |
|---|---|---|---|---|---|---|---|
| END | TAA | DNU | 40.7 | | AGT | 18.2 | 17.1 |
| | TAG | DNU | 22.7 | | TCA | 21.9 | 20.6 |
| | TGA | 100.0 | 36.6 | | TCC | 18.0 | 16.9 |
| GLN (Q) | CAA | 55.5 | 55.5 | | TCG | DNU | 6.1 |
| | CAG | 44.5 | 44.5 | | TCT | 25.8 | 24.2 |
| GLU (E) | GAA | 50.5 | 50.5 | THR (T) | ACA | 32.4 | 29.7 |
| | GAG | 49.5 | 49.5 | | ACC | 30.2 | 27.7 |
| GLY (G) | GGA | 31.9 | 31.9 | | ACG | DNU | 8.3 |
| | GGC | 19.3 | 19.3 | | ACT | 37.4 | 34.3 |
| | GGG | 18.4 | 18.4 | TRP (W) | TGG | 100.0 | 100 |
| | GGT | 30.4 | 30.4 | TYR (Y) | TAC | 48.2 | 48.2 |
| HIS (H) | CAC | 44.8 | 44.8 | | TAT | 51.8 | 51.8 |
| | CAT | 55.2 | 55.2 | VAL (V) | GTA | 11.5 | 11.5 |
| ILE (I) | ATA | 23.4 | 23.4 | | GTC | 17.8 | 17.8 |
| | ATC | 29.9 | 29.9 | | GTG | 32.0 | 32.0 |
| | ATT | 46.7 | 46.7 | | GTT | 38.7 | 38.7 |

*DNU = Do Not Use

To derive a soybean-optimized DNA sequence encoding the doubly mutated EPSPS protein, the protein sequence of SEQ ID NO:21 was reverse-translated by the OptGene™ program using the soybean-biased genetic code derived above. The initial DNA sequence thus derived was then modified by compensating codon changes (while retaining overall weighted average representation for the codons) to reduce the numbers of CG and TA doublets between adjacent codons, increase the numbers of CT and TG doublets between adjacent codons, remove highly stable intrastrand secondary structures, remove or add restriction enzyme recognition sites, and to remove other sequences that might be detrimental to expression or cloning manipulations of the engineered gene. Further refinements of the sequence were made to eliminate potential plant intron splice sites, long runs of A/T or C/G residues, and other motifs that might interfere with RNA stability, transcription, or translation of the coding region in plant cells. Other changes were made to eliminate long internal Open Reading Frames (frames other than +1). These changes were all made within the constraints of retaining the soybean-biased codon composition as described above, and while preserving the amino acid sequence disclosed as SEQ ID NO:21.

The soybean-biased DNA sequence that encodes the EPSPS protein of SEQ ID NO:21 is given as bases 1-1575 of SEQ ID NO:22. Synthesis of a DNA fragment comprising SEQ ID NO:22 was performed by a commercial supplier (PicoScript, Houston Tex.).

5.3.4—Cloning of Additional Binary Constructs.

The completion of pDAB3295 and pDAB3757 incorporated the use of the GateWay Cloning Technology (Invitrogen, cat #11791-043 and cat #12535-019). The GateWay Technology uses lambda phage-based site-specific recombination to insert a gene cassette into a vector. For more information refer to *Gateway Technology: A universal technology to clone DNA sequence for functional analysis and expression in multiple systems,* © 1999-2003, Invitrogen Corp., 1600 Faraday Ave., Carlsbad, Calif. 92008 (printed—2003). All other constructs created for transformation into appropriate plant species were built using similar procedures as above and other standard molecular cloning methods (Maniatis et al., 1982). Table 14 lists all the transformation constructs used with appropriate promoters and features defined, as well as the crop transformed.

The sacB gene was added to the binary vector pDAB3289 as a bacterial negative selection marker to reduce the persistence of *Agrobacterium* associated with transformed plant tissue. SacB is a levan-sucrase enzyme produced by *Bacillus* spp. and is toxic to most Gram negative bacteria when grown in the presence of sucrose (Gay et al., 1983). The sacB gene was recovered on a Hind III fragment from plasmid pRE112 (Edwards, et al., 1998) and cloned into the unique Hind III site in pDAB3289.

TABLE 14

Binary constructs used in transformation of various plant species.

| pDAB # | pDAS # | Species * Transformed into | Gene of interest (GOI) | Promoter | Feature 1 | Feature 2 | GOI 2 | Promoter | Bacterial Selection gene | Bacterial Selection gene 2 | Plant Selection gene | Promoter | Trxn Method |
|---|---|---|---|---|---|---|---|---|---|---|---|---|---|
| 721 | | A, T, Ct, S, Ca | AAD1 v3 | AtUbi10 | NtOsm | — | — | — | Erythromycin | — | pat | CsVMV | Agro binary |
| 3230 | | A | EPSPS | AtUbi10 | NtOsm | RB7 Mar v2 | — | — | Spectinomycin | — | AAD1 v3 | CsVMV | Agro binary |
| 3289 | | S | AAD1 v3 | CsVMV | NtOsm | RB7 Mar v2 | EPSPS | AtUbi10 | Spectinomycin | sacB | HptII | AtUbi3 | Agro binary |
| 3291 | | S | AAD1 v3 | CsVMV | NtOsm | RB7 Mar v2 | EPSPS | AtUbi10 | Spectinomycin | — | HptII | AtUbi3 | Agro binary |

TABLE 14-continued

Binary constructs used in transformation of various plant species.

| 3295 | | S | AAD1 v3 | CsVMV | NtOsm | RB7 Mar v2 | — | — | Spectinomycin | — | pat | AtUbi10 | Aerosol beam |
|---|---|---|---|---|---|---|---|---|---|---|---|---|---|
| 3297 | 1270 | A, T | AAD1 v3 | CsVMV | NtOsm | RB7 Mar v2 | — | — | Spectinomycin | — | pat | AtUbi10 | Agro binary |
| 3403 | | Cn, R | AAD1 v3 | ZmUbi1 | — | RB7 Mar v2 | — | — | Ampicillin | — | Same as GOI | | Whiskers/ Gun |
| 3404 | | Cn | AAD1 v3 | ZmUbi1 | — | RB7 Mar v2 | — | — | Ampicillin | — | pat | OsAct1 | Whiskers |
| 3415 | 1283 | Cn | AAD1 v3 | ZmUbi1 | — | RB7 Mar v2 | — | — | Ampicillin | — | AHAS v3 | OsAct1 | Whiskers |
| 3602 | 1421 | Cn | AAD1 v3 | ZmUbi1 | — | RB7 Mar v2 | — | — | Spectinomycin | — | AHAS v3 | OsAct1 | Agro Super- binary |
| 3757 | | Ca | AAD1 v3 | CsVMV | NtOsm | RB7 Mar v2 | EPSPS | AtUbi10 | Spectinomycin | — | pat | AtUbi11 | Agro binary |
| 3705 | | A | AAD2 v2 | AtUbi10 | NtOsm | RB7 Mar v2 | — | — | Erythromycin | — | pat | CsVMV | Agro binary |

* A = *Arabidopsis*  CsVMV = Cassava Vein Mosaic Virus Promoter  ZmUbi1 = *Zea mays* Ubiquitin 1 Promoter
T = Tobacco  AtUbi10 = *Arabidopsis thaliana* Ubiquitin 10 Promoter  HptII = hygromycin phosphotransferase
S = Soybean  RB7 Mar v2 = *Nicotiana tabacum* matrix associated region (MAR)
Ct = Cotton  Nt Osm = *Nicotiana tabacum* Osmotin 5' Untranslated Region and the *Nicotiana tabacum* Osmotin 3' Untranslated Region
R = Rice
Cn = Corn  (721 and 793) Atu ORF1 3' UTR = *Agrobacterium tumefaciens* Open Reading Frame 1 3' Untranslated Region
Ca = Canola  (3295 and 3757) Atu ORF24 3' UTR = *Agrobacterium tumefaciens* Open Reading Frame 24 3' Untranslated Region Example 6—Transformation into *Arabidopsis* and Selection 6.1—*Arabidopsis thaliana* Growth Conditions.

Wildtype *Arabidopsis* seed was suspended in a 0.1% Agarose (Sigma Chemical Co., St. Louis, Mo.) solution. The suspended seed was stored at 4° C. for 2 days to complete dormancy requirements and ensure synchronous seed germination (stratification).

Sunshine Mix LP5 (Sun Gro Horticulture, Bellevue, Wash.) was covered with fine vermiculite and sub-irrigated with Hoagland's solution until wet. The soil mix was allowed to drain for 24 hours. Stratified seed was sown onto the vermiculite and covered with humidity domes (KORD Products, Bramalea, Ontario, Canada) for 7 days.

Seeds were germinated and plants were grown in a Conviron (models CMP4030 and CMP3244, Controlled Environments Limited, Winnipeg, Manitoba, Canada) under long day conditions (16 hours light/8 hours dark) at a light intensity of 120-150 µmol/m² sec under constant temperature (22° C.) and humidity (40-50%). Plants were initially watered with Hoagland's solution and subsequently with deionized water to keep the soil moist but not wet.

6.2—*Agrobacterium* Transformation.

An LB+agar plate with erythromycin (Sigma Chemical Co., St. Louis, Mo.) (200 mg/L) or spectinomycin (100 mg/L) containing a streaked DH5α colony was used to provide a colony to inoculate 4 ml mini prep cultures (liquid LB+erythromycin). The cultures were incubated overnight at 37° C. with constant agitation. Qiagen (Valencia, Calif.) Spin Mini Preps, performed per manufacturer's instructions, were used to purify the plasmid DNA.

Electro-competent *Agrobacterium tumefaciens* (strains Z707s, EHA101s, and LBA4404s) cells were prepared using a protocol from Weigel and Glazebrook (2002). The competent *Agrobacterium* cells were transformed using an electroporation method adapted from Weigel and Glazebrook (2002). 50 µl of competent agro cells were thawed on ice and 10-25 ng of the desired plasmid was added to the cells. The DNA and cell mix was added to pre-chilled electroporation cuvettes (2 mm) An Eppendorf Electroporator 2510 was used for the transformation with the following conditions, Voltage: 2.4 kV, Pulse length: 5 msec.

After electroporation, 1 ml of YEP broth (per liter: 10 g yeast extract, 10 g Bacto-peptone, 5 g NaCl) was added to the cuvette, and the cell-YEP suspension was transferred to a 15 ml culture tube. The cells were incubated at 28° C. in a water bath with constant agitation for 4 hours. After incubation, the culture was plated on YEP+agar with erythromycin (200 mg/L) or spectinomycin (100 mg/L) and streptomycin (Sigma Chemical Co., St. Louis, Mo.) (250 mg/L). The plates were incubated for 2-4 days at 28° C.

Colonies were selected and streaked onto fresh YEP+agar with erythromycin (200 mg/L) or spectinomycin (100 mg/L) and streptomycin (250 mg/L) plates and incubated at 28° C. for 1-3 days. Colonies were selected for PCR analysis to verify the presence of the gene insert by using vector specific primers. Qiagen Spin Mini Preps, performed per manufacturer's instructions, were used to purify the plasmid DNA from selected *Agrobacterium* colonies with the following exception: 4 ml aliquots of a 15 ml overnight mini prep culture (liquid YEP+erythromycin (200 mg/L) or spectinomycin (100 mg/L)) and streptomycin (250 mg/L)) were used for the DNA purification. An alternative to using Qiagen Spin Mini Prep DNA was lysing the transformed *Agrobacterium* cells, suspended in 10 µl of water, at 100° C. for 5 minutes. Plasmid DNA from the binary vector used in the *Agrobacterium* transformation was included as a control. The PCR reaction was completed using Taq DNA polymerase from Takara Minis Bio Inc. (Madison, Wis.) per manufacturer's instructions at 0.5× concentrations. PCR reactions were carried out in a MJ Research Peltier Thermal Cycler programmed with the following conditions; 1) 94° C. for 3 minutes, 2) 94° C. for 45 seconds, 3) 55° C. for 30 seconds, 4) 72° C. for 1 minute, for 29 cycles then 1 cycle of 72° C. for 10 minutes. The reaction was maintained at 4° C. after cycling. The amplification was analyzed by 1% agarose gel electrophoresis and visualized by ethidium bromide staining A colony was selected whose PCR product was identical to the plasmid control.

6.3—*Arabidopsis* Transformation.

*Arabidopsis* was transformed using the floral dip method. The selected colony was used to inoculate one or more 15-30 ml pre-cultures of YEP broth containing erythromycin (200 mg/L) or spectinomycin (100 mg/L) and streptomycin (250 mg/L). The culture(s) was incubated overnight at 28° C. with constant agitation at 220 rpm. Each pre-culture was used to inoculate two 500 ml cultures of YEP broth containing erythromycin (200 mg/L) or spectinomycin (100 mg/L) and streptomycin (250 mg/L) and the cultures were incubated overnight at 28° C. with constant agitation. The cells were then pelleted at approx. 8700×g for 10 minutes at room temperature, and the resulting supernatant discarded. The cell pellet was gently resuspended in 500 ml infiltration media containing: ½× Murashige and Skoog salts/Gamborg's B5 vitamins, 10% (w/v) sucrose, 0.044 µM benzylamino purine (10 µl/liter of 1 mg/ml stock in DMSO) and 300 µl/liter Silwet L-77. Plants approximately 1 month old were dipped into the media for 15 seconds, being sure to submerge the newest inflorescence. The plants were then laid down on their sides and covered (transparent or opaque) for 24 hours, then washed with water, and placed upright. The plants were grown at 22° C., with a 16-hour light/8-hour dark photoperiod. Approximately 4 weeks after dipping, the seeds were harvested.

6.4—Selection of Transformed Plants.

Freshly harvested $T_1$ seed (transformed with native [AAD-1 (v2)] or plant optimized [AAD-1 (v3)] gene) was allowed to dry for 7 days at room temperature. $T_1$ seed was sown in 26.5×51-cm germination trays (T.O. Plastics Inc., Clearwater, Minn.), each receiving a 200 mg aliquots of stratified $T_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet, then allowed to gravity drain. Each 40 ml aliquot of stratified seed was sown evenly onto the vermiculite with a pipette and covered with humidity domes (KORD Products, Bramalea, Ontario, Canada) for 4-5 days. Domes were removed 1 day prior to initial transformant selection using glufosinate postemergence spray (selecting for the co-transformed PAT gene).

Five to six days after planting (DAP) and again 10 DAP, $T_1$ plants (cotyledon and 2-4-1f stage, respectively) were sprayed with a 0.2% solution of Liberty herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (plants actively growing) were identified 5-7 days after the final spraying and transplanted individually into 3-inch pots prepared with potting media (Metro Mix 360). Transplanted plants were covered with humidity domes for 3-4 days and placed in a 22° C. growth chamber as before. Domes were subsequently removed and plants moved to the greenhouse (22±5° C., 50±30% RH, 14 h light:10 dark, minimum 500 µE/m$^2$ s$^1$ natural+supplemental light) at least 1 day prior to testing for the ability of AAD-1 (v3) (plant optimized gene) or AAD-1 (v2) (native microbial gene) to provide phenoxy auxin herbicide resistance.

Random individual $T_1$ plants selected for glufosinate resistance above were confirmed for expression of the PAT protein using a PAT ELISA kit (Part no. 7000045, Strategic Diagnostics, Inc., Newark, Del.) to non-destructively confirm fidelity of selection process (manufacturer's protocol). Plants were then randomly assigned to various rates of phenoxy herbicides (dichlorprop or 2,4-D). Phenoxy rates initially applied were 12.5 g ae/ha 2,4-D and 50 or 200 g ae/ha dichlorprop. $GR_{99}$ for *Arabidopsis* is about 50 g ae/ha 2,4-D and 200 g ae/ha dichlorprop. Elevated rates were applied in subsequent trials (50, 200, 800, or 3200 g ae/ha).

All auxin herbicide applications were made using the DeVilbiss sprayer as described above to apply 703 L/ha spray volume (0.4 ml solution/3-inch pot) or applied by track sprayer in a 187 L/ha spray volume. 2,4-D used was either technical grade (Sigma, St. Louis, Mo.) dissolved in DMSO and diluted in water (<1% DMSO final concentration) or the commercial dimethylamine salt formulation (456 g ae/L, NuFarm, St Joseph, Mo.). Dichlorprop used was technical grade (Sigma, St. Louis, Mo.) dissolved in DMSO and diluted in water (<1% DMSO final concentration). As herbicide rates increased beyond 800 g ae/ha, the pH of the spray solution became exceedingly acidic, burning the leaves of young, tender *Arabidopsis* plants and complicating evaluation of the primary effects of the herbicides. It became standard practice to apply these high rates of phenoxy herbicides in 200 mM Tris buffer (pH 9.0) to a final pH of ~7-8.

Some $T_1$ individuals were subjected to alternative commercial herbicides instead of a phenoxy auxin. One point of interest was determining whether haloxyfop could be effectively degraded in planta.

Although *Arabidopsis*, being a dicot, is not an optimal system for testing ACCase-inhibiting AOPP grass herbicides, AAD-1 (v3)-transformed $T_1$ plants were subjected to elevated rates (400-1600 g ae/ha) of RS-haloxyfop acid (internally synthesized) that do cause growth abnormalities and death of wildtype *Arabidopsis* using the DeVilbiss sprayer as described above Injury ratings were taken 7 and 14 days after treatment. Likewise, $T_1$ individuals were treated with the pyridyloxyacetate auxin herbicide, fluroxypyr.

6.5—Results of Selection of Transformed Plants.

The first *Arabidopsis* transformations were conducted using AAD-1 (v3) (plant optimized gene). $T_1$ transformants were first selected from the background of untransformed seed using a glufosinate selection scheme. Over 400,000 $T_1$ seed were screened and 493 glufosinate resistant plants were identified (PAT gene), equating to a transformation/selection frequency of 0.12%. Depending on the lot of seed tested, this ranged from 0.05-0.23% (see Table 15). A small lot of AAD-1 (v2) (native)-transformed seed were also selected using the glufosinate selection agent. Two hundred seventy eight glufosinate-resistant $T_1$ individuals were identified out of 84,000 seed screened (0.33% transformation/selection frequency).

TABLE 15

Selection of AAD-1 (v3) (plant optimized), or AAD-1 (v2) (native), AAD-2 (v1) (native), or plant optimized AAD-2 (v2)-transformed T₁ individual plants using glufosinate and 2,4-D.

| Selection agent | Gene | Codon bias | Total seed sown and screened | Number of resistant T₁ | Selection rate | Selection rate range | % of selected plants expressing PAT[3] |
|---|---|---|---|---|---|---|---|
| Glufosinate[1] | AAD-1 (v2) | n | 84,000 | 278 | 0.33% | 0.33% | nd[4] |
| Glufosinate[1] | AAD-1 (v3) | p | 400,500 | 493 | 0.12% | 0.05 to 0.23% | 97% |
| 2,4-D[2] | AAD-1(v3) | p | 70,000 | 53 | 0.08% | 0.07 to 0.08% | 96% |
| Glufosinate[1] | AAD-2 (v1) | n | 1,301,500 | 228 | 0.018% | 0.007 to 0.021% | 100% |
| Glufosinate[1] | AAD-2(v2) | p | 200,000 | 224 | 0.11% | 0.11% | nd[4] |

[1]Glufosinate selection scheme: 280 g ai/ha glufosinate applied 5-6 + 10 DAP
[2]2,4-D selection scheme: 50 g ai/ha 2,4-D applied 5-7 + 10-14 DAP
[3]PAT protein expression determined by PAT ELISA strips
[4]nd, not determined
[5]codon bias, n-native microbial gene, p = plant optimized T₁ plants selected above were subsequently transplanted to individual pots and sprayed with various rates of commercial aryloxyalkanoate herbicides. Table 16 compares the response of native AAD-1 (v2) and plant optimized AAD-1 (v3) genes to impart 2,4-D resistance to *Arabidopsis* T₁ transformants. Both genes imparted resistance to individual T₁ *Arabidopsis* plants. Within a given treatment, the level of plant response varied greatly and can be attributed to the fact each plant represents an independent transformation event. Of important note, at each 2,4-D rate tested, there were individuals that were unaffected while some were severely affected. An overall population injury average by rate is presented in Table 16 simply to demonstrate the significant difference between the plants transformed with AAD-1 (v2) or AAD-1 (v3) versus the wildtype or PAT/Cry1F transformed controls. Also evident is that tolerance appears to be significantly greater (frequency and overall level of individual response) for the plant optimized sequence AAD-1 (v3) versus the native sequence AAD-1 (v2) (see Table 16). Higher rates of 2,4-D (up to 3,200 g ae/ha) have been applied to additional T₁ individuals expressing AAD-1 (v3). Injury levels tend to be greater and the frequency of highly resistant plants is lower at these elevated rates (6× field rates). Also at these high rates, the spray solution becomes highly acidic unless buffered. *Arabidopsis* grown mostly in the growth chamber has a very thin cuticle and severe burning effects can complicate testing at these elevated rates. Nonetheless, some individuals have survived 3,200 g ae/ha 2,4-D with little or no injury.

Table 16.

AAD-1 v3 (plant optimized), or AAD-1 v2 (native), or AAD-2 (native)-transformed T₁ *Arabidopsis* response to a range of 2,4-D rates applied postemergence. Response is presented in terms of % visual injury 2 WAT. Data are presented as a histogram of individuals exhibiting little or no injury (<20%), moderate injury (20-40%), or severe injury (>40%). Since each T₁ is an independent transformation event, one can expect significant variation of individual T₁ responses within a given rate. An arithmetic mean and standard deviation is presented for each treatment. The range in individual response is also indicated in the last column for each rate and transformation. PAT/Cry1F-transformed *Arabidopsis* served as an auxin-sensitive transformed control. Wildtype *Arabidopsis* is untransformed.

TABLE 16

AAD-1 v3 (plant optimized), or AAD-1 v2 (native), or AAD-2 (native)- transformed T₁ *Arabidopsis* response to a range of 2,4-D rates applied postemergence.

| | % Injury | | | % Injury | |
|---|---|---|---|---|---|
| Averages | <20% | 20-40% | >40% | Ave | Std Dev |
| Native AAD-1 (v2) gene | | | | | |
| Untreated control-buffer | 20 | 6 | 7 | 25.3 | 34.7 |
| 50 g ae/ha 2,4-D | 55 | 16 | 9 | 14.8 | 22.7 |
| 200 g ae/ha 2,4-D | 45 | 11 | 24 | 34.1 | 39.3 |
| 800 g ae/ha 2,4-D | 11 | 32 | 37 | 52.5 | 34.2 |
| Native AAD-2 gene | | | | | |
| Untreated control-buffer | 4 | 1 | 1 | 25.0 | 21.7 |
| 50 g ae/ha 2,4-D | 1 | 2 | 11 | 68.2 | 30.2 |
| 200 g ae/ha 2,4-D | 0 | 3 | 11 | 82.7 | 28.8 |
| 800 g ae/ha 2,4-D | 0 | 0 | 14 | 99.8 | 0.8 |
| Rebuilt AAD-1 (v3) gene | | | | | |
| Untreated control-buffer | 9 | 0 | 0 | 0.0 | 0.0 |
| 50 g ae/ha 2,4-D | 10 | 1 | 5 | 24.3 | 35.9 |
| 200 g ae/ha 2,4-D | 11 | 4 | 1 | 14.0 | 25.9 |
| 800 g ae/ha 2,4-D | 11 | 4 | 1 | 14.7 | 26.1 |
| Wildtype | | | | | |
| Untreated control-buffer | 11 | 0 | 0 | 0.0 | 0.0 |
| 50 g ae/ha 2,4-D | 0 | 0 | 15 | 90.0 | 0.0 |
| 200 g ae/ha 2,4-D | 0 | 0 | 15 | 95.1 | 0.5 |
| 800 g ae/ha 2,4-D | 0 | 0 | 15 | 100.0 | 0.0 |
| PAT/Cry1F (transformed control) | | | | | |
| Untreated control-buffer | 11 | 0 | 0 | 0.0 | 0.0 |
| 50 g ae/ha 2,4-D | 0 | 0 | 15 | 90.7 | 4.2 |
| 200 g ae/ha 2,4-D | 0 | 0 | 15 | 97.2 | 1.7 |
| 800 g ae/ha 2,4-D | 0 | 0 | 15 | 100.0 | 0.0 |

Table 17 shows a similar dose response of T₁ *Arabidopsis* to the phenoxypropionic acid, dichlorprop. Similar trends were seen as with 2,4-D, indicating the chiral propionic side chain indeed serves as an acceptable substrate. Next, it was determined that a degree of increased haloxyfop tolerance could be imparted to transformed *Arabidopsis* at elevated rates of 400-1,600 g ae/ha (Table 18). Normal field use rate for haloxyfop (a grass-specific herbicide) is around 50-70 g ae/ha. Dicots are generally considered naturally tolerant to AOPP herbicides; however, severe physiological effects do occur in *Arabidopsis* at these elevated rates. Some AAD1 (v3) transformed individuals did exhibit increased tolerance to haloxyfop. This provides the first in planta data that AAD-1 (v3) will provide AOPP resistance. No resistance was observed with fluroxypyr (a pryridyloxyacetate auxin)

in transformed *Arabidopsis*, consistent with in vitro work using heterologously expressed enzyme.

Table 17.

$T_1$ *Arabidopsis* response to a range of dichlroprop rates applied postemergence. Response is presented in terms of % visual injury 2 WAT. Data are presented as a histogram of individuals exhibiting little or no injury (<20%), moderate injury (20-40%), or severe injury (>40%). Since each $T_1$ is an independent transformation event, one can expect significant variation of individual $T_1$ responses within a given rate. An arithmetic mean and standard deviation is presented for each treatment. The range in individual response is also indicated in the last column for each rate and transformation. PAT/Cry1F-transformed *Arabidopsis* served as an auxin-sensitive transformed control. Wildtype *Arabidopsis* is untransformed.

TABLE 17

$T_1$ *Arabidopsis* response to a range of dichlroprop rates applied postemergence.

| Averages | % Injury <20% | % Injury 20-40% | % Injury >40% | Ave | Std Dev | Range |
|---|---|---|---|---|---|---|
| AAD-1 v3 | | | | | | |
| Untreated control | 3 | 0 | 0 | 0.0 | 0.0 | 0 |
| 12.5 g ae/ha RS-dichlorprop | 7 | 1 | 0 | 5.0 | 7.6 | 0-20 |
| 50 g ae/ha RS-dichlorprop | 7 | 1 | 0 | 3.1 | 8.8 | 0-25 |
| 200 g ae/ha RS-dichlorprop | 4 | 1 | 3 | 40.0 | 50.1 | 0-100 |
| 800 g ae/ha RS-dichlorprop | 0 | 5 | 3 | 51.9 | 40.0 | 20-100 |
| PAT/Cry1F | | | | | | |
| Untreated control | 3 | 0 | 0 | 0.0 | 0.0 | 0 |
| 12.5 g ae/ha RS-dichlorprop | 0 | 6 | 2 | 38.1 | 25.3 | 20-95 |
| 50 g ae/ha RS-dichlorprop | 0 | 0 | 8 | 80.0 | 25.3 | 50-100 |
| 200 g ae/ha RS-dichlorprop | 0 | 0 | 8 | 98.3 | 2.2 | 95-100 |
| 800 g ae/ha RS-dichlorprop | 0 | 0 | 8 | 100.0 | 0.0 | 100 |
| Wildtype | | | | | | |
| Untreated control | 3 | 0 | 0 | 0.0 | 0.0 | 0 |
| 12.5 g ae/ha RS-dichlorprop | 3 | 0 | 0 | 13.3 | 2.9 | 10-15 |
| 50 g ae/ha RS-dichlorprop | 0 | 0 | 3 | 53.3 | 5.8 | 50-60 |
| 200 g ae/ha RS-dichlorprop | 0 | 0 | 3 | 95.0 | 5.0 | 90-100 |
| 800 g ae/ha RS-dichlorprop | 0 | 0 | 3 | 100.0 | 0.0 | 100 |

Table 18.

T1 *Arabidopsis* response to a range of haloxyfop rates applied postemergence at artificially high rates attempting to show tolerance of the dicot *Arabidopsis* to the graminicide. Response is presented in terms of % visual injury 2 WAT. Data are presented as a histogram of individuals exhibiting little or no injury (<20%), moderate injury (20-40%), or severe injury (>40%). Since each T1 is an independent transformation event, one can expect significant variation of individual T1 responses within a given rate. An arithmetic mean and standard deviation is presented for each treatment. The range in individual response is also indicated in the last column for each rate and transformation. PAT/Cry1F-transformed *Arabidopsis* served as an auxin-sensitive transformed control. Wildtype *Arabidopsis* is untransformed.

TABLE 18

T1 *Arabidopsis* response to a range of haloxyfop rates applied postemergence at artificially high rates attempting to show tolerance of the dicot *Arabidopsis* to the graminicide.

| Averages | % Injury <20% | % Injury 20-40% | % Injury >40% | Ave | Std Dev | Range |
|---|---|---|---|---|---|---|
| AAD-1 v3 | | | | | | |
| Untreated control | 3 | 0 | 0 | 0.0 | 0.0 | 0 |
| 100 g ae/ha haloxyfop | 4 | 0 | 0 | 0.0 | 0.0 | 0 |
| 200 g ae/ha haloxyfop | 4 | 0 | 0 | 0.0 | 0.0 | 0 |
| 400 g ae/ha haloxyfop | 3 | 1 | 0 | 6.3 | 9.5 | 0-20 |
| 800 g ae/ha haloxyfop | 1 | 1 | 2 | 46.3 | 42.7 | 0-85 |
| 1600 g ae/ha haloxyfop | 1 | 0 | 3 | 65.0 | 47.3 | 0-100 |
| PAT/Cry1F | | | | | | |
| Untreated control | 3 | 0 | 0 | 0.0 | 0.0 | 0 |
| 100 g ae/ha haloxyfop | 4 | 0 | 0 | 0.0 | 0.0 | 0 |
| 200 g ae/ha haloxyfop | 4 | 0 | 0 | 10.0 | 0.0 | 10 |
| 400 g ae/ha haloxyfop | 0 | 4 | 0 | 27.5 | 5.0 | 20-30 |
| 800 g ae/ha haloxyfop | 0 | 0 | 4 | 78.8 | 6.3 | 70-85 |
| 1600 g ae/ha haloxyfop | 0 | 0 | 4 | 47.5 | 43.5 | 80-100 |
| Wildtype | | | | | | |
| Untreated control | 3 | 0 | 0 | 0.0 | 0.0 | 0 |
| 100 g ae/ha haloxyfop | 3 | 0 | 0 | 0.0 | 0.0 | 0 |
| 200 g ae/ha haloxyfop | 3 | 0 | 0 | 0.0 | 0.0 | 0 |
| 400 g ae/ha haloxyfop | 0 | 3 | 0 | 20.0 | 0.0 | 20 |
| 800 g ae/ha haloxyfop | 0 | 0 | 3 | 73.3 | 10.4 | 70-85 |
| 1600 g ae/ha haloxyfop | 0 | 0 | 3 | 93.3 | 11.5 | 80-100 |

6.6—AAD-1 (v3) as a Selectable Marker.

The ability to use AAD-1 (v3) as a selectable marker using 2,4-D as the selection agent was analyzed initially with *Arabidopsis* transformed with as described above. $T_1$ seed transformed with PAT and AAD1 (v3) (pDAB 721) were sown into flats and germinated as described above and compared to similar seed treated with the normal glufosinate selection scheme (5 and 10 DAP). 2,4-D (50 g ae/ha) was applied to seedling *Arabidopsis* as previously done with glufosinate. Variation in number of applications and timing of application were tested. Each tray of plants received either one or two application timings of 2,4-D in one of the following treatment schemes: 5+10 DAP, 5+14 DAP, 10 DAP, 10+14 DAP, 14 DAP. Plants were identified as Resistant or Sensitive 19 DAP and ELISA test strips run to determine frequency of successfully co-transforming an active PAT gene.

Fifty-three out of 70,000 seed planted were identified as resistant to 2,4-D. ELISA was used to screen a subset of 44-individuals from this population for PAT protein expression. Ninety six percent of the individuals were positive indicating the presence of the co-transformed gene, PAT. The low number of negative ELISA results (4%) is in line with a 3% error rate in populations of glufosinate-resistant plants (Table 15). The efficiency of selection appears to be somewhat less with 2,4-D (0.08%) vs. glufosinate (0.12%); however, the range of selection rates across all experiments would indicate both selection agents are equally good for selecting *Arabidopsis* transformed with AAD-1 (v3) or PAT genes, respectively. Two successive applications most accurately identify resistant individuals with both herbicides tested.

6.7—Heritability.

A variety of $T_1$ events were self-pollinated to produce $T_2$ seed. These seed were progeny tested by applying 2,4-D (200 g ae/ha) to 100 random $T_2$ siblings. Each individual $T_2$ plant was transplanted to 7.5-cm square pots prior to spray application (track sprayer at 187 L/ha applications rate). More than 60% of the $T_1$ families ($T_2$ plants) segregated in the anticipated 3 Resistant:1 Sensitive model for a dominantly inherited single locus with Mendelian inheritance as determined by Chi square analysis (P>0.05).

Seed were collected from 12 to 20 $T_2$ individuals ($T_3$ seed). Twenty-five $T_3$ siblings from each of eight randomly-selected $T_2$ families were progeny tested as previously described. Approximately one-third of the $T_2$ families anticipated to be homozygous (non-segregating populations) have been identified in each line tested: ranging in frequency from one to four out of the eight families tested. These data show AAD1 (v3) is stably integrated and inherited in a Mendelian fashion to at least three generations.

6.8—Additional Herbicide Resistance Attributable to AAD-1 in *Arabidopsis*.

The ability of AAD-1 (v3) to provide resistance to other aryloxyphenoxyalkanoate herbicides in transgenic *Arabidopsis* was determined using a modified in vitro plate assay. Seeds from wild-type *Arabidopsis thaliana* as well as *Arabidopsis thaliana* containing the plant optimized AAD-1 (v3) gene ($T_4$ homozygous plants id=PAAD1.315.064) were sterilized by agitating for 10 min in a 50% bleach solution. These seeds were then rinsed four times with sterile water to remove the bleach.

Dose response assays utilized a nutrient media (see below) supplemented with various rates of test compounds. The test compounds were added to the heated media (55° C.) as concentrated solutions in DMSO. Control wells had the appropriate amount of DMSO without any additional compound. The final concentration of DMSO never exceeded 1% (v/v). After thorough mixing, a 6 mL aliquot of the warm media containing the appropriate concentration of compound was added to each well of a 6-well, flat bottom, polystyrene tissue culture tray (Falcon 353046, Becton Dickson and Company, Franklin Lakes, N.J.). After the media solidified, approximately 20 to 30 *Arabidopsis* seeds were applied on top of the solidified media and the remaining 2 mL of media was poured over the seeds. The plates were lightly agitated to disperse the seeds, covered and allowed to cool until the media had completely solidified. The plates were incubated for 7 days at 25° C. under continual fluorescent lighting (75 µE $m^{-2}$ $s^{-1}$). Nutrient Media Composition was as described in Example 2.2 and in Somerville and Orgen (1982).

Assessment of Growth Reduction.

The apical portion of the *Arabidopsis* plants grown in the treated media was assessed visually relative to the apical portion of the plants grown in the media containing only DMSO. Values were recorded as % growth reduction.

Assessments of root growth inhibition of the *Arabidopsis* plants grown in the treated media were achieved by carefully extracting the plants from the media and measuring the length of the root. These root lengths were then compared to the root length of the control plants to determine a % growth reduction. A minimum of five plants were assessed for each treatment. The values recorded are an average of all the plants assessed. The calculated concentration to reach 50% inhibition effect ($I_{50}$) were determined for both root and shoots of wildtype and AAD-1-transformed *Arabidopsis*. The ratios of resistant to sensitive biotypes are included in Table 19. A ratio >2 for both root and shoot measurements generally signifies significant resistance. The higher the ratio, the greater the level of resistance. All commercial phenoxy auxins showed significant levels of resistance including oxyacetic acids (2,4-D and MCPA) as well as oxypropionic acids (dichlorprop and mecoprop). In fact, the chronic root assessment shows resistance to the oxypropionic acid is higher with AAD-1 (v3) than for the oxyacetic acids, consistent with enzymatic characteristics of AAD-1 (v1). Assessment of other auxins containing pyridine rings showed AAD-1 (v3) did not effectively protect *Arabidopsis* form pyridyloxyacetates herbicides, triclopyr and fluroxypyr, or the picolinic acid herbicide, picloram. The broad phenoxy auxin resistance is the first reported in planta. The alternative auxins to which AAD-1 does not protect would be viable tools for the control and containment of AAD-1-transformed commercial crops or experimental plant species.

TABLE 19

In vitro plate test assessment of herbicide substrate cross resistance afforded by AAD-1 (v3) in homozygous $T_4$ *Arabidopsis* (ARBTH).

| Compound | Structure | wt ARBTH shoot I50 | PAAD1.315.064 T3 ARBTH shoot I50 | wt ARBTH root I50 | PAAD1.315.064 ARBTH root I50 | shoot ratio | root ratio |
|---|---|---|---|---|---|---|---|
| | | ppm | | | | | |
| Phenoxy auxins | | | | | | | |
| 2,4-D | [structure] | 0.2 | 10 | <0.01 | 0.04 | 50 | >4 |
| dichlorprop | [structure] | 2 | 5 | 0.01 | 1.5 | 2.5 | 150 |

TABLE 19-continued

In vitro plate test assessment of herbicide substrate cross resistance afforded by
AAD-1 (v3) in homozygous T₄ Arabidopsis (ARBTH).

| Compound | Structure | wt ARBTH shoot I50 | PAAD1.315.064 T3 ARBTH shoot I50 | wt ARBTH root I50 ppm | PAAD1.315.064 ARBTH root I50 | shoot ratio | root ratio |
| --- | --- | --- | --- | --- | --- | --- | --- |
| Mecoprop | 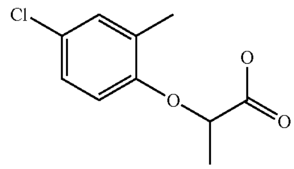 | 2 | 25 | 0.01 | 1.5 | 12.5 | 150 |
| MCPA | 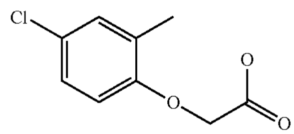 | 0.2 | 1 | 0.01 | 0.03 | 5 | 3 |
| 2,4,5-T | 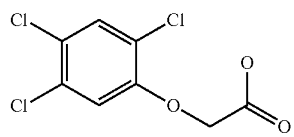 [SMILES: O=C(O)COc1cc(Cl)c(Cl)cc1Cl] | 1.5 | 10 | <0.01 | <0.01 | 6.67 | NA |
| Pyridine auxins | | | | | | | |
| Fluroxypyr | 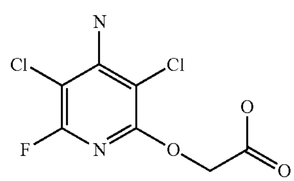 [SMILES: Nc1c(Cl)c(F)nc(OCC(=O)O)c1Cl] | 2 | 1 | 0.2 | 0.2 | 0.5 | 1 |
| Triclopyr | 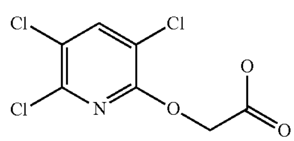 [SMILES: O=C(O)COc1nc(Cl)c(Cl)cc1Cl] | 0.2 | 0.04 | 0.02 | 0.02 | 0.2 | 1 |
| Picloram | 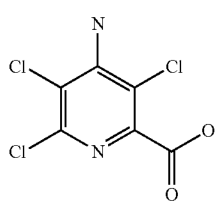 [SMILES: Nc1c(Cl)c(Cl)nc(C(=O)O)c1Cl] | 1 | 0.5 | 0.3 | 0.15 | 0.5 | 0.5 |

6.9—Foliar Applications Herbicide Resistance in AAD-1 Arabidopsis.

The ability of AAD-1 (v3) to provide resistance to other aryloxyphenoxyalkanoate auxin herbicides in transgenic Arabidopsis was determined by foliar application of various substrates described in Example 6.8. T₄ generation Arabidopsis seed, homozygous for AAD-1 (v3) (line AAD1.01.315.076) was stratified, and sown into selection trays much like that of Arabidopsis (Example 6.4). A transformed-control line containing PAT and the insect resistance gene Cry1F was planted in a similar manner. Seedlings were transferred to individual 3-inch pots in the greenhouse. All plants were sprayed with the use of a track sprayer set at 187 L/ha. The plants were sprayed from a range of phenoxy auxin herbicides: 12.5-1600 g ae/ha 2,4-D dimethylamine salt (DMA) (Riverside Chemicals), 12.5-1600 g ae/ha mecoprop (AH Marks), 50-3200 g ae/ha R-dichlorprop (AH Marks), 8.75-1120 g ae/ha 2,4,5-T (technical grade); pyridyloxyacetates herbicides 50-3200 g ae/ha triclopyr (Dow AgroSciences) and 50-3200 g ae/ha fluroxypyr (Dow AgroSciences); and the 2,4-D metabolite resulting from AAD-1 activity, 2,4-dichlorophenol (DCP, Sigma) (at 50-3200 g ae/ha, technical grade). All applications were formulated in 200 mM Hepes buffer (pH 7.5). Each treatment was replicated 3-4 times. Plants were evaluated at 3 and 14 days after treatment and are averaged over two experiments.

These results (see Table 20) confirm that AAD-1 (v3) in Arabidopsis provides robust resistance to the phenoxyacetic auxins, phenoxypropionic auxins, but have not shown significant cross resistance to the pyridyloxyacetic auxins tested and corroborates the in vitro enzyme and whole plate substrate specificity data. Additionally, there is no effect of the metabolite, 2,4-dichlorphohenol (DCP), on wildtype or transgenic *Arabidopsis*.

TABLE 20

Comparison of homozygous $T_4$ AAD-1 (v3) and wildtype *Arabidopsis* plant response to various foliar-applied auxinic herbicides.

Phenoxypropionic auxins

| Herbicide Treatment | Ave % Injury 14DAT | |
|---|---|---|
| | AAD1.01.315.076.$T_4$ homozygous AAD1 plants | PatCry1f-Control |
| 50 g ae/ha R-Dichlorprop | 3 | 31 |
| 200 g ae/ha R-Dichlorprop | 3 | 73 |
| 800 g ae/ha R-Dichlorprop | 3 | 89 |
| 3200 g ae/ha R-Dichlorprop | 3 | 95 |
| 12.5 g ae/ha Mecoprop | 3 | 0 |
| 25 g ae/ha Mecoprop | 0 | 2 |
| 50 g ae/ha Mecoprop | 0 | 17 |
| 100 g ae/ha Mecoprop | 0 | 33 |
| 200 g ae/ha Mecoprop | 3 | 62 |
| 400 g ae/ha Mecoprop | 0 | 78 |
| 800 g ae/ha Mecoprop | 0 | 93 |
| 1600 g ae/ha Mecoprop | 0 | 100 |

| Herbicide Treatment | Ave % Injury 14DAT | |
|---|---|---|
| | AAD1.01.315.076.$T_4$ homozygous AAD1 plants | Pat/Cry1f-Control |
| Phenoxyacetic auxins | | |
| 12.5 g ae/ha 2,4-D DMA | 0 | 67 |
| 25 g ae/ha 2,4-D DMA | 0 | 78 |
| 50 g ae/ha 2,4-D DMA | 0 | 93 |
| 100 g ae/ha 2,4-D DMA | 0 | 100 |
| 200 g ae/ha 2,4-D DMA | 0 | 100 |
| 400 g ae/ha 2,4-D DMA | 0 | 100 |
| 800 g ae/ha 2,4-D DMA | 0 | 100 |
| 1600 g ae/ha 2,4-D DMA | 0 | 100 |
| 8.75 g ae/ha 2,4,5-T | 0 | 0 |
| 17.5 g ae/ha 2,4,5-T | 3 | 20 |
| 35 g ae/ha 2,4,5-T | 0 | 43 |
| 70 g ae/ha 2,4,5-T | 3 | 85 |
| 140 g ae/ha 2,4,5-T | 0 | 95 |
| 280 g ae/ha 2,4,5-T | 0 | 98 |
| 560 g ae/ha 2,4,5-T | 17 | 100 |
| 1120 g ae/ha 2,4,5-T | 3 | 100 |
| Pyridyloxyacetic auxins | | |
| 50 g ae/ha Triclopyr | 31 | 36 |
| 200 g ae/ha Triclopyr | 58 | 65 |
| 800 g ae/ha Triclopyr | 74 | 84 |
| 3200 g ae/ha Triclopyr | 97 | 95 |
| 50 g ae/ha Fluroxypyr | 48 | 76 |
| 200 g ae/ha Fluroxypyr | 75 | 85 |
| 800 g ae/ha Fluroxypyr | 88 | 85 |
| 3200 g ae/ha Fluroxypyr | 95 | 95 |
| Inactive DCP metabolite | | |
| 50 g ae/ha 2,4-DCP | 0 | 0 |
| 200 g ae/ha 2,4-DCP | 0 | 0 |
| 800 g ae/ha 2,4-DCP | 0 | 0 |
| 3200 g ae/ha 2,4-DCP | 0 | 0 |

6.10—Relationship of Plant Growth to AAD-1 (v3) Expression in *Arabidopsis*.

Figure 8A:
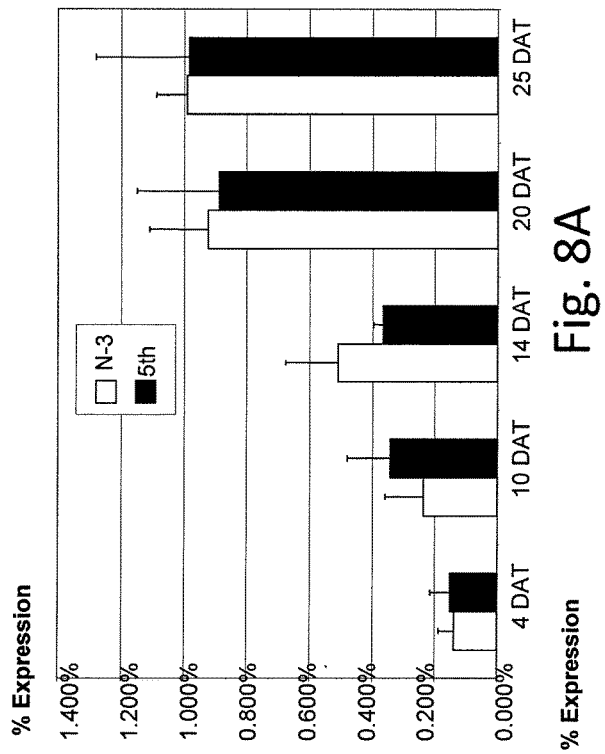
FIGS. 8A and 8B show that AAD-1 (v3) was expressed equally in Arabidopsis leaves of different ages but continued to accumulate throughout the 25 days of experiment. Plants that were not sprayed with the herbicide 2,4-D (panel A) expressed a little more AAD-1 (v3) than those had been sprayed (panel B). Bars represent the mean±SEM of 5 leaves from 5 different plants, with percent expression of AAD-1 (v3) normalized to total soluble protein. Light bars represent the third young leaves (N-3) collected from the top, dark bars represent the $5^{th}$ oldest leaves from the bottom.
Figure 8B:
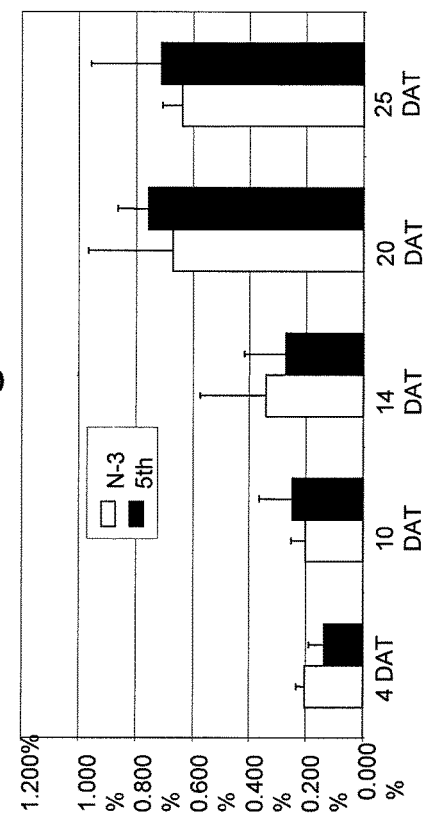

An experiment was designed to examine if the level of AAD-1 (v3) expression in *Arabidopsis* varies at different growth stages. A high-tolerance, homozygous, AAD-1 (v3) $T_4$ line (id=PAAD1.01.345.163) was grown in greenhouse. Half of the plants were treated with 800 g ae/ha of 2,4-D (as previously described) while the other half were not treated. Two leaves, the 3rd leaf from the top and the 5th leaf from the bottom, were harvested from 5 plants, both treated and untreated, and analyzed by ELISA and Western Blotting (as described in Example 11) experiments at 4, 10, 14, 20 and 25 DAT. FIGS. 8A and 8B showed that there was statistically no difference in AAD-1 (v3) expression between young and old leaves. In addition, the herbicide 2,4-D had little impact on the expression level of AAD-1 (v3) protein. The protein levels accumulated in older plants with some significant protein degradation at the later time points.

Figure 9A:
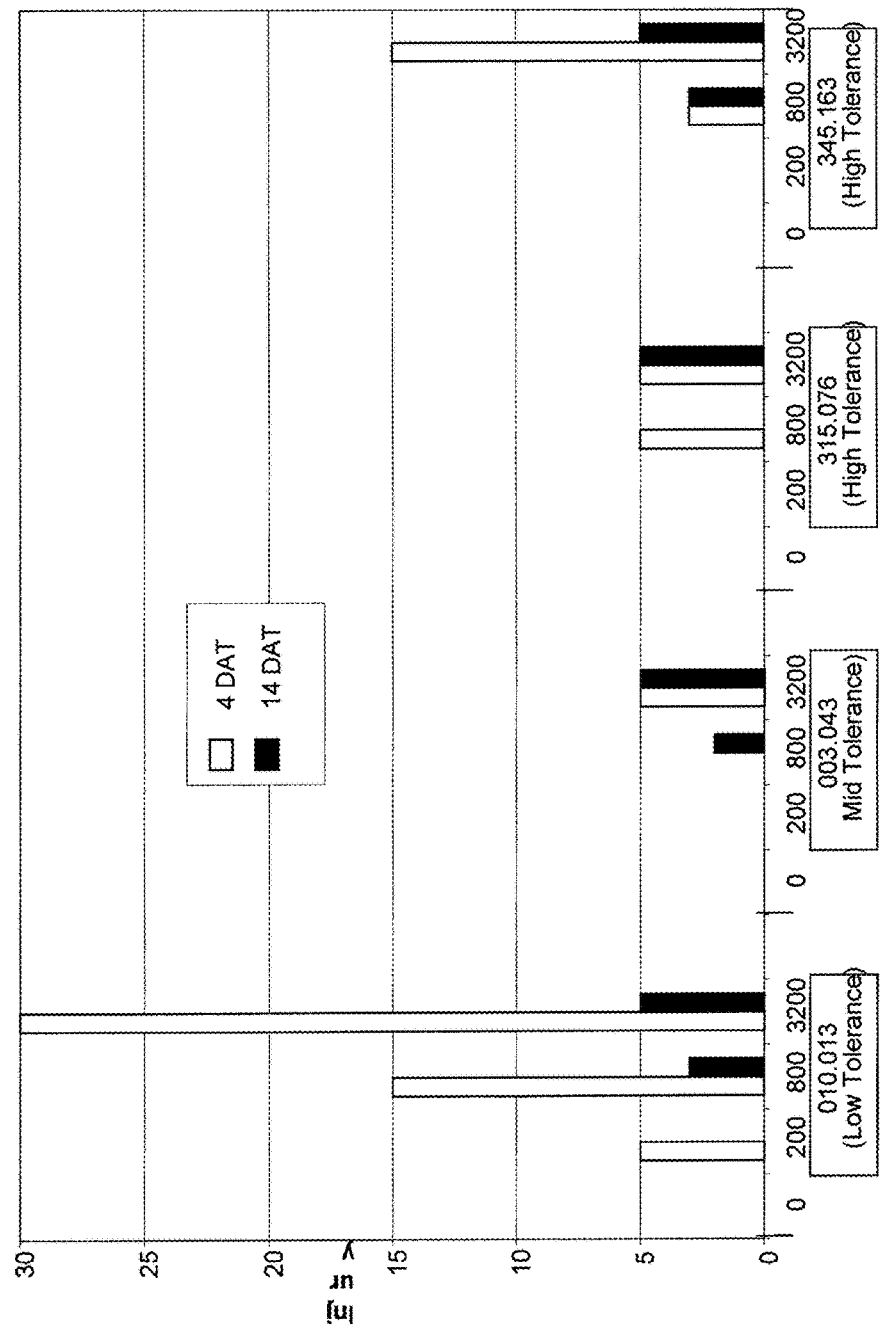
Figure 9B:
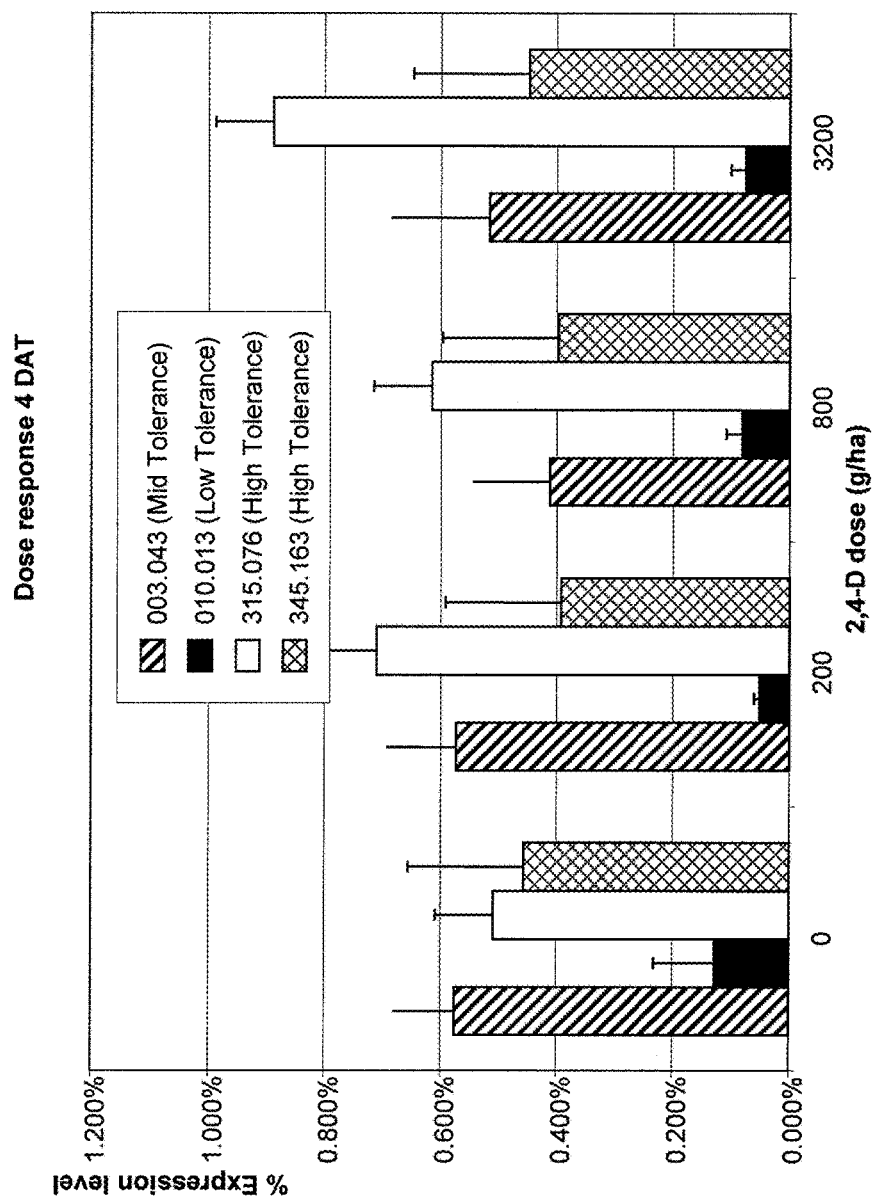

In a separate experiment, four different homozygous $T_4$ lines of *Arabidopsis* displaying different tolerance level to the herbicide 2,4-D were sprayed with various levels (0, 200, 800 and 3200 g/ha) of 2,4-D and their herbicide injury and AAD-1 (v3) expression were examined. Four days after the herbicide treatment, little injury was observed in three of the four lines, even at the highest dose tested (FIG. 9A). These plants also expressed high level of AAD-1 (v3), from 0.1 to 0.25% of (FIG. 9B). On the contrary, the low tolerance line expressed less than 0.1% of AAD-1 (v3) in TSP and suffered observable injury. More importantly, they recovered from the injury on 14 DAT (FIG. 9A), indicating that the low level of AAD-1 (v3) expression was able to protect the plants from the serious herbicide damage. All control plants suffered serious injury and died 14 DAT at doses 800 g ae/ha 2,4-D and above.

6.11—Molecular Analysis of AAD-1 (v3) *Arabidopsis*.

Invader Assay (methods of Third Wave Agbio Kit Procedures) for PAT gene copy number and/or Southern blot analysis was performed with total DNA obtained from Qiagen DNeasy kit on multiple AAD-1 (v3) homozygous lines to determine stable integration of the plant transformation unit containing PAT and AAD-1 (v3). Analysis assumed direct physical linkage of these genes as they were contained on the same plasmid.

For Southern analysis, a total of 1 µg of DNA was subjected to an overnight digest of Nsi I for pDAB721 to obtain integration data. The samples were run on a large 0.85% agarose gel overnight at 40 volts. The gel was then denatured in 0.2 M NaOH, 0.6 M NaCl for 30 minutes. The gel was then neutralized in 0.5 M Tris HCl, 1.5 M NaCl pH of 7.5 for 30 minutes. A gel apparatus containing 20 SSC was then set up to obtain a gravity gel to nylon membrane (Millipore INYC00010) transfer overnight. After the overnight transfer the membrane was then subjected to UV light via a crosslinker (stratagene UV stratalinker 1800) at 1200× 100 microjoules. The membrane was then washed in 0.1% SDS, 0.1 SSC for 45 minutes. After the 45 minute wash, the membrane was baked for 3 hours at 80° C. and then stored at 4° C. until hybridization. The hybridization template fragment consisted of the prepared primers (Pat 5-3 AGA-TACCCTTGGTTGGTTGC) (SEQ ID NO:23) and (Pat 3-3 CAGATGGATCGTTTGGAAGG) (SEQ ID NO:24) designed to obtain the coding region of PAT. The product was run on a 1% agarose gel and excised and then gel extracted using the Qiagen (28706) gel extraction procedure. The membrane was then subjected to a pre-hybridization at 60° C. step for 1 hour in Perfect Hyb buffer (Sigma H7033). The Prime it RmT dCTP-labeling rxn (Stratagene 300392) procedure was used to develop the p32 based probe (Perkin Elmer). The probe was cleaned up using the Probe Quant. G50 columns (Amersham 27-5335-01). Two million counts CPM per ml of Perfect Hyb buffer was used to hybridize the southern blots overnight. After the overnight hybridization the blots were then subjected to two 20 minute washes at 65° C. in 0.1% SDS, 0.1 SSC. The blots were then exposed to film overnight, incubating at −80° C.

Results showed all 2,4-D resistant plants assayed contained PAT (and thus by inference, AAD-1 (v3)). Copy number analysis showed total inserts ranged from 1 to >10 copies. This correlates, too, with the AAD-1 (V3) protein expression data indicating that the presence of the enzyme yields significantly high levels of resistance (>>200 fold) to all commercially available phenoxyacetic and phenoxypropionic acids.

6.12—*Arabidopsis* Transformed with Molecular Stack of AAD-1 (v3) and Glyphosate Resistance Gene.

Figure 10:
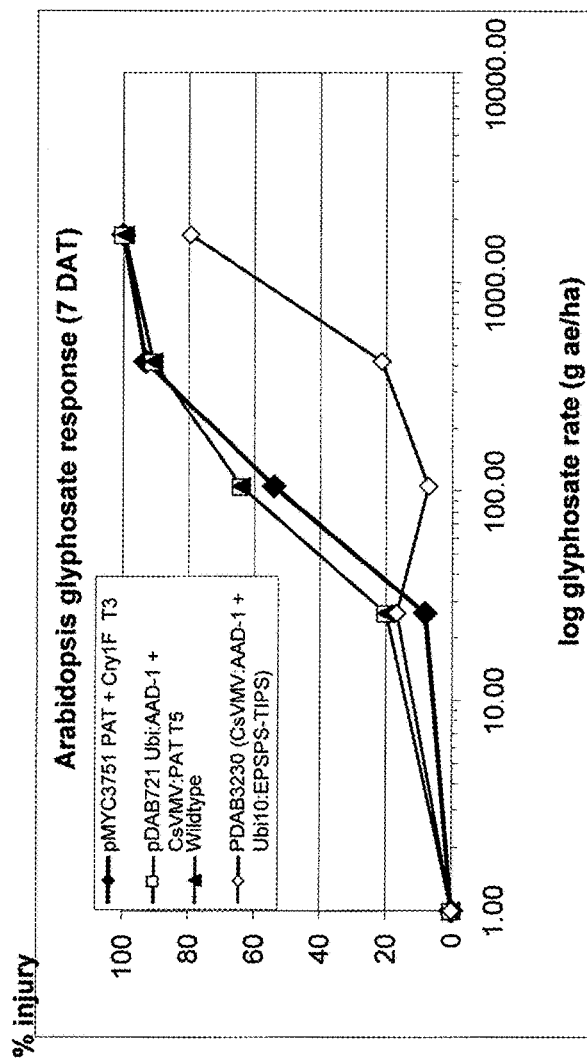
FIG. 10 illustrates that pDAB3230-transformed Arabidopsis (AAD-1+EPSPS) shows >14-fold level of glyphosate tolerance 7 DAT vs. wildtype and transformed control Arabidopsis lines.

T1 *Arabidopsis* seed was produced, as previously described, containing pDAB3230 plasmid (AAD-1 (v3)+ EPSPS) coding for a putative glyphosate resistance trait. $T_1$ transformants were selected using AAD-1 (v3) as the selectable marker as described in example 6.6, except the 2,4-D rate used was 75 g ae/ha. Twenty-four $T_1$ individually transformed events were recovered from the first selection attempt and transferred to three-inch pots in the greenhouse as previously described. Three different control *Arabidopsis* lines were also tested: wildtype Columbia-0, AAD-1 (v3)+ PAT $T_5$ homozygous lines (pDAB721-transformed), and PAT+Cry1F homozygous line (transformed control). Only pDAB3230 plants were pre-selected at the seedling stage for 2,4-D tolerance. Four days after transplanting, plants were evenly divided for foliar treatment by track sprayer as previously described with 0, 26.25, 105, 420, or 1680 g ae/ha glyphosate (Glyphomax Plus, Dow AgroSciences) in 200 mM Hepes buffer (pH 7.5). All treatments were replicated 4 or 5 times. Plants were evaluated 7 and 14 days after treatment. $I_{50}$ values were calculated and show >14 fold level of tolerance imparted by EPSPS molecularly stacked with AAD-1 (v3) (see FIG. 10). AAD-1 (v3) did not provide resistance to glyphosate itself (re: pDAB721 response). These $T_1$ plants will be grown to seed, self-pollinated to yield $T_2$ seed. The pDAB 3230 $T_1$ plants have demonstrated tolerance to lethal doses of 2,4-D and glyphosate. $T_2$ plants will be further tested to demonstrate these co-transformed plants will withstand glyphosate+2,4-D treatments applied in tankmix as described in Example 21 and shown for AAD-1 (v3)-transformed corn in Example 8.

Example 7—WHISKERS-Mediated Transformation into Maize, and Use of AAD-1 (v3) as a Selectable Marker 7.1—Cloning of AAD-1 (v3).

The AAD-1 (v3) fragment was received on an NcoI/SacI fragment. Construct pDAB4005 was digested with NcoI and SacI and the 5175 bp backbone fragment isolated. The two fragments were ligated together using T4 DNA ligase and transformed into DH5α cells. Minipreps were performed on the resulting colonies using Qiagen's QIA Spin mini prep kit, and the colonies were digested to check for orientation. The correct intermediate plasmid was named pDAB3403. Both pDAB3403 and pDAB8505 (OsAct1/PAT/ZmLip) were digested with NotI. The 3442 bp band from pDAB3403 and the 11017 bp band from pDAB8505 were isolated and purified. The fragments were ligated together, transformed into DH5α, and the resulting plasmids were screened for orientation. The final construct was designated pDAB3404, which contains ZmUbi1/po-aad1/ZmPer5::OsAct1/PAT/ZmLip.

7.2—Callus/Suspension Initiation.

To obtain immature embryos for callus culture initiation, $F_1$ crosses between greenhouse-grown Hi-II parents A and B (Armstrong et al. 1991) were performed. When embryos were 1.0-1.2 mm in size (approximately 9-10 days post-pollination), ears were harvested and surface sterilized by scrubbing with Liqui-Nox® soap, immersed in 70% ethanol for 2-3 minutes, then immersed in 20% commercial bleach (0.1% sodium hypochlorite) for 30 minutes.

Ears were rinsed in sterile, distilled water, and immature zygotic embryos were aseptically excised and cultured on 15Ag10 medium (N6 Medium (Chu et al., 1975), 1.0 mg/L 2,4-D, 20 g/L sucrose, 100 mg/L casein hydrolysate (enzymatic digest), 25 mM L-proline, 10 mg/L AgNO$_3$, 2.5 g/L Gelrite, pH 5.8) for 2-3 weeks with the scutellum facing away from the medium. Tissue showing the proper morphology (Welter et al., 1995) was selectively transferred at biweekly intervals onto fresh 15Ag10 medium for about 6 weeks, then transferred to 4 medium (N6 Medium, 1.0 mg/L 2,4-D, 20 g/L sucrose, 100 mg/L casein hydrolysate (enzymatic digest), 6 mM L-proline, 2.5 g/L Gelrite, pH 5.8) at bi-weekly intervals for approximately 2 months.

To initiate embryogenic suspension cultures, approximately 3 ml packed cell volume (PCV) of callus tissue originating from a single embryo was added to approximately 30 ml of H9CP+ liquid medium (MS basal salt mixture (Murashige and Skoog, 1962), modified MS Vitamins containing 10-fold less nicotinic acid and 5-fold higher thiamine-HCl, 2.0 mg/L 2,4-D, 2.0 mg/L α-naphthaleneacetic acid (NAA), 30 g/L sucrose, 200 mg/L casein hydrolysate (acid digest), 100 mg/L myo-inositol, 6 mM L-proline, 5% v/v coconut water (added just before subculture), pH 6.0). Suspension cultures were maintained under dark conditions in 125 ml Erlenmeyer flasks in a temperature-controlled shaker set at 125 rpm at 28° C. Cell lines typically became established within 2 to 3 months after initiation. During establishment, suspensions were subcultured every 3.5 days by adding 3 ml PCV of cells and 7 ml of conditioned medium to 20 ml of fresh H9CP+ liquid medium using a wide-bore pipette. Once the tissue started doubling in growth, suspensions were scaled-up and maintained in 500 ml flasks whereby 12 ml PCV of cells and 28 ml conditioned medium was transferred into 80 ml H9CP+ medium. Once the suspensions were fully established, they were cryopreserved for future use.

7.3—Cryopreservation and Thawing of Suspensions.

Two days post-subculture, 4 ml PCV of suspension cells and 4 ml of conditioned medium were added to 8 ml of cryoprotectant (dissolved in H9CP+ medium without coconut water, 1 M glycerol, 1 M DMSO, 2 M sucrose, filter sterilized) and allowed to shake at 125 rpm at 4° C. for 1 hour in a 125 ml flask. After 1 hour 4.5 ml was added to a chilled 5.0 ml Corning cryo vial. Once filled individual vials were held for 15 minutes at 4° C. in a controlled rate freezer, then allowed to freeze at a rate of −0.5° C./minute until reaching a final temperature of −40° C. After reaching the final temperature, vials were transferred to boxes within racks inside a Cryoplus 4 storage unit (Forma Scientific) filled with liquid nitrogen vapors.

For thawing, vials were removed from the storage unit and placed in a closed dry ice container, then plunged into a water bath held at 40-45° C. until "boiling" subsided. When thawed, contents were poured over a stack of ~8 sterile 70 mm Whatman filter papers (No. 4) in covered 100×25 mm Petri dishes. Liquid was allowed to absorb into the filters for several minutes, then the top filter containing the cells was transferred onto GN6 medium (N6 medium, 2.0 mg/L 2,4-D, 30 g/L sucrose, 2.5 g/L Gelrite, pH 5.8) for 1 week. After 1 week, only tissue with promising morphology was transferred off the filter paper directly onto fresh GN6 medium. This tissue was subcultured every 7-14 days until 1 to 3 grams was available for suspension initiation into approximately 30 mL H9CP+ medium in 125 ml Erlenmeyer flasks. Three milliliters PCV was subcultured into fresh H9CP+ medium every 3.5 days until a total of 12 ml PCV was obtained, at which point subculture took place as described previously.

7.4—Dose Response of Non-Transformed Tissue to Haloxyfop Acid.

Figure 11:
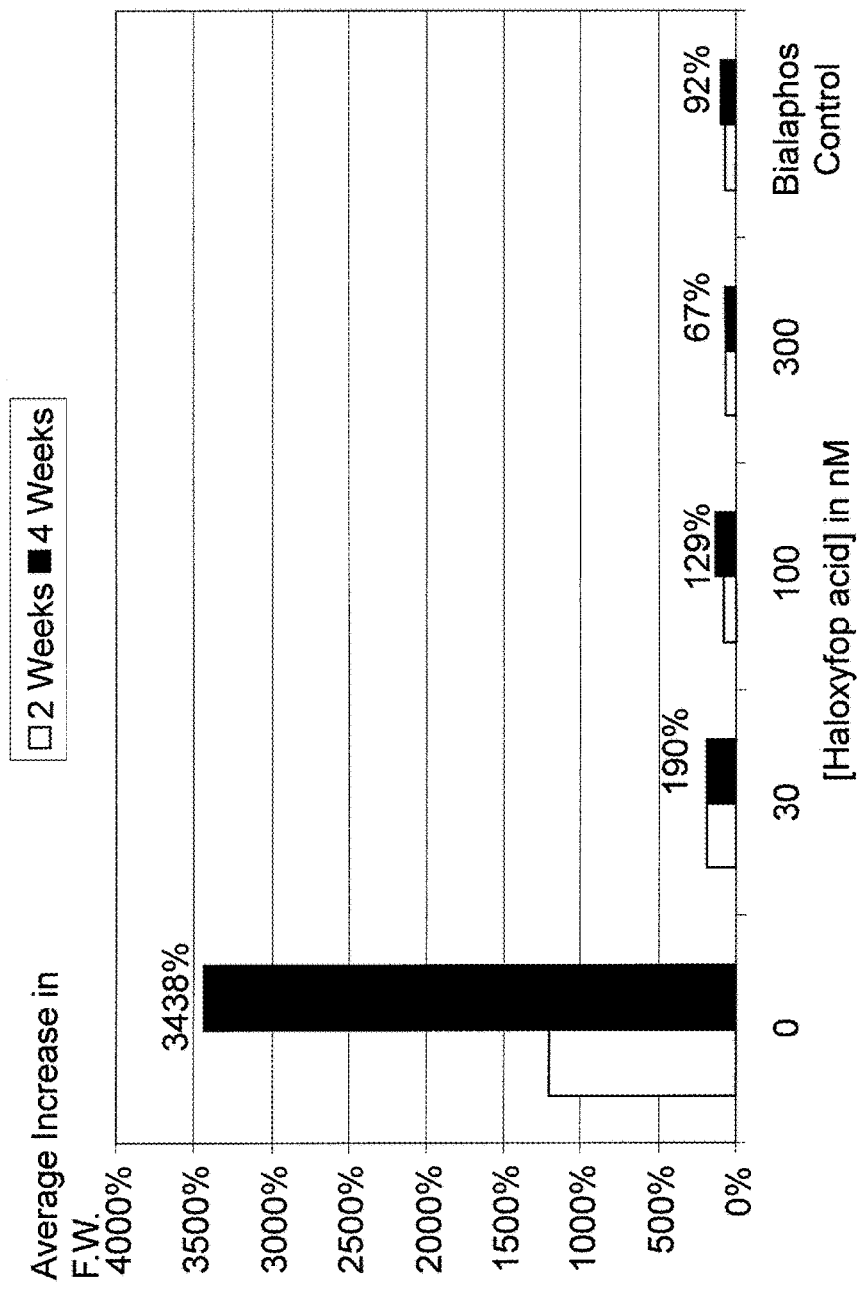
FIG. 11 shows dose response of callused maize suspensions to R-haloxyfop.

Non-transformed donor Hi-II cell lines were pooled together, WHISKERS-treated without DNA, filtered onto GN6 medium at the rate of 6 ml per filter, and allowed to callus for 2-3 weeks at 28° C. Approximately 200 mg of callused suspension tissue was transferred per treatment to selection media in 60×20 mm plates containing 30, 100 or 300 nM R-haloxyfop acid. Three replicates were used per concentration. A control medium containing 1 mg/L bialaphos (from Herbiace commercial formulation, Meiji Seika, Japan), GN6 (1H), was also included for comparison. Callus was removed after 2 weeks, weighed, and transferred to fresh media of the same concentration for another 2 weeks. After a total of 4 weeks elapsed time, tissue was removed, weighed a final time, and then discarded. Results are shown in FIG. 11.

Figure 12:
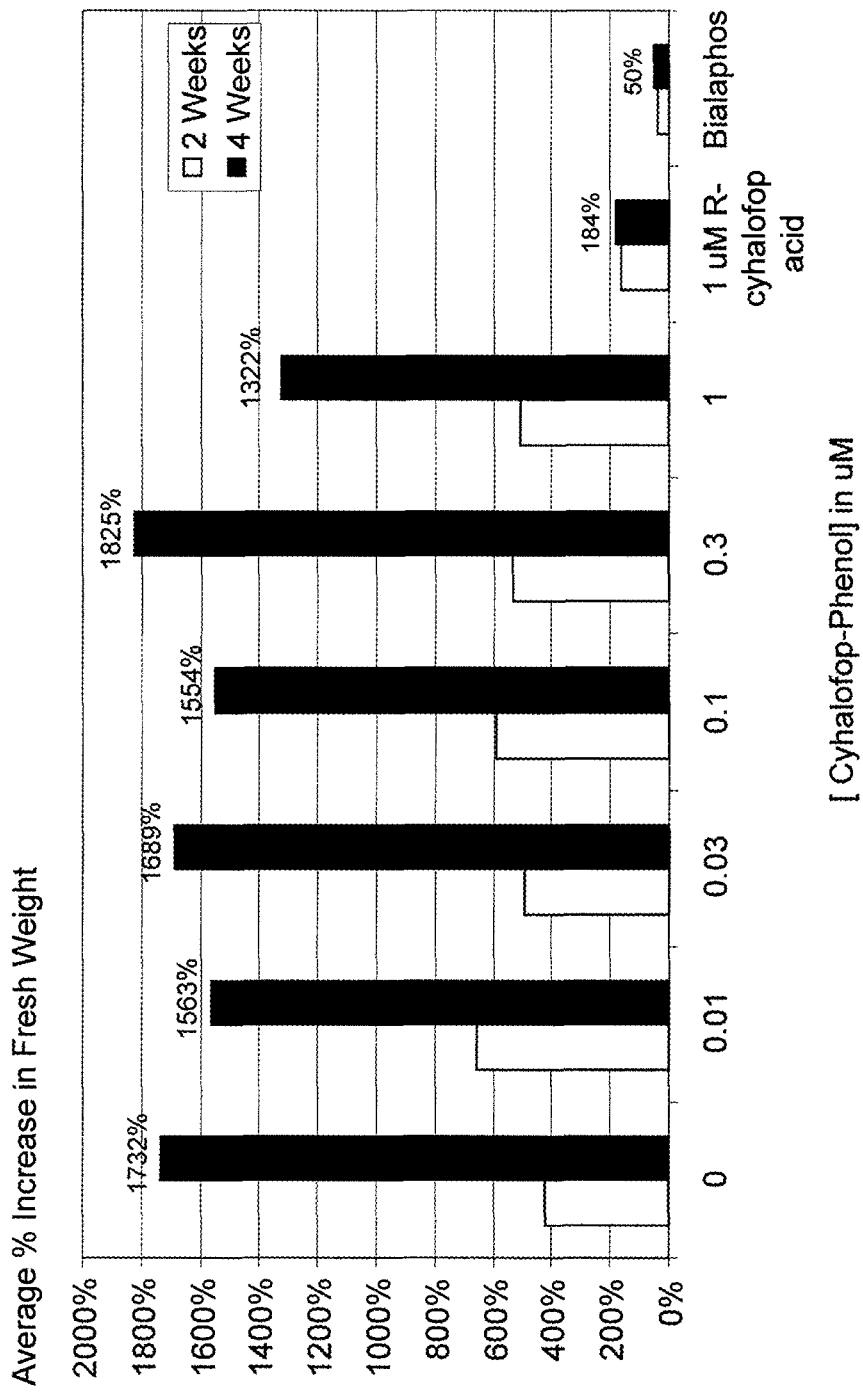
FIG. 12 shows that at 1 μM cyhalofop phenol, growth is still 76% as high as the control without cyhalofop phenol.

Two separate dose response studies of callus tissue to the phenol degradation products of haloxyfop and cyhalofop, respectively, were also completed to confirm that this end product would not be deleterious to callus growth. Data from a cyhalofop phenol dose response (see FIG. 12) shows that at 1 µM cyhalofop phenol, growth is still 76% as high as the control without cyhalofop phenol. Data from a haloxyfop phenol dose response showed that even at 300 nM haloxyfop phenol, growth was equal to or greater than the control lacking haloxyfop phenol (data not shown).

7.5—WHISKERS-Mediated Transformation Using Bialaphos Selection.

Approximately 24 hours prior to transformation, 12 ml PCV of previously cryopreserved embryogenic maize suspension cells plus 28 ml of conditioned medium was subcultured into 80 ml of GN6 liquid medium (GN6 medium lacking Gelrite) in a 500 ml Erlenmeyer flask, and placed on a shaker at 125 rpm at 28° C. This was repeated 2 times using the same cell line such that a total of 36 ml PCV was distributed across 3 flasks. After 24 hours the GN6 liquid media was removed and replaced with 72 ml GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0) per flask in order to plasmolyze the cells. The flasks were placed on a shaker in the dark for 30-35 minutes, and during this time a 50 mg/ml suspension of silicon carbide whiskers was prepared by adding the appropriate volume of GN6 S/M liquid medium to ~405 mg of pre-autoclaved, silicon carbide whiskers (Advanced Composite Materials, Inc.).

After incubation in GN6 S/M, the contents of each flask were pooled into a 250 ml centrifuge bottle. Once all cells settled to the bottom, all but ~14 ml of GN6 S/M liquid was drawn off and collected in a sterile 1-L flask for future use. The pre-wetted suspension of whiskers was vortexed for 60 seconds on maximum speed and 8.1 ml was added to the bottle, to which 170 µg DNA was added as a last step. The bottle was immediately placed in a modified Red Devil 5400 commercial paint mixer and agitated for 10 seconds. After agitation, the cocktail of cells, media, whiskers and DNA was added to the contents of the 1-L flask along with 125 ml fresh GN6 liquid medium to reduce the osmoticant. The cells were allowed to recover on a shaker for 2 hours before being filtered onto Whatman #4 filter paper (5.5 cm) using a glass cell collector unit that was connected to a house vacuum line.

Either 3 or 6 mL of dispersed suspension was pipetted onto the surface of the filter as the vacuum was drawn. Filters were placed onto 60×20 mm plates of GN6 medium. Plates were cultured for 1 week at 28° C. in a dark box that was loosely sealed with a single layer of plastic (<2 mils thick) to minimize evaporation of the individual plates.

After 1 week, filter papers were transferred to 60×20 mm plates of GN6 (1H) medium (N6 Medium, 2.0 mg/L 2,4-D, 30 g/L sucrose, 100 mg/L myo-inositol, 1.0 mg/L bialaphos, 2.5 g/L Gelrite, pH 5.8) or GN6D (1H) medium (same as GN6 (1H) except with 8.0 mg/L dicamba and 0.8 mg/L 2,4-D).

Plates were placed in boxes and cultured as before for an additional week. Two weeks post-transformation, the tissue was embedded by scraping either ½ the cells on the plate or else all cells on the plate into 3.0 mL of melted GN6 agarose medium (N6 medium, 2.0 mg/L 2,4-D, 30 g/L sucrose, 100 mg/L myo-inositol, 7 g/L Sea Plaque agarose, pH 5.8, autoclaved for only 10 minutes at 121° C.) containing 1 mg/L bialaphos. The tissue was broken up and the 3 mL of agarose and tissue were evenly poured onto the surface of a 100×15 mm plate of GN6 (1H) or GN6D (1H) medium. This was repeated for all remaining plates. Once embedded, plates were individually sealed with Nescofilm® or Parafilm M®, and then cultured for 1 week at 28° C. in dark boxes.

Putatively transformed isolates were typically first visible 5-8 weeks post-transformation. Any potential isolates were removed from the embedded plate and transferred to fresh selection medium of the same concentration in 60×20 mm plates. If sustained growth was evident after approximately 2 weeks, an event was deemed to be resistant and was submitted for molecular analysis.

Regeneration was initiated by transferring callus tissue to a cytokinin-based induction medium, 28 (1H), containing 1 mg/L bialaphos, MS salts and vitamins, 30.0 g/L sucrose, 5 mg/L BAP, 0.25 mg/L 2,4-D, 2.5 g/L Gelrite; pH 5.7. Cells were allowed to grow in low light (13 $\mu Em^{-2} s^{-1}$) for one week then higher light (40 $\mu Em^{-2} s^{-1}$) for another week before being transferred to regeneration medium, 36 (1H), which was identical to 28 (1H) except that it lacked plant growth regulators. Small (3-5 cm) plantlets were removed and placed into 150×25-mm culture tubes containing selection-free SHGA medium (Schenk and Hildebrandt basal salts and vitamins, 1972; 1 g/L myo-inositol, 10 g/L sucrose, 2.0 g/L Gelrite, pH 5.8). Once plantlets developed a sufficient root and shoot system, they were transplanted to soil in the greenhouse.

7.6—WHISKERS-Mediated Transformation Using Haloxyfop Selection.

DNA delivery parameters for direct selection on "fops" were identical to the bialaphos selection procedure except that 85 µg of pDAB3403 and 85 µg of construct containing a GFP (Green Fluorescent Protein) reporter gene were co-transformed together, and only 3 mL of suspension was filtered onto GN6 medium following the 2-hour recovery.

After 0-7 days on GN6 selection-free medium, filter papers were transferred to 60×20-mm plates of GN6 medium containing 2 mg/L 2,4-D plus 50, 100, or 200 nM R-haloxyfop acid. Plates were placed in boxes and cultured for one additional week. After one week, the tissue was embedded by scraping all cells from the plate into 3.0 mL of melted GN6 agarose medium containing the same concentration of selection agent as in the previous transfer. All steps afterward were identical to the PAT selection/regeneration protocol except that 100 nM R-haloxyfop acid was included in the regeneration media instead of 1 mg/L bialaphos.

7.7—Results.

Multiple experiments testing various levels of haloxyfop and cyhalofop were initiated, and 47 isolates were recovered from direct selection. A subset of the callus events were submitted for screening using PCR and Western analyses. Following these expression data, 21 lead events were submitted for Southern analysis. Results using NcoI, a unique cutter, to obtain integration data following probing with AAD-1 (v3), unequivocally demonstrate stable integration of AAD-1 (v3) following Whiskers-mediated transformation coupled with "fop" selection.

7.8—Quantitative Demonstration of In Vitro Tolerance from AAD-1 (v3) Expressing Callus Events from Bialaphos Selection Ninety-seven callus isolates recovered from bialaphos selection were submitted for PAT copy number via Invader analysis and AAD-1 (v3) PTU analysis via PCR (see Example 7.10). AAD-1 (v3) protein expression using Western blot/Sandwich ELISA (Example 11) was completed on a subset of the events. A summary is described in Table 21 below. At least 15 $T_0$ plants were regenerated from each of these events and sent for spray testing and seed production.

TABLE 21

| Event | PAT Copy # | PCR for AAD-1 (v3) PTU | Callus Western |
|---|---|---|---|
| 3404-001 | 2 | + | + |
| 3404-006 | 2 | + | + |
| 3404-013 | 3 | + | + |
| 3404-017 | 1 | + | + |
| 3404-020 | 3 | + | nd |
| 3404-022 | 2 | + | + |
| 3404-025 | 2 | + | + |
| 3404-027 | 3 | + | + |
| 3404-031 | 1 | + | + |
| 3404-033 | 2 | + | nd |
| 3404-036 | 3 | + | + |
| 3404-044 | 3 | + | + |
| 3404-050 | 3 | + | + |
| 3404-053 | 3 | + | + |
| 3404-074 | 2 | + | + |
| 3404-082 | 2 | + | + |

Figure 13:
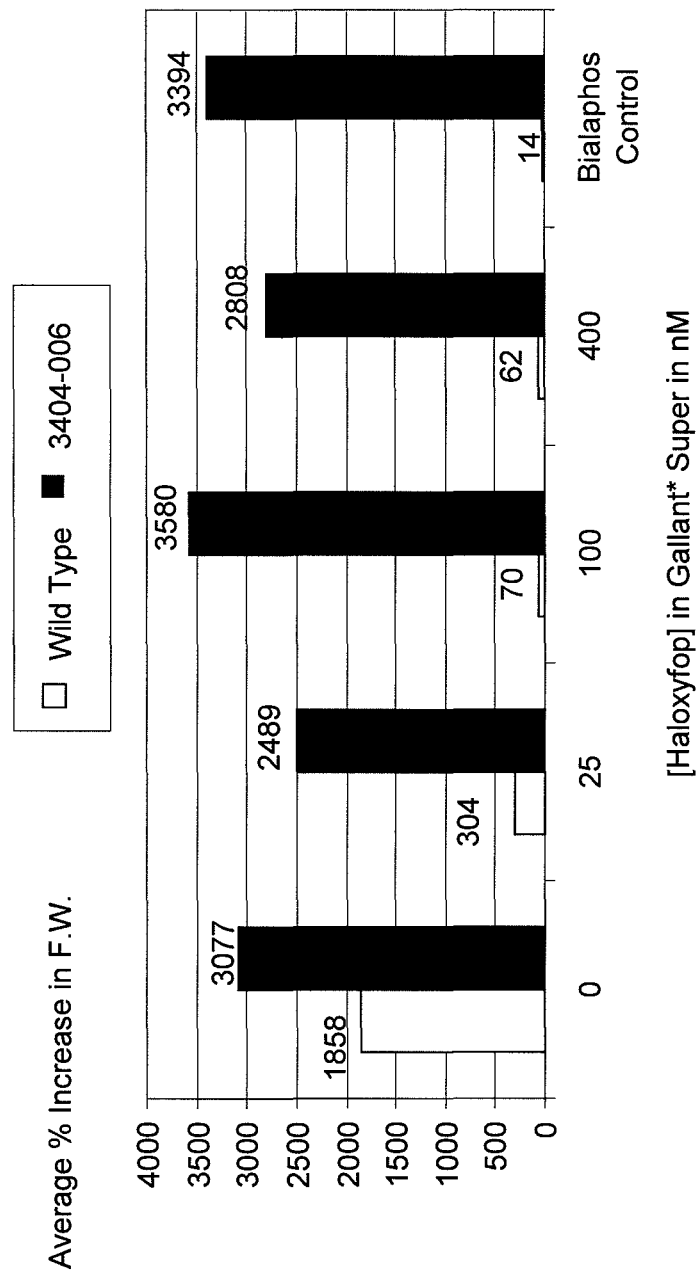
FIG. 13 illustrates dose-response data on one transgenic event, 3404-006, to haloxyfop.

A smaller subset of these events was assessed in dose-response studies in comparison to a non-transformed control. A range of concentrations of haloxyfop (from Gallant Super formulation), up to 400 nM, were tested. Dose response data for one event, 3404-006, was generated using the general methods of Example 7.4, and is shown in FIG. 13. This demonstrates that event 3404-006 showed no significant reduction in callus growth at haloxyfop concentrations up to 400 nM whereas non-transgenic corn callus tissue growth was inhibited at this rate. These data have not been normalized to account for inherent growth differences that are not related to the expression of the transgene.

7.9—WHISKERS-Mediated Transformation Using Imazethapyr Selection.

The ZmUbi1/AAD-1 (v3)/ZmPer5 cassette was removed from pDAB3404 with AscI/SwaI and inserted into pDAB2212 to create the AAD-1 (v3) and AHAS Whiskers transformation vector pDAB3415, which is also referred to as pDAS1283) Once completed, this construct was transformed into maize via silicon carbide whiskers-mediated transformation as described in Example 7.4 except 2 mL of cells were filtered, followed by a 7-day recovery on GN6 medium followed by selection on media containing 3 μM imazethapyr from Pursuit® DG herbicide. Following Invader analysis, 36 events were identified that contained the AAD-1 (v3) and the AHAS genes.

Fifty-three corn calli events from these transformations were tested in both ELISA and Western Blotting experiments for their AAD-1 (v3) expression—a subset of the data is shown below. For the events listed in Table 22, the expression levels of those detected positive ranged from 90 to over 1000 ppm of total soluble proteins.

TABLE 22

| AAD-1 Event ID Number | Expression Level (ppm) | Western Blot |
|---|---|---|
| 1283[1]-001 | 2 | − |
| 1283[1]-002 | 206 | +++ |
| 1283[1]-003 | 1 | − |
| 1283[1]-004 | 90 | +++ |
| 1283[1]-005 | 1 | − |
| 1283[1]-006 | 105 | +++ |
| 1283[1]-007 | 212 | ++ |
| 1283[1]-008 | 114 | ± |
| 1283[1]-009 | 305 | + |
| 1283[1]-010 | 2 | − |
| 1283[1]-011 | 4 | − |
| 1283[1]-012 | 200 | +++ |
| 1283[1]-013 | 134 | +++ |
| 1283[1]-014 | 4 | − |
| 1283[1]-015 | 194 | +++ |
| 1283[1]-016 | 4 | − |
| 1283[1]-017 | 196 | +++ |
| 1283[1]-018 | 3 | − |
| 1283[1]-019 | 178 | + |
| 1283[1]-020 | 260 | ++ |
| 1283[1]-021 | 144 | +++ |
| 1283[1]-022 | 140 | +++ |
| 1283[1]-023 | 191 | +++ |
| 1283[1]-024 | 392 | ++ |
| 1283[1]-025 | 368 | ++ |
| 1283[1]-026 | 14 | − |
| 1283[1]-027 | 1006 | ++ |
| Neg Control | 3 | − |
| Neg Control | 3 | − |
| Standard (0.5 μg/mL) |  | ++ |
| Standard (5 μg/mL) |  | ++++ |

7.10—Molecular Analysis: Maize Materials and Methods.

7.10.1—Tissue Harvesting DNA Isolation and Quantification.

Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, DNeasy 69109). An aliquot of the extracted DNA was then stained with Pico Green (Molecular Probes P7589) and read in the fluorometer (BioTek) with known standards to obtain the concentration in ng/μl.

7.10.2—Invader Assay Analysis.

The DNA samples are diluted to 20 ng/μl then denatured by incubation in a thermocycler at 95° C. for 10 minutes. Signal Probe mix was then prepared using the provided oligo mix and $MgCl_2$ (Third Wave Technologies). An aliquot of 7.5 μl was placed in each well of the Invader assay plate followed by an aliquot of 7.5 μl of controls, standards, and 20 ng/µl diluted unknown samples. Each well was overlaid with 15 µl of mineral oil (Sigma). The plates are then incubated at 63° C. for 1 hour and read on the fluorometer (Biotek). Calculation of % signal over background for the target probe divided by the % signal over background internal control probe will calculate the ratio. The ratio of known copy standards developed and validated with Southern blot analysis was used to identify the estimated copy of the unknown events.

7.10.3—Polymerase Chain Reaction.

A total of 100 ng of total DNA was used as the template. 20 mM of each primer was used with the Takara Ex Taq PCR Polymerase kit (Mirus TAKRROO1A). Primers for the AAD-1 (v3) PTU were (Forward—ATAATGCCAGC CTGTTAAACGCC) (SEQ ID NO:25) and (Reverse—CT-CAAGCATATGAATGACCT CGA) (SEQ ID NO:26). The PCR reaction was carried out in the 9700 Geneamp thermocycler (Applied Biosystems), by subjecting the samples to 94° C. for 3 minutes and 35 cycles of 94° C. for 30 seconds, 63° C. for 30 seconds, and 72° C. for 1 minute and 45 seconds followed by 72° C. for 10 minutes. Primers for Coding Region PCR AAD-1 (v3) were (Forward—ATG-GCTCATGCTGCCCTCAGCC) (SEQ ID NO:27) and (Reverse—CGGGC AGGCCTAACTCCACCAA) (SEQ ID NO:28). The PCR reaction was carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 1 minute and 45 seconds followed by 72° C. for 10 minutes. PCR products were analyzed by electrophoresis on a 1% agarose gel stained with EtBr.

7.10.4—Southern Blot Analysis.

Southern blot analysis was performed with total DNA obtained from Qiagen DNeasy kit. A total of 2 µg of DNA was subjected to an overnight digestion of Afl II and also EcoRV for pDAB3404, NcoI for pDAB3403, and SpeI for pDAB1421 to obtain integration data. After the overnight digestion an aliquot of ~100 ng was run on a 1% gel to ensure complete digestion. After this assurance the samples were run on a large 0.85% agarose gel overnight at 40 volts. The gel was then denatured in 0.2 M NaOH, 0.6 M NaCl for 30 minutes. The gel was then neutralized in 0.5 M Tris HCl, 1.5 M NaCl pH of 7.5 for 30 minutes. A gel apparatus containing 20×SSC was then set up to obtain a gravity gel to nylon membrane (Millipore INYC00010) transfer overnight. After the overnight transfer the membrane was then subjected to UV light via a crosslinker (Stratagene UV stratalinker 1800) at 1200×100 microjoules. The membrane was then washed in 0.1% SDS, 0.1 SSC for 45 minutes. After the 45 minute wash, the membrane was baked for 3 hours at 80° C. and then stored at 4° C. until hybridization. The hybridization template fragment was prepared using the above coding region PCR using plasmid pDAB3404. The product was run on a 1% agarose gel and excised and then gel extracted using the Qiagen (28706) gel extraction procedure. The membrane was then subjected to a pre-hybridization at 60° C. step for 1 hour in Perfect Hyb buffer (Sigma H7033). The Prime it RmT dCTP-labeling rxn (Stratagene 300392) procedure was used to develop the p32 based probe (Perkin Elmer). The probe was cleaned up using the Probe Quant. G50 columns (Amersham 27-5335-01). Two million counts CPM were used to hybridize the southern blots overnight. After the overnight hybridization the blots were then subjected to two 20 minute washes at 65° C. in 0.1% SDS, 0.1 SSC. The blots were then exposed to film overnight, incubating at −80° C.

Example 8—In Vivo Tolerance and Field Tolerance Data Generated from PAT-Selected (pDAB3404) AAD-1 (v3) Events 8.1—Tolerance of $T_0$ Corn Plants to AOPP Herbicides.

If more than 15 clone plants per event were successfully regenerated, then extra plants were transferred to the greenhouse for preliminary tolerance screening with postemergence-applied AOPP herbicides on $T_0$ corn plants. Greenhouse-acclimated plants were allowed to grow until 2-4 new, normal looking leaves had emerged from the whorl (i.e., plants had transitioned from tissue culture to greenhouse growing conditions). Plants were grown at 27° C. under 16 hour light: 8 hour dark conditions in the greenhouse. Plants were then treated with commercial formulations of one of three AOPP herbicides: Assure® II (DuPont), Clincher* (Dow AgroSciences), or Gallant Super* (Dow AgroSciences) for quizalofop, cyhalofop, or haloxyfop, respectively. Herbicide applications were made with a track sprayer at a spray volume of 187 L/ha, 50-cm spray height, and all sprays contained 1% v/v Agridex crop oil concentrate adjuvant. The number of clones of each event varied from week to week due to the rate of regeneration and acclimation of each event. Overall, an attempt was made to treat representative clones of each event with a range of herbicide doses ranging from 1× lethal dose (~⅛× field dose) up to 8× field doses (64× lethal dose). A lethal dose is defined as the rate that causes >95% injury to the Hi-II inbred. Hi-II is the genetic background of the transformants of the present invention.

AOPP's are generally very potent corn-killing herbicides. Three to four leaf Hi-II corn grown from seed is effectively killed (>95% injury) with 8.8, 62.5, and 4.4 g ae/ha of haloxyfop, cyhalofop, and quizalofop, respectively. Each AAD-1 (v3)-transformed line tested survived a minimally lethal dose of each AOPP herbicide tested. In fact, most lines tested survived with no visible injury (14 DAT) even when treated with an 8× field dose (64× lethal dose) of quizalofop. Several individual clones from events "017" and "038," however, did incur significant injury at elevated rates. This could be a function of lower gene expression due to how or where the gene was inserted.

The high level of AOPP tolerance was demonstrated in most events, even when applications were made to plants just coming out of tissue culture ($T_0$ stage). Significantly, this tolerance was shown for all three AOPP herbicides and likely will extend to all AOPP herbicides as previously shown for AAD-1 in vitro.

Figure 14:
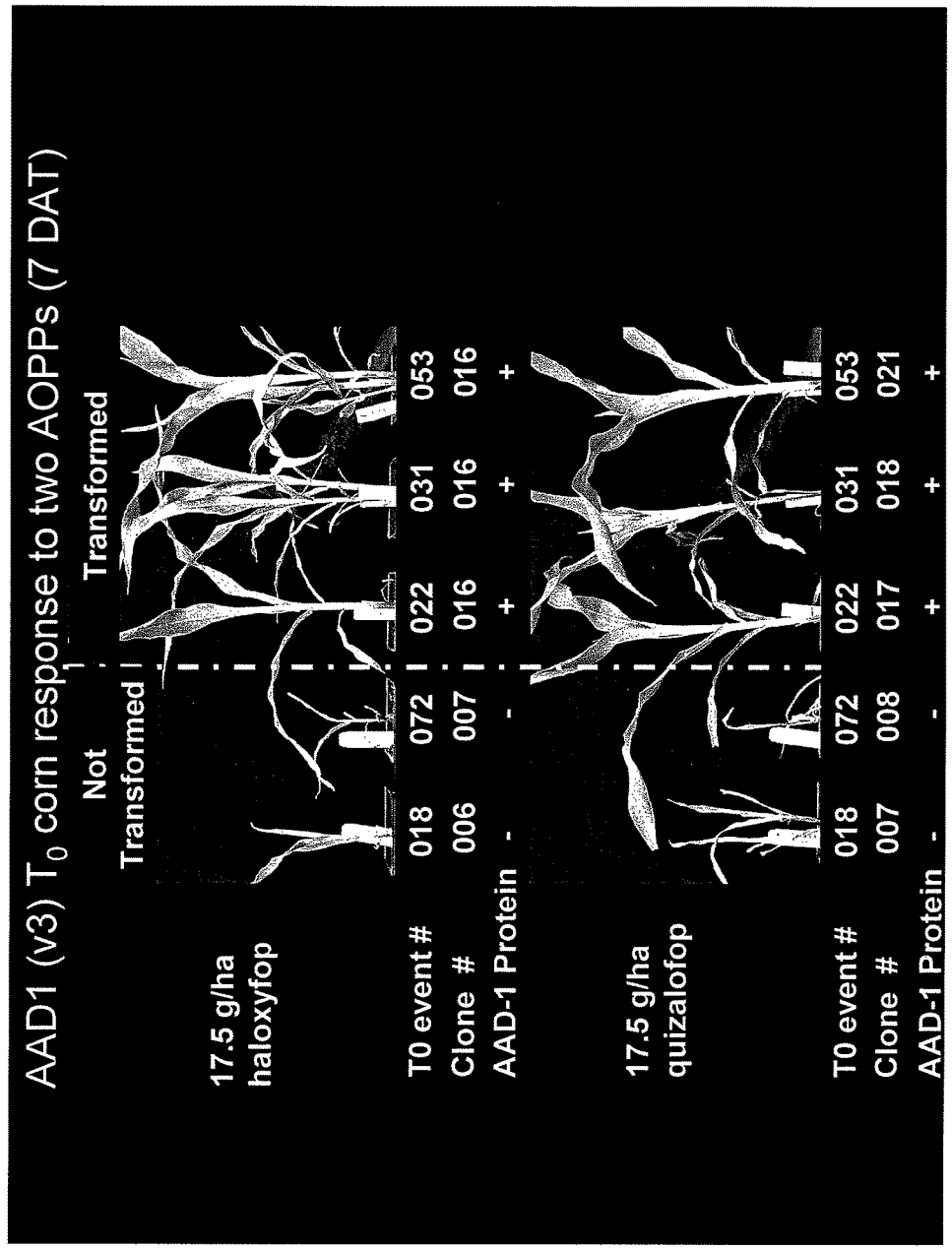
FIG. 14 shows the responses of several AAD-1 (v3)-transformed and non-transformed event clones to lethal doses of two AOPP herbicides (haloxyfop and quizalofop) applied as a postemergence spray 1 week prior.

FIG. 14 shows the responses of several AAD-1 (v3)-transformed and non-transformed event clones to lethal doses of two AOPP herbicides (haloxyfop and quizalofop) applied 1 week prior.

Table 23 shows data for the responses of selected AAD-1 (v3)-transformed $T_0$ corn events to three AOPP herbicides applied postemergence.

TABLE 23

Selected AAD-1 (v3)-transformed T0 corn events response to three AOPP herbicides applied postemergence.

| Construct | Event | Clone | Haloxyfop* g ae/ha | Cyhalofop** g ae/ha | Quizalofop*** g ae/ha | % Injury 14 DAT |
|---|---|---|---|---|---|---|
| 3404 | 001 | 016 | 8.8 | | | 0 |
| 3404 | 001 | 018 | | 62.5 | | 0 |
| 3404 | 001 | 017 | | | 8.8 | 0 |
| 3404 | 001 | 019 | | | 8.8 | 30 |
| 3404 | 001 | 020 | | | 35 | 0 |
| 3404 | 017 | 018 | | | 35 | 0 |
| 3404 | 017 | 019 | | | 35 | 0 |
| 3404 | 017 | 020 | | | 70 | 0 |
| 3404 | 017 | 021 | | | 70 | 0 |
| 3404 | 017 | 022 | | | 140 | 0 |
| 3404 | 017 | 023 | | | 140 | 30 |
| 3404 | 017 | 024 | | | 280 | 30 |
| 3404 | 017 | 025 | | | 280 | 20 |
| 3404 | 022 | 019 | 8.8 | | | 0 |
| 3404 | 022 | 020 | 17.5 | | | 0 |
| 3404 | 022 | 016 | 17.5 | | | 0 |
| 3404 | 022 | 024 | | 62.5 | | 0 |
| 3404 | 022 | 018 | | 125 | | 0 |
| 3404 | 022 | 021 | | | 8.8 | 0 |
| 3404 | 022 | 017 | | | 17.5 | 0 |
| 3404 | 022 | 022 | | | 35 | 0 |
| 3404 | 022 | 023 | | | 70 | 0 |
| 3404 | 033 | 012 | | | 35 | 0 |
| 3404 | 033 | 013 | | | 70 | 0 |
| 3404 | 033 | 014 | | | 70 | 0 |
| 3404 | 033 | 015 | | | 140 | 0 |
| 3404 | 033 | 016 | | | 280 | 0 |
| 3404 | 038 | 016 | 8.8 | | | 0 |
| 3404 | 038 | 018 | | 62.5 | | 0 |
| 3404 | 038 | 017 | | | 8.8 | 0 |
| 3404 | 038 | 019 | | | 35 | 70 |
| 3404 | 038 | 020 | | | 35 | 80 |
| 3404 | 038 | 021 | | | 70 | 80 |
| 3404 | 038 | 022 | | | 70 | 80 |
| | | | (lethal dose = 8.8 g ae/ha) | (lethal dose = 62.5 g ae/ha) | (lethal dose = 4.4 g ae/ha) | |

*Gallant super# + 1% COC (v/v)
**Clincher# + 1% COC (v/v)
***Assure II + 1% COC (v/v)
Trademark of Dow AgroSciences, LLC 8.2—Field Tolerance of pDAB3404 $T_1$ Corn Plants to Quizalofop 2,4-D, and Glufosinate Herbicides.

Two field trials were established at field stations in Hawaii and Indiana. Corn seed from inbred $T_1$ plants were utilized to evaluate sixteen AAD1 event lines for tolerance against quizalofop and 2,4-D. Three non-transformed hybrids were included for comparison purposes. The hybrid Hi-IIx 5XH571 is of the same parentage as the AAD-1 (v3) event lines. The hybrid Croplan 585SR is a sethoxydim resistant line.

The experimental design was a split-plot with four replications. The main plot was herbicide treatment and the sub-plot was AAD-1 (v3) event or comparison hybrid. Plots were one row by 3.7 meters with approximately twenty-five seeds planted in each row. For AAD1 events, seeds from a different lineage within the event were planted in each replicate.

Glufosinate at 560 g ai/ha was applied to AAD-1 (v3) plots at the V2 stage to eliminate non-transformed plants. Experimental treatments included commercial formulations of quizalofop applied at 70 and 140 g ae/ha, 2,4-D (dimethylamine salt) at 560 and 1120 g ae/ha, and an untreated control. Treatments were applied using backpack broadcast boom equipment delivering 187 L/ha carrier volume at 130-200 kpa pressure. Quizalofop treatments were applied at the V3-V4 corn stage and 2,4-D treatments were applied at the V5-V6 stage.

Quizalofop treated plots were visually assessed for crop injury at one and three weeks after application (WAA) using a 0-100% scale, where 0 equals no injury and 100 equals complete death. 2,4-D treated plots were visually assessed for plant leaning at 2 days after application (DAA) using 0-100% scale where 0 equals no leaning from any plant and 100 equals all plants prone. Additionally, 2,4-D plots were visually assessed at 3-4 WAA for brace root deformation using a 0-10 scale.

8.2.1—Results.

AAD-1 (v3) event response to the highest rates tested of quizalofop and 2,4-D are shown in Table 24. These rates represent approximately twice the normal commercial use rates. Non-transformed hybrids were severely injured (80-100%) by quizalofop at 70 g ae/ha including the sethoxydim resistant line, although it displayed slightly better tolerance than the other two hybrids. All AAD-1 (v3) events except one lineage of event 3404.001 displayed excellent tolerance to quizalofop at 70 g ae/ha. No visible symptoms were observed on the AAD-1 (v3) events except with the events noted above.

TABLE 24

| | Treatment (rate) = | | | | | | | | | |
|---|---|---|---|---|---|---|---|---|---|---|
| | Quizalofop (140 g ae/ha) | | 2,4-D amine (1120 g ae/ha) | | 2,4-D amine (1120 g ae/ha) | Analysis Results Evaluation = | | | Resistance Segregation Ratios following Liberty Spray | |
| | % Injury 3 WAA (0-100 scale) | | % Leaning 2 DAA (0-100 scale) | | Braceroot Deformation 3-4 WAA (0-10 scale) | AAD-1 copy number leaf (Southern | AAD-1 Leaf Western | AAD-1 Leaf | $T_1$ Population Average | $T_2$ Population Average |
| Event or Hybrid | IN | HI | IN | HI | IN | HI | analysis) | Blot $T_0$ | ELISA $T_0$ | IN | HI | HI |
| 3404.001 | 25 | 25 | 0 | 5 | 1 | 2 | 3 | +++ | +++ | 40% | 47% | X |
| 3404.006 | 0 | 0 | 0 | 0 | 0 | 0 | 1 | ++ | +++ | 33% | 26% | X |
| 3404.013 | 0 | 0 | 0 | 0 | 0 | 0 | 1 | + | +++ | 63% | 58% | X |
| 3404.017 | 0 | 0 | 1 | 0 | 0 | 0 | 2 | +/− | ++ | 48% | 47% | X |
| 3404.020 | 0 | 0 | 0 | 0 | 0 | 0 | 2 | ++ | +++ | 50% | 51% | X |
| 3404.022 | 0 | 0 | 1 | 0 | 0 | 0 | 1 | + | ++ | 51% | 57% | 76%* |
| 3404.025 | 0 | 0 | 0 | 0 | 0 | 0 | 2 | +++ | ++++ | 55% | 59% | X |
| 3404.027 | 0 | 0 | 3 | 0 | 0 | 0 | 5 | + | ++ | 51% | 50% | X |
| 3404.031 | 0 | 0 | 1 | 0 | 0 | 0 | 1 | ++ | ++++ | 47% | 43% | 61%* |
| 3404.033 | 0 | 0 | 0 | 0 | 0 | 0 | 2 or 3 | + | ++ | 52% | 49% | X |
| 3404.036 | 0 | 0 | 0 | 0 | 0 | 0 | 4 | ++ | +++ | 52% | 48% | X |
| 3404.044 | 0 | 0 | 1 | 0 | 0 | 1 | 1 | + | +/− | 50% | 48% | X |
| 3404.050 | 0 | 0 | 0 | 1 | 0 | 1 | 2 | nd | nd | 38% | 28% | X |
| 3404.053 | 0 | 0 | 1 | 0 | 0 | 0 | 2 | +++ | +++ | 48% | 56% | X |
| 3404.074 | 0 | 0 | 0 | 0 | 0 | 0 | 1 | ++ | +++ | 53% | 52% | 73%* |
| 3404.082 | 0 | 0 | 0 | 0 | 0 | 1 | 3 | nd | nd | 38% | 36% | X |
| DK493 | 100 | 100 | 20 | 23 | 8 | 9 | | | | | | |
| HI-II X 5XH571 | 100 | 100 | 13 | 34 | 7 | 9 | | | | | | |
| CROPLAN 585SR | 80 | 96 | 11 | 33 | 9 | 9 | | | | | | |

*Fits single locus dominant trait segregation as determined by chi square analysis (P > 0.05)

2,4-D at the 1120 g ae/ha rate caused significant levels (11-33%) of epinastic leaning in the non-transformed hybrids, a normal response when applied beyond the V4 growth stage. Little or no leaning was observed with all AAD-1 (v3) events except one lineage of 3404.001 (Indiana location only) where moderate levels (5-13%) of leaning occurred.

Brace roots of non-transformed hybrids were severely deformed (rating of 9 on a 0-10 scale) by 2,4-D at the 1120 g ae/ha rate. Again, this is a normal response to 2,4-D applied beyond the V4 growth stage. As with the leaning response, little or no brace root injury was observed with all AAD-1 (v3) events except one lineage of 3404.001.

Similar trends occurred with lower tested rates of quizalofop and 2,4-D although at reduced but still significant response levels in the non-transformed hybrids (data not shown).

Figure 16:
FIG. 16 shows AAD-1 (v3)-transformed corn tolerant to 8× field rates of quizalofop (Assure II) under field conditions.

These results indicate that most AAD-1 (v3) transformed event lines displayed a high level of resistance to quizalofop and 2,4-D at rates that were lethal or caused severe epinastic malformations to non-transformed corn hybrids. See also FIG. 16.

8.2.2—Expected Mendelian Segregation Ratios on Three $T_2$ Events.

Plants from individual lineages of each event were randomly self-pollinated in the field. $T_2$ seed were hand harvested at physiological maturity. Based on single gene copy number (see Table 24 above) and overall performance in $T_1$ generation (segregation, herbicide tolerance, and vigor), three events (022, 031, and 074) were chosen for further evaluation in the field. Breeding rows of each event were planted using a precision cone planter each consisting of 2500-3000 seeds. At the V2 growth stage, all AAD-1 (v3) lines were sprayed with 140 g ae/ha quizalofop (Assure® II) using a backpack sprayer as previously described. This rate rapidly killed all "null" (untransformed) segregants. Each event had a segregation ratio consistent with Mendelian inheritance of a single locus, dominant gene (3 resistant:1 sensitive, or 75% survival) (see Table 24). Homozygotes and hemizygotes from event 74 were identified by zygosity testing (refer to AAD-1 (v3) Invader assay description for corn). Hemizygous plants were removed and homozygous AAD-1 (v3) plants were crossed with BE1146 corn inbred introgressed and homozygous for glyphosate resistance trait, NK603, creating a homogeneous $F_1$ hybrid seed that is hemizygous for glyphosate resistance, AAD-1 (v3), and glufosinate resistance.

8.3—Stacking of AAD-1 (v3) and PAT with Glyphosate Resistance Genes in Corn.

Homozygous $T_2$ AAD-1 (v3)/PAT corn plants were crossed with glyphosate resistant corn plants producing $F_1$ seed containing AAD-1 (v3), PAT, and glyphosate resistance genes as described in the previous example.

$F_1$ seeds were planted individually into 3-inch pots prepared with Metro-Mix® 360 growing medium (Sun Gro Horticulture). The pots were initially subirrigated with Hoagland's solution until wet, then allowed to gravity drain, and grown at 27° C. under 16 hour light:8 hour dark conditions in the greenhouse. For the remainder of the study the plants were subirrigated with deionized water.

Plants were allowed to grow until 2-4 leaves had emerged from the whorl. At this point herbicide applications were made with a track sprayer at a spray volume of 187 L/ha, 50-cm spray height. The plants were sprayed with rates of 2,4-D DMA, glyphosate, glufosinate, and various combinations of the three. All applications were formulated in 200 mM Hepes buffer (pH 7.5). In spray applications where glufosinate was present the treatment was formulated with the addition of 2% w/v ammonium sulfate.

At 3 and 14 days after treatment (DAT) plants were evaluated. Plants were assigned injury rating with respect to stunting, chlorosis, and necrosis. Plants assigned an injury rating of 90% or above are considered dead. Results of the study at 14 DAT can be seen in Table 25.

TABLE 25

| | | % Injury at 14 DAT | |
|---|---|---|---|
| | Field Rate | Hi II X 5XH751 Ave | RR/PAT/AAD1 Ave |
| Untreated control | — | 0 | 0 |
| 840 g ae/ha glyphosate | 1X | 98 | 0 |
| 1680 g ae/ha glyphosate | 2X | 100 | 0 |
| 3360 g ae/ha glyphosate | 4X | 100 | 0 |
| 560 g ae/ha 2,4-D DMA | 1X | 10 | 0 |
| 1120 g ae/ha 2,4-D DMA | 2X | 14 | 0 |
| 2240 g ae/ha 2,4-D DMA | 4X | 29 | 0 |
| 470 g ae/ha glufosinate | 1X | 80 | 0 |
| 940 g ae/ha glufosinate | 2X | 90 | 3 |
| 1880 g ae/ha glufosinate | 4X | 96 | 15 |
| 840 g ae/ha glyphosate + 560 g ae/ha 2,4-D DMA | 1X + 1X | 96 | 1 |
| 1680 g ae/ha glyphosate + 1120 g ae/ha 2,4-D DMA | 2X + 2X | 100 | 2 |
| 3360 g ae/ha glyphosate + 2240 g ae/ha 2,4-D DMA | 4X + 4X | 100 | 1 |
| 470 g ae/ha glufosinate + 560 g ae/ha 2,4-D DMA | 1X + 1X | 89 | 5 |
| 940 g ae/ha glufosinate + 1120 g ae/ha 2,4-D DMA | 2X + 2X | 91 | 10 |
| 1880 g ae/ha glufosinate + 2240 g ae/ha 2,4-D DMA | 4X + 4X | 97 | 13 |
| 840 g ae/ha glyphosate + 470 g ae/ha glufosinate | 1X + 1X | 90 | 5 |
| 1680 g ae/ha glyphosate + 940 g ae/ha glufosinate | 2X + 2X | 98 | 15 |
| 3360 g ae/ha glyphosate + 1880 g ae/ha glufosinate | 4X + 4X | 100 | 15 |

This study demonstrated that the AAD-1 (v3) gene in corn can be stacked with a glyphosate resistance gene and a glufosinate resistance gene to provide robust field-level tolerance to 2,4-D, glyphosate, and glufosinate alone or in tank mix combinations.

8.3.1—Resistance of AAD-1 (v3) Corn Using a Tank Mix of 2,4-D DMA and Quizalofop.

$T_2BC_1$ seeds of hemizygous event number 3404-025.001R/R001 Bulked.001.S058 were planted individually into 3-inch pots prepared with Metro-Mix® 360 growing medium. The pots were initially sub-irrigated with Hoagland's solution until wet, then allowed to gravity drain, and grown at 27° C. under 16 hour light:8 hour dark conditions in the greenhouse. For the remainder of the study the plants were sub-irrigated with de-ionized water.

Plants were allowed to grow until V1 stage in the greenhouse. At this point the plants were selected with 560 g ae/ha Assure® II with the addition of 1% Agridex crop oil concentrate in 200 mM Hepes buffer with the research track sprayer set at 187 L/ha. Plants were allowed 4 days to show symptoms of the selection. All plants were uninjured. Herbicide applications were made with a track sprayer at a spray volume of 187 L/ha, 18-in spray height. All applications were formulated in 200 mM Hepes buffer (pH 7.5) with the addition of 1% v/v Agridex.

At 3 and 14 days after treatment (DAT) plants were evaluated. Plants were assigned injury rating with respect to stunting, chlorosis, and necrosis. Plants assigned an injury rating of 90% or above are considered dead. Plants from this particular lineage had 0% injury at 14 DAT for all tank mixed combinations, while the wild-type had 100% injury. These results indicate AAD-1 (v3) not only provides robust field level resistance to 2,4-D and quizalofop individually, but also to exaggerated rates of multiple combinations of the two chemistries. One could logically expect to implement novel weed control measures with combinations of phenoxy auxins and AOPP graminicides in corn (or other crops transformed with AAD-1) not previously enabled by a single gene HTC.

8.3.2—Tolerance of (pDAB3403) $T_0$ Corn Plants to Quizalofop Herbicide.

A target of approximately eight $T_0$ plant clones from each of 17 events were regenerated and transferred to the greenhouse for preliminary tolerance screening with postemergence-applied discriminating rate of quizalofop herbicide applied by track sprayer at 35 g ae/ha (1× field rate, 4× lethal dose) to 3-leaf, greenhouse-adapted $T_0$ corn plants using track sprayer conditions previously described. Plants were rated as Resistant or Sensitive 7 days after treatment. Control, non-transgenic corn was included with each spray application. Two events, Event 014 and 047, had two or more $T_0$ clones sensitive to 35 g ae/ha quizalofop, indicating an unexpected level of sensitivity for this event. The 15 other events showed stable integration, protein expression, and the ability to tolerate a 4× lethal dose of quizalofop at the whole plant level.

8.3.3 Expression of AAD-1 (v3) with Respect to Quizalofop Tolerance.

Figure 15:
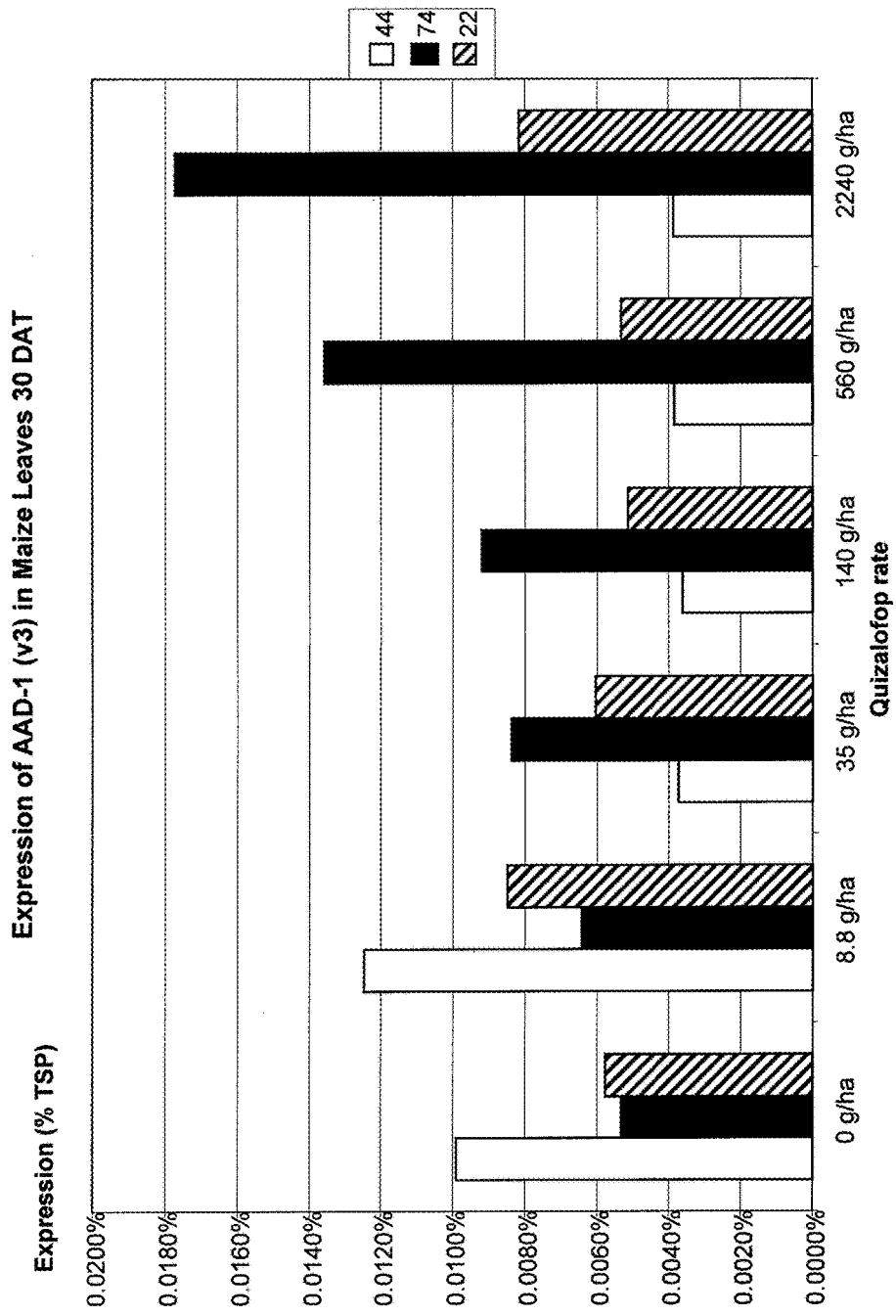
FIG. 15 shows three different T2 lineages from 3404 transformations that were pre-screened with Liberty® to remove nulls, which were chosen to compare their tolerance to quizalofop with respect to their AAD-1 expression. Expression was measured at 14 DAT (data not shown) and at 30 DAT.

Three different T2 lineages from 3404 transformations that were pre-screened with Liberty® (as described previously) to remove nulls were chosen to compare their tolerance to quizalofop with respect to their AAD-1 (v3) expression. Expression was measured at 14 DAT (data not shown) and at 30 DAT (see FIG. 15.). The highest tolerance line, event 3404-074, always expressed with a higher amount of AAD-1 (v3) than the other two events at 1× and higher field rates. This data concludes that corn expressing AAD-1 (v3) can be protected from quizalofop injury at the highest level tested (2,240 g/ha), which is 16 times the 1× field dose of 35 g/ha. In addition, the expression level was consistent throughout the period of the experiment.

Example 9—*Agrobacterium*-Mediated Transformation of Maize with AAD-1 (v3)

9.1—Plant Material.

Seeds of a "High II" (i.e., Parent A and B) $F_1$ cross (Armstrong et al., 1991) are planted directly into 5 gallon-pots containing 95:5 Metro-Mix® 360: Mineral soil. The plants are grown in the greenhouse with a 16 hour photoperiod supplemented by a combination of high pressure sodium and metal halide lamps.

9.2—Tissue Source.

For obtaining immature Hi-II (F2) embryos, controlled sib-pollinations were performed. On the day of pollination, actively shedding tassels are bagged, and fresh pollen is collected and applied carefully onto the silks. Immature embryos were isolated as described in Example 7.2.

9.3—Preparation of a Superbinary Vector.

Construction of an *Agrobacterium* construct, pDAB2272, containing the AAD-1 (v3) gene in combination with the AHAS selectable marker gene was accomplished by isolating the 3443 base pair NotI fragment from pDAB3404 containing ZmUbi1 v2/AAD-1 (v3)/ZmPer5 v2 and inserting it into the NotI site of pDAB8549. The resulting plasmid contains the ZmUbi1 v2/AAD-1 (v3)/ZmPer5 v2 and the OsAct1 v2/AHAS v3/ZmLip v1 cassettes flanked by non-identical MAR regions in the direct orientation. This was subsequently transformed into LBA4404/pSB1 to create the superbinary vector, which was named pDAB3602 but was also referred to as pDAS1421.

9.4—Bacterial Supply.

All transformations use the "Super Binary" vector from Japan Tobacco described in U.S. Pat. No. 5,591,616 ("Method for Transforming Monocotyledons"). To prepare the *Agrobacterium* suspension for treatment, 1-2 loops of pDAS1421 recombinant bacteria from a YP streak plate was put into 5 ml of LS-inf. Mod medium (LS Basal Medium (Linsmaier and Skoog, 1965), N6 vitamins, 1.5 mg/L 2,4-D, 68.5 g/L sucrose, 36.0 g/L glucose, 6 mM L-proline, pH 5.2). The mixture was vortexed until a uniform suspension was achieved. The bacterial concentration was taken using a Klett-Summerson Photoelectric Colorimeter by reading the density of the solution. The solution was adjusted to a concentration of Klett 200 (~1×10$^9$ cfu/ml) and 100 µM actetosyringone added to the solution.

9.5—Infection and Cocultivation.

The immature embryos are isolated directly into a microfuge tube containing 2 ml LS-inf. Mod liquid medium. Each tube, containing ~100 embryos, is vortexed for 3-5 sec. The medium is removed and replaced with fresh liquid medium and the vortex is repeated. The liquid medium is again removed and this time replaced with an *Agrobacterium* solution at the Klett 200 concentration. The *Agrobacterium* and embryo mixture is vortexed for 30 sec. Following a 5 minute incubation at room temperature, the embryos were transferred to LS-As Mod medium (LS Basal Medium, N6 vitamins, 1.5 mg/L 2,4-D, 30.0 g/L sucrose, 6 mM L-proline, 0.85 mg/L AgNO$_3$, 1, 100 µM actetosyringone, 3.0 g/L Gelrite, pH 5.8) for a 5-day co-cultivation at 25° C.

9.6—Dose Response Using Immature Embryos.

Figure 17:
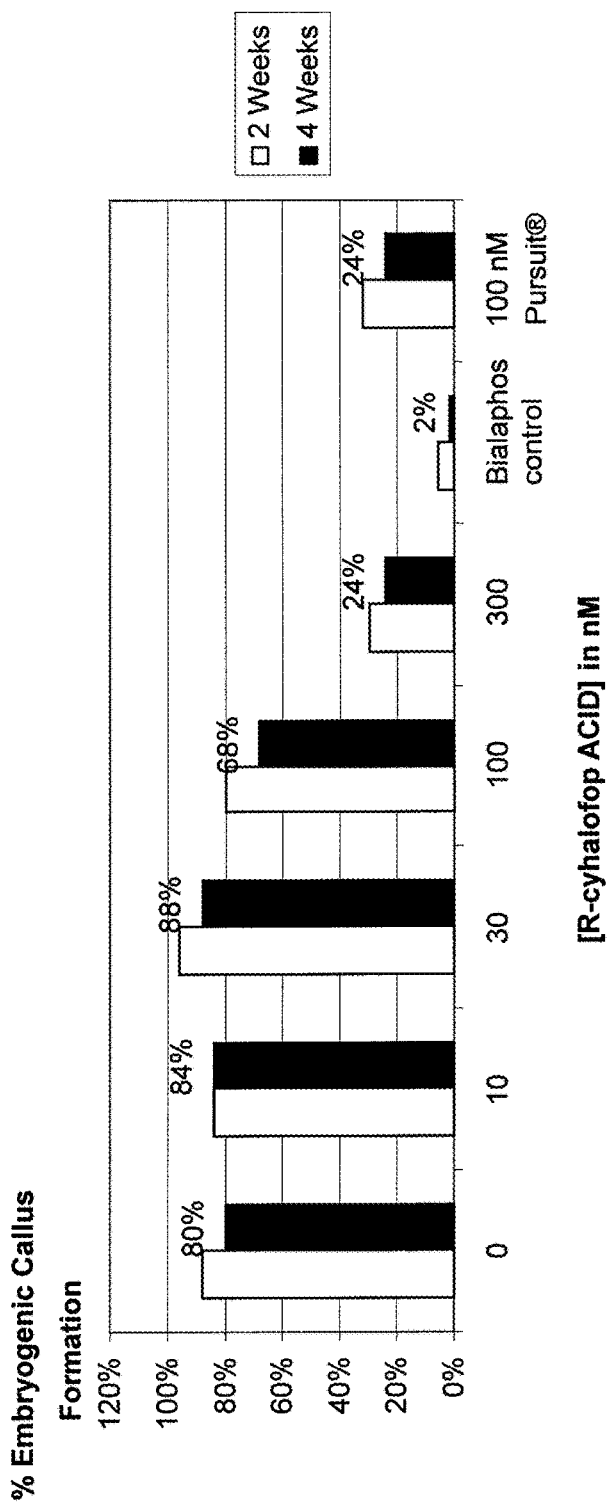
FIG. 17 illustrates data from immature maize embryos grown on cyhalofop-containing media.

Dose response studies were initiated using immature embryos treated with *Agrobacterium* strain LBA4404 lacking a plasmid as described previously. Once treated, embryos were allowed to co-cultivate for 5 days at 25° C. and were then transferred to selection media containing various levels of R-haloxyfop or R-cyhalofop. Embryos were also transferred to media containing 1 mg/L bialaphos and 100 nM imazethapyr as negative controls. Embryos were scored for % embryogenic callus formation after 2 weeks, and then again after 4 weeks. Embryos were tested on R-haloxyfop levels up to 30 nM; however, insufficient reduction of callus formation was seen at the highest levels, so higher concentrations (50-100 nM) were used during transformation experiments. Data from embryos grown on cyhalofop-containing media is shown in FIG. 17.

9.7—Selection.

After co-cultivation, the embryos were moved through a 2-step selection scheme after which transformed isolates were obtained. For selection, LSD Mod medium (LS Basal Medium, N6 vitamins, 1.5 mg/L 2,4-D, 0.5 g/L MES, 30.0 g/L sucrose, 6 mM L-proline, 1.0 mg/L AgNO$_3$, 250 mg/L cephotaxime, 2.5 g/L Gelrite, pH 5.7) was used along with one of two selection levels of either haloxyfop, cyhalofop, or imazethapyr. Throughout the selection phase, the embryos are cultured in the dark at 28° C. The embryos were first transferred to an initial level of selection (50-100 nM R-haloxyfop or 300 nM R-cyhalofop) for 14 days, then moved up to a higher selection level (250-500 nM R-haloxyfop acid or 1.5 µM cyhalofop) at a rate of 5 embryos/plate. A subset of embryos were similarly stepped-up from 100 to 500 nM imazethapyr from Pursuit® DG as a positive control. Pursuit® is used as the chemical selection agent when the AHAS gene is used, based on U.S. Pat. No. 5,731,180. Tissue was transferred at biweekly intervals on the same medium until embryogenic colonies were obtained. These colonies were maintained on the high selection pressure for the remainder of the culture period. The recovered transgenic colonies were bulked up by transferring to fresh selection medium at 2-week intervals for regeneration and further analysis.

9.8.—Regeneration and Seed Production.

For regeneration, the cultures are transferred to 28 "induction" medium and 36 "regeneration" medium as described previously containing either 100 nM R-haloxyfop or 1.5 cyhalofop for differentiation of plantlets. When plantlets were established, they were transferred to SHGA tubes to allow for further growth and development of the shoot and roots as described previously. Controlled pollinations for seed production were conducted as described previously.

9.9—Event Recovery and Analysis Particulars; Whole Plant Screening of T$_0$ Corn Lineages Containing AAD-1 (v3) and AHAS (pDAS1421).

Seventy-two *Agrobacterium*-transformed events were selected on various levels of R-haloxyfop acid and R-cyhalofop acid in vitro. Twenty-two callus samples were analyzed by Southern blot analysis for stable integration of AAD-1 (v3) into the genome as described previously. Ten single copy events, as indicated in Table 26, were chosen to be regenerated.

TABLE 26

| Corn event | In vitro Selection agent (nM) | Southern Copy # (callus) AAD-1 | Western Blot (AAD-1) T$_0$ Callus | Assessment of T$_0$ lineages resistant to 35 g ae/ha quizalofop | |
|---|---|---|---|---|---|
| | | | | Resistant | Sensitive |
| 1421[21]-016 | 50 Haloxyfop | 1 | + | 8 | 0 |
| 1421[22]-020 | 100 Haloxyfop | 1 | ++ | 8 | 0 |
| 1421[22]-022 | 100 Haloxyfop | 1 | + | 8 | 0 |
| 1421[22]-023 | 100 Haloxyfop | 1 | ++ | 8 | 0 |
| 1421[3]-036 | 100 Haloxyfop | 1 | ++ | 8 | 0 |
| 1421[4]-031 | 300 Cyhalofop | 1 | ++ | 9 | 0 |
| 1421[4]-032 | 300 Cyhalofop | 1 | ++ | 8 | 0 |
| 1421[4]-033 | 300 Cyhalofop | 1 | ++ | 12 | 0 |
| 1421[4]-034 | 300 Cyhalofop | 1 | ++ | 8 | 0 |
| 1421[4]-035 | 300 Cyhalofop | 1 | ++ | 6 | 0 |

Events with more than 1 copy were not taken to the greenhouse

A minimum six regenerated clonal lineages per event were moved to soil in the greenhouse and screened using a track sprayer as previously described to apply 35 g ae/ha quizalofop when 2-4 new, normal leaves had emerged (see section 8.3.3). Presence of AAD-1 protein on a Western blot correlated perfectly with herbicide resistance in the $T_0$ generation regardless of which AOPP herbicide was used for selection. There is no negative impact of the second HTC gene (AHAS) on the function of the AAD-1 (v3).

Example 10—Purification of AAD-1 (v1) for Antibody Creation and Biochemical Characterization All operations during purification were carried out at 4° C. Frozen or fresh *E. coli* cells from approximately 1 L culture, grown and induced as in Example 3, were re-suspended in 200 ml of extraction buffer containing 20 mM Tris-HCl, 1 mM EDTA, and 2 ml of Protease Inhibitor Cocktail (Sigma), and disrupted by ultrasonication treatment on ice using a Branson sonifier. The soluble extract was obtained by centrifugation in a GSA rotor (Sorvall) at 12,000 rpm (24,000 g) for 20 minutes. The supernatant was then loaded onto a Mono Q ion exchange column (Pharmacia HR 10/10) equilibrated with 20 mM Tris-HCl, 1 mM EDTA, pH 8.0, and the column was washed with same buffer for 10 CV (80 ml). The protein was eluted with 80 ml of a 0 to 0.25 M NaCl linear gradient in column buffer, while 2 ml fractions were collected. The fractions containing AAD-1 (v1) were pooled and concentrated using MWCO 30 kDa membrane centrifugation spin columns (Millipore). The sample was then further separated on a Superdex 200 size exclusion column (Pharmacia, XK 16/60) with buffer containing 20 mM Tris-HCl, 0.15 M NaCl, and 1 mM DTT, pH 8.0 at a flow rate of 1 ml/min. Purification procedures were analyzed by SDS-PAGE, and protein concentration was determined by Bradford assay using bovine serum albumin as standard.

Example 11—Recombinant AAD1 Purification and Antibody Production

Plasmid pDAB3203 containing the AAD-1 (v1) gene was maintained frozen at −80° C. in TOP10F' cells (Invitrogen) as Dow Recombinant strain DR1878. For expression, plasmid DNA purified from TOP10F' cell culture using Promega's Wizard Kit (Fisher cat. #PR-A1460) was transformed into BL-21 Star (DE3) cells (Invitrogen cat. #C6010-03) following manufacturer's protocol. After transformation, 50 µL of the cells were plated onto LB S/S agar plates, and incubated overnight at 37° C. All colonies from the entire agar plate were scraped into 100 mL LB in a 500 mL tribaffled flask and incubated at 37° C. with 200 rpm shaking for 1 hr. Gene expression was then induced with 1 mM IPTG, and incubated for 4 hrs at 30° C. with 200 rpm shaking. All 100 mL of culture was centrifuged at 4000 rpm for 20 min. The supernatant were then discarded, and the pellets were resuspended in 200 mL of extraction containing 20 mM Tris-HCl (pH 8.0), 1 mM EDTA, and 2 mL of Protease Inhibitor Cocktail (Sigma), and disrupted by ultrasonication treatment on ice using a Branson sonifier. The lysate was centrifuged at 24,000×g for 20 min to remove cell debris. The supernatant containing the AAD-1 protein was then subjected to purification protocol.

All AAD-1 (v1) purifications were conducted at 4° C. as discussed in Example 10, unless otherwise stated. The cell lysate was loaded onto a Mono Q ion exchange column (Pharmacia Cat. #HR 10/10) equilibrated with 20 mM Tris-HCl (pH 8.0) 1 mM EDTA, followed by 80 mL of washing with the same buffer. The proteins were eluted with 80 mL of a 0 to 0.25 M NaCl linear gradient in column buffer, while 2 mL fractions were collected. The fractions containing AAD-1 were pooled and concentrated using MWCO 30 kDa membrane centrifugation spin columns (Millipore). The sample was then further separated on a Superdex 200 size exclusion column (Pharmacia, XK 16/60) with buffer containing 20 mM Tris-HCl (pH 8.0), 0.15 M NaCl and 1 mM DTT. Protein concentration was determined by Bradford assay using bovine serum albumin as standard.

Five milligrams purified AAD-1 (v1) was delivered to Zymed Laboratories, Inc. (South San Francisco, Calif.) for rabbit polyclonal antibody production. The rabbit received 5 injections in the period of 5 weeks with each injection containing 0.5 mg of the purified protein suspended in 1 mL of Incomplete Freund's Adjuvant. Sera were tested in both ELISA and Western blotting experiments to confirm specificity and affinity before affinity purification and horseradish peroxidase (HRP) conjugation (Zymed Lab Inc).

11.1—Extracting AAD-1 (v3) from Plant Leaves.

Approximately 50 to 100 mg of leaf tissue was cut into small pieces and put into microfuge tubes containing 2 stainless steel beads (4.5 mm; Daisy Co., cat. #145462-000) and 300 µL plant extraction buffer (PBS containing 0.1% Triton X-100 and 10 mM DTT). The tubes were shaken for 4 min with a bead beater at maximum speed followed by centrifugation for 10 min at 5,000×g. The supernatant containing the plant soluble proteins were analyzed for both total soluble protein (TSP) and AAD-1 (v3) concentrations.

11.2—Bradford Assay.

Total soluble protein concentration from plant leaf tissues were determined by Bradford assay using bovine serum albumin (BSA) as standard. Five micro-liter of serially diluted BSA in PBS or plant extract was transferred to 96-well microtiter plate in triplicates. For standards, concentrations were ranged from 2000 to 15.6 µg/mL. The protein assay concentrate was first diluted 5 fold in PBS and 250 µL was added to each well and incubated at room temp for 5 min. Each optical density (OD) was measured at 595 nm using a microplate reader. The protein concentration of each sample was extrapolated from standard curve using the Softmax® Pro (ver. 4.0) (Molecular Devices).

11.3—Enzyme Linked Immuno-Sorbent Assay (ELISA).

The assay was conducted at room temperature unless otherwise stated. One hundred micro-liter of purified anti-AAD-1 antibody (0.5 µg/mL) was coated on 96-well microtiter well and incubated at 4° C. for 16 hours. The plate was washed four times with washing buffer (100 mM phosphate buffered saline (PBS; pH 7.4) containing 0.05% Tween 20) using a plate washer, followed by blocking with 4% skim milk dissolved in PBS for 1 hour. After washing, 100 µL standard AAD-1 of known concentrations or plant extract (see previous section) was incubated in the wells. For standard curve, purified AAD-1 concentrations ranged from 100 to 1.6 ng/mL in triplicates. Plant extracts were diluted 5, 10, 20, and 40 fold in PBS and analyzed in duplicates. After 1 hour incubation, the plate was washed as above. One hundred micro-liter anti-AAD-1 antibody-HRP conjugate (0.25 ug/mL) was incubated in each well for 1 hour before washing. One hundred micro-liter HRP substrate, 1-Step™ Ultra TMB-ELISA (Pierce), was incubated in each well for 10 minutes before the reaction was stopped by adding 100 µL 0.4N $H_2SO_4$. The OD of each well was measured using a microplate reader at 450 nm. To determine the concentrations of AAD-1 in plant extract, the OD value of duplicates were averaged and extrapolated from the standard curve using the Softmax® Pro ver. 4.0 (Molecular Devices).

For comparison, each sample was normalized with its TSP concentration and percent expression to TSP was calculated.

11.4—Western Blotting Analysis.

Plant extracts or AAD-1 standards (5 and 0.5 µg/mL) were incubated with Laemmli sample buffer at 95° C. for 10 minutes and electrophoretically separated in 8-16% Tris-Glycine Precast gel. Proteins were then electro-transferred onto nitrocellulose membrane using standard protocol. After blocking in 4% skim milk in PBS, AAD-1 protein was detected by anti-AAD1 antiserum followed by goat anti-rabbit/HRP conjugates. The detected protein was visualized by chemiluminescence substrate ECL Western Analysis Reagent (Amersham cat. #RPN 21058).

Example 12—Tobacco Transformation

Tobacco transformation with *Agrobacterium tumefaciens* was carried out by a method similar, but not identical, to published methods (Horsch et al., 1988). To provide source tissue for the transformation, tobacco seed (*Nicotiana tabacum* cv. Kentucky 160) was surface sterilized and planted on the surface of TOB-medium, which is a hormone-free Murashige and Skoog medium (Murashige and Skoog, 1962) solidified with agar. Plants were grown for 6-8 weeks in a lighted incubator room at 28-30° C. and leaves collected sterilely for use in the transformation protocol. Pieces of approximately one square centimeter were sterilely cut from these leaves, excluding the midrib. Cultures of the *Agrobacterium* strains (EHA101S containing pDAB721, AAD-1 (v3)+PA7), grown overnight in a flask on a shaker set at 250 rpm at 28° C., were pelleted in a centrifuge and resuspended in sterile Murashige & Skoog salts, and adjusted to a final optical density of 0.5 at 600 nm. Leaf pieces were dipped in this bacterial suspension for approximately 30 seconds, then blotted dry on sterile paper towels and placed right side up on TOB+ medium (Murashige and Skoog medium containing 1 mg/L indole acetic acid and 2.5 mg/L benzyladenine) and incubated in the dark at 28° C. Two days later the leaf pieces were moved to TOB+ medium containing 250 mg/L cefotaxime (Agri-Bio, North Miami, Fla.) and 5 mg/L glufosinate ammonium (active ingredient in Basta, Bayer Crop Sciences) and incubated at 28-30° C. in the light. Leaf pieces were moved to fresh TOB+ medium with cefotaxime and Basta twice per week for the first two weeks and once per week thereafter. Four to six weeks after the leaf pieces were treated with the bacteria, small plants arising from transformed foci were removed from this tissue preparation and planted into medium TOB-containing 250 mg/L cefotaxime and 10 mg/L Basta in Phytatray™ II vessels (Sigma). These plantlets were grown in a lighted incubator room. After 3 weeks, stem cuttings were taken and re-rooted in the same media. Plants were ready to send out to the greenhouse after 2-3 additional weeks.

Plants were moved into the greenhouse by washing the agar from the roots, transplanting into soil in 13.75 cm square pots, placing the pot into a Ziploc® bag (SC Johnson & Son, Inc.), placing tap water into the bottom of the bag, and placing in indirect light in a 30° C. greenhouse for one week. After 3-7 days, the bag was opened; the plants were fertilized and allowed to grow in the open bag until the plants were greenhouse-acclimated, at which time the bag was removed. Plants were grown under ordinary warm greenhouse conditions (30° C., 16 hour day, 8 hour night, minimum natural+supplemental light=500 µE/m$^2$ s$^1$).

Prior to propagation, $T_0$ plants were sampled for DNA analysis to determine the insert copy number. The PAT gene which was molecularly linked to AAD-1 (v3) was assayed for convenience. Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, DNeasy 69109). An aliquot of the extracted DNA was then stained with Pico Green (Molecular Probes P7589) and read in the florometer (BioTek) with known standards to obtain the concentration in ng/µl.

The DNA samples were diluted to 9 ng/µl, then denatured by incubation in a thermocycler at 95° C. for 10 minutes. Signal Probe mix was then prepared using the provided oligo mix and MgCl2 (Third Wave Technologies). An aliquot of 7.5 µl was placed in each well of the Invader assay plate followed by an aliquot of 7.5 µl of controls, standards, and 20 ng/µl diluted unknown samples. Each well was overlaid with 15 µl of mineral oil (Sigma). The plates were then incubated at 63° C. for 1.5 hours and read on the florometer (Biotek). Calculation of % signal over background for the target probe divided by the % signal over background internal control probe will calculate the ratio. The ratio of known copy standards developed and validated with southern blot analysis was used to identify the estimated copy of the unknown events (Table 27).

TABLE 27

Tobacco T0 events transformed with pDAB721 (AAD-1(v3) + PAT).

| Event | PAT copy number (Southern) | Coding Region PCR for AAD-1 | ELISA (µg AAD-1/ml plant extract) | Relative tolerance T0 spray with 2,4-D * |
|---|---|---|---|---|
| 721(1)1 | 1 | + | 0.9 | Medium |
| 721(2)1 | nd | nd | 0.6 | Medium |
| 721(2)2 | 5 | + | 0.3 | Low |
| 721(2)3 | 3 | + | 2.6 | Medium |
| 721(2)5 | 5 | + | 4.1 | Variable |
| 721(2)6 | 3 | + | 0.5 | Variable |
| 721(2)8 | 5 | + | 0.3 | High |
| 721(2)11 | 3 | + | n/a | High |
| 721(2)12 | 3 | + | 4.1 | Medium |
| 721(2)13 | 2 | + | 0.5 | Medium |
| 721(2)14 | 5 | + | 0.2 | High |
| 721(2)16 | 4 | + | 3.2 | Medium |
| 721(2)17 | 3 | + | nd | High |
| 721(2)18 | 5 | + | nd | High |
| 721(2)19 | >10 | + | nd | Low |
| 721(2)20 | 5 | + | nd | Medium |
| 721(2)21 | 4 | + | nd | High |
| 721(2)22 | 7 | + | nd | Medium |
| 721(2)23 | >10 | + | nd | Variable |
| 721(3)003 | 3 | + | nd | Variable |
| 721(3)008 | 2 | + | nd | High |
| 721(3)012 | 1 | + | nd | High |
| 721(3)4 | 2 | + | 0.5 | High |
| 721(3)5 | 9 | + | 3.3 | High |
| 721(3)6 | 4 | + | 7.1 | Variable |
| 721(3)9 | 2 | + | 1 | Low |
| 721(3)10 | 3 | + | 0.6 | High |
| 721(3)11 | 7 | + | 6 | Low |
| 721(3)13 | 4 | + | 0.1 | High |
| 721(3)014 | 2 | + | 0.1 | Medium | nd = not done

Legend: Relative tolerance* Injury at 3200 g ae/ha 2,4-D (14DAT)
Low        >50% injury
Medium     20-50% injury
High       <20% injury
Variable   inconsistent Copy number estimations were confirmed by Southern Analysis on several events. Southern blot analysis was performed with total DNA obtained from Qiagen DNeasy kit. A total of 2 μgs of DNA was subjected to an overnight digest of NsiI and also HindIII for pDAB721 to obtain integration data. After the overnight digestion an aliquot of ~100 ngs was run on a 1% gel to ensure complete digestion. After this assurance the samples were processed using same protocol as in Example 6 section 11.

All events were also assayed for the presence of the AAD-1 (v3) gene by PCR using the same extracted DNA samples. A total of 100 ng of total DNA was used as template. 20 mM of each primer was used with the Takara Ex Taq PCR Polymerase kit (Mirus TAKRROO1A). Primers for the Coding Region PCR AAD-1 were (RdpAcodF ATG-GCTCA TGCTGCCCTCAGCC) (SEQ ID NO:27) and (Rd-pAcodR CGGGCAGGCCTAACTCCACC AA) (SEQ ID NO:28). The PCR reaction was carried out in the 9700 Geneamp thermocycler (Applied Biosystems), by subjecting the samples to 94° C. for 3 minutes and 35 cycles of 94° C. for 30 seconds, 64° C. for 30 seconds, and 72° C. for 1 minute and 45 seconds followed by 72° C. for 10 minutes. PCR products were analyzed by electrophoresis on a 1% agarose gel stained with EtBr. Four to 12 clonal lineages from each of 30 PCR positive events were regenerated and moved to the greenhouse.

A representative plant from each of 19 events was assayed for AAD-1 (v3) expression by ELISA methods previously described. All events assayed showed detectable levels of AAD-1 (v3) (Table 27). Protein expression varied across events.

$T_0$ plants from each of the 30 events were challenged with a wide range of 2,4-D sprayed on plants that were 3-4 inches tall. Spray applications were made as previously described using a track sprayer at a spray volume of 187 L/ha. 2,4-D dimethylamine salt (Riverside Corp) was applied at 0, 50, 200, 800, or 3200 g ae/ha to representative clones from each event mixed in deionized water. Each treatment was replicated 1-3 times. Injury ratings were recorded 3 and 14 DAT. Every event tested was more tolerant to 2,4-D than the untransformed control line KY160. In several events, some initial auxinic herbicide-related epinasty occurred at doses of 800 g ae/ha or less. Some events were uninjured at this rate (equivalent to 1.5× field rate). All events suffered some level temporary auxinic damage 3 DAT when treated with 3200 g ae/ha. Some leaf burning also occurred at this high rate due to the acidity of the spray solution. Future trials at high 2,4-D rates were buffered. Response of $T_0$ plants treated with 3200 g ae/ha 2,4-D (~6× field rate) was used to discern relative tolerance of each event into "low" (>50% injury 14 DAT), "medium" (20-50% injury), "high" (<20% injury). Some events were inconsistent in response among replicates and were deemed "variable" (Table 27).

Verification of High 2,4-D Tolerance.

Two to four $T_0$ individuals surviving high rates of 2,4-D were saved from each event and allowed to self fertilize in the greenhouse to give rise to $T_1$ seed. Two AAD-1 (v3) tobacco lines (event 721(2)-013.010 and 721(3)-008.005) were chosen from the $T_0$ generation. The $T_1$ seed was stratified, and sown into selection trays much like that of *Arabidopsis* (Example 6.4), followed by selective removal of untransformed nulls in this segregating population with 280 g ai/ha glufosinate (PAT selection). Survivors were transferred to individual 3-inch pots in the greenhouse. These lines provided medium and high levels of robustness to 2,4-D in the $T_0$ generation. Improved consistency of response is anticipated in $T_1$ plants not having come directly from tissue culture. These plants were compared against wildtype KY 160 tobacco. All plants were sprayed with the use of a track sprayer set at 187 L/ha. The plants were sprayed from a range of 70-4480 g ae/ha 2,4-D dimethylamine salt (DMA), R-Dichlorprop, and a 50/50 mix of the two herbicides. All applications were formulated in 200 mM Hepes buffer (pH 7.5). Each treatment was replicated 4 times. Plants were evaluated at 3 and 14 days after treatment. Plants were assigned injury rating with respect to stunting, chlorosis, and necrosis. The $T_1$ generation is segregating, so some variable response is expected due to difference in zygosity. (Table 28). No injury was observed at rates below 1× field rates (560 g ae/ha) for 2,4-D or R-dichlorprop in either event. Very little injury was observed even up to 8 times field rates (4480 g ae/ha) and this was exhibited as stunting, not auxinic herbicide damage. These results indicated commercial level tolerance can be provided by AAD-1 (v3), even in a very auxin-sensitive dicot crop like tobacco. These results also show resistance can be imparted to both chiral (2,4-dichlorophenoxypropionic acid) and achiral (2,4-dichlorophenoxyacetic acid) phenoxy auxin herbicides alone or in tank mix combination.

TABLE 28

Segregating AAD-1 $T_1$ tobacco plants' response to phenoxy auxin herbicides.

| Herbicide | KY160-Wildtype | 721(2)013.010 (medium tolerance in $T_0$ generation) | 721(3)008.005 (high tolerance in $T_0$ generation) |
|---|---|---|---|
| | Average % Injury of Replicates 14 DAT | | |
| 560 g ae/ha 2,4-D DMA | 75 | 5 | 0 |
| 1120 g ae/ha 2,4-D DMA | 80 | 5 | 2 |
| 2240 g ae/ha 2,4-D DMA | 90 | 5 | 0 |
| 4480 g ae/ha 2,4-D DMA | 95 | 5 | 5 |
| 560 g ae/ha R-dichlorprop | 70 | 5 | 0 |
| 1120 g ae/ha R-dichlorprop | 75 | 5 | 0 |
| 2240 g ae/ha R-dichlorprop | 88 | 5 | 0 |
| 4480 g ae/ha R-dichlorprop | 95 | 10 | 5 |
| 560 g ae/ha 2,4-D DMA/R-dichlorprop | 80 | 5 | 5 |
| 1120 g ae/ha 2,4-D DMA/R-dichlorprop | 80 | 10 | 10 |
| 2240 g ae/ha 2,4-D DMA/R-dichlorprop | 95 | 15 | 15 |
| 4480 g ae/ha 2,4-D DMA/R-dichlorprop | 95 | 15 | 15 |

A 100 plant progeny test was also conducted on each of the two AAD-1 (v3) lines (events 721(2)-013.010 and 721 (3)-008.005). The seeds were stratified, sown, and transplanted with respect to the procedure above except null plants were not removed by Liberty selection. All plants were then sprayed with 560 g ae/ha 2,4-D DMA as previously described. After 14 DAT, resistant and sensitive plants were counted. Both event '013' and '008' segregated as a single locus, dominant Mendelian trait (3R:1S) as determined by Chi square analysis. AAD-1 is heritable as a robust phenoxy auxin resistance gene in multiple species.

Field level tolerance will be demonstrated by planting $T_1$ or $T_2$ seed in the greenhouse, selectively removing the null plants by Liberty selection as previously described, and rearing individual seedlings in 72-well transplant flats (Hummert International) in Metro 360 media according to growing conditions indicated above. Individual plants will be transplanted into the field plots using an industrial vegetable planter. Drip or overhead irrigation will be used to keep plants growing vigorously. Once plants reach 6-12 inches in height, tobacco plants will be sprayed with a broad range of phenoxy auxins and rated as shown above. Environmental stresses are more significant under field conditions; however, based on previous experience with AAD-1 (v3)-transformed corn, robust translation of resistance from the greenhouse to the field is expected.

Example 13—Soybean Transformation

Soybean improvement via gene transfer techniques has been accomplished for such traits as herbicide tolerance (Padgette et al., 1995), amino acid modification (Falco et al., 1995), and insect resistance (Parrott et al., 1994). Introduction of foreign traits into crop species requires methods that will allow for routine production of transgenic lines using selectable marker sequences, containing simple inserts. The transgenes should be inherited as a single functional locus in order to simplify breeding. Delivery of foreign genes into cultivated soybean by microprojectile bombardment of zygotic embryo axes (McCabe et al., 1988) or somatic embryogenic cultures (Finer and McMullen, 1991), and *Agrobacterium*-mediated transformation of cotyledonary explants (Hinchee et al., 1988) or zygotic embryos (Chee et al., 1989) have been reported.

Transformants derived from *Agrobacterium*-mediated transformations tend to possess simple inserts with low copy number (Birch, 1991). There are benefits and disadvantages associated with each of the three target tissues investigated for gene transfer into soybean, zygotic embryonic axis (Chee et al., 1989; McCabe et al., 1988), cotyledon (Hinchee et al., 1988) and somatic embryogenic cultures (Finer and McMullen, 1991). The latter have been extensively investigated as a target tissue for direct gene transfer. Embryogenic cultures tend to be quite prolific and can be maintained over a prolonged period. However, sterility and chromosomal aberrations of the primary transformants have been associated with age of the embryogenic suspensions (Singh et al., 1998) and thus continuous initiation of new cultures appears to be necessary for soybean transformation systems utilizing this tissue. This system needs a high level of 2,4-D, 40 mg/L concentration, to initiate the embryogenic callus and this poses a fundamental problem in using the AAD-1 (v3) gene since the transformed locus could not be developed further with 2,4-D in the medium. So, the meristem based transformation is ideal for the development of 2,4-D resistant plant using AAD-1 (v3).

13.1—Transformation Method 1: Cotyledonary Node Transformation of Soybean Mediated by *Agrobacterium tumefaciens*.

The first reports of soybean transformation targeted meristematic cells in the cotyledonary node region (Hinchee et al., 1988) and shoot multiplication from apical meristems (McCabe et al., 1988). In the *A. tumefaciens*-based cotyledonary node method, explant preparation and culture media composition stimulate proliferation of auxiliary meristems in the node (Hinchee et al., 1988). It remains unclear whether a truly dedifferentiated, but totipotent, callus culture is initiated by these treatments. The recovery of multiple clones of a transformation event from a single explant and the infrequent recovery of chimeric plants (Clemente et al., 2000; Olhoft et al., 2003) indicates a single cell origin followed by multiplication of the transgenic cell to produce either a proliferating transgenic meristem culture or a uniformly transformed shoot that undergoes further shoot multiplication. The soybean shoot multiplication method, originally based on microprojectile bombardment (McCabe et al., 1988) and, more recently, adapted for *Agrobacterium*-mediated transformation (Martinell et al., 2002), apparently does not undergo the same level or type of dedifferentiation as the cotyledonary node method because the system is based on successful identification of germ line chimeras. The range of genotypes that have been transformed via the *Agrobacterium*-based cotyledonary node method is steadily growing (Olhoft and Somers, 2001). This de novo meristem and shoot multiplication method is less limited to specific genotypes. Also, this is a non 2,4-D based protocol which would be ideal for 2,4-D selection system. Thus, the cotyledonary node method may be the method of choice to develop 2,4-D resistant soybean cultivars. Though this method was described as early as 1988 (Hinchee et al., 1988), only very recently has it been optimized for routine high frequency transformation of several soybean genotypes (Zhang et al., 1999; Zeng et al., 2004).

13.1.1—*Agrobacterium* Preparation.

The plasmid, pDAB721, contains the AAD-1 (v3) gene under the control of the *Arabidopsis* Ubi10 promoter. This plasmid also carries the PAT gene under the control of rice actin promoter coding for an enzyme that degrades glufosinate which can be used as a selection agent for transformants. This vector can be used in the transformation experiment described below. The construct pDAB721 was mobilized into the *Agrobacterium* strain EHA101S by electroporation.

*Agrobacterium* cultures harboring pDAB721 used in the transformations can be grown in YEP medium (10 g/L peptone, 5 g/L yeast extract and 5 g/L NaCl, pH 7.0). *Agrobacterium* cultures are pelleted at low speed and resuspended in SCM liquid medium (see below) to OD660 of 0.6 for use in the inoculations.

13.1.2—Plant Transformation.

Seeds of "Thorne," "Williams82," or "NE3001," public genotypes of soybean, can be disinfected by a 20-minute wash in 20% (v/v) commercial bleach (NaClO) amended with 2 drops of Liqui-Nox®. The seeds should be rinsed five times with sterile water on hormone-free SHGA medium and allowed to germinate for 5 days at 24° C., with an 18/6 hour light/dark regime. B5 medium consists of macro and micro nutrients and vitamins described by Gamborg et al. (1968) (Sigma, cat. #G 5893, St. Louis). All media are solidified with 0.8% (w/v) washed agar (Sigma cat. #A 8678). Alternatively, certain genotypes of soybean can undergo a dry surface sterilization procedure using chlorine gas ($Cl_2$) whereby mature seeds are placed into 100×25 mm Petri plates in a single layer using about 130 seeds per plate. Approximately 3-4 plates are placed into a desiccator within a fume hood in such a way that all the plates are half open and that there is enough space for a 250 ml beaker in the middle of the desiccator. The beaker is filled with 95 ml of commercial bleach, to which 5 ml of concentrated (12N) HCl is added dropwise along the side of the beaker. The desiccator is immediately closed and allowed to stand for at least 16 hours in a fume hood. Following sterilization, the plates are closed, then brought to a laminar flow hood and left open for about 30 minutes to remove any excessive $Cl_2$ gas. Seeds are then germinated as described previously. The dry surface sterilized seeds will remain sterile at room temperature for about 2 weeks. Explants are prepared for inoculation as previously described (Hinchee et al., 1988).

Explants should be inoculated for 30 minutes. Cocultivation and *Agrobacterium* re-suspension medium consists of B5 medium supplemented with 1 mg/L BAP, 1 mg/L GA3, 3% (w/v) sucrose, 20 mM MES (2-[N-morpholino]ethane sulfonic acid), 400 mg/L L-cysteine (Olhoft and Somers, 2001) pH 5.7, 0.99 mM dithiothreitol (DTT), and 200 µM acetosyringone (AS). Explants are cocultivated for 5 days at 25° C. Following cocultivation, explants were washed in the cocultivation medium containing 100 mg/L timentin and 200 mg/L cefotaxime, without MES and AS.

Explants are to be placed on shoot induction medium and transferred every 14 days for a total of 28 days prior to herbicide selection. The shoot induction medium consists of full-strength B5 medium supplemented with 1.7 mg/L BAP, 100 mg/L timentin, 200 mg/L cefotaxime pH 5.7 and 3% (w/v) sucrose. Cotyledons should be placed adaxial side up with the cotyledonary nodal region flush to the medium, amended with increasing levels of Basta (2, 5, 6 then 7 mg/L glufosinate ammonium) or sublethal levels of 2,4-D ranging from 10 mg to 400 mg/L every 2 weeks for a total of 8 weeks.

Differentiating explants are subsequently transferred to shoot elongation medium for an additional 4 to 10 weeks under the same glufosinate selection or under decreased 2,4-D selection pressure ranging from 10 mg to 100 mg/L. The elongation medium consisted of B5 medium (Sigma cat. #M0404) amended with 1 mg/L zeatin riboside, 0.1 mg/L IAA (indole-3-acetic acid), 0.5 mg/L GA3, 50 mg/L glutamine, 50 mg/L asparagine, and 3% (w/v) sucrose, pH 5.8. Elongated shoots should be rooted, without further selection, on half-strength MS/B5 medium with full-strength vitamins plus 0.5 mg/L NAA (α-naphthaleneacetic acid) or 0.1 mg/L IAA and 2% (w/v) sucrose.

The antibiotics, timentin and cefotaxime, are maintained within the media throughout selection. Cultures are transferred to fresh medium every 2 weeks. Plantlets are acclimated for 1 to 2 weeks prior to transfer to the greenhouse.

13.1.3—Progeny Evaluation.

$T_0$ plants will be allowed to self fertilize in the greenhouse to give rise to $T_1$ seed. $T_1$ plants (and to the extent enough $T_0$ plant clones are produced) will be sprayed with a range of herbicide doses to determine the level of herbicide protection afforded by AAD-1 (v3) and PAT genes in transgenic soybean. Rates of 2,4-D used on $T_0$ plants will typically use one or two selective rates in the range of 100-400 g ae/ha. $T_1$ seed will be treated with a wider herbicide dose ranging from 50-3200 g ae/ha 2,4-D. Likewise, $T_0$ and $T_1$ plants can be screened for glufosinate resistance by postemergence treatment with 200-800 and 50-3200 g ae/ha glufosinate, respectively. Analysis of protein expression will occur as described in Example 9 for *Arabidopsis* and corn. Determination of the inheritance of AAD-1 (v3) will be made using $T_1$ and $T_2$ progeny segregation with respect to herbicide tolerance.

13.2—Transformation Method 2: "No-Shake" *Agrobacterium* Mediated Trans-Formation of Non-Regenerable Soybean Suspension Cells.

The DAS Soybean cell suspensions were cultured on a 3 d cycle with 10 ml of settled suspension volume transferred to 115 ml of fresh liquid medium. Settled cell volume was determined by allowing the cell suspension to settle for 2 min in the 125-mL flask after vigorous swirling and then drawing cells from the bottom of the flask with a wide bore 10 ml pipette. The flasks were then transferred to orbital shakers at 140 rpm.

Aliquots of 4 ml of the suspension cells at 0.72 $OD^{600}$ was transferred along with 200 µM acetosyringone (AS) onto a 100×25 sterile Petri plate. EHA105 *Agrobacterium* suspension at a density of 1.2 $OD^{650}$ in a 100 µL volume was added and mixed well. The *Agrobacterium* and suspension cell mixture was swirled well and the plate was transferred to dark growth chamber where the temperature was maintained at 25° C.

13.2.1—Selection of Soybean Suspension Cells and Isolation of Transformed Colonies.

After 4 days of co-cultivation the plate was swirled again to mix the suspension well and a 1.5 ml aliquot was transferred to the selection medium and spread on the gel medium on a 100×15 ml Petri-plate. The selection medium consisted of full-strength B5 medium supplemented with 1.7 mg/L BAP, 100 mg/L timentin, 200 mg/L cefotaxime pH 5.7 and 3% (w/v) sucrose and the medium was amended with glufosinate ammonium at 5 mg/L level. After a 10 min drying in the hood the plates were incubated for 4 weeks in dark at 28° C. Colonies appeared in selection and a total of 11 colonies were transferred to fresh medium from 3 different experiments and maintained for 3-4 months. All the 11 resistant colonies produced calli that were growing on the 5 mg/L glufosinate containing selection medium. The non-transformed suspension cells were sensitive when plated on to 0.5 mg/l glufosinate ammonium medium. However, the transformed colonies were resistant to 5× concentration of glufosinate ammonium and were maintained for up to 4 months.

Figure 18:
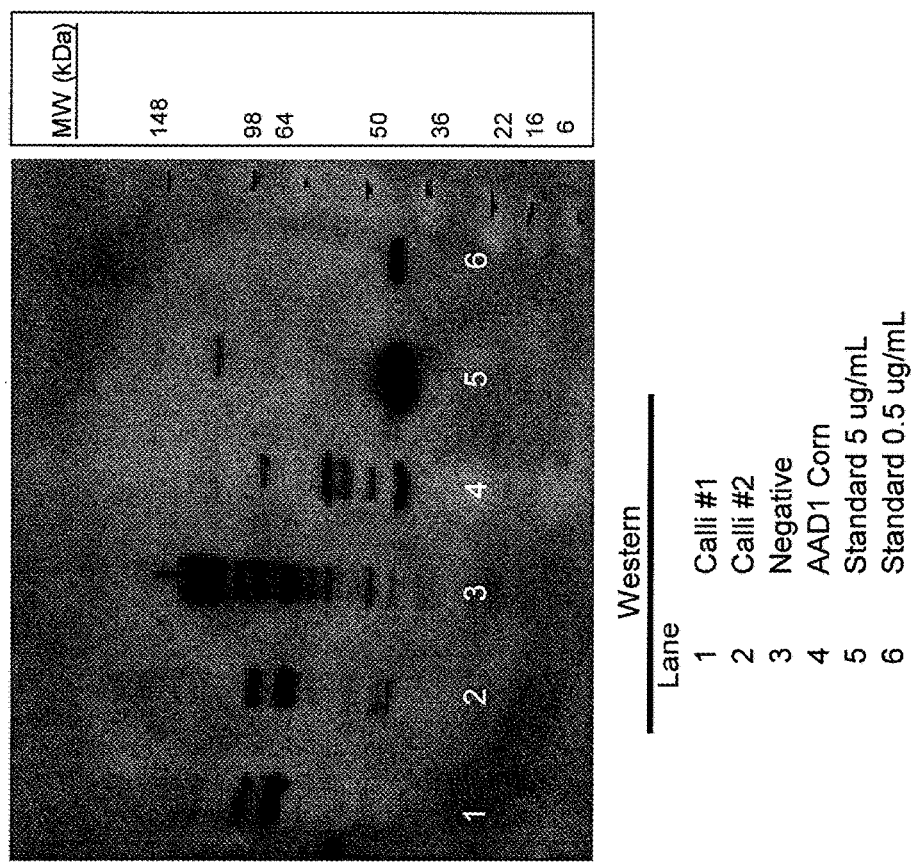
FIG. 18 shows Western Blotting analysis on soybean calli transformed with AAD-1 (V3) gene indicating that the callus cells are expressing AAD-1 (v3) protein.

Callus events were sampled for analyses when they reached 2 to 3 cm in diameter. At least two of colony isolates, one each from two different experiments, were analyzed for AAD1 protein expression. The ELISA and Western analysis carried out on these two isolates showed positive expression of AAD1 proteins. Both ELISA (Table 29) and Western Blotting (FIG. 18) analysis on two separate soybean calli transformed with AAD-1 (v3) gene indicated that the callus cells are expressing AAD-1 (v3) protein. The sandwich ELISA detected 0.0318% and 0.0102% total soluble protein of AAD-1 (v3) in two different callus tissue samples. Due to the sensitivity and cross reactivity of the antiserum, multiple bands were observed in the western blot. However, AAD-1 (v3) specific band was observed in both callus samples but not in the wild type (negative) tissue. Coding region PCR analyses showed the expected size products of the AAD1 and the PAT coding regions in these colonies indicating that they were transformed.

TABLE 29

PCR and ELISA data for transgenic soybean events.

| Event | AAD-1 Coding region PCR | PAT Coding region PCR | T SP (µg/mL) | AAD-1 (ng/mL) | % Expression |
|---|---|---|---|---|---|
| 1-1 | + | + | 1995.13 | 633.89 | 0.0318% |
| 2-1 | + | + | 2018.91 | 205.92 | 0.0102% |
| Negative Control | − | − | 2074.63 | −1.22 | −0.0001% |

13.3—Transformation Method 3: Aerosol-Beam Mediated Transformation of Embryogenic Soybean Callus Tissue.

Culture of embryogenic soybean callus tissue and subsequent beaming were as described in U.S. Pat. No. 6,809,232 (Held et al.).

Embryogenic calluses of several Stine elite varieties, including 96E750, 96E94, 97E986, 96E144 and 96E692, were separately collected into the center of plates of B1-30 3Co5My or B1-30 3Co5My0.25PA0.5K three days after transfer to fresh medium. The tissue was then beamed with pDAB3295 using linearized DNA at a concentration of approximately 0.2 µg/ml. After beaming, the embryogenic callus was transferred to fresh B1-30 3Co5My or B1-30 3Co5My0.25PA0.5K for one passage of a month. The tissue was then transferred to selective medium containing 1 mg/l bialaphos. With bialaphos, selection typically was maintained at 1 mg/l for the first two one-month passages and then increased to 2 mg/l for the following three to seven months. Transgenic events were identified when callus tissue generated by transformation experiments began to organize and develop into embryogenic structures while still on selective media containing 2,4-D plus bialaphos. Once identified, the maturing structures were regenerated into plants according to the following protocol: Embryogenic structures were transferred off B1-30 3Co5My or B1-30 3/co5My0.25PA0.5K to B3 medium. After 3 to 4 weeks' growth on B3 medium, individual structures were transferred to fresh medium. After another 3 to 4 weeks, maturing embryos were transferred to B5G medium and placed in the light. Embryos that had elongated and produced roots were transferred to tubes containing ½ B5G medium where they continued development into plantlets; and these plantlets were removed from the tubes and placed into pots.

Variations of media referred to in Table 30 were tested, e.g., B1-30 3Co5My, which was made by adding 3% coconut water and 5 gm/l myo-inositol to B1-30. Other variations included: B1-30 3Co5My0.25 PA0.5K which contained B1-30 basal medium plus 3% coconut water, 5 gm/l myo-inositol, 0.25 gm/l phytic acid, and 0.5 gm/l additional $KH_2PO_4$ and ½ B5G which contained all ingredients of B5G medium at half strength.

TABLE 30

Growth Media for Soybean

| | Ingredients in 1 Liter | | |
|---|---|---|---|
| | B1-30 | B3 | B5G |
| Ms Salts | 4.43 g | 4.43 g | |
| B5 Salts | | | 3.19 g |
| NaEDTA | 37.3 mg | 37.3 mg | 37.3 mg |
| 2,4-D | 30 mg | | |
| Activated charcoal | | 5 g | |
| Phytagar | 8 g | 8 g | |
| Gelrite | | | 2 g |
| pH | 5.8 | 5.8 | 5.8 |

Example 14—AAD-1 (v3) Enablement in Cotton 14.1—Cotton Transformation Protocol.

Cotton seeds (Co310 genotype) are surface-sterilized in 95% ethanol for 1 minute, rinsed, sterilized with 50% commercial bleach for twenty minutes, and then rinsed 3 times with sterile distilled water before being germinated on G-media (Table 31) in Magenta GA-7 vessels and maintained under high light intensity of 40-60 µE/m2, with the photoperiod set at 16 hours of light and 8 hours dark at 28° C.

Cotyledon segments (~5 mm) square are isolated from 7-10 day old seedlings into liquid M liquid media (Table 31) in Petri plates (Nunc, item #0875728). Cut segments are treated with an *Agrobacterium* solution (for 30 minutes) then transferred to semi-solid M-media (Table 31) and undergo co-cultivation for 2-3 days. Following co-cultivation, segments are transferred to MG media (Table 31). Carbenicillin is the antibiotic used to kill the *Agrobacterium* and glufosinate-ammonium is the selection agent that would allow growth of only those cells that contain the transferred gene.

*Agrobacterium* Preparation.

Inoculate 35 ml of Y media (Table 31) (containing streptomycin (100 mg/ml stock) and erythromycin (100 mg/ml stock)), with one loop of bacteria to grow overnight in the dark at 28° C., while shaking at 150 rpm. The next day, pour the *Agrobacterium* solution into a sterile oakridge tube (Nalge-Nunc, 3139-0050), and centrifuge for in Beckman J2-21 at 8,000 rpm for 5 minutes. Pour off the supernatant and resuspend the pellet in 25 ml of M liquid (Table 31) and vortex. Place an aliquot into a glass culture tube (Fisher, 14-961-27) for Klett reading (Klett-Summerson, model 800-3). Dilute the new suspension using M liquid media to a Klett-meter reading of $10^8$ colony forming units per mL with a total volume of 40 ml.

After three weeks, callus from the cotyledon segments is isolated and transferred to fresh MG media. The callus is transferred for an additional 3 weeks on MG media. Callus is then transferred to CG-media (Table 31), and transferred again to fresh selection medium after three weeks. After another three weeks the callus tissue is transferred to D media (Table 31) lacking plant growth regulators for embryogenic callus induction. After 4-8 weeks on this media, embryogenic callus is formed, and can be distinguished from the non-embryogenic callus by its yellowish-white color and granular cells. Embryos start to regenerate soon after and are distinct green in color.

Larger, well-developed embryos are isolated and transferred to DK media (Table 31) for embryo development. After 3 weeks (or when the embryos have developed), germinated embryos are transferred to fresh media for shoot and root development. After 4-8 weeks, any well-developed plants are transferred into soil and grown to maturity. Following a couple of months, the plant has grown to a point that it can be sprayed to determine if it has resistance to 2,4-D.

TABLE 31

Media for Cotton Transformation

| Ingredients in 1 liter | G | M liquid | M | MG | CG | D | DK | Y |
|---|---|---|---|---|---|---|---|---|
| LS Salts (5X) | 200 ml | 200 ml | 200 ml | 200 ml | 200 ml | | | |
| Glucose | | 30 grams | 30 grams | 30 grams | 30 grams | 20 grams | | |
| modified B5 vit (1000x) | 1 ml | 1 ml | 1 ml | 1 ml | 1 ml | 10 ml | 1 ml | |

TABLE 31-continued

Media for Cotton Transformation

| Ingredients in 1 liter | G | M liquid | M | MG | CG | D | DK | Y |
|---|---|---|---|---|---|---|---|---|
| kinetin (1 mM) | | 1 ml | 1 ml | 1 ml | 4.6 ml | | 0.5 ml | |
| 2,4-D (1 mM) | | 1 ml | 1 ml | 1 ml | | | | |
| agar | 8 grams | | 8 grams | 8 grams | 8 grams | 8 grams | 8 grams | |
| DKW salts (D190) | | | | | | 1 package | 1 package | |
| MYO-Inositol (100x) | | | | | | 1 ml | 10 ml | |
| Sucrose 3% | 30 grams | | | | | | 30 grams | 10 grams |
| NAA | | | | | | | | |
| Carbenicillin (250 mg/ml) | | | | 2 ml | 0.4 ml | | | |
| GLA (10 mg/ml) | | | | 0.5 ml | 0.3 ml | | | |
| Peptone | | | | | | | | 10 grams |
| Yeast Extract | | | | | | | | 10 grams |
| NaCl | | | | | | | | 5 grams |

14.2—Experiment Specifics.

For this experiment 500 cotyledon segments were treated with pDAB721. Of the 500 segments treated, 475 had callus isolated while on selection (95% transformation frequency). The callus was selected on glufosinate-ammonium, due to the inclusion of the PAT gene in the construct, since there was already a selection scheme developed. Callus line analysis in the form of PCR and Invader were initiated to determine the insertion patterns and to be sure the gene was present at the callus stage, then callus lines that were embryogenic were sent for Western analysis.

14.3—Callus Analysis Results.

The object of the analysis is to eliminate any lines that do not have the complete PTU, show no expression or that have high copy number, so those lines are not regenerated. Of the 475 pDAB721 transformed callus lines, 306 were sent for PCR analysis and Invader assay (Table 32). Very few lines were PCR negative. The Invader results are not complete at this time, because some samples had low DNA amounts when extracted, and these have been resubmitted. However, the current Invader data shows a few of the lines submitted have high copy number (copy number of >2) (Table 32). Due to the large number of lines that passed analysis, it was necessary to decrease the number of embryogenic callus lines being maintained due to the volume. Ninety lines have been sent for Western analysis, and eight of those were negative. The western analysis showed high expression from the majority of the lines (Table 32). Eighty-two embryogenic callus lines are being maintained for plant regeneration based on analysis results (and results pending).

TABLE 32

Analysis of cotton callus

| Line | Copy # | PTU | Western |
|---|---|---|---|
| 1 | 2 | pos | *** |
| 2 | 1 | pos | *** |
| 3 | 1 | pos | *** |
| 4 | 2 | pos | *** |
| 5 | 1 | pos | *** |
| 6 | 1 | pos | neg |
| 7 | 1 | pos | **** |
| 8 | 1 | pos | ***** |
| 9 | 2 | pos | * |
| 10 | 1 | pos | * |
| 11 | 1 | pos | ***** |
| 12 | 1 | pos | * |
| 13 | 1 | pos | * |
| 14 | 1 | pos | ** |
| 15 | 1 | pos | **** |
| 16 | 1 | pos | ***** |
| 17 | 1 | pos | * |
| 18 | 1 | pos | *** |
| 19 | 1 | pos | ** |
| 20 | 1 | pos | ***** |
| 21 | 2 | pos | ***** |
| 22 | 1 | pos | ***** |
| 23 | 1 | pos | ***** |
| 24 | 4 | pos | * or neg |
| 25 | 1 | pos | **** |
| 26 | 1 | pos | **** |
| 27 | low DNA | pos | ***** |
| 28 | low DNA | pos | ** |
| 29 | low DNA | pos | ***** |
| 30 | 17 | pos | * |
| 31 | low DNA | pos | ***** |
| 32 | low DNA | pos | ***** |
| 33 | low DNA | pos | **** |
| 34 | low DNA | faint pos | ***** |
| 35 | low DNA | pos | **** |
| 36 | low DNA | pos | neg |
| 37 | low DNA | pos | **** |
| 38 | low DNA | neg | ***** |
| 39 | 1 | pos | **** |
| 40 | low DNA | pos | * |
| 41 | low DNA | pos | * |
| 42 | low DNA | pos | ** |
| 43 | 1 | pos | ***** |
| 44 | low DNA | pos | ***** |
| 45 | 1 | pos | ***** |
| 46 | 2 | pos | ***** |
| 47 | 1 | pos | *** |
| 48 | 1 | pos | *** |
| 49 | 3 | faint pos | neg |
| 50 | 1 | pos | **** |
| 51 | 4 | pos | neg |
| 52 | 2 | pos | **** |
| 53 | 1 | pos | *** |
| 54 | 1 | pos | **** |
| 55 | 1 | pos | neg |
| 56 | 5 | pos | * |
| 57 | 2 | faint pos | neg |
| 58 | 8 | pos | **** |
| 59 | 2 | pos | **** |
| 60 | 5 | pos | ***** |
| 61 | 1 | pos | ** |
| 62 | 1 | pos | ** |
| 63 | 1 | pos | *** |
| 64 | 1 | pos | *** |
| 65 | 3 | pos | **** |
| 66 | 5 | pos | * |
| 67 | 6 | pos | * |
| 68 | Low DNA | pos | neg |

TABLE 32-continued

Analysis of cotton callus

| Line | Copy # | PTU | Western |
|---|---|---|---|
| 69 | Low DNA | pos | **** |
| 70 | low DNA | pos | ** |
| 71 | low DNA | faint pos | ** |
| 72 | low DNA | pos | **** |
| 73 | low DNA | neg | *** |
| 74 | low DNA | faint pos | *** |
| 75 | Low DNA | pos | *** |
| 76 | Low DNA | pos | neg |
| 77 | low DNA | faint pos | **** |
| 78 | low DNA | pos | **** |
| 79 | 1 | pos | ** |
| 80 | low DNA | pos | *** |
| 81 | low DNA | pos | *** |
| 82 | low DNA | pos | *** |
| 83 | low DNA | neg | **** |
| 84 | low DNA | pos | *** |
| 85 | low DNA | pos | ** |
| 86 | low DNA | pos | * |
| standard | AAD1 | 5 ug/ml | ***** |
| standard | AAD1 | 0.5 ug/ml | ** |

14.4—Plant Regeneration.

Two AAD-1 (v3) cotton lines have produced plants according to the above protocol that have been sent to the greenhouse. To demonstrate the AAD-1 (v3) gene provides resistance to 2,4-D in cotton, both the AAD-1 (v3) cotton plant and wild-type cotton plants were sprayed with a track sprayer set at 187 L/ha. The plants were sprayed at 560 g ae/ha 2,4-DMA formulated in 200 mM Hepes buffer (pH 7.5). The plants were evaluated at 3, 7, and 14 days after treatment. Plants were assigned injury ratings with respect to stunting, chlorosis, and necrosis. Plants assigned an injury rating of 90% or above are considered dead. Three days after treatment (DAT) the wild-type plant began showing epinasy and received a rating of 15%; in contrast, the AAD-1 (v3) plant showed 0% injury. By 7 DAT epinasy continued on the wild-type and the new growth shoots began turning brown. It received a rating of 50% at this time. At 14 DAT the AAD-1 (v3) plant was still uninjured, whereas the wild-type was severely stunted, and the new growth areas were brown and shriveled. Thus, the wild-type received a rating of 90% at 14 DAT.

This study demonstrates that the AAD-1 (v3) gene in cotton provides substantial tolerance to 2,4-D up to at least 560 g ae/ha.

Example 15—*Agrobacterium* Transformation of Other Crops

In light of the subject disclosure, additional crops can be transformed according to the subject invention using techniques that are known in the art. For *Agrobacterium*-mediated trans-formation of rye, see, e.g., Popelka and Altpeter (2003). For *Agrobacterium*-mediated transformation of soybean, see, e.g., Hinchee et al., 1988. For *Agrobacterium*-mediated transformation of *sorghum*, see, e.g., Zhao et al., 2000. For *Agrobacterium*-mediated transformation of barley, see, e.g., Tingay et al., 1997. For *Agrobacterium*-mediated transformation of wheat, see, e.g., Cheng et al., 1997. For *Agrobacterium*-mediated transformation of rice, see, e.g., Hiei et al., 1997.

The Latin names for these and other plants are given below. It should be clear that these and other (non-*Agrobacterium*) transformation techniques can be used to transform AAD-1 (v3), for example, into these and other plants, including but not limited to Maize (*Gramineae Zea mays*), Wheat (*Pooideae Triticum* spp.), Rice (*Gramineae Oryza* spp. and *Zizania* spp.), Barley (*Pooideae Hordeum* spp.), Cotton (*Abroma Dicotyledoneae Abroma augusta*, and *Malvaceae Gossypium* spp.), Soybean (*Soya Leguminosae Glycine max*), Sugar beet (*Chenopodiaceae Beta vulgaris altissima*), Sugar cane (*Arenga pinnata*), Tomato (*Solanaceae Lycopersicon esculentum* and other spp., *Physalis ixocarpa, Solanum incanum* and other spp., and *Cyphomandra betacea*), Potato, Sweet potato, Rye (*Pooideae Secale* spp.), Peppers (*Solanaceae Capsicum annuum, sinense,* and *frutescens*), Lettuce (*Compositae Lactuca sativa, perennis,* and *pulchella*), Cabbage, Celery (*Umbelliferae Apium graveolens*), Eggplant (*Solanaceae Solanum melongena*), Sorghum (all *Sorghum* species), Alfalfa (*Leguminosae Medicago sativum*), Carrot (*Umbelliferae Daucus carota sativa*), Beans (*Leguminosae Phaseolus* spp. and other genera), Oats (*Avena Sativa* and *Strigosa*), Peas (*Leguminosae Pisum, Vigna,* and *Tetragonolobus* spp.), Sunflower (*Compositae Helianthus annuus*), Squash (*Dicotyledoneae Cucurbita* spp.), Cucumber (*Dicotyledoneae genera*), Tobacco (*Solanaceae Nicotiana* spp.), Arabidopsis (*Cruciferae Arabidopsis thaliana*), Turfgrass (*Lolium, Agrostis,* and other families), and Clover (*Leguminosae*). Such plants, with AAD-1 (v3) genes, for example, are included in the subject invention.

Example 16—Stacking AAD-1 (v3) with AHAS Herbicide Resistance Gene

Stacking AAD-1 (v3) with an AHAS herbicide resistance gene is described in Example 7.9.

Example 17—Further Evidence of Surprising Results: AAD-1 vs. AAD-2

17.1—AAD-2 (v1) Initial Cloning.

Another gene was identified from the NCBI database (see the ncbi.nlm.nih.gov website; accession #AP005940) as a homologue with only 44% amino acid identity to tfdA. This gene is referred to herein as AAD-2 (v1) for consistency. Percent identity was determined by first translating both the AAD-2 and tfdA DNA sequences (SEQ ID NO:12 and GENBANK Accession No. M16730, respectively) to proteins (SEQ ID NO:13 and GENBANK Accession No. M16730, respectively), then using ClustalW in the VectorNTI software package to perform the multiple sequence alignment.

The strain of *Bradyrhizobium japonicum* containing the AAD-2 (v1) gene was obtained from Northern Regional Research Laboratory (NRRL, strain #B4450). The lyophilized strain was revived according to NRRL protocol and stored at −80° C. in 20% glycerol for internal use as Dow Bacterial strain DB 663. From this freezer stock, a plate of Tryptic Soy Agar was then struck out with a loopful of cells for isolation, and incubated at 28° C. for 3 days. A single colony was used to inoculate 100 ml of Tryptic Soy Broth in a 500 ml tri-baffled flask, which was incubated overnight at 28° C. on a floor shaker at 150 rpm. From this, total DNA was isolated with the gram negative protocol of Qiagen's DNeasy kit (Qiagen cat. #69504). The following primers were designed to amplify the target gene from genomic DNA, Forward: 5' ACT AGT AAC AAA GAA GGA GAT ATA CCA TGA CGA T 3' [(brjap 5'(speI) SEQ ID NO:14 (added Spe I restriction site and Ribosome Binding Site (RBS))] and Reverse: 5' TTC TCG AGC TAT CAC TCC GCC GCC TGC TGC TGC 3' [(br jap 3' (xhoI) SEQ ID NO:15 (added a Xho I site)].

Fifty microliter reactions were set up as follows: Fail Safe Buffer 25 ea. primer 1 nl (50 ng/µl), gDNA 1 µl (200 ng/µl), H$_2$O 21 µl, Taq polymerase 1 µl (2.5 units/µl). Three Fail Safe Buffers—A, B, and C—were used in three separate reactions. PCR was then carried out under the following conditions: 95° C. 3.0 minutes heat denature cycle; 95° C. 1.0 minute, 50° C. 1.0 minute, 72° C. 1.5 minutes, for 30 cycles; followed by a final cycle of 72° C. 5 minutes, using the FailSafe PCR System (Epicenter cat. #FS99100). The resulting ~4 kb PCR product was cloned into pCR 2.1 (Invitrogen cat. #K4550-40) following the included protocol, with chemically competent TOP10F' *E. coli* as the host strain, for verification of nucleotide sequence.

Ten of the resulting white colonies were picked into 3 µl Luria Broth+1000 µg/ml Ampicillin (LB Amp), and grown overnight at 37° C. with agitation. Plasmids were purified from each culture using Nucleospin Plus Plasmid Miniprep Kit (BD Biosciences cat. #K3063-2) and following included protocol. Restriction digestion of the isolated DNA's was completed to confirm the presence of the PCR product in the pCR2.1 vector. Plasmid DNA was digested with the restriction enzyme EcoRI (New England Biolabs cat. #R0101S). Sequencing was carried out with Beckman CEQ Quick Start Kit (Beckman Coulter cat. #608120) using M13 Forward [5' GTA AAA CGA CGG CCA GT 3'] (SEQ ID NO:16) and Reverse [5' CAG GAA ACA GCT ATG AC 3'] (SEQ ID NO:17) primers, per manufacturers instructions. This gene sequence and its corresponding protein was given a new general designation AAD-2 (v1) for internal consistency.

17.2—Completion of AAD-2 (v1) Binary Vector.

The AAD-2 (v1) gene was PCR amplified from pDAB3202. During the PCR reaction alterations were made within the primers to introduce the AflIII and SacI restriction sites in the 5' primer and 3' primer, respectively. The primers "NcoI of Brady" [5' TAT ACC ACA TGT CGA TCG CCA TCC GGC AGC TT 3'] (SEQ ID NO:18) and "SacI of Brady" [5' GAG CTC CTA TCA CTC CGC CGC CTG CTG CTG CAC 3'] (SEQ ID NO:19) were used to amplify a DNA fragment using the Fail Safe PCR System (Epicentre). The PCR product was cloned into the pCR 2.1 TOPO TA cloning vector (Invitrogen) and sequence verified with M13 Forward and M13 Reverse primers using the Beckman Coulter "Dye Terminator Cycle Sequencing with Quick Start Kit" sequencing reagents. Sequence data identified a clone with the correct sequence (pDAB716). The AflIII/SacI AAD-2 (v1) gene fragment was then cloned into the NcoI/SacI pDAB726 vector. The resulting construct (pDAB717); AtUbi10 promoter: Nt OSM 5'UTR: AAD-2 (v1): Nt OSM3'UTR: ORF1 polyA 3'UTR was verified with restriction digests (with NcoI/SacI). This construct was cloned into the binary pDAB3038 as a NotI-NotI DNA fragment. The resulting construct (pDAB767); AtUbi10 promoter: Nt OSM5'UTR: AAD-2 (v1): Nt OSM 3'UTR: ORF1 polyA 3'UTR: CsVMV promoter: PAT: ORF25/26 3'UTR was restriction digested (with NotI, EcoRI, HinDIII, NcoI, PvuII, and SalI) for verification of the correct orientation. The completed construct (pDAB767) was then used for transformation into *Agrobacterium*.

17.3—Comparison of Substrate Specificities of AAD-2 (v1) and AAD-1 (v1)

Figure 22:
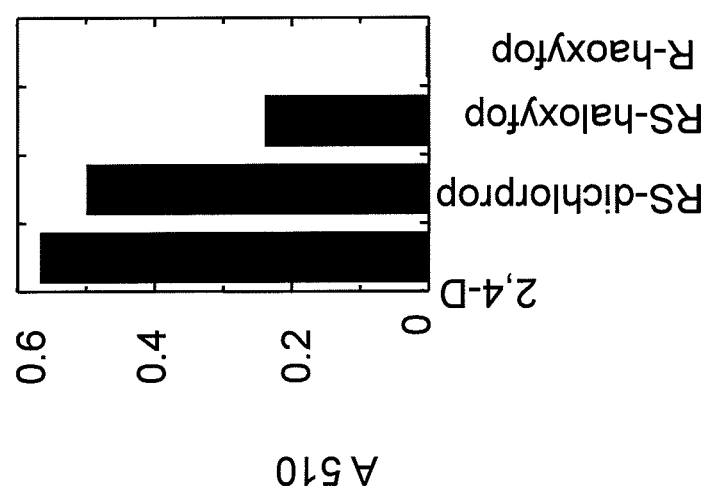
FIG. 22 shows that the relative AAD-2 (v1) activity on the substrates was 2,4-D=dichlorprop >(R,S)-haloxyfop>>(R)-haloxyfop.

The activity of an extract from *E. coli* expressing AAD-2 (v1) (pDAB3202) prepared as in Example 11 was tested on four herbicides, 2,4-D, (R,S)-dichlorprop, (R,S)-haloxyfop and (R)-haloxyfop (all at a final concentration of 0.5 mM) using 3 µl (42 µg) of *E. coli* extract per assay with a 15 min assay period. FIG. 22 shows that the relative AAD-2 (v1) activity on the substrates was 2,4-D=dichlorprop>(R,S)-haloxyfop>>(R)-haloxyfop. Thus AAD-2 (v1) differs from AAD-1 (v1) in that it has a similar level of activity on 2,4-D as on dichlorprop (whereas the activity of AAD-1 (v1) on 2,4-D is ~10% that of dichlorprop). AAD-2 (v1) also differs from AAD-1 (v1) in that it is unable to act on (R)-haloxyfop. Table 33 shows data from additional substrates tested with AAD-1 (v1) and AAD-2 (v1) that confirm that AAD-2 (v1) is specific for (S)-enantiomer substrates, in contrast to AAD-1 (v1) which is specific for (R)-enantiomers. In another test, AAD-2 (v1) was found to differ from AAD-1 (v1) in that it releases little or no detectable phenol from 2,4-D sulfonate (in which a sulfonate group replaces the carboxylate of 2,4-D) whereas AAD-1 (v1) produces significant levels of phenol from this compound (~25% of 2,4-D.)

TABLE 33

Comparison of AAD1 and AAD2 activity on various substrates. Substrates were assayed at 0.5 mM for 15 min in 25 mM MOPS pH 6.8, 200 µM Fe$^{2+}$, 200 µM Na ascorbate, 1 mM α-ketoglutarate using 4 µl AAD1 (32 µg protein) extract or 3 µl AAD2 extract (42 µg protein).

|  |  |  |  | A510 | |
| --- | --- | --- | --- | --- | --- |
| STRUCTURE | Reg ID | Compound | Enantiomer | AAD1 | AAD2 |
|  | 18706 | quizalofop | R | 0.27 | 0.01 |

TABLE 33-continued

Comparison of AAD1 and AAD2 activity on various substrates. Substrates were assayed at 0.5 mM for 15 min in 25 mM MOPS pH 6.8, 200 μM Fe²⁺, 200 μM Na ascorbate, 1 mM α-ketoglutarate using 4 μl AAD1 (32 μg protein) extract or 3 μl AAD2 extract (42 μg protein).

| STRUCTURE | Reg ID | Compound | Enantiomer | A510 AAD1 | A510 AAD2 |
|---|---|---|---|---|---|
| 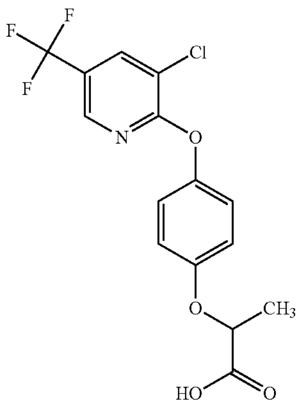 [SMILES: CC(Oc1ccc(Oc2ncc(C(F)(F)F)cc2Cl)cc1)C(=O)O] | 8671 | haloxyfop | R | 0.12 | 0 |
| 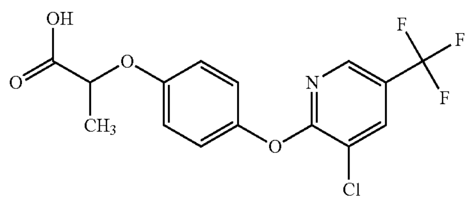 [SMILES: CC(Oc1ccc(Oc2ncc(C(F)(F)F)cc2Cl)cc1)C(=O)O] | 66905 | haloxyfop | R,S | 0.1 | 0.3 |
| 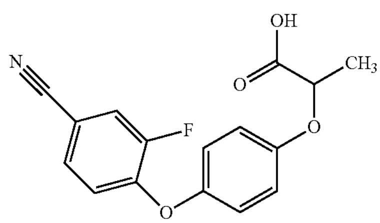 [SMILES: CC(Oc1ccc(Oc2ccc(C#N)cc2F)cc1)C(=O)O] | 14623 | cyhalofop | R,S | 0.12 | 0.1 |
| 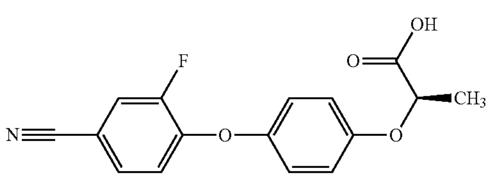 [SMILES: C[C@@H](Oc1ccc(Oc2ccc(C#N)cc2F)cc1)C(=O)O] | 14603 | cyhalofop | R | 0.14 | 0 |
| 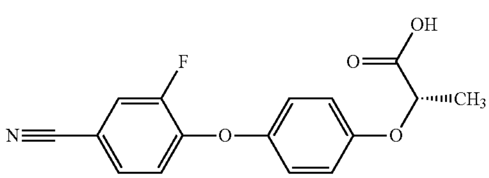 [SMILES: C[C@H](Oc1ccc(Oc2ccc(C#N)cc2F)cc1)C(=O)O] | 7466 | cyhalofop | S | 0 | 0.15 |
| 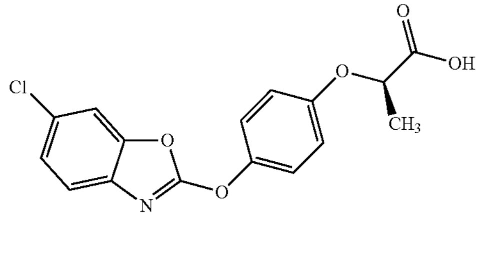 | 11044492 | fenoxaprop | R | 0.14 | 0 |

TABLE 33-continued

Comparison of AAD1 and AAD2 activity on various substrates. Substrates were assayed at 0.5 mM for 15 min in 25 mM MOPS pH 6.8, 200 µM $Fe^{2+}$, 200 µM Na ascorbate, 1 mM α-ketoglutarate using 4 µl AAD1 (32 µg protein) extract or 3 µl AAD2 extract (42 µg protein).

| STRUCTURE | Reg ID | Compound | Enantiomer | A510 AAD1 | A510 AAD2 |
|---|---|---|---|---|---|
| [structure image] | 43865 | haloxyfop-acetate | — | 0 | 0.22 |

Figure 19:
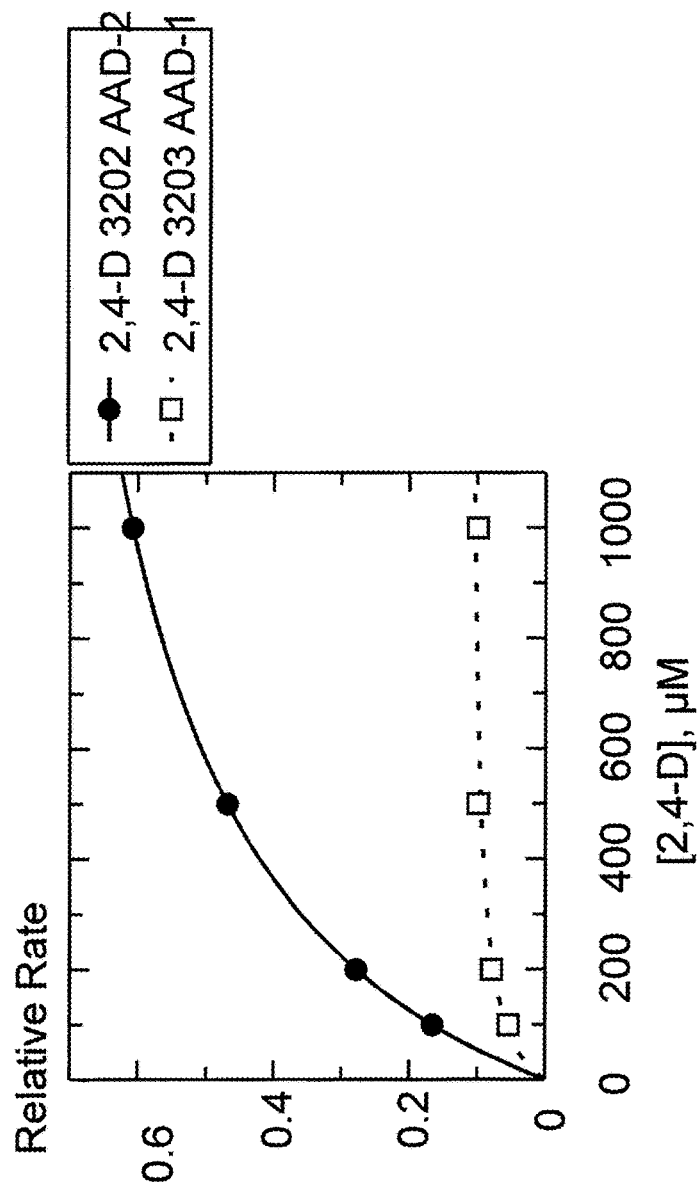
FIG. 19 shows fitted curves for 2,4-D degradation rates by AAD-2 (v1) vs. AAD-1 (v1).

The enzyme kinetics of partially purified AAD-1 (v1) and AAD-2 (v1) were compared using 2,4-D as substrate. See FIG. 19. The $K_m$ values for 2,4-D were 97 and 423 µM for AAD-1 (v1) and AAD-2 (v1) respectively and the apparent $V_{max}$ values were 0.11 and 0.86 $A_{510}$ units, respectively (Table 34). Because equivalent amounts of enzyme were used in the assays (as determined by SDS-PAGE analysis), it can be concluded that the $k_{cat}$ of AAD-2 (v1) for 2,4-D is almost 8-fold higher than AAD-1 (v1) and the $k_{cat}/K_m$ is 2-fold higher. Thus AAD-2 (v1) is significantly more efficient at cleaving 2,4-D in vitro than AAD-1 (v1). This is in surprising contrast to the in planta findings reported below, where plants expressing AAD-1 (v1) are significantly better in conferring 2,4-D resistance relative to AAD-2 (v1).

TABLE 34

Comparison of the Km and "Vmax" values for the aryloxyalkanoate dioxygenases (AADs) from pDAB3202 (AAD-2) and pDAB3203 [AAD-1 (v1)] with different herbicide substrates:

| Enzyme | Compound | Km (µM) ± SE | Vmax (A510 units) | Km/Vmax (arbitrary units) |
|---|---|---|---|---|
| AAD-2 | 2,4-D | 423 (±1) | 0.86 | 2.03 |
| AAD-1 (v1) | 2,4-D | 97 (±21) | 0.11 | 1.16 |

Notes:
Assays were performed in MOPS pH 6.75 + 1 mM α-ketoglularate + 0.1 mM Na ascorbate + 0.1 mM Fe2+ and the released phenols colorimetrically detected using 4-aminoantipyrinc/ferricyanide.

17.4—Evaluation of Transformed *Arabidopsis*.

Freshly harvested $T_1$ seed transformed with a native [AAD-1 (v2)], plant optimized [AAD-1 (v3)], or native AAD-2 (v1) gene was allowed to dry for 7 days at room temperature. $T_1$ seed was sown in 26.5×51-cm germination trays (T.O. Plastics Inc., Clearwater, Minn.), each receiving a 200 mg aliquots of stratified $T_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet and then allowed to gravity drain. Each 40 ml aliquot of stratified seed was sown evenly onto the vermiculite with a pipette and covered with humidity domes (KORD Products, Bramalea, Ontario, Canada) for 4-5 days. Domes were removed 1 day prior to initial transformant selection using glufosinate postemergence spray (selecting for the co-transformed PAT gene).

Five to six days after planting (DAP) and again 10 DAP, $T_1$ plants (cotyledon and 2-4-1f stage, respectively) were sprayed with a 0.2% solution of Liberty herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (plants actively growing) were identified 5-7 days after the final spraying and transplanted individually into 3-inch pots prepared with potting media (Metro Mix 360). Transplanted plants were covered with humidity domes for 3-4 days and placed in a 22° C. growth chamber as before. Domes were subsequently removed and plants moved to the greenhouse (22±5° C., 50±30% RH, 14 hours light:10 dark, minimum 500 µE/$m^2$ $s^1$ natural+supplemental light) at least 1 day prior to testing for the ability of AAD-1 (v3), AAD-1 (v2), or AAD-2 (v1) to provide phenoxy auxin herbicide resistance.

Random individual $T_1$ plants selected for glufosinate resistance above were confirmed for expression of the PAT protein using a PAT ELISA kit (Part no. 7000045, Strategic Diagnostics, Inc., Newark, Del.) to non-destructively confirm fidelity of selection process (manufacturer's protocol). Plants were then randomly assigned to various rates of 2,4-D (50-800 g ae/ha).

Herbicide applications were applied by track sprayer in a 187 L/ha spray volume. 2,4-D used was the commercial dimethylamine salt formulation (456 g ae/L, NuFarm, St Joseph, Mo.) mixed in 200 mM Tris buffer (pH 9.0).

17.5—Results of Selection of Transformed Plants.

The first *Arabidopsis* transformations were conducted using AAD-1 (v3). $T_1$ transformants were first selected from the background of untransformed seed using a glufosinate selection scheme. Over 400,000 $T_1$ seed were screened and 493 glufosinate resistant plants were identified (PAT gene), equating to a transformation/selection frequency of 0.12%. Depending on the lot of seed tested, this ranged from 0.05-0.23% (see Table 15 in Example 6.5 above). A small lot of native AAD-1 (v2) transformed seed were also selected using the glufosinate selection agent. Two hundred seventy eight glufosinate-resistant $T_1$ individuals were identified out of 84,000 seed screened (0.33% transformation/selection frequency). Surprisingly, *Arabidopsis* transformations using the native AAD-2(v1) gene provided a very low transformation frequency when selected for glufosinate tolerance (PAT selectable marker function). Approximately 1.3 million seed have been screened and only 228 glufosinate transformants were recovered, equating to a transformation/selection frequency of 0.018% (see Table 15). Transformation frequency for native AAD-2 (v1) was only 6% of that of native AAD-1 (v2). The native AAD2 (v1) gene was subsequently synthetically optimized, cloned, and transformed as pDAB3705, into *Arabidopsis* using methods previously described (see Example 5). The plant optimized AAD2 (v2) (SEQ ID NO:29, which encodes SEQ ID NO:30) yielded a normal $T_1$ *Arabidopsis* selection frequency using Liberty herbicide of approximately 0.11% (see Table 15).

$T_1$ plants selected above were subsequently transplanted to individual pots and sprayed with various rates of commercial aryloxyalkanoate herbicides. Table 16 (in Example 6.5 above) compares the response of AAD-1 (v2), AAD-1 (v3), AAD-2 (v1) and AAD-1(v2) genes to impart 2,4-D resistance to *Arabidopsis* $T_1$ transformants. All genes did provide some significant 2,4-D resistance versus the transformed and untransformed control lines; however, individual constructs were widely variable in their ability to impart 2,4-D resistance to individual $T_1$ *Arabidopsis* plants. Within a given treatment, the level of plant response varied greatly and can be attributed to the fact each plant represents an independent transformation event. Of important note, at each 2,4-D rate tested, there were individuals that were unaffected while some were severely affected. An overall population injury average by rate is presented in Table 16 simply to demonstrate the significant difference between the plants transformed with AAD-1 (v2), AAD-1 (v3), AAD-2 (v1) or AAD-2 (v2) versus the wildtype or PAT/Cry1F transformed controls.

Figure 20:
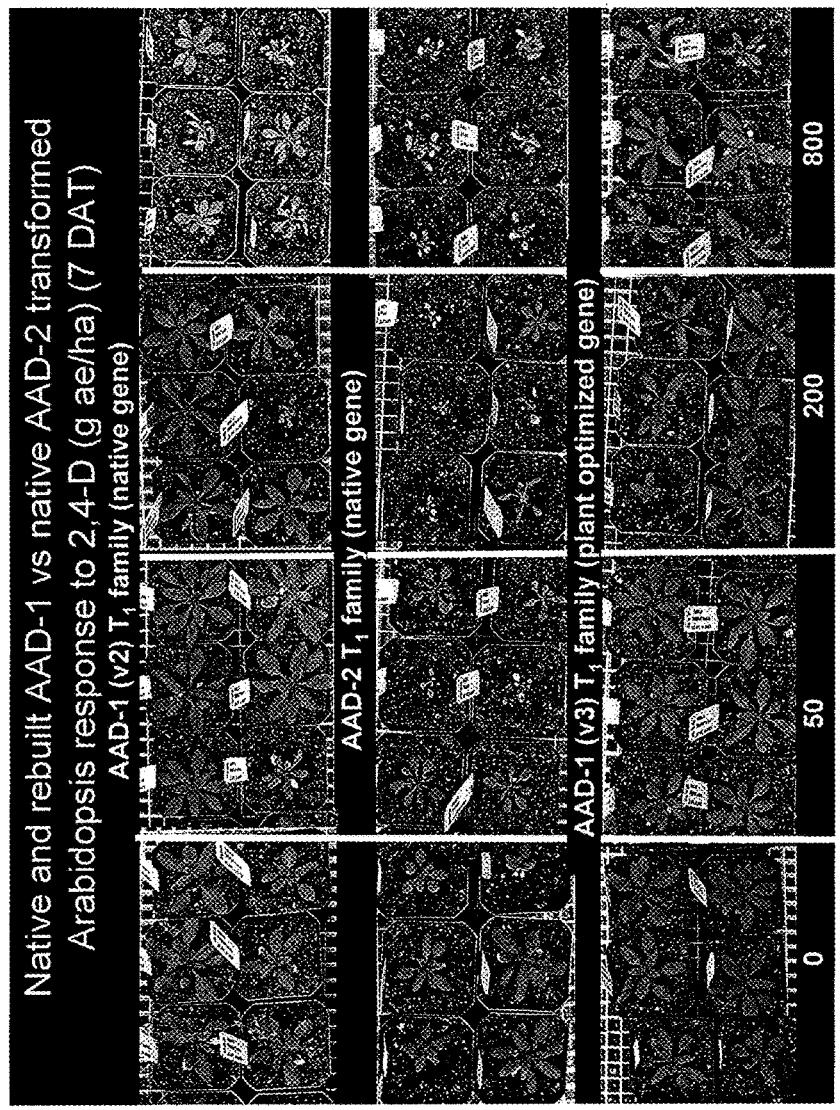
FIG. 20 shows the response of AAD-1 v3 (plant optimized), or AAD-1 (v2) (native), AAD-2 (v1) (native), or AAD-2 (v2) (plant optimized)-transformed $T_1$ Arabidopsis to a range of 2,4-D rates applied postemergence. Each pot represents an individual transformation event within each gene $T_1$ family.

Surprisingly, AAD-2 (v1) transformants were far less resistant to 2,4-D than either AAD-1 (v2) or AAD-1 (v3) genes (Table 16) both from a frequency of highly tolerant plants as well as overall average injury. No plants transformed with AAD-2 (v1) survived 200 g ae/ha 2,4-D relatively uninjured (<20% visual injury), and overall population injury was about 83%. Conversely, 56% (45 of 80) AAD-1 (v2)-transformed $T_1$ plants survived 200 g ae/ha 2,4-D uninjured (population injury average=34%), and >73% (11 of 15) AAD-1 (v3) $T_1$ plants were uninjured (population injury average=14%). See FIG. 20. Tolerance improved slightly for plant-optimized AAD2 (v2) versus the native gene; however, comparison of both AAD-1 and -2 plant optimized genes indicates a significant advantage for AAD-1 (v3) in planta (see Table 16).

Figure 21:
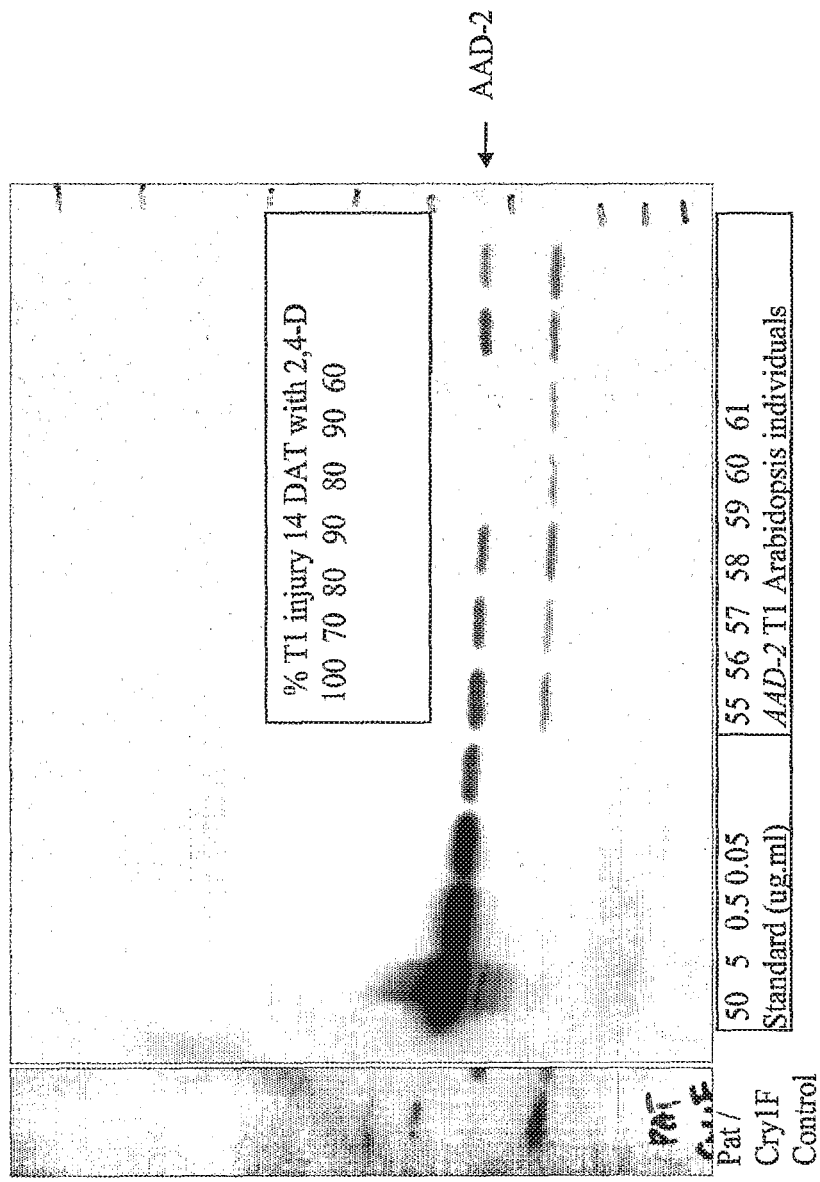
FIG. 21 shows western blot analysis of individual native AAD-2 (v1)-transformed $T_1$ Arabidopsis plants. This shows that plants expressing the AAD-2 (v1) protein are suffering severe injury from 200 g ae (acid equivalent)/ha 2,4-D treatments, which normally causes little injury to native AAD-1 (v2) or plant optimized AAD-1 (v3)-transformed Arabidopsis. AAD-2 protein is identified on the gel. Several background bands were detected in AAD-2-transformed and Pat/Cry1F-transformed samples.

These results are unexpected given that in vitro comparison of native AAD-1 (v2) and AAD-2 (v1) indicated 2,4-D was better degraded by AAD-2 (v1). AAD-2 (v1) is expressed in individual $T_1$ plants to varying levels with the anticipated size; however, little protection from 2,4-D injury is afforded by this expressed protein. Little correlation exists between expression level noted on the Western blot and the level of injury from 2,4-D on the same plants. See FIG. 21. No large difference was evident in protein expression level (in planta) for the native and plant optimized AAD-2 genes. These data corroborate earlier findings that make the functional expression of AAD-1 (v3) in planta for imparting herbicide resistance to 2,4-D and AOPP herbicides is unexpected.

Example 18—Preplant Burndown Applications

This and the following Examples are specific examples of novel herbicide uses made possible by the subject AAD-1 invention.

Preplant burndown herbicide applications are intended to kill weeds that have emerged over winter or early spring prior to planting a given crop. Typically these applications are applied in no-till or reduced tillage management systems where physical removal of weeds is not completed prior to planting. An herbicide program, therefore, must control a very wide spectrum of broadleaf and grass weeds present at the time of planting. Glyphosate, gramoxone, and glufosinate are examples of non-selective, non-residual herbicides widely used for preplant burndown herbicide applications. Some weeds, however, are difficult to control at this time of the season due to one or more of the following: inherent insensitivity of the weed species or biotype to the herbicide, relatively large size of winter annual weeds, and cool weather conditions limiting herbicide uptake and activity. Several herbicide options are available to tankmix with these herbicides to increase spectrum and activity on weeds where the non-selective herbicides are weak. An example would be 2,4-D tankmix applications with glyphosate to assist in the control of Conyza *canadensis* (horseweed). Glyphosate can be used from 420 to 1680 g ae/ha, more typically 560 to 840 g ae/ha, for the preplant burndown control of most weeds present; however, 280-1120 g ae/ha of 2,4-D can be applied to aid in control of many broadleaf weed species (e.g., horseweed). 2,4-D is an herbicide of choice because it is effective on a very wide range of broadleaf weeds, effective even at low temperatures, and extremely inexpensive. However, if the subsequent crop is a sensitive dicot crop, 2,4-D residues in the soil (although short-lived) can negatively impact the crop. Soybeans are a sensitive crop and require a minimum time period of 7 days (for 280 g ae/ha 2,4-D rate) to at least 30 days (for 2,4-D applications of 1120 g ae/ha) to occur between burndown applications and planting. 2,4-D is prohibited as a burndown treatment prior to cotton planting (see federal labels, most are available through CPR, 2003 or online at cdms.net/manuf/manuf.asp). With AAD-1 (v3) transformed cotton or soybeans, these crops should be able to survive 2,4-D residues in the soil from burndown applications applied right up to and even after planting before emergence of the crop. The increased flexibility and reduced cost of tankmix (or commercial premix) partners will improve weed control options and increase the robustness of burndown applications in important no-till and reduced tillage situations. This example is one of many options that will be available. Those skilled in the art of weed control will note a variety of other applications including, but not limited to gramoxone+2,4-D or glufosinate+2,4-D by utilizing products described in federal herbicide labels (CPR, 2003) and uses described in Agriliance Crop Protection Guide (2003), as examples. Those skilled in the art will also recognize that the above example can be applied to any 2,4-D-sensitive (or other phenoxy auxin herbicide) crop that would be protected by the AAD-1 (v3) gene if stably transformed.

Example 19—In-Crop Use of Phenoxy Auxins Herbicides in AAD-1 (v3) Only Transformed Soybeans, Cotton, and Other Dicot Crops AAD-1 (v3) can enable the use of phenoxy auxin herbicides (e.g., 2,4-D, dichlorprop, MCPA, et al.) for the control of a wide spectrum of broadleaf weeds directly in crops normally sensitive to 2,4-D. Application of 2,4-D at 280 to 2240 g ae/ha would control most broadleaf weed species present in agronomic environments. More typically, 560-1120 g ae/ha is used. For a complete weed control system, grass weeds must be controlled. A variety of broad spectrum graminicide herbicides, including but not limited to haloxyfop, quizalofop, fenoxaprop, fluazifop, sethoxydim, and clethodim are currently registered for use in most dicot crops which are naturally tolerant to these herbicides. A combination of quizalofop (20-100 g ae/ha) plus 2,4-D (420-840 g ae/ha) could provide two herbicide modes of action in an AAD-1 (v3)-transformed dicot crop (i.e., soybean or cotton) that would control most agronomic weeds in a similar fashion to glyphosate in glyphosate tolerant crops (see weed control spectra by reference to Agriliance Crop Protection Guide performance ratings).

An advantage to this additional tool is the extremely low cost of the broadleaf herbicide component and potential short-lived residual weed control provided by higher rates of 2,4-D and/or AOPP herbicides when used at higher rates, whereas a non-residual herbicide like glyphosate would provide no control of later germinating weeds. This tool also provides a mechanism to rotate herbicide modes of action with the convenience of HTC as an integrated herbicide resistance and weed shift management strategy in a glyphosate tolerant crop/AAD-1 (v3) HTC rotation strategy, whether one rotates crops species or not. Additionally, the grass and broadleaf weed control components of this system are independent of one another, thus allowing one skilled in the are of weed control to determine the most cost effective and efficacious ratio of auxin and AOPP herbicide. For example, if broadleaf weeds were the only significant weeds present when herbicide applications were needed, an herbicide application of 560 to 1120 g ae/ha 2,4-D could be made without another herbicide. This would reduce unnecessary herbicide applications, provide flexibility to reduce input costs and reduce environmental loads of pesticides, and reduce unnecessary selection pressure for the development of herbicide resistant weeds.

Further benefits could include tolerance to 2,4-D drift or volatilization as mechanisms for off-site 2,4-D injury to dicot crops; no interval required before planting following 2,4-D application (see previous example); and fewer problems from contamination injury to dicot crops resulting from incompletely cleaned bulk tanks that had contained 2,4-D. Dicamba (and other herbicides) can still be used for the subsequent control of AAD-1 (v3)-transformed dicot crop volunteers.

Those skilled in the art will also recognize that the above example can be applied to any 2,4-D-sensitive (or other phenoxy auxin herbicide) crop that would be protected by the AAD-1 (v3) gene if stably transformed. One skilled in the art of weed control will now recognize that use of various commercial phenoxy auxin herbicides alone or in combination with any commercial AOPP herbicide is enabled by AAD-1 (v3) transformation. Specific rates of other herbicides representative of these chemistries can be determined by the herbicide labels compiled in the CPR (Crop Protection Reference) book or similar compilation or any commercial or academic crop protection references such as the Crop Protection Guide from Agriliance (2003). Each alternative herbicide enabled for use in HTCs by AAD-1 (v3), whether used alone, tank mixed, or sequentially, is considered within the scope of this invention.

Example 20—In-Crop Use of Phenoxy Auxins and AOPP Herbicides in AAD-1 (v3) Only Transformed Corn, Rice, and Other Monocot Species In an analogous fashion, transformation of grass species (such as, but not limited to, corn, rice, wheat, barley, or turf and pasture grasses) with AAD-1 (v3) would allow the use of highly efficacious AOPP graminicides in crops normally sensitive to these herbicides. Most grass species have a natural tolerance to auxinic herbicides such as the phenoxy auxins (i.e., 2,4-D, dichlorprop, et al.). However, a relatively low level of crop selectivity has resulted in diminished utility in these crops due to a shortened window of application timing and alternative broadleaf weeds. AAD-1 (v3)-transformed monocot crops would, therefore, enable the use of a similar combination of treatments described for dicot crops such as the application of 2,4-D at 280 to 2240 g ae/ha to control most broadleaf weed species. More typically, 560-1120 g ae/ha would be used. A variety of broad spectrum AOPP graminicide herbicides (including but not limited to haloxyfop, quizalofop, fenoxaprop, and fluazifop) could be utilized for effectively controlling a wide selection of grass weeds. Cyclohexanedione graminicidal herbicides like sethoxydim, clethodim, et al. could not be used in this system as shown for dicot crops since AAD-1 would not protect from this chemistry, and grass crops will be naturally sensitive to the cyclohexanedione chemistries. However, this attribute would enable the use of cyclohexanedione herbicides for the subsequent control of AAD-1 (v3)-transformed grass crop volunteers. Similar weed control strategies are now enabled by AAD-1 for the dicot crop species. A combination of quizalofop (20-100 g ae/ha) plus 2,4-D (420-840 g ae/ha) could provide two herbicide modes of action in an AAD-1 (v3) transformed monocot crop (e.g., corn and rice) that would control most agronomic weeds in a similar fashion to glyphosate in glyphosate tolerant crops (see weed control spectra by reference to Agriliance Crop Protection Guide performance ratings).

An advantage to this additional tool is the extremely low cost of the broadleaf herbicide component and potential short-lived residual weed control provided by higher rates of 2,4-D and/or AOPP herbicides when used at higher rates. In contrast, a non-residual herbicide like glyphosate would provide no control of later-germinating weeds. This tool would also provide a mechanism to rotate herbicide modes of action with the convenience of HTC as an integrated-herbicide-resistance and weed-shift-management strategy in a glyphosate tolerant crop/AAD-1 (v3) HTC rotation strategy, whether one rotates crops species or not. Additionally, the grass and broadleaf weed control components of this system are independent of one another, thus allowing one skilled in the are of weed control to determine the most cost effective and efficacious ratio of auxin and AOPP herbicide. For example, if broadleaf weeds were the only significant weeds present when herbicide applications were needed, an herbicide application of 560 to 1120 g ae/ha 2,4-D could be made without another herbicide. This would reduce unnecessary herbicide applications, provide flexibility to reduce input costs and reduce environmental loads of pesticides, and reduce unnecessary selection pressure for the development of herbicide resistant weeds. The increased tolerance of corn, and other monocots to the phenoxy auxins shall enable use of these herbicides in-crop without growth stage restrictions or the potential for crop leaning, unfurling phenomena such as "rat-tailing," crop leaning, growth regulator-induced stalk brittleness in corn, or deformed brace roots.

Those skilled in the art will now also recognize that the above example can be applied to any monocot crop that would be protected by the AAD-1 (v3) gene from injury by any AOPP herbicide. One skilled in the art of weed control will now recognize that use of various commercial phenoxy auxin herbicides alone or in combination with any commercial AOPP herbicide is enabled by AAD-1 (v3) transformation. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2003). Each alternative herbicide enabled for use in HTCs by AAD-1 (v3), whether used alone, tank mixed, or sequentially, is considered within the scope of this invention.

Example 21—AAD-1 (v3) Stacked with Glyphosate Tolerance Trait in any Crop

The vast majority of cotton, canola, and soybean acres planted in North America contain a glyphosate tolerance (GT) trait, and adoption of GT corn is on the rise. Additional GT crops (e.g., wheat, rice, sugar beet, and turf) have been under development but have not been commercially released to date. Many other glyphosate resistant species are in experimental to development stage (e.g., alfalfa, sugar cane, sunflower, beets, peas, carrot, cucumber, lettuce, onion, strawberry, tomato, and tobacco; forestry species like poplar and sweetgum; and horticultural species like marigold, petunia, and begonias; isb.vt.edu/cfdocs/fieldtests1.cfm, 2005 on the World Wide Web). GTC's are valuable tools for the sheer breadth of weeds controlled and convenience and cost effectiveness provided by this system. However, glyphosate's utility as a now-standard base treatment is selecting for glyphosate resistant weeds. Furthermore, weeds that glyphosate is inherently less efficacious on are shifting to the predominant species in fields where glyphosate-only chemical programs are being practiced. By stacking AAD-1 (v3) with a GT trait, either through conventional breeding or jointly as a novel transformation event, weed control efficacy, flexibility, and ability to manage weed shifts and herbicide resistance development could be improved. As mentioned in previous examples, by transforming crops with AAD-1 (v3), one can selectively apply AOPP herbicides in monocot crops, monocot crops will have a higher margin of phenoxy auxin safety, and phenoxy auxins can be selectively applied in dicot crops. Several scenarios for improved weed control options can be envisioned where AAD-1 (v3) and a GT trait are stacked in any monocot or dicot crop species:
  a) Glyphosate can be applied at a standard postemergent application rate (420 to 2160 g ae/ha, preferably 560 to 840 g ae/ha) for the control of most grass and broadleaf weed species. For the control of glyphosate resistant broadleaf weeds like Conyza canadensis or weeds inherently difficult to control with glyphosate (e.g., Commelina spp), 280-2240 g ae/ha (preferably 560-1120 g ae/ha) 2,4-D can be applied sequentially, tank mixed, or as a premix with glyphosate to provide effective control.
  b) Glyphosate can be applied at a standard postemergent application rate (420 to 2160 g ae/ha, preferably 560 to 840 g ae/ha) for the control of most grass and broadleaf weed species. For the control of glyphosate resistant grass species like Lolium rigidum or Eleusine indica, 10-200 g ae/ha (preferably 20-100 g ae/ha) quizalofop can be applied sequentially, tank mixed, or as a premix with glyphosate to provide effective control.
  c) Currently, glyphosate rates applied in GTC's generally range from 560 to 2240 g ae/ha per application timing. Glyphosate is far more efficacious on grass species than broadleaf weed species. AAD-1 (v3)+GT stacked traits would allow grass-effective rates of glyphosate (105-840 g ae/ha, more preferably 210-420 g ae/ha). 2,4-D (at 280-2240 g ae/ha, more preferably 560-1120 g ae/ha) could then be applied sequentially, tank mixed, or as a premix with grass-effective rates of glyphosate to provide necessary broadleaf weed control. An AOPP herbicide like quizalofop at 10-200 g ae/ha (preferably 20-100 g ae/ha and more preferably 20-35 g ae/ha), could be for more robust grass weed control and/or for delaying the development of glyphosate resistant grasses. The low rate of glyphosate would also provide some benefit to the broadleaf weed control; however, primary control would be from the 2,4-D.

One skilled in the art of weed control will recognize that use of one or more commercial phenoxy auxin herbicides alone or in combination (sequentially or independently) with one or more commercial AOPP herbicide is enabled by AAD-1 (v3) transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2003). Each alternative herbicide enabled for use in HTCs by AAD-1 (v3), whether used alone, tank mixed, or sequentially, is considered within the scope of this invention.

Example 22—AAD-1 (v3) Stacked with Glufosinate Tolerance Trait in any Crop

Glufosinate tolerance (PAT or bar) is currently present in a number of crops planted in North America either as a selectable marker for an input trait like insect resistance proteins or specifically as an HTC trait. Crops include, but are not limited to, glufosinate tolerant canola, corn, and cotton. Additional glufosinate tolerant crops (e.g., rice, sugar beet, soybeans, and turf) have been under development but have not been commercially released to date. Glufosinate, like glyphosate, is a relatively non-selective, broad spectrum grass and broadleaf herbicide. Glufosinate's mode of action differs from glyphosate. It is faster acting, resulting in desiccation and "burning" of treated leaves 24-48 hours after herbicide application. This is advantageous for the appearance of rapid weed control. However, this also limits translocation of glufosinate to meristematic regions of target plants resulting in poorer weed control as evidenced by relative weed control performance ratings of the two compounds in many species (Agriliance, 2003).

By stacking AAD-1 (v3) with a glufosinate tolerance trait, either through conventional breeding or jointly as a novel transformation event, weed control efficacy, flexibility, and ability to manage weed shifts and herbicide resistance development could be improved. As mentioned in previous examples, by transforming crops with AAD-1 (v3), one can selectively apply AOPP herbicides in monocot crops, monocot crops will have a higher margin of phenoxy auxin safety, and phenoxy auxins can be selectively applied in dicot crops. Several scenarios for improved weed control options can be envisioned where AAD-1 (v3) and a glufosinate tolerance trait are stacked in any monocot or dicot crop species:
  a) Glufosinate can be applied at a standard postemergent application rate (200 to 1700 g ae/ha, preferably 350 to 500 g ae/ha) for the control of many grass and broadleaf weed species. To date, no glufosinate-resistant weeds have been confirmed; however, glufosinate has a greater number of weeds that are inherently more tolerant than does glyphosate.

i) Inherently tolerant grass weed species (e.g., *Echinochloa* spp or *Sorghum* spp) could be controlled by tank mixing 10-200 g ae/ha (preferably 20-100 g ae/ha) quizalofop.

ii) Inherently tolerant broadleaf weed species (e.g., *Cirsium arvensis* and *Apocynum cannabinum*) could be controlled by tank mixing 280-2240 g ae/ha, more preferably 560-2240 g ae/ha, 2,4-D for effective control of these more difficult-to-control perennial species and to improve the robustness of control on annual broadleaf weed species.

b) A three-way combination of glufosinate (200-500 g ae/ha)+2,4-D (280-1120 g ae/ha)+quizalofop (10-100 g ae/ha), for example, could provide more robust, overlapping weed control spectrum. Additionally, the overlapping spectrum provides an additional mechanism for the management or delay of herbicide resistant weeds.

One skilled in the art of weed control will recognize that use of one or more commercial phenoxy auxin herbicides alone or in combination (sequentially or independently) with one or more commercial AOPP herbicide is enabled by AAD-1 (v3) transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2003). Each alternative herbicide enabled for use in HTCs by AAD-1 (v3), whether used alone, tank mixed, or sequentially, is considered within the scope of this invention.

Example 23—AAD-1 (v3) Stacked with AHAS Trait in any Crop

Imidazolinone herbicide tolerance (AHAS, et al.) is currently present in a number of crops planted in North America including, but not limited to, corn, rice, and wheat. Additional imidazolinone tolerant crops (e.g., cotton and sugar beet) have been under development but have not been commercially released to date. Many imidazolinone herbicides (e.g., imazamox, imazethapyr, imazaquin, and imazapic) are currently used selectively in various conventional crops. The use of imazethapyr, imazamox, and the non-selective imazapyr has been enabled through imidazolinone tolerance traits like AHAS et al. Imidazolinone tolerant HTCs to date have the advantage of being non-transgenic. This chemistry class also has significant soil residual activity, thus being able to provide weed control extended beyond the application timing, unlike glyphosate or glufosinate-based systems. However, the spectrum of weeds controlled by imidazolinone herbicides is not as broad as glyphosate (Agriliance, 2003). Additionally, imidazolinone herbicides have a mode of action (inhibition of acetolactate synthase, ALS) to which many weeds have developed resistance (Heap, 2004). By stacking AAD-1 (v3) with an imidazolinone tolerance trait, either through conventional breeding or jointly as a novel transformation event, weed control efficacy, flexibility, and ability to manage weed shifts and herbicide resistance development could be improved. As mentioned in previous examples, by transforming crops with AAD-1 (v3), one can selectively apply AOPP herbicides in monocot crops, monocot crops will have a higher margin of phenoxy auxin safety, and phenoxy auxins can be selectively applied in dicot crops. Several scenarios for improved weed control options can be envisioned where AAD-1 (v3) and an imidazolinone tolerance trait are stacked in any monocot or dicot crop species:

a) Imazethapyr can be applied at a standard postemergent application rate of (35 to 280 g ae/ha, preferably 70-140 g ae/ha) for the control of many grass and broadleaf weed species.

i) ALS-inhibitor resistant broadleaf weeds like *Amaranthus rudis, Ambrosia trifida, Chenopodium album* (among others, Heap, 2004) could be controlled by tank mixing 280-2240 g ae/ha, more preferably 560-1120 g ae/ha, 2,4-D.

ii) Inherently more tolerant broadleaf species to imidazolinone herbicides like *Ipomoea* spp. can also be controlled by tank mixing 280-2240 g ae/ha, more preferably 560-1120 g ae/ha, 2,4-D.

iii) ALS-inhibitor resistant grass weeds like *Sorghum halepense* and *Lolium* spp. can be controlled by tank mixing 10-200 g ae/ha (preferably 20-100 g ae/ha) quizalofop.

iv) Inherently tolerant grass weed species (e.g., *Agropyron repens*) could also be controlled by tank mixing 10-200 g ae/ha (preferably 20-100 g ae/ha) quizalofop.

b) A three-way combination of imazethapyr (35 to 280 g ae/ha, preferably 70-140 g ae/ha)+2,4-D (280-1120 g ae/ha)+quizalofop (10-100 g ae/ha), for example, could provide more robust, overlapping weed control spectrum. Additionally, the overlapping spectrum provides an additional mechanism for the management or delay of herbicide resistant weeds.

One skilled in the art of weed control will recognize that use of any of various commercial imidazolinone herbicides, phenoxy auxin herbicides, or AOPP herbicide, alone or in multiple combinations, is enabled by AAD-1 (v3) transformation and stacking with any imidazolinone tolerance trait either by conventional breeding or genetic engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2003). Each alternative herbicide enabled for use in HTCs by AAD-1 (v3), whether used alone, tank mixed, or sequentially, is considered within the scope of this invention.

Example 24—AAD-1 (v3) in Rice 24.1—Media Description.

Culture media employed were adjusted to pH 5.8 with 1 M KOH and solidified with 2.5 g/l Phytagel (Sigma). Embryogenic calli were cultured in 100×20 mm Petri dishes containing 40 ml semi-solid medium. Rice plantlets were grown on 50 ml medium in Magenta boxes. Cell suspensions were maintained in 125-ml conical flasks containing 35 ml liquid medium and rotated at 125 rpm. Induction and maintenance of embryogenic cultures took place in the dark at 25-26° C., and plant regeneration and whole-plant culture took place in a 16-h photoperiod (Zhang et al. 1996).

Induction and maintenance of embryogenic callus took place on NB basal medium as described previously (Li et al. 1993), but adapted to contain 500 mg/l glutamine. Suspension cultures were initiated and maintained in SZ liquid medium (Zhang et al. 1998) with the inclusion of 30 g/l sucrose in place of maltose. Osmotic medium (NBO) consisted of NB medium with the addition of 0.256 M each of mannitol and sorbitol. Hygromycin-B-resistant callus was selected on NB medium supplemented with 50 mg/l hygromycin B for 3-4 weeks. Pre-regeneration took place on medium (PRH50) consisting of NB medium without 2,4-dichlorophenoxyacetic acid (2,4-D), but with the addition of 2 mg/l 6-benzylaminopurine (BAP), 1 mg/l α-naphthaleneacetic acid (NAA), 5 mg/l abscisic acid (ABA) and 50 mg/l hygromycin B for 1 week. Regeneration of plantlets followed via culture on regeneration medium (RNH50) comprising NB medium without 2,4-D, and supplemented with 3 mg/l BAP, 0.5 mg/l NAA, and 50 mg/l hygromycin B until shoots regenerated. Shoots were transferred to rooting medium with half-strength Murashige and Skoog basal salts and Gamborg's B5 vitamins, supplemented with 1% sucrose and 50 mg/l hygromycin B (½MSH50).

24.2—Tissue Culture Development.

Mature desiccated seeds of Oryza sativa L. japonica cv. Taipei 309 were sterilized as described in Zhang et al. 1996. Embryogenic tissues were induced by culturing sterile mature rice seeds on NB medium in the dark. The primary callus approximately 1 mm in diameter, was removed from the scutellum and used to initiate cell suspension in SZ liquid medium. Suspensions were then maintained as described in Zhang 1995. Suspension-derived embryogenic tissues were removed from liquid culture 3-5 days after the previous subculture and placed on NBO osmotic medium to form a circle about 2.5 cm across in a Petri dish and cultured for 4 h prior to bombardment. Sixteen to 20 h after bombardment, tissues were transferred from NBO medium onto NBH50 hygromycin B selection medium, ensuring that the bombarded surface was facing upward, and incubated in the dark for 14-17 days. Newly formed callus was then separated from the original bombarded explants and placed nearby on the same medium. Following an additional 8-12 days, relatively compact, opaque callus was visually identified, and transferred to PRH50 pre-regeneration medium for 7 days in the dark. Growing callus, which became more compact and opaque was then subcultured onto RNH50 regeneration medium for a period of 14-21 days under a 16-h photoperiod. Regenerating shoots were transferred to Magenta boxes containing ½ MSH50 medium. Multiple plants regenerated from a single explant are considered siblings and were treated as one independent plant line. A plant was scored as positive for the hph gene if it produced thick, white roots and grew vigorously on ½ MSH50 medium. Once plantlets had reached the top of Magenta boxes, they were transferred to soil in a 6-cm pot under 100% humidity for a week, then moved to a growth chamber with a 14-h light period at 30° C. and in the dark at 21° C. for 2-3 weeks before transplanting into 13-cm pots in the greenhouse. Seeds were collected and dried at 37° C. for one week prior to storage at 4° C.

24.3—Microprojectile Bombardment.

All bombardments were conducted with the Biolistic PDS-1000/He™ system (Bio-Rad, Laboratories, Inc.). Three milligrams of 1.0 micron diameter gold particles were washed once with 100% ethanol, twice with sterile distilled water and resuspended in 50 µl water in a siliconized Eppendorf tube. Five micrograms plasmid DNA representing a 1:6 molar ratio of pDOW3303(Hpt-containing vector) to pDAB3403, 20 µl spermidine (0.1 M) and 50 µl calcium chloride (2.5 M) were added to the gold suspension. The mixture was incubated at room temperature for 10 min, pelleted at 10000 rpm for 10 s, resuspended in 60 µl cold 100% ethanol and 8-9 µl was distributed onto each macrocarrier. Tissue samples were bombarded at 1100 psi and 27 in of Hg vacuum as described by Zhang et al. (1996).

24.4—Tolerance Testing.

Rice plantlets at the 3-5 leaf stage were sprayed with a 0.3% (v/v) solution of DuPont™ Assure® II containing 1% (v/v) Agridex crop oil concentrate using a DeVilbiss bulb sprayer (model 15-RD glass atomizer). This concentration corresponds to approximately 140 g ae/ha. Each plant was spayed in a fume hood at a distance of 8-12 inches with 6 full squirts of the sprayer directed so that the entire plant was covered with an equal portion of herbicide. Each squirt delivered approximately 100 µl solution to the plantlet. Once sprayed, plantlets were allowed to dry for one hour before being moved out of the fume hood. Rating for sensitivity or resistance was done at 10-14 days after treatment (DAT) and is shown in Table 35 below.

TABLE 35

| Sample Name | 140 g ae/ha quizalofop |
|---|---|
| Control | Dead |
| 63-1A | No injury |
| 63-1F | No injury |
| 63-4B | No injury |
| 63-4D | No injury |
| 63-6C | Dead |

24.5—Tissue Harvesting, DNA Isolation and Quantification.

Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, Dneasy 69109). An aliquot of the extracted DNA was then stained with Pico Green (Molecular Probes P7589) and scanned in the florometer (BioTek) with known standards to obtain the concentration in ng/µl.

24.6—Southern Blot Analysis.

Southern blot analysis was performed with total DNA obtained from the Qiagen DNeasy kit. A total of 2 µg of DNA was subjected to an overnight digest of HindIII for pDAB3403 to obtain integration data. Likewise a total of 2 ug of DNA was subjected to an overnight digest of MfeI to obtain the PTU data. After the overnight digestion an aliquot of ~100 ng was run on a 1% gel to ensure complete digestion. After this assurance the samples were run on a large 0.85% agarose gel overnight at 40 volts. The gel was then denatured in 0.2 M NaOH, 0.6 M NaCl for 30 minutes. The gel was then neutralized in 0.5 M Tris HCl, 1.5 M NaCl pH of 7.5 for 30 minutes. A gel apparatus containing 20×SSC was then set-up to obtain a gravity gel to nylon membrane (Millipore INYC00010) transfer overnight. After the overnight transfer the membrane was then subjected to UV light via a crosslinker (Stratagene UV stratalinker 1800) at 1200×100 microjoules. The membrane was then washed in 0.1% SDS, 0.1 SSC for 45 minutes. After the 45 minute wash, the membrane was baked for 3 hours at 80° C. and then stored at 4° C. until hybridization. The hybridization template fragment was prepared using coding region PCR using plasmid pDAB3404. A total of 100 ng of total DNA was used as template. 20 mM of each primer was used with the Takara Ex Taq PCR Polymerase kit (Mims TAKRROO1A). Primers for Southern fragment PCR AAD-1 were (Forward—ATGGCTCATGCTGCCCTCA-GCC) (SEQ ID NO:31) and (Reverse—GGGCAGGC-CTAACTCCACCAA) (SEQ ID NO:32). The PCR reaction was carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 1 minute and 45 seconds followed by 72° C. for 10 minutes.

The product was run on a 1% agarose gel and excised then gel extracted using the Qiagen (28706) gel extraction procedure. The membrane was then subjected to a pre-hybridization at 60° C. step for 1 hour in Perfect Hyb buffer (Sigma H7033). The Prime it RmT dCTP-labeling reaction (Stratagene 300392) procedure was used to develop the p32 based probe (Perkin Elmer). The probe was cleaned-up using the Probe Quant. G50 columns (Amersham 27-5335-01). Two million counts CPM were used to hybridize the Southern blots overnight. After the overnight hybridization the blots were then subjected to two 20 minute washes at 65° C. in 0.1% SDS, 0.1 SSC. The blots were then exposed to a phosphor image screen overnight and scanned using a storm scanner (MOLECULAR DEVICES). A summary of the results is presented in Table 36.

TABLE 36

Southern Results.

| Event | Integration Southern data Number of bands | PTU Southern data Expected size 3049 bp |
|---|---|---|
| 63-1 A | 8 | yes, 7 distinct bands |
| 63-1 F | 5 | yes, 9 distinct bands |
| 63-4 A | 20 | yes, 20 distinct bands |
| 63-4 D | 20 | yes, 19 distinct bands |
| 63-6 C | 2 | Insufficient DNA yield for both cuts |

Plants 63-1 A and 63-1 F are not the same event; Plants 63-4 A and 63-4 D are the same event. These events have the expected size PTU's, but they are very complex. This Southern blot PTU data correlates with expression data and the spray data. Sample 63-6 C did not have enough DNA present to perform both Integration and PTU southern blots.

24.7—Western Data

Sample preparation and analysis conditions were as described previously. Five transgenic rice lines and 1 non-transgenic control were analyzed for AAD-1 expression using ELISA and Western blot. AAD-1 was detected in four lines (63-1A, 63-1F, 63-4B and 63-4D) but not in line 63-1C or the control plant. Expression levels ranged from 15.6 to 183 ppm of total soluble protein. A summary of the results is presented in Table 37.

TABLE 37

| | | | ELISA | | |
|---|---|---|---|---|---|
| Lane | Sample Name | TSP (μg/mL) | [AAD1] (ng/mL) | Expression (ppm) | Western |
| 1 | Control | 6719.58 | 0.00 | 0.00 | − |
| 2 | 63-1A | 8311.87 | 351.17 | 42.25 | ± |
| 3 | 63-1F | 11453.31 | 2092.35 | 182.69 | ++ |
| 4 | 63-4B | 13835.09 | 216.00 | 15.61 | + |
| 5 | 36-4D | 13656.49 | 717.05 | 52.51 | ++ |
| 6 | 63-6C | 5343.63 | 0.00 | 0.00 | − |
| 7 | AAD1 Standard (0.5 μg/mL) | | | | +++ |
| 8 | AAD1 Standard (5.01 μg/mL) | | | | +++++ |

Example 25—Turf Grass Transformation Procedures

Genetic transformation, with AAD-1 (v3) substituted for the "bar" gene as described below, of creeping bentgrass mediated by *Agrobacterium tumefaciens* could be achieved through embryogenic callus initiated from seeds (cv. Penn-A-4), as described generally below. See "Efficiency of *Agrobacterium tumefaciens*-mediated turfgrass (*Agrostis stolonifera* L) transformation" (Luo et. al., 2004).

Callus is infected with an *A. tumefaciens* strain (LBA4404) harboring a super-binary vector that contained an herbicide-resistant bar gene driven either by a rice ubiquitin promoter. The overall stable transformation efficiency ranged from 18% to 45%. Southern blot and genetic analysis confirmed transgene integration in the creeping bentgrass genome and normal transmission and stable expression of the transgene in the $T_1$ generation. All independent transformation events carried one to three copies of the transgene, and a majority (60-65%) contained only a single copy of the foreign gene with no apparent rearrangements.

25.1—Seed Preparation for Embryogenic Callus Induction.

Mature seeds were dehusked with sand paper and surface sterilized in 10% (v/v)

Clorox bleach (6% sodium hypochlorite) plus 0.2% (v/v) Tween 20 (Polysorbate 20) with vigorous shaking for 90 min. Following rinsing five times in sterile distilled water, the seeds were placed onto callus-induction medium (MS basal salts and vitamins, 30 g/l sucrose, 500 mg/l casein hydrolysate, 6.6 mg/l 3,6-dichloro-o-anisic acid (dicamba), 0.5 mg/l 6-benzylaminopurine (BAP) and 2 g/l Phytagel. The pH of the medium was adjusted to 5.7 before autoclaving at 120° C. for 20 min)

25.2—Embryogenic Callus Induction.

The culture plates containing prepared seed explants were kept in the dark at room temperature for 6 weeks. Embryogenic calli were visually selected and subcultured on fresh callus-induction medium in the dark at room temperature for 1 week before co-cultivation.

25.3—*Agrobacterium* Infection and Co-Cultivation.

One day before agro-infection, the embryogenic callus was divided into 1- to 2-mm pieces and placed on callus-induction medium containing 100 μM acetosyringone. A 10-ul aliquot of *Agrobacterium* (LBA4404) suspension (OD=1.0 at 660 nm) was then applied to each piece of callus, followed by 3 days of co-cultivation in the dark at 25° C.

25.4—Resting Stage and *Agrobacterium* Control.

For the antibiotic treatment step, the callus was then transferred and cultured for 2 weeks on callus-induction medium plus 125 mg/l cefotaxime and 250 mg/l carbenicillin to suppress bacterial growth.

25.5—Selection and Potential Transgenic Colony Identification.

Subsequently, for selection, the callus was moved to callus-induction medium containing 250 mg/l cefotaxime and 10 mg/l phosphinothricin (PPT) for 8 weeks. Antibiotic treatment and the entire selection process were performed at room temperature in the dark. The subculture interval during selection was typically 3 weeks.

25.6—Regeneration of Transgenic Plants.

For plant regeneration, the PPT-resistant proliferating callus events are first moved to regeneration medium (MS basal medium, 30 g/l sucrose, 100 mg/l myo-inositol, 1 mg/l BAP and 2 g/l Phytagel) supplemented with cefotaxime, PPT or hygromycin. These calli were kept in the dark at room temperature for 1 week and then moved into the light for 2-3 weeks to develop shoots. No Albino plants with PPT selection (Hygromycin if used as a selection agent, produces a high level of albino plants).

25.7—Root Induction and Transfer to Greenhouse.

Small shoots were then separated and transferred to hormone-free regeneration medium containing PPT and cefotaxime to promote root growth while maintaining selection pressure and suppressing any remaining *Agrobacterium* cells. Plantlets with well-developed roots (3-5 weeks) were then transferred to soil and grown either in the greenhouse or in the field.

25.8—Vernalization and Out-Crossing of Transgenic Plants.

Transgenic plants were maintained out of doors in a containment nursery (3-6 months) until the winter solstice in December. The vernalized plants were then transferred to the greenhouse and kept at 25° C. under a 16/8 h photoperiod and surrounded by non-transgenic wild-type plants that physically isolated them from other pollen sources. The plants started flowering 3-4 weeks after being moved back into the greenhouse. They were out-crossed with the pollen from the surrounding wild type plants. The seeds collected from each individual transgenic plant were germinated in soil at 25° C., and T1 plants were grown in the greenhouse for further analysis.

25.9—Other Target Grasses.

Other grasses that can be targeted for AAD-1 transformation according to the subject invention include Annual meadowgrass (*Poa annua*), Bahiagrass, Bentgrass, Bermudagrass, Bluegrass, Bluestems, Bromegrass, Browntop bent (*Agrostis capillaries*), Buffalograss, Canary Grass, Carpetgrass, Centipedegrass, Chewings fescue (*Festuca rubra commutate*), Crabgrass, Creeping bent (*Agrostis stolonifera*), Crested hairgrass (*Koeleria macrantha*), Dallisgrass, Fescue, Festolium, Hard/sheeps fescue (*Festuca ovina*), Gramagrass, Indiangrass, Johnsongrass, Lovegrass, mixes (Equine, Pasture, etc.), Native Grasses, Orchardgrass, Perennial ryegrass (*Lolium perenne*), Redtop, Rescuegrass, annual and perennial Ryegrass, Slender creeping red fescue (*Festuca rubra trichophylla*), Smooth-stalked meadowgrass (*Poa pratensis*), St. Augustine, Strong creeping red fescue (*Festuca rubra rubra*), Sudangrass, Switchgrass, Tall fescue (*Festuca arundinacea*), Timothy, Tufted hairgrass (*Deschampsia caespitosa*), Turfgrasses, Wheatgrass, and Zoysiagrass.

Example 26—AAD-1 (v3) in Canola 26.1—Canola Transformation.

The AAD-1 (v3) gene conferring resistance to 2,4-D was used to transform *Brassica napus* var. Nexera* 710 with *Agrobacterium*-mediated transformation. The construct contained AAD-1 (v3) gene driven by CsVMV promoter and Pat gene driven by AtUbi10 promoter.

Seeds were surface-sterilized with 10% commercial bleach for 10 minutes and rinsed 3 times with sterile distilled water. The seeds were then placed on one half concentration of MS basal medium (Murashige and Skoog, 1962) and maintained under growth regime set at 25° C., and a photoperiod of 16 hrs light/8 hrs dark.

Hypocotyl segments (3-5 mm) were excised from 5-7 day old seedlings and placed on callus induction medium K1D1 (MS medium with 1 mg/l kinetin and 1 mg/l 2,4-D) for 3 days as pre-treatment. The segments were then transferred into a petri plate, treated with *Agrobacterium* Z7075 or LBA4404 strain containing pDAB721. The *Agrobacterium* was grown overnight at 28° C. in the dark on a shaker at 150 rpm and subsequently re-suspended in the culture medium. After 30 min treatment of the hypocotyl segments with *Agrobacterium*, these were placed back on the callus induction medium for 3 days. Following co-cultivation, the segments were placed K1D1TC (callus induction medium containing 250 mg/l Carbenicillin and 300 mg/l Timentin) for one week of recovery. Alternately, the segments were placed directly on selection medium K1D1H1 (above medium with 1 mg/l Herbiace). Carbenicillin and Timentin were the antibiotics used to kill the *Agrobacterium*. The selection agent Herbiace allowed the growth of the transformed cells.

Callus samples from 35 independent events were tested by PCR. All the 35 samples tested positive for the presence of AAD-1 (v3), whereas the non-transformed controls were negative (section on PCR assay). Ten callus samples were confirmed to express the AAD-1 protein as determined by ELISA (section on protein analysis).

Callused hypocotyl segments were then placed on B3Z1H1 (MS medium, 3 mg/l benzylamino purine, 1 mg/l Zeatin, 0.5 gm/l MES [2-(N-morpholino) ethane sulfonic acid], 5 mg/l silver nitrate, 1 mg/l Herbiace, Carbenicillin and Timentin) shoot regeneration medium. After 3 weeks shoots started regenerating. Hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l Herbiace, Carbenicillin and Timentin) for another 3 weeks.

Shoots were excised from the hypocotyl segments and transferred to shoot elongation medium MESH10 (MS, 0.5 gm/l MES, 10 mg/l Herbiace, Carbenicillin, Timentin) for 2-4 weeks. The elongated shoots are cultured for root induction on MSI.1 (MS with 0.1 mg/l Indolebutyric acid). Once the plants had a well established root system, these were transplanted into soil. The plants were acclimated under controlled environmental conditions in the Conviron for 1-2 weeks before transfer to the greenhouse.

The transformed T0 plants were self-pollinated in the greenhouse to obtain T1 seed. The T0 plants and T1 progeny were sprayed with a range of herbicide concentrations to establish the level of protection by the AAD-1 (v3) gene.

26.2—"Molecular Analysis": Canola Materials and Methods 26.2.1—Tissue Harvesting DNA Isolation and Quantification.

Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, DNeasy 69109). An aliquot of the extracted DNA was then stained with Pico Green (Molecular Probes P7589) and read in the florometer (BioTek) with known standards to obtain the concentration in ng/ul.

26.2.2—Polymerase Chain Reaction.

A total of 100 ng of total DNA was used as the template. 20 mM of each primer was used with the Takara Ex Taq PCR Polymerase kit (Minis TAKRROO1A). Primers for Coding Region PCR AAD-1 (v3) were (Forward—ATGGCTCATG CTGCCCTCAGCC) (SEQ ID NO:27) and (Reverse—CGGGCAGGCCTAACTCCACCAA) (SEQ ID NO:28). The PCR reaction was carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 2 minutes followed by 72° C. for 10 minutes. PCR products were analyzed by electrophoresis on a 1% agarose gel stained with EtBr. 35 samples from 35 plants with AAD-1 (v3) events tested positive. Three negative control samples tested negative.

26.3—ELISA.

Using established ELISA described in previous section, AAD-1 protein was detected in 10 different canola transformation events. Expression levels ranged from 150 to over 1000 ppm of total soluble protein (TSP). Three different untransformed calli samples were tested in parallel with little signal detected, indicating that the antibodies used in the assay have minimal cross reactivity to the canola cell matrix. A summary of the results is presented in Table 38.

TABLE 38

Expression of AAD1 in Canola calli.

| Sample # | Weight (mg) | [TSP] (μg/mL) | [AAD1] (ng/mL) | Expression (ppm TSP) | PCR for AAD1 |
|---|---|---|---|---|---|
| 1 | 114 | 757.02 | 119.36 | 157.67 | + |
| 2 | 55 | 839.79 | 131.84 | 156.99 | + |
| 3 | 53 | 724.41 | 202.12 | 279.01 | + |
| 4 | 52 | 629.01 | 284.89 | 452.92 | + |
| 5 | 55 | 521.75 | 175.88 | 337.08 | + |
| 6 | 61 | 707.69 | 74.24 | 153.71 | + |
| 7 | 51 | 642.02 | 559.11 | 1026.73 | + |
| 8 | 65 | 707.69 | 270.73 | 382.56 | + |
| 9 | 51 | 642.02 | 197.90 | 308.25 | + |
| 10 | 51 | 1417.42 | 220.63 | 156.66 | + |
| Control 1 | 53 | 2424.67 | 18.67 | 7.70 | − |
| Control 2 | 61 | 2549.60 | 35.00 | 13.73 | − |
| Control 3 | 59 | 2374.41 | 22.79 | 9.60 | − |

REFERENCES

Adang, M. J., M. J. Stayer, T. A. Rocheleau, J. Leighton, R. F. Barker, and D. V. Thompson. 1985. Characterized full-length and truncated plasmid clones of the crystal protein of Bacillus thuringiensis subsp kurstaki HD-73 and their toxicity to Manduca sexta. Gene 36:289-300.

Agriliance Crop Protection Guide. 2003. Agriliance, LLC. St Paul, Minn. 588 p.

Altschul, S. F., W. Gish, W. Miller, E. W. Myers, and D. J. Lipman. 1990. Basic local alignment search tool. J. Mol. Biol. 215:403-410.

Altschul, S. F., T. L. Madden, A. A. Schaffer, J. Zhang, Z, Zhang, W. Miller, and D. J. Lipman. 1997. Gapped BLAST and PSIBLAST: a new generation of protein databasesearch programs. Nucl. Acids Res. 25:3389-3402.

An, G., B. D. Watson, S. Stachel, M. P. Gordon, E. W. Nester. 1985. New cloning vehicles for transformation of higher plants. EMBO J. 4:277-284.

Armstrong C. L., C. E. Green, R. L. Phillips. 1991. Development and availability of germplasm with high Type II culture formation response. Maize Genet Coop News Lett 65:92-93.

Beltz, G. A., K. A. Jacobs, T. H. Eickbush, P. T. Cherbas, and F. C. Kafatos. 1983 Methods of Enzymology, R. Wu, L. Grossman and K. Moldave [eds.] Academic Press, New York 100:266-285

Birch R. G. and T. Franks. 1991. Development and optimization of microprojectile systems for plant genetic transformation. Aust. J. Plant Physiol. 18:453-469.

CDMS. Crop Data Management Systems Labels and MSDS. Online. Internet. Mar. 13, 2004. Available at net/manufimanufasp.

Chee P. P., K. A. Fober, J. L. Slightom. 1989. Transformation of soybean (Glycine max) by infecting germinating seeds with Agrobacterium tumefaciens. Plant Physiol. 91:1212-1218.

Cheng M., J. E. Fry, S. Pang, H. Zhou, C. M. Hironaka, D. R. Duncan, T. W. Conner, and Y. Wan. 1997. Genetic transformation of wheat mediated by Agrobacterium tumefaciens. Plant Physiol 115: 971-980.

Chu C. C., C. C. Wang, C. S. Sun, C. Hsu, K. C. Yin, C. Y. Chu, F. Y. Bi. 1975. Establishment of an efficient medium for anther culture of rice through comparative experiments on the nitrogen sources. Sci. Sinica 18:659-668.

Clemente T. E., B. J. LaVallee, A. R. Howe, D. Conner-Ward, R. J. Rozman, P. E. Hunter, D. L. Broyles, D. S. Kasten, M. A. Hinchee. 2000. Progeny analysis of glyphosate selected transgenic soybeans derived from Agrobacterium-mediated transformation. Crop Sci 40: 797-803.

CPR: Crop Protection Reference. 2003 Chemical and Pharmaceutical Press, New York, N.Y. 2429 p.

Devine, M. D. 2005. Why are there not more herbicide-tolerant crops? Pest Manag. Sci. 61:312-317.

Dietrich, Gabriele Elfriede (1998) Imidazolinone resistant AHAS mutants. U.S. Pat. No. 5,731,180.

Didierjean L, L. Gondet, R. Perkins, S. M. Lau, H. Schaller, D. P. O'Keefe, D. Werck-Reichhart. 2002. Engineering Herbicide Metabolism in Tobacco and Arabidopsis with CYP76B1, a Cytochrome P450 Enzyme from Jerusalem Artichoke. Plant Physiol 2002, 130:179-189.

Ditta, G. S. Stranfield, D. Corbin, and D. R. Helinski. 1980. Broad host range DNA cloning system for Gram-negative bacteria: Construction ofa gene bank of Rhizobium leliloti. PNAS 77:7347-7351.

Edwards, R. A., L. H. Keller, and D. M. Schifferli. 1998. Improved allelic exchange vectors and their use to analyze 987P fimbria gene expression. Gene 207:149-157.

Falco S. C., T. Guida, M. Locke, J. Mauvais, C. Sanders, R. T. Ward, P. Webber. 1995. Transgenic canola and soybean seeds with increased lysine. Bio/Technology 13:577-582.

Finer J. and M. McMullen. 1991. Transformation of soybean via particle bombardment of embryogenic suspension culture tissue. In Vitro Cell. Dev. Biol. 27P:175-182.

Fraley, R. T., D. G. Rogers, and R. B. Horsch. 1986. Genetic transformation in higher plants. Crit. Rev. Plant Sci. 4:1-46.

Frame B. R., P. R. Drayton, S. V. Bagnall, C. J. Lewnau, W. P. Bullock, H. M. Wilson, J. M. Dunwell, J. A. Thompson, and K. Wang. 1994. Production of fertile maize plants by silicon carbide whisker-mediated transformation. Plant J. 6:941-948.

Fukumori, F., and R. P. Hausinger. 1993. Purification and characterization of 2,4-dichlorophenoxyacetate/α-ketoglutarate dioxygenase. J. Biol. Chem. 268: 24311-24317.

Gamborg, O. L., R. A. Miller, and K. Ojima. 1968. Nutrient requirements of suspensions of cultures of soybean root cells. Exp. Cell Res. 50:151-158.

Gay, P., D. Le Coq, M. Steinmetz, E. Ferrari, and J. A. Hoch. 1983. Cloning structural gene sacB, which codes for exoenzyme levansucrase of Bacillus subtilis: expression of the gene in Eschericia coli. J. Bacteriol. 153:1424-1431.

Gianessi, L. R. 2005 Economic and herbicide use impacts of glyphosate-resistant crops. Pest. Manag. Sci. 61:241-245.

Heap, I. The International Survey of Herbicide Resistant Weeds. Online. Internet. Mar. 18, 2005. Available at weedscience.com.

Hiei Y., T. Komari, and T. Kubo. 1997. Tranformation of rice mediated by Agrobacterium tumefaciens, Plant Mol. Biol. 35:205-218.

Hiei, Y., T. Komari (1997) Method for Transforming Monocotyledons. U.S. Pat. No. 5,591,616.

Hinchee M. A. W., D. V. Conner-Ward, C. A. Newell, R. E. McDonnell, S. J. Sato, C. S. Gasser, D. A. Fischhoff, D. B. Re, R. T. Fraley, R. B. Horsch. 1988. Production of transgenic soybean plants using *Agrobacterium*-mediated DNA transfer. Bio/Technology 6:915-922.

Höfte, H. and H. R. Whiteley. 1989. Insecticidal cristal proteins of *Bacillus thuringiensis*. 1989. Microbiol. Rev. 53:242-255.

Hoekema, A. 1985. In: *The Binary Plant Vector System*, Offset-durkkerij Kanters B. V., Alblasserdam, Chapter 5.

Hogan, D. A.; S. R. Smith, E. A. Saari, J. McCracken, R. P. Hausinger. 2000. Site-directed mutagenesis of 2,4-dichlorophenoxyacetic acid/α-ketoglutarate dioxygenase.

Identification of residues involved in metallocenter formation and substrate binding. J. Biol. Chem. 275:12400-12409.

Holsters, M., D. De Waele, A. Depicker, E. Messens, M. Van Montagu, and J. Schell. 1978. Transfection and transformation of *Agrobacterium tumefaciens*. Mol Gen. Genet. 163:181-187.

Horsch, R., J. Fry, N. Hoffman, J. Neidermeyer, S. Rogers, and R. Fraley. 1988. In Plant Molecular Biology Manual, S. Gelvin et al., eds., Kluwer Academic Publishers, Boston Horvath, M., G. Ditzelmüller, M. Lodl, and F. Streichsbier. 1990. Isolation and characterization of a 2-(2,4-dichlorophenoxyl)propionic acid-degrading soil bacterium. Appl. Microbiol Biotechnol. 33:213-216.

Jefferson, R. A. M. Bevan, and T. Kavanagh. 1987. The use of *Escherichia coli* B-glucuronidase gene as a gene fustion marker for studies of gene expression in higher plants. Biochem. Soc. Trans. 15: 17-19.

Karlin, S. and S. F. Altschul. 1990. Methods for assessing the statistical significance of molecular sequence features by using general scoring schemes. PNAS 87:2264-2268.

Karlin, S. and S. F. Altschul. 1993. Applications and statistics for multiple high-scoring segments in molecular sequences. PNAS 90:5873-5877

Keller, G. H., and M. M. Manak. 1987. DNA Probes. Stockton Press, New York, N.Y., pp. 169-170.

Kohler, H. P. E. 1999. *Sphingobium herbicidovorans* MH: a versatile phenoxyalkanoic acid herbicide degrader. J. Ind Microbiol and Biotech. 23:336-340.

Li L, Qu R, Kochko A de, Fauquet C M, Beachy R N (1993) An improved rice transformation system using the biolistic method. Plant Cell Rep 12:250-255

Linsmaier, E. M. and F. Skoog (1965) Organic growth factor requirements of tobacco tissue cultures. Physiol. Plant. 18:100-127.

Lorraine-Colwill, D. F., S. B. Powles, T. R. Hoawkes, P. H. Hollingshead, S. A. J. Arner, and C. Preston. 2003. Investigations into the mechanism of glyphosate resistance in *Lolium rigidum*. Pestic. Biochem. Physiol. 74:62-73.

Luo, H., Q. Hu, K. Nelson, C. Longo, A. P. Kausch, J. M. Chandlee, J. K. Wipff and C. R. Fricker. 2004. *Agrobacterium tumefaciens*-mediated creeping bentgrass (*Agrostis stolonifera* L.) transformation using phosphinothricin selection results in a high frequency of single-copy transgene integration. Plant Cell Reports 22: 645-652.

Lyon, B. R., D. J. Llewellyn, J. L. Huppatz, E. S. Dennis, and W. J. Peacock. 1989. Expression of a bacterial gene in transgenic tobacco confers resistance to the herbicide 2,4-dichlorophenoxyacetic acid. Plant Mol. Bio. 13:533-540.

Lyon, B. R., Y. L. Cousins, D. J. Llewellyn, and E. S. Dennis. 1993. Cotton plants transformed with a bacterial degradation gene are protected from accidental spray drift damage by the herbicide 2,4-dichlorophenoxyacetic acid. Transgenic Res. 2: 166-169.

Maniatis, T., E. F. Fritsch, J. Sambrook. 1982. Molecular Cloning: A Laboratory Manual, Cold Spring Harbor Laboratory, Cold Spring Harbor, N.Y.

Martin, J. R. and W. W. Witt. 2002. Response of glyphosate tolerant and susceptible biotypes of horseweed (Conyza canadensis) to foliar applied herbicides. Proc. North Cent. Weed Sci. Soc. 57:185.

Martinell B. J., L. S. Julson, C. A. Emler, H. Yong, D. E. McCabe, E. J. Williams. 2002. Soybean *Agrobacterium* transformation method. U.S. Pat. No. 6,384,301

McCabe D. E., W. F. Swain, B. J. Martinell, P. Christou. 1988. Stable transformation of soybean (*Glycine max*) by particle acceleration. Bio/Technology 6:923-926.

Miller S. D., P. W. Stahlman, P. Westra, G. W. Wicks, R. G. Wilson, J. M. Tichota. 2003. Risks of weed spectrum shifts and herbicide resistance in glyphosate-resistant cropping systems. Proc. West. Soc. Weed Sci. 56:61-62.

Muller R, S. Jorks, S. Kleinsteuber, W. Babel. 1999. *Comamonas acidovorans* strain MC1: a new isolate capable of degrading the chiral herbicides dichlorprop and mecoprop and the herbicides 2,4-D and MCPA. Microbiol. Res. 154:241-246.

Murashige T. and F. Skoog. 1962. A revised medium for rapid growth and bioassays with tobacco tissue cultures. Physiol. Plant. 15:473-497.

Murphy G. P., T. E. Dutt, R. F. Montgomery, T. S. Willard, G. A. Elmore. 2002. Control of horseweed with glyphosate. Proc. North Cent. Weed Sci. Soc. 57:194.

Ng, C. H., R. Wickneswari, S. Salmigah, Y. T. Teng, and B. S. Ismail. 2003. Gene polymorphisms in glyphosate-resistant and -susceptible biotypes of *Eleusine indica* from Malaysia. Weed Res. 43:108-115.

Olhoft P. M. and D. A. Somers. 2001. L-Cysteine increases *Agrobacterium*-mediated T-DNA delivery into soybean cotyledonary-node cells. Plant Cell Rep 20: 706-711

Olhoft, P. M., L. E. Flagel, C. M. Donovan, and D. A. Somers. 2003. Efficient soybean transformation using hygromycin B selection in the cotyledonary-node method. Planta 216:723-735

Padgette S. R., K. H. Kolacz, X. Delannay, D. B. Re, B. J. LaVallee, C. N. Tinius, W. K. Rhodes, Y. I. Otero, G. F. Barry, D. A. Eichholtz, V. M. Peschke, D. L. Nida, N. B. Taylor, and G. M. Kishore. 1995. Development, identification, and characterization of a glyphosate-tolerant soybean line. Crop Sci. 1995; 35:1451-1461.

Parrott W. A., J. N. All, M. J. Adang, M. A. Bailey, H. R. Boerma, and C. N. Stewart, Jr. 1994. Recovery and evaluation of soybean plants transgenic for a *Bacillus thuringiensis* var. *kurstaki* insecticidal gene. In Vitro Cell. Dev. Biol. 30P:144-149.

Popelka, J. C. and F. Altpeter 2003. *Agrobacterium tumefaciens*-mediated genetic transformation of rye (*Secale cereale* L) Mol. Breed 11:203-211

Saari, R. E., D. A. Hogan, and R. P. Hausinger. 1999. Stereospecific degradation of the pheonxypropionate herbicide dichlorprop. J. Mol. Catal. B: Enz. 6:421-428.

Saiki, R. K., S. Scharf, F. Faloona, K. B. Mullis, G. T. Horn, H. A. Erlich, and N. Arnheim. 1985. Enzymatic Amplification of β-Globin Genomic Sequences and Restriction Site Analysis for Diagnosis of Sickle Cell Anemia. Science 230:1350-1354.

Sambrook, J., E. F. Fritsch, and T. Maniatis. 1989. Molecular Cloning, A Laboratory Manual, Cold Spring Harbor Press.

Sambrook, J. and D. W. Russell. 2000. *Molecular Cloning*. Cold Spring Harbor Laboratory Press, Cold Spring Harbor, N.Y.

Schenk, R. U. and A. C. Hildebrandt (1972) Methods and techniques for induction and growth of monocotyledenous and dicotyledenous plant cell cultures. Can. J. Bot. 50:199-204.

Sfiligoj, E. 2004. Spreading resistance. Crop Life. March issue.

Simarmata, M., J. E. Kaufmann, and D. Penner. 2003. Potential basis of glyphosate resistance in California rigid ryegrass (*Lolium rigidum*). Weed Sci. 51:678-682.

Singh R. J., T. M. Klein, C. J. Mauvais, S. Knowlton, T. Hymowitz, C. M. Kostow. Cytological characterization of transgenic soybean. Theor. Appl. Genet. 1998; 96:319-324.

Smejkal, C. W., T. Vallaeys, S. K. Burton, and H. M. Lappin-Scott. 2001. Substrate specificity of chlorophenoxyalkanoic acid-degrading bacteria is not dependent upon phylogenetically related tfdA gene types. Biol. Fertil. Sols 33:507-513.

Streber, W. and L. Willmitzer. 1989. Transgenic tobacco plants expressing a bacterial detoxifying enzyme are resistant to 2,4-D. Bio/Technology 7:811-816.

Streber, W. R., K. N. Timmis, and M. H. Zenk. 2000. Microorganisms and plasmids for 2,4-dichlorophenoxyacetic acid (2,4-D) monooxygenase formation and process for the production of these plasmids and strains. U.S. Pat. No. 6,153,401.

Streber, W. R., K. N. Timmis, and M. H. Zenk. 1987. Analysis, cloning, and high-level expression of 2,4-dichlorophenixyacetic monooxygenase gene tfdA of *Alcaligenes eutrophus* JMP134. J. Bacteriol. 169:2950-2955.

Suggs, S. V., T. Miyake, E. H. Kawashime, M. J. Johnson, K. Itakura, and R. B. Wallace. 1981. *ICN-UCLA Symp. Dev. Biol. Using Purified Genes*, D. D. Brown [ed.], Academic Press, New York, 23:683-693.

Tingay, S., D. McElroy, R. Kalla, S. Fieg, W. Mingbo, S. Thornton, and R. Bretell. 1997. *Agrobacterium tumefaciens*-mediated barley transformation. Plant J. 11:1369-1376.

Weigel, D. and J. Glazebrook. 2002. *Arabidopsis*: A Laboratory Manual. Cold Spring Harbor Lab Press, Cold Spring Harbor, N.Y. 358 pp.

Weising, K., J. Schell, and G. Kahl. 1988. Foreign genes in plants: transfer, structure, expression and applications. Ann. Rev. Genet. 22:421-477.

Welter, M. E., D. S. Clayton, M. A. miler, and J. F. Petolino. 1995. Morphotypes of friable embryogenic maize callus. Plant Cell Rep. 14:725-729.

Westendorf A., D. Benndorf, R. Muller, W. Babel. 2002. The two enantiospecific dichlorprop/α-ketoglutarate-dioxygenases from *Delftia acidovorans* MC1-protein and sequence data of RdpA and SdpA. Microbiol. Res. 157: 317-22.

Westendorf, A., R. H. Muller, and W. Babel. 2003. Purification and characterization of the enantiospecific dioxygenases from *Delftia acidovorans* MC1 initiating the degradation of phenoxypropionates and phenoxyacetate herbicides. Acta Biotechnol. 23: 3-17.

WSSA. 2002. Herbicide Handbook (8$^{th}$ ed). Weed Science Society of America. Lawrence, Kans. 492 pp.

Zeng P, D. Vadnais, Z. Zhang, and J. Polacco. 2004. Refined glufosinate selection in *Agrobacterium*-mediated transformation of soybean [*Glycine max* (L.) Merr.]. Plant Cell Rep. 22: 478-482.

Zhang S (1995) Efficient plant regeneration from indica (group 1) rice protoplasts of one advanced breeding line and three varieties. Plant Cell Rep 15:68-71

Zhang S, Chen L, Qu R, Marmey P, Beachy R N, Fauquet C M (1996) Efficient plant regeneration from indica (group 1) rice protoplasts of one advanced breeding line and three varieties. Plant Cell Rep 15:465-469.

Zhang S, Song W, Chen L, Ruan D, Taylor N, Ronald P, Beachy R N, Fauquet C M (1998) Transgenic elite Indica rice varieties, resistant to *Xanthomonas oryzae* pv. *oryzae*. Mol Breed 4:551-558.

Zhang, Z., A. Xing, P. E. Staswick, and T. E. Clemente. 1999. The use of glufosinate as a selective agent in *Agrobacterium*-mediated transformation of soybean. Plant Cell, Tissue, and Organ Culture 56:37-46.

Zhao, Z. Y., T. Cai, L. Tagliani, M. Miller, N. Wang, H. Pang, M. Rudert, S. Schroeder, D. Hondred, J. Seltzer, and D. Pierce. 2000. *Agrobacterium*-mediated *sorghum* transformation, Plant Mol. Biol. 44:789-798.

Zipper, C., M. Bunk, A. Zehnder, H. Kohler. 1998. Enantioselective uptake and degradation of the chiral herbicide dichlorprop [(RS)-2-(2,4-dichlorophenoxy)propanoic acid] by *Sphingobium herbicidovorans* MH. J. Bact. 13:3368-3374

---

The invention claimed is:

1. A plant cell comprising an expression cassette, wherein said expression cassette comprises a polynucleotide encoding a protein comprising the amino acid sequence selected from the group consisting of SEQ ID NO:9, SEQ ID NO: 10 and SEQ ID NO: 11, wherein said polynucleotide is operably linked to a heterologous promoter that is functional in a plant cell and expression of said polynucleotide renders said transgenic plant cell tolerant to a phenoxy auxin herbicide as compared to an untransformed plant cell of the same plant.

2. The plant cell of claim 1, wherein said polynucleotide is selected from the group consisting of SEQ ID NO:3, SEQ ID NO:4 and SEQ ID NO:5.

3. A plant comprising the plant cell of claim 1.

4. A seed from the plant of claim 3, wherein plant cells of said seed comprise said expression cassette.

5. A method of protecting a crop plant from damage by an aryloxyalkanoate herbicide, said method comprising growing the plant of claim 3, and applying said herbicide to said plant.

6. A method of making the plant cell of claim 1 wherein said method comprises subjecting a plurality of plant cells to transformation with said polynucleotide, then growing said cells in a concentration of a herbicide that permits transformed cells that express said polynucleotide to grow while killing or inhibiting the growth of nontransformed cells.

7. The plant cell of claim 1 wherein said promoter is selected from the group consisting of cassava vein mosaic virus promoter (CsVMV), AtUbi10 promoter, AtUbi3 promoter, OsActl promoter and ZmUbil promoter.

8. The plant of claim 3 wherein said plant further comprises an insect-resistance gene derived from an organism selected from the group consisting of *Bacillus thuringiensis*, *Photorhabdus*, and *Xenorhabdus*.

9. The plant of claim 3 wherein said plant further comprises a gene for an agronomic trait selected from the group consisting of fungal resistance, stress tolerance, increased yield, improved oil profile, improved fiber quality, viral resistance, delayed ripening, cold tolerance, and salt tolerance.

10. The plant of claim 3, wherein said plant is a monocot.

11. The plant of claim 10, wherein said monocot is selected from the group consisting of corn, rice, wheat, barley, rye, turf grass, oats, *sorghum*, and pasture grasses.

12. A plant grown from the seed of claim 4.

13. A regenerable part, progeny, or asexual propagate of the plant of claim 3, wherein said regenerable part, progeny, or asexual propagate comprises an expression cassette comprising a polynucleotide encoding a protein comprising an amino acid sequence selected from the group consisting of SEQ ID NO:9, SEQ ID NO: 10 and SEQ ID NO: 11, wherein said polynucleotide is operably linked to a heterologous promoter that is functional in a plant cell.

* * * * *